(12) United States Patent
Leong et al.

(10) Patent No.: US 7,115,712 B1
(45) Date of Patent: Oct. 3, 2006

(54) CYTOKINE POLYPEPTIDES

(75) Inventors: Steven R. Leong, Berkeley, CA (US); Juha Punnonen, Palo Alto, CA (US)

(73) Assignee: Maxygen, Inc., Redwood City, CA (US)

( * ) Notice: Subject to any disclaimer, the term of this patent is extended or adjusted under 35 U.S.C. 154(b) by 75 days.

(21) Appl. No.: 09/725,324

(22) Filed: Nov. 28, 2000

Related U.S. Application Data

(60) Provisional application No. 60/169,035, filed on Dec. 2, 1999.

(51) Int. Cl.
C07K 14/52 (2006.01)
(52) U.S. Cl. .......................................... 530/350; 514/2
(58) Field of Classification Search ................ 530/350; 536/23.1; 514/1
See application file for complete search history.

(56) References Cited

U.S. PATENT DOCUMENTS

| | | | |
|---|---|---|---|
| 4,683,202 A | 7/1987 | Mullis | |
| 5,001,065 A | 3/1991 | Larrick et al. | |
| 5,279,833 A | 1/1994 | Rose | |
| 5,348,867 A | 9/1994 | Georgiou et al. | |
| 5,457,038 A | 10/1995 | Trinchieri et al. | |
| 5,512,463 A | 4/1996 | Stemmer | |
| 5,514,588 A | 5/1996 | Varadaraj | |
| 5,547,852 A | 8/1996 | Seiler et al. | |
| 5,569,454 A | 10/1996 | Trinchieri et al. | |
| 5,571,515 A | 11/1996 | Scott et al. | |
| 5,573,764 A | 11/1996 | Sykes et al. | |
| 5,605,793 A | 2/1997 | Stemmer | |
| 5,641,662 A | 6/1997 | Debs et al. | |
| 5,648,072 A | 7/1997 | Trinchieri et al. | |
| 5,648,467 A | 7/1997 | Trinchieri et al. | |
| 5,650,492 A | 7/1997 | Gately et al. | |
| 5,665,347 A | 9/1997 | Metzger et al. | |
| 5,674,483 A | 10/1997 | Tu et al. | |
| 5,723,127 A | 3/1998 | Scott et al. | |
| 5,744,132 A | 4/1998 | Warne et al. | |
| 5,756,085 A | 5/1998 | Sykes et al. | |
| 5,763,239 A | 6/1998 | Short et al. | |
| 5,766,914 A | 6/1998 | Deits | |
| 5,789,228 A | 8/1998 | Lam et al. | |
| 5,798,208 A | 8/1998 | Crea | |
| 5,811,238 A | 9/1998 | Stemmer et al. | |
| 5,811,523 A | 9/1998 | Trinchieri et al. | |
| 5,814,473 A | 9/1998 | Warren et al. | |
| 5,824,469 A | 10/1998 | Horwitz et al. | |
| 5,830,650 A | 11/1998 | Crea | |
| 5,830,696 A | 11/1998 | Short | |
| 5,830,721 A | 11/1998 | Stemmer et al. | |
| 5,833,975 A * | 11/1998 | Paoletti et al. ............. | 424/93.2 |
| 5,834,252 A | 11/1998 | Stemmer et al. | |
| 5,837,458 A | 11/1998 | Minushull et al. | |
| 5,853,714 A | 12/1998 | Deetz et al. | |
| 5,866,363 A | 2/1999 | Pieczenik | |
| 5,876,997 A | 3/1999 | Kretz | |
| 5,891,680 A | 4/1999 | Lieschke et al. | |
| 5,906,815 A | 5/1999 | Tu et al. | |
| 5,922,685 A | 7/1999 | Rakhmilevich et al. | |
| 5,925,749 A | 7/1999 | Mathur et al. | |
| 5,928,905 A | 7/1999 | Stemmer et al. | |
| 5,939,250 A | 8/1999 | Short | |
| 5,939,300 A | 8/1999 | Robertson et al. | |
| 5,942,430 A | 8/1999 | Robertson et al. | |
| 5,948,666 A | 9/1999 | Callen et al. | |
| 5,958,672 A | 9/1999 | Short | |
| 5,958,751 A | 9/1999 | Murphy et al. | |
| 5,962,258 A | 10/1999 | Mathur et al. | |
| 5,962,283 A | 10/1999 | Warren et al. | |
| 5,965,408 A | 10/1999 | Short | |
| 5,976,539 A | 11/1999 | Scott et al. | |
| 5,985,646 A | 11/1999 | Murphy et al. | |
| 6,001,574 A | 12/1999 | Short et al. | |
| 6,004,788 A | 12/1999 | Short | |
| 6,030,779 A | 2/2000 | Short | |
| 6,054,267 A | 4/2000 | Short | |
| 6,057,103 A | 5/2000 | Short | |
| 6,096,548 A | 8/2000 | Stemmer | |
| 6,117,679 A | 9/2000 | Stemmer | |
| 6,132,970 A | 10/2000 | Stemmer | |
| 6,165,793 A | 12/2000 | Stemmer | |
| 6,168,919 B1 | 1/2001 | Short | |
| 6,168,923 B1 | 1/2001 | Scott et al. | |
| 6,171,820 B1 | 1/2001 | Short | |
| 6,174,673 B1 | 1/2001 | Short et al. | |

(Continued)

FOREIGN PATENT DOCUMENTS

EP 0 527 809 B1 4/1991

(Continued)

OTHER PUBLICATIONS

Chang, C., et al. (1999) "Evolution of a cytokine using DNA family shuffling." *Nature Biotechnology* 17:793-797.

(Continued)

*Primary Examiner*—Marjorie A. Moran
*Assistant Examiner*—Carolyn L. Smith
(74) *Attorney, Agent, or Firm*—Margaret A. Powers; Joanne R. Petithory

(57) ABSTRACT

New cytokine polypeptides, and nucleic acids encoding them, are provided. Compositions including these polypeptides and nucleic acids, recombinant cells comprising said polypeptides and nucleic acids, methods of making the polypeptides and nucleic acid, antibodies to the polypeptides, and methods of using the polypeptides and nucleic acids are provided. Integrated systems comprising the sequences of the nucleic acids or polypeptides are also provided.

12 Claims, 16 Drawing Sheets

U.S. PATENT DOCUMENTS

| | | |
|---|---|---|
| 6,180,406 B1 | 1/2001 | Stemmer |
| 6,231,850 B1 | 5/2001 | Okano et al. |

FOREIGN PATENT DOCUMENTS

| | | |
|---|---|---|
| EP | 0 433 827 B1 | 6/1991 |
| EP | 0 441 900 B1 | 8/1991 |
| EP | 0911396 A2 | 4/1999 |
| EP | 0911396 A3 | 5/1999 |
| EP | 0 919 241 A1 | 6/1999 |
| EP | 0 820 299 B1 | 4/2002 |
| EP | 0 750 509 B1 | 5/2002 |
| WO | WO 96/24369 | 8/1996 |
| WO | WO 97/00321 | 1/1997 |
| WO | WO 97/07205 | 2/1997 |
| WO | WO 97/20078 | 6/1997 |
| WO | WO 97/25410 | 7/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42727 A1 | 10/1998 |
| WO | WO 98/42832 | 10/1998 |
| WO | WO 98/48034 | 10/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | 0934999 A1 | 8/1999 |
| WO | WO 99/41368 | 8/1999 |
| WO | WO 99/41368 A2 | 8/1999 |
| WO | WO 99/41369 | 8/1999 |
| WO | WO 99/41369 A2 | 8/1999 |
| WO | WO 99/41383 | 8/1999 |
| WO | WO 99/41383 A2 | 8/1999 |
| WO | WO 99/41402 | 8/1999 |
| WO | WO 99/41402 A2 | 8/1999 |
| WO | WO 99/45154 | 9/1999 |
| WO | WO 99/57128 | 11/1999 |
| WO | WO 99/65927 | 12/1999 |
| WO | WO 00/42560 | 7/2000 |
| WO | WO 00/42561 | 7/2000 |
| WO | WO 00/46344 A2 | 8/2000 |
| WO | WO 00/46344 A3 | 8/2000 |
| WO | WO 00/53744 | 9/2000 |
| WO | WO 00/58517 | 10/2000 |

OTHER PUBLICATIONS

Christians, F.C. et al., (1999) "Directed evolution of thymidine kinase for AZT phosphorylation using DNA family shuffling."*Nature Biotechnology* 17:259-264.

Coco et al., (2001) "DNA shuffling method for generating highly recombined genes and evolved enzymes" *Nature Biotechnology* vol. 19 pp. 354-359.

Crameri et al., (1993) "10(20)-Fold aptamer library amplification without gel purification," *Nuc. Acids Res.* 21(18):4410.

Crameri, A. & Stemmer W.P.C. (1995) "Combinatorial multiple cassette mutagenesis creates all the premutations of mutant and wildtype cassettes." *Biotechniques* 18:194-195.

Crameri, A. et al. (1996) "Improved green fluorescent protein by molecular evolution using DNA shuffling." *Nature Biotechnology* 14:315-319.

Crameri, A. et al. (1996) "Construction and evolution of antibody-phage libraries by DNA shuffling." *Nature Medicine* 2:100-103.

Crameri, A. et al., (1997) "Molecular evolution of an arsenate detoxification pathway by DNA shuffling." *Nature Biotechnology* 15:436-438.

Crameri, A. et al., (1998) "DNA shuffling of a family of genes from diverse species accelerates directed evolution." *Nature* 391:288-291.

Gates, C.M. et al., (1996) "Affinity selective isolation of ligands from peptide libraries through display on a lac repressor headpiece dimer". *Journal of Molecular Biology* 255:373-386.

Minshull, J., Stemmer, W.P.C. (1999) "Protein evolution by molecular breeding." *Current Opinion in Chemical Biology* 3:284-290.

Ness, J. et al., (1999) "DNA shuffling of subgenominc sequences of subtilisin." *Nature Biotechnology* 17:893-896.

Patten, P.A. et al., (1997) "Application of DNA Shuffling to Pharmaceuticals and Vaccines." *Current Opinion in Biotechnology* 8:724-733.

Pelletier, Joelle N., (2001) "A Rachitt for our toolbox" *Nature Biotechnology* vol. 19, p. 314-315.

Stemmer, W.P.C. (1994) "DNA Shuffling by random fragmentation and reassembly: In vitro recombination for molecular evolution." *PNAS* 91:10751.

Stemmer, W.P.C. (1994) "Rapid evolution of a protein in vitro by DNA shuffling." *Nature* 370:389-391.

Stemmer, W.P.C. (1995) "The Evolution of Molecular Computation." *Science* 270:1510.

Stemmer, W.P.C. (1995) "Searching Sequence Space." *Bio/Technology* 13:549-553.

Stemmer, W.P.C. (1996) "Sexual PCR and Assembly PCR." In: *The Encyclopedia of Molecular Biology.* VCH Publishers, New York. pp. 447-457.

Stemmer, W.P.C. & Soong, N.W. (1999) "Molecular breeding of viruses for targeting and other clinical properties." *Tumor Targeting* 4:59-62.

Zhang, J. et al., (1997) "Directed evolution of an effective fucosidase from galactosidase by DNA shuffling and screening." *Proceedings of the National Academy of Sciences, USA* 94:4504-4509.

Altschul et al. (1990) "Basic Local Alignment Search Tool." J. Mol. Biol. 215:403-410.

Arkin and Youvan (1992) Optimizing nucleotide mixtures to encode specific subsets of amino acids for semi-random mutagenesis. Biotechnology 10:297-300.

Bass et al. (1988) "Mutant Trp repressors with new DNA-binding specifications," Science 242:240-245.

Botstein and Shortle (1985) "Strategies and applications in invitro mutagenesis." Science 229:1193-1201.

Breyer and Sauer (1989) "Mutational analysis of the fine specificity of binding of monoclonal antibody 51F to lambda repressor." J. Biol. Chem 264:13355-13360.

Cadwell et al. (1992) "Randomization of Genes by PCR Mutagenesis." PCR Methods Applications 2:28-33.

Carter (1986) "Site -directed mutagenesis." Biochem. J. 237:1-7.

Carter (1987) "Improved oligonucleotide-directed mutagenesis using M13 vectors." Methods in Enzymol 154:382-403.

Carter et al. (1985) "Improved oligonucleotide site-directed mutagenesis using M13 vectors." Nucl. Acids Res. 13:4431-4443.

Chatelain et al. (1992) "IL-4 Induces a Th2 Response in *Leishmania major*-Infected Mice." J. Immunol 148:1182-1187.

Chen et al. (1994) "Gene therapy for brain tumors: Regression of experimental gliomas by adenovirus-meadiated gene transfer in vivo." Proc. Natl. Acad. Sci. USA 91:3054-3057.

Dale et al. (1996) "Oligonucleotides-directed random mutagenesis using the phosphorothioate method." Methods Mol. Biol. 57:369-374.

De Vries and Punnonen (1996) "In Cytokine regulation of humoral immunity: basic and clinical aspects." Eds. Snapper C.M. John Wiley & Sons, LTD West Sussex UK p. 195-215.

Devergne et al. (1997) "Epstein-Barr virus-induced gene 3 and the p35 subunit of Interleukin 12 form a novel heterodimeric hematopoietin." Proc. Nat'l Acad. Sci USA 94:12041-12046.

Eghtedarzadeh and Henikoff (1986) "Use of Oligonucleotides to generate large deletions." Nucl. Acids Res. 14:5115.

Feng & Doolittle (1987) "Progressive Sequence Alignment as a Prerequisite to Correct Phylogenetic Trees." J. Mol. Evol. 35:351-360.

Foss et al. (1997) "Molecular cloning and mRNA expression of porcine interleukin-12." *Veterinary Immunology and Immunopathology* 57:121-134.

Foss et al. (1995) "Cloning and Characterization of Porcine Interleukin-12" *Unpublished* (XP-002165227).

Fritz et al. (1988) "Oligonucleotide directed construction of mutations: a gapped duplex DNA procedure without enzymatic reactions in vitro." Nucl. Acids. Res. 16:6987-6999.

Gately et al. (1996) "Interleukin-12 Antagonist Activity of Mouse Interleukin-12 p40 Homodimer in Vitro and in Vivo." Ann. NY Acad. Sci. 795-:1-12.

Gately et al. (1998) "The Interleukin-12/Interleukin-12-Receptor System: Role in Normal and Pathologic Immune Response." Annu. Rev. Immunol. 16:495-521.

Grundstrom et al. (1985) "Oligonucleotide-directed mutagenesis by microscale 'shot-gun' gene synthesis." Nucl. Acids Res. 13:3305-3316.

Henikoff and Henikoff (1992) "Amino acid substitution matrices from protein blocks." Proc. Nat'l. Acad. Sci. USA 89:10915-10919.

Karlin and Altschul (1993) "Applications and statistics for multiple high-scoring segments in molecular sequences." Proc. Nat'l. Acad. Sci. USA 90:5873-5887.

Kramer and Fritz (1987) "Oligonucleotide directed construction of mutations via gapped duplex DNA." Methods in Enzymol 154:350-367.

Kramer et al. (1984) "The gapped duplex DNA approach to oligonucleotide directed mutation construction." Nucl. Acids. Res. 12:9441-9456.

Kramer et al. (1994) "Different Base/Base Mismatches Are Corrected with Different Efficiencies by the Methyl-Directed DNA Mismatch-Repair System of *E. coli*." Cell 38:879-887.

Kramer et al. (1998) "Improved enzymatic in vitro reactions in the gapped duplex DNA Approach to olignucleotide directed construction of mutations." Nucl. Acids. Res. 16:7207.

Kunkel (1985) "Rapid and efficient site-specific mutagenesis without phenotype selection." Proc. Nat'l Acad. Sci. UDS 82:448-492.

Kunkel (1987) "Rapid and efficient site-specific mutagenesis without phenotype selection." Methods in Enzymol. 154:367-382.

Leung et al. (1989) "A Method for Random Mutagenesis of a Defined DNA segment Using a Modified Polymerase Chain Reaction." Technique 1:11-15.

Ling et al. (1994) "Human IL-12 p40 Homodimer Binds to the IL-12 Receptor but Does Not Mediate Biologic Activity." J. Immunol 154:116-127.

Ling et al. (1997) "Approaches to DNA Mutagenesis: an Overview." Anal Biochem. 254(2):157-178.

Logan and Shenk (1984) "Adenovirus tripartite leader sequence enhances translation of mRNAs late after injection." Proc. Natl. Acad Sci 81:3655-3659.

Mandeck (1986) Oligonucleotide-directed double-strand break repair in plasmids of *Escherichia coli*: a method for site-specific mutagenesis. Proc. Nat'l Acad. Sci. USA 83:7177-7181.

Miller et al. (1990) "Gene Transfer by Retrovirus Vectors Occurs Only in Cells That Are Actively Replicating at the Time of Infection." Mol. Cell Biol. 10(8):4239 (1990).

Miller et al. (1993) "Use of Retroviral Vectors for Gene Transfer and Expression." Methods in Enzymology 217:581-599.

Murphy et al. (1985) "γ Interferon and Lymphotoxin, Released by Activated T Cells, Synergized to Inhibit Granulocyte/Momocyte Colony Formation." Journal of Experimental Medicine 164:263-279.

Murray, E. et al. (1989) "Codon usage in plant genes." Nuc. Acids Res. 17:477-508.

Nambiar et al. (1984) "Total synthesis and cloning of a gene coding for the ribonuclease S protein." Science 223:1299-1301.

Paul and Seder (1994) "Lymphocyte Responses and Cytokines." Cell 76:241-251.

Pearson and Lipman (1998) "Improved tools for biological sequences comparison." Proc. Nat'l Acad. Sci. USA 85:2444-2448.

Porath et al. (1992) "Immobilized Metal Ion Affinity Chromatography." Protein Expression and Purification 3:263-281.

Punnonen and De Vries (1994) "IL-13 Induces Proliferation, Ig Isotype Switching, and Ig Synthesis by Immature Human Fetal B Cells." Journal of Immunology 152: 1094.

Rakhmilevich et al. (1999) "Gene Gun-Mediated IL-12 Gene Therapy Induces Antitumer Effects in the Absence of Toxicity: A Direct Comparison With systemic IL-12 Protein Therapy." J. Immunother 22(2):135-144.

Reidhaar-Olson et al. (1991) "Random Mutagenesis of protein sequences using olignucleotide cassettes." Method in Enzymol 208:564-586.

Sayers et al. (1988) "Strand specific cleavage of phosphorothioate-containing DNA by reaction with restriction endonucleases in the presence of ethidium bromide." Nucl. Acids. Res. 16:803-814.

Scharf D et al. (1994) 6 Heat Stress Promoters and Transcription Factors Results Probl Cell Differ 20:125-165.

Smith (1985) "In Vitro Mutagenesis." Ann. Rev. Genet 19:423-462.

Smith and Waterman (1981) "Compatison of Biosequences." Adv. Appl. Math 2:428-489.

Soong et al. (2000) "Molecular Breeding of Viruses." Nature Genetice 25:436-439.

Sun et al. (1998) "Vaccination with IL-12 gene-modified autologous melanoma cells: preclinical results and a first clinical phase I Study." Gene Ther. 5(4): 481-490.

Thompson et al. (1994) "Clustal W: improving the sensitivity of progressive multiple sequence alignment through sequence weighting, position-specific gap penlities and weight matrix choice." Nucl. Acids Res. 22:4673-4680.

Trinchieri and Scott (1999) "Current Topics in Microbiology and Immunology." Curr. Top. Microbiol. Immunol 238:57-78.

Van Heeke & Schuster (1989) "Expression of Human Asparagine Synthetase in *Eschichia coli*." J. Bio Chem. 264:5503-5509.

Wells (1985) "Cassette mutagenesis: an efficient method for generation of multiple mutations at defined sited." Gene 34:315-323.

Wells et al. (1986) "Importance of hydrogen-bond formation in stabilizing the transition state of subtilisin." Phil Trans. R. Soc. Lond A 317:415-423.

Wilson I. et al. (1984) "The Structure of an Antigenic Determinant in a Protein." Cell 37:767-778.

Wolff et al. (1990) "Direct Transfer into Mouse Muscle in Vivo." Science 247:1465-1468.

Wu and Wu (1998) "Receptor-mediated Gene Delivery and Expression in Vivo." J. Biol. Chem. 263:14621-14624.

Arkin and Youvan (1992) "An algorithm for protein engineering: Simulations of recursive ensemble mutagenesis." Proc. Nat'l. Acad. Sci. USA 89:7811-7815.

Zhang, S.P. et al. (1991) "Low-uage codons in *Escherichia coli*, yeast, fruit fly and primates." Gene 105:61-72.

Zoller and Smith (1982) "Oligonucleotide directed mutagenesis using M13-derived vectors." Nucleic Acid Res. 10:6487-6500.

Zoller and Smith (1983) "Oligonucleotide directed mutagenesis of DNA fragments cloned into M13 vectors." Methods in Enzymol 100:468-500.

Zoller and Smith (1987) "Oligonucleotide directed mutagenesis: a simple method using two oligonucleotide primers and a single-stranded DNA template." Methods in Enzymol 154:329-350.

Zou et al. (1995) "Structure-Function Analysis of the p35 Subunit of Mouse Interleukin 12" *The Journal of Biological Chemsitry* 270(11):5864-5871.

Chang, C.-C.J., et al., "Evolution of a cytokine using DNA family shuffling," Nature Biotechnology 17:793-797 (1999).

Chaplin, P.J., et al., "Production of Interleukin-12 as a Self-Processing 2A Polypeptide," J. Interferon Cytokine Research 19:235-241 (1999).

Collins, R.A., et al., "Bovine interleukin-12 and modulation of IFNy production," Veterinary Immunology and Immunopathy 68:193-207 (1999).

Crameri, A., et al., "DNA shuffling of a family of genes from diverse species accelerates directed evolution," Nature 391:288-291 (1998).

Foss, D.L., et al., "Molecular cloning and mRNA expression of porcine interleukin-12," Veterinary Immunology and Immunopathy 57:121-134 (1997).

Foss, D.L., et al., "Sus scrofa interleukin-12 mRNA, complete cds.," Database EMBL [Online] Accession No. U08317, XP002165227 (Apr. 19, 1995).

Kokuho, T., et al., "Production of biologically active, heterodimeric porcine interleukin-12 using a monocistronic baculoviral expression system," Veterinary Immunology and Immunopathy 72:289-302 (1999).

Leong S.R., et al., "Maximizing the genetic diversity by molecular breeding: Evolution of DNA vaccine vectors and adjuvant cytokines." 1999 Winter Biotechnology Conference: Molecular Approaches to Vaccine Design, Cold Spring Harbor, NY, Dec. 2-5, 1999.

Minshull, J., et al., "Protein evolution by molecular breeding," Current Opinion in Chemical Biology 3(3):284-290 (Jun. 1999).

Oppmann, B., et al., "Novel p19 Protein Engages IL-12p40 to Form a Cytokine, IL-23, with Biological Activities Similar as Well as Distinct from IL-12," Immunity 13:715-725 (2000).

Patten, P.A., et al., "Applications of DNA shuffling to pharmaceuticals and vaccines," Pharmaceutical Biotechnology 8:724-733 (1997).

Punnonen, J., "Molecular Breeding of Allergy Vaccine and Antiallergic Cytokines," Int. Arch. Allergy Immunol. 121:173-182 (Mar. 2000).

Punnonen, J., et al., "Molecular Breeding by DNA Shuffling," Science & Medicine 7(2):38-47 (Mar./Apr. 2000).

Punnonen, J., et al., "Evolution of DNA vaccine vectors, antigens, and adjuvant cytokines by DNA shuffling." Keystone Symposia on Molecular and Cellular Biology, DNA VAccines: Immune Responses, Mechanisms and Manipulating Antigen Processing Snowbird, UT, Apr. 12-17, 1999.

Stemmer, W.P.C., "DNA shuffling by random fragmentation and reassembly: In vitro recombination for molecular evolution," Proceedings of the National Academy of Sciences U.S.A. 91(22):10747-10751 (Oct. 25, 1994).

Stemmer, W.P.C., "Rapid evolution of a protein in vitro by DNA shuffling," Nature 370(6488):389-391 (Aug. 4, 1994).

Swinburne, S.J., et al., "Ovine Interleukin 12 has biological activity on ovine and human activated peripheral blood mononuclear cells," Cytokine, 12(10):1546-1552 (2000).

Yoon, C., et al., "Charged residues dominate a unique interlocking topography in the heterodimeric cytokine interleukin-12," The EMBO Journal 19(14):3530-3541 (2000).

Zou, J.J., et al., "Structure-Function Analysis of the p35 Subunit of Mouse Interleukin 12," J. of Biological Chemistry 270(11):5864-5871 (1995).

Kukuho, T. et al. "Production of biologically active, heterodimeric porcine interleukin-12 using a monocistronic baculoviral expression system," Vet. Immunol. Immunopathol., 72:289-302 (1999).

Swinburne, S., et al., "Ovine Interleukin 12 has biological activity on ovine and human activated peripheral blood mononuclear cells," Cytokine, 12:1546-1552 (2000).

Yoon, C. et al, "Charged residues dominate a unique interlocking topography in the heterodimeric cytokine interleukin-12," EMBO J., 19:3530-3541 (2000).

* cited by examiner

```
                 1                                                                          70
SEQ 15    (1)    MCHQQLVISWFSLVFLASPLVAIWELKLKKDVYVVELDWYPDAPGEMVLTCDTPEEDGITWTLDQSSEVLG
SEQ 08    (1)    MCHQQLVISWFSLVFLASPLVAIWELKLKKDVYVVELDWYPDAPGEMVLTCDTPEEDGITWTSDQSSEVLG
SEQ 09    (1)    MCHQQLVISWFSLVFLASPLMAIWELKLEKNVYVVELDWYPNAPGETVLACDTPEEDGITWTSDQSSEVLG
SEQ 10    (1)    MCHQQLVISWFSLVFLASPLVAIWELEKNVYVVELDWYPDAPGETVLACDTPEEDGITWTSDQSSEVLG
SEQ 11    (1)    MHHQQLVMSWFSLVMLASPLVAIWELEKNVYVVELDWYPDAPGETVLACDTPEEDGITWTSDQSSEVLG
SEQ 12    (1)    MCHQQLVISWFSLVFLASPLVAIWELELEKNVYVVELDWYPDAPGETVLACDTPEEDGITWTSDQSSEVLG
SEQ 13    (1)    MCHQQLVISWFSLVFLASPLMAIWELKLKKDVYVVELDWYPDAPGEMVLACDTPEEDGITWTSDQSSEVLG
SEQ 14    (1)    MCHQQLVISWFSLVFLASPLVAIWELEKNVYVVELDWYPDAPGEMVLACDTPEEDGITWTSDQSSEVLG 71                                                                         140
SEQ 15    (71)   SGKTLTIQVKEFGDAGQYTCHKGGEVLSHSLLLLHKKEDGIWSTDILKDQKEPKNKTFLRCEAKNYSGRF
SEQ 08    (71)   IGKTLTITHVKEFGDAGQYTCRKGGEALSRSLLLLHKKEDGIWSTDILKDQKEPKNKSFLKCEAKNYSGRF
SEQ 09    (71)   IGKTLTITHVKEFGDAGQYTCRKGGAVLSQSLLLLHKKEDGIWSTDILKDQKEPKNKSFLKCEAKDYSGHF
SEQ 10    (71)   IGKTLTITHVKEFGDAGQYTCRKGGAVLSQSLLLLHKKEDGIWSTDILKDQKEPKAKSFLKCEAKNYSGRF
SEQ 11    (71)   IGKTLTITHVKEFGDAGQYTCRKGGAVLSRSLLLLHKKEDGIWSTDILKDQKEPKNKFLKCEAKNYSGRF
SEQ 12    (71)   IGKTLTITHVKEFGDAGQYTCHKGGKVLSRSLLLLHKKEDGIWSTDILKDQKEPKNKSFLKCEAKNYSGRF
SEQ 13    (71)   IGKTLTITHVKEFGDAGQYTCHKGGTVLSQSLLLLHKKEDGIWSTDILKDQKEPKNKSFLKCEAKNYSGRF
SEQ 14    (71)   IGKTLTITHVKEFGDAGQYTCRKGGAVLSQSLLLLHKKEDGIWSTDILKDQKEPKNKSFLKCEAKNYSGRF 141                                                                        209
SEQ 15    (141)  TCWWLTTISTDLTFSVKSSRGSSDPQGVTCGAATLSAERVRGDN-KEYEYSVECQEDSACPAAEESLPIE
SEQ 08    (141)  TCWWLTTISTDLKFSVKSSRGSSDPQRGVTCGTATLSEDLG---EYKKYSLEHREYKKYRVECQEGSACPAAEESLPIE
SEQ 09    (141)  TCWWLTTISTDLKFSVKSSRGSSDPPRGVTCGAATLSAEKVSLEHREYNKYTVECQEGSACPAAEESLPIE
SEQ 10    (141)  TCWWLTTISTDLKFSVKSSRGSSDPQGVTCGAVTLSAERVSMDHREYNKYTVECQEGSACPAAEESLPIE
SEQ 11    (141)  TCWWLTTAISTDLKFTVKSSRGSSDPPHGVTCGAVTLSAERVSMDHREYNKYTVECQEGSACPAAEESLPIE
SEQ 12    (141)  TCWWLTTAISTDLKFTVKSSRGSSDPQGVTCGAVTLSEDLG---EYKKYSMDHREYNKYTVECQEGSACPAAEESLPIE
SEQ 13    (141)  TCWWLTAAISTDLKFHVKSSRGSSDPPRGVTCGAVTLSEDLG---EYKKYSMDHREYNKYTVECQEGSACPAAEESLPIE
SEQ 14    (141)  TCWWLTAAISTDLKFTVKSSRGSSDPQGVTCGAVTLSAERVSMDHREYNKYTVECQEGSACPSAEESLPIE
```

Fig. 1A

```
             210                                                          279
SEQ 15 (210) VMVDAVHKLKYENYTSSFFIRDIIKPDPPKNLQLKPLKNSRQVEVSWEYPDTWSTPHSYFSLTFCVQVQG
SEQ 08 (206) VVLEAVHKLKYENYTSSFFIRDIIKPDPPKNLQLKPLKNSRQVEVSWEYPDTWSTPHSYFSLTFCVQVQG
SEQ 09 (211) VVLEAVHKLKYENYTSSFFIRDIIKPDPPKNLQLKPLKNSRQVEVSWGYPDTWSTPHSYFSLTFCVQVQG
SEQ 10 (211) VVVDATHKLKYENYTSSFFIRDIIKPDPPKNLQLRPLKNSRQVEVNWEYPDTWSTPHSYFSLTFCVQVQG
SEQ 11 (211) VVVDATHKLKYENYTSSFFIRRFFIRDIIKPDPPKNLQLRPLKNSRQVEVNWEYPDTWSTPHSYFSLTFCVQVQG
SEQ 12 (206) VVLEAVHKLKYENYTSSFFIRDIIKPDPPKNLQLRPLKNSRHVEISWEYPDTWSTPHSYFSLTFCVQVQG
SEQ 13 (206) VVLEAVHKLKYENYTSSFFIRDIIKPDPPKNLQLRPLKNSRHVEVSWEYPDTWSAPHSYFSLTFGVQVQG
SEQ 14 (211) VVVDATHKLKYENYTSSFFIRDIIKPDPPKNLQLKPLKNSRHVEISWEYPDTWSIPHSYFSLMFGVQVQG 280                                                          328
SEQ 15 (280) KSKREKKDRVFTDKTSATVICRKNASISVRAQDRYYSSSWSEWASVPCS--
SEQ 08 (276) KSKREKKDRIFTDKTSATVICRKNAKIRVQARDRYYSSSWSEWASVSCS--
SEQ 09 (281) KNKREKK--LFMDQTSAKVTCHKDAKIRVQARDRYYSSSWSEWASVPCS--
SEQ 10 (281) KNKREKK--LFMDQTSAKVICHKDAKIRVQARDRYYSSSWSEWASVPCS--
SEQ 11 (281) KNKREKK--LFMDQTSAKVICHKDAKIRVQARDRYHSSSWSEWASVPCS--
SEQ 12 (276) RNKREKK--LFMDQTSAKVVCHKDAKIRVQARDRYYSSSWSDWASVSCG--
SEQ 13 (276) RNKREDR--LFMDQTSAKVVCHKDAKIRVQARDRYYSSSWSDWASVSLQSV
SEQ 14 (281) KNKREKKDRLSVDKTSAKVMCHKDAKIRVQARDRYYSSSWSEWASVPCS--
```

Fig. 1B

```
                                1                                                                                67
SEQ_36     (1)  MCPARSLLLVATLVLLDHL----SLARNLPVATPDPGMFPCLHHSQNLLRAVSNMLQKARQTLEFYPCTSE
SEQ 26     (1)  MCPTRSLLLLTSTLVLLHHLPHTSLGRSLPTTTASPGRS-CLDMSQNLLKAASNTLQKARQTLEFYPCTSE
SEQ 27     (1)  MVPTRSLLLLTSTLVLLHHLPHHSLGRSLPTTTASPGRS-CLDMSQNLLKAASNTLQRARQTLEFYPCTSE
SEQ 28     (1)  MCPARGLLLVATLVLLDHL----SLARNLPVATPGPGMFPCLHHSQNLLRAVSNMLQKARQTLEFYPCTSE
SEQ 29     (1)  MCPARSLLLVATLVLLDHL----SLARNLPVATPGPGMLPCLHHSQNLLRAVSNMLQKAKQTLEFYPCTSE
SEQ 30     (1)  MCPARSLLLVATLVLLDHL----SLARNLPVATPDPGMFPCLHHSQNLLRAVSNMLQKARQTLEFYCCTSE
SEQ 31     (1)  MCPBRGLLLVATLVLLDHL----SLARNLPVATPGPGMFPCLHHSQNLLRAVSNTLQKAKQTLEFYCCTSE
SEQ 32     (1)  MCPBRGLLLVATLVLLDHL----SLARNLPVATPGPGMFPCLHHSQNLLRAVSNTLQKAKQTLEFYCCTSE
SEQ 33     (1)  MCPBRGLLLVATLVLLDHL----SLARNLPVATPGPGMFPCLHHSQNLLRAVSNTLQKAKQTLEFYCCTSE
SEQ 34     (1)  MCPARSLLLVATLVLLDHL----SLARNLPVATPDPGMFPCLHHSQNLLRAVSNMLQKARQTLEFYPCTSE
SEQ 35     (1)  MCPBRGLLLVATLVLLDHL----SLARNLPVATPGPGMFPCLHHSQNLLRAVSNTLQKAKQTLEFYCCTSE 68                                                                              137
SEQ_36    (68)  EIDHEDITKDKTSTVEACLPLELTKNESCLNSRETSFITNGSCLASRKTSFMALCLSSIYEDLKMYQVE
SEQ 26    (70)  EIDHEDITKDKTSTVEACLPLELTKNESCLNSRETSFITNGSCLASREHSHITNGSCLASRKTSFMLLCHSSIYEDLKMYQME
SEQ 27    (70)  EIDHEDITKDKTSTVEACLPLELTKNESCLNSRETSFITNGSCLASREHSHITNGSCLASRKTSFMLLCHSSIYEDLKMYQME
SEQ 28    (68)  EIDHEDITKDKTSTVEACLPLELTKNESCLNSRETSFITNGSCLASRKTSFMTLCLSSIYEDLKMYQVE
SEQ 29    (68)  EIDHEDITDKTSTVEACLPLELTKNESCLATNESCLNSRETSFITNGSCLASRKTSFMTLCLSSIYEDLKMYQVE
SEQ 30    (68)  EIDHEDITKDKTSTVEACLPLELTKNESCLATNESCLNSRETSFITNGSCLASRKTSFMTLCLSSIYEDLKMYQVE
SEQ 31    (68)  EDHEDITKDKTSTVEACLPLELTKNESCLATNESCLNSRETSFITNGSCLASRKTSFMTLCLGSIYEDLKMYQVE
SEQ 32    (68)  EIDHEDITKDKTSTVEACLPLELTKNESCLATNESCLNSRETSFITNGSCLASRKTSFMTLCLSSIYEDLKMYQVE
SEQ 33    (68)  EIDHEDITKDKTSTVEACLPLELTKNESCLATNESCLNSRETSFITNGSCLASRKTSFMTLCLSSIYEDLKMYQVE
SEQ 34    (68)  EIDHEDITKDKTSTVEACLPLELTKNESCLATNESCLNSRETSFITNGSCLASRKTSFMTLCLSSIYEDLKMYQVE
SEQ 35    (68)  EIDHEDITKDKTSTVEACLPLELTKNESCLATNESCLNSRETSFITNGSCLASRKTSFMTLCLSSIYEDLKMYQVE
```

Fig. 11A

```
                 138                                                                207
SEQ_36  (138)    FKTMNAKLLMDPKRQIFLDQNMLAVIDELMQALNFNSETVPQKSSLEEPDFYKTKIKLCILLHAFRIRAV
SEQ 26  (140)    FKAMNAKLLMDPKRQIFLDQNMLAVIDELMQALNFNSETVPQKSSLEEPDFYKTKIKLCILLHAFRIRAV
SEQ 27  (140)    FKAMNAKLLMDPKRQIFLDQNMLAVIDELMQALNFNSETVPQKSSLEEPDFYKTKIKLCILLHAFRIRAV
SEQ 28  (138)    FKTMNAKLLMDPKRQIFLDQNMLTAIDELMQALNFNSETVPQKPSLEEDFYKTKIKLCILLHAFRIRAV
SEQ 29  (138)    FKAMNAKLLMDPKRQIFLDQNMLAAIAELMQALNVNSETAPQKSSLEEPDFYKTKIKLCILLHAFRIRAV
SEQ 30  (138)    FKAMNAKLLMDPKRQIFLDQNMLAAIAELMQALNVNSETAPQKSSLEEPDFYKTKIKLCILLHAFRIRAV
SEQ 31  (138)    FKTMNAKLLMNPKRQIFLDQNMLTAIDELQALNFNSETVPQKSSLEEPDFYKTKIKLCILLHAFRIRAV
SEQ 32  (138)    FKTMNAKLLMDPKRQIFLDQNMLTAIDELQALNFNSETVPQKSSLEEPDFYKTKIKLCILLHAFRIRAV
SEQ 33  (138)    FKAMNAKLLMDPKRQIFLDQNMLAAIAELMQALNVNSETAPQKSSLEEPDFYKTKIKLCILLHAFRIRAV
SEQ 34  (138)    FKAMNAKLLMDPKRQIFLDQNMLAAIAELMQALNVNSETAPQKSSLEEPDFYKTKIKLCILLHAFRIRAV
SEQ 35  (138)    FKTMNAKLLMNPKRQIFLDQNMLTAIDELQALNFNSETVPQKSSLEEPDFYKTKIKLCILLHAFRIRAV 208                 219
SEQ_36  (208)    TIDRVTSYLNAS
SEQ 26  (210)    TIDRMMSYLNSS
SEQ 27  (210)    TINRMMSYLNSS
SEQ 28  (208)    TINRMMSYLNSS
SEQ 29  (208)    TINRMMSYLNSS
SEQ 30  (208)    TINRMMSYLNSS
SEQ 31  (208)    TINRMMSYLNSS
SEQ 32  (208)    TINRMMSYLNSS
SEQ 33  (208)    TIDRMMSYLNSS
SEQ 34  (208)    TIDRMMSYLNSS
SEQ 35  (208)    TINRMMSYLNSS
```

Fig. 11B

CYTOKINE POLYPEPTIDES

CROSS REFERENCE TO RELATED APPLICATIONS

This application is a continuation-in-part application of and claims the benefit of and priority to U.S. Patent Application Ser. No. 60/169,035, filed Dec. 2, 1999, the disclosure of which is incorporated herein by reference in its entirety for all purposes.

STATEMENT REGARDING FEDERALLY SPONSORED RESEARCH

This invention was made with government support under Grant No. N65236-98-1-5401 awarded by the Defense Advanced Research Agency (DARPA). The Government may have certain rights in the invention.

COPYRIGHT NOTIFICATION

Pursuant to 37 C.F.R. 1.71(e), a portion of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to the generation of new cytokine polypeptides and nucleic acids which encode them.

BACKGROUND OF THE INVENTION

T helper ($T_H$) cells, key regulators of the immune system, are divided into two subsets, $T_H1$ and $T_H2$, based upon their pattern of cytokine synthesis (Paul and Seder (1994) *Cell* 76: 241–251). $T_H1$ cells predominantly produce high levels of interleukin-2 (IL-2) and interferon-gamma (IFN-γ). $T_H1$ cells also activate antigen-presenting cells (macrophages and dendritic cells) and enhance the cytotoxic activity of $CD8^+$ Cytotoxic T-lymphocyte (CTL) and Natural Killer (NK) cells. In contrast, $T_H2$ cells produce elevated levels of IL-4, IL-5 and IL-13, and mediate allergic responses as a result of inducing IgE isotype switching and differentiation of B cells into IgE secreting cells (De Vries and Punnonen (1996) In *Cytokine regulation of humoral immunity: basic and clinical aspects*. Eds. Snapper, C. M., John Wiley & Sons, Ltd., West Sussex, UK, p. 195–215).

It is desirable to modify the relative populations of $T_H1$ and $T_H2$ cells in various circumstances. Modulators which up-regulate $T_H1$-mediated responses by, for example, directing the differentiation of naive T cells into $T_H1$ cells, inducing $T_H1$ cell proliferation, and increasing IFN-γ production and macrophage activation, are useful in promoting cell-mediated immunity to infectious agents such as bacterial, protozoan, intracellular parasitic and viral infections. Modulators which down-regulate $T_H1$-mediated responses are useful in situations where a decreased cell-mediated immune response is desired, for example, in treatment of autoimmune diseases such as multiple sclerosis.

The discovery of novel cytokine polypeptides which modulate $T_H1$-mediated responses, and nucleic acids encoding them, satisfies a need in the art by providing new compositions useful in modifying host immune responses and in treating disease.

SUMMARY OF THE INVENTION

The invention provides modified cytokine polypeptides (also referred to herein as "modified p40 polypeptides" and as "modified p35 polypeptides"), nucleic acids encoding the polypeptides and complementary nucleotide sequences thereof, fragments of said polypeptides and nucleic acids, antibodies to the polypeptides, and uses therefor, a computer or computer readable medium comprising a sequence record comprising one or more data sets containing character strings of new cytokine sequences, and automated systems for using the character strings.

In one aspect, the invention includes an isolated or recombinant nucleic acid encoding a modified cytokine polypeptide of the invention. Included are polynucleotide sequences comprising a mature polypeptide coding region of a sequence selected from SEQ ID NO:1 to SEQ ID NO:7, or SEQ ID NO:16 to SEQ ID NO:25, and complementary polynucleotide sequences thereof. Polynucleotide sequences encoding a polypeptide comprising a mature polypeptide region of an amino acid sequence selected from SEQ ID NO:8 to SEQ ID NO:14 or SEQ ID NO:26 to SEQ ID NO:35, and complementary polynucleotide sequences thereof, are also a feature of the invention. Similarly, a polynucleotide sequence which hybridizes under at least highly stringent conditions over substantially the entire length of any one of the preceding polynucleotide sequences is a feature of the invention. A polynucleotide sequence which encodes a polypeptide comprising an amino acid sequence having at least about 90% sequence identity to a mature polypeptide region of a sequence selected from SEQ ID NO:8 to SEQ ID NO:14 and SEQ ID NO:39, or to a mature polypeptide region of a sequence selected from SEQ ID NO:26 to SEQ ID NO:35 and SEQ ID NO:40, is also a feature of the invention. In various embodiments, the polynucleotide sequence encodes a polypeptide comprising an amino acid sequence having at least about 90%, 92%, 95%, 96%, 97%, 98%, or 99% identical to a mature polypeptide region of a sequence selected from SEQ ID NO:8 to SEQ ID NO:14 and SEQ ID NO:39, or to a mature polypeptide region of a sequence selected from SEQ ID NO:26 to SEQ ID NO:35 and SEQ ID NO:40. In addition, a polynucleotide sequence comprising a nucleotide fragment of any of the preceding polynucleotide sequences, which nucleotide fragment encodes a polypeptide having T-cell proliferative activity and/or IFN-gamma induction activity in T-cells (e.g., human T-cells) in the presence of a p35 polypeptide or a p40 polypeptide is also a feature of the invention.

Any of the polynucleotides described above may optionally include a leader peptide coding region, which encodes a leader peptide region. In one embodiment, the optional leader peptide coding region encodes a leader peptide region comprising an amino acid sequence at least about 90% identical to the amino acid sequence set forth as the leader peptide region of any one of SEQ ID NO:8 to SEQ ID NO:14, or SEQ ID NO:26 to SEQ ID NO:35. In various embodiments, the optional leader peptide coding region encodes a leader peptide region comprising an amino acid sequence at least about 90%, 92%, 95%, 96%, 97%, 98%, or 99% identical to the amino acid sequence set forth as the leader peptide region of any one of SEQ ID NO:8 to SEQ ID NO:14, or SEQ ID NO:26 to SEQ ID NO:35. In another embodiment, the optional leader peptide coding region encodes a leader peptide region comprising an amino acid sequence set forth as the leader peptide region of any one of SEQ ID NO:8 to SEQ ID NO:14, or SEQ ID NO:26 to SEQ ID NO:35.

The invention also includes an isolated or recombinant nucleic acid, comprising a polynucleotide sequence encoding a modified p40 polypeptide comprising an amino acid modification located at an amino acid position equivalent to (i.e., an "equivalent position" to) that in the amino acid sequence of a naturally-occurring or wild-type p40 polypeptide (SEQ ID NO:15). The modification can include: (a) a substitution of the specified amino acid for a different amino acid at one or more equivalent position to that of SEQ ID NO:15 selected from Leu62, Ser71, Gln78, His99, Thr127, Arg130, Lys185, Glu186, Tyr187, Glu188, Ser190, Asp196, Met211, Val289, Ser305, Ser307, Arg309, and Gln311; (b) a deletion of one or more amino acid residues at equivalent position Arg181 to Asn184 inclusive, or a substitution, of the amino acid residues at equivalent positions Arg181 to Asn184 inclusive, for the amino acid residues Ser-(Leu or Met)-(Glu or Asp)-His-Arg; (c) a deletion of one or more amino acid residues at equivalent positions Asp287 and Arg288. The modified p40 polypeptide may optionally include two or more of modification (a), (b) or (c). The modified p40 polypeptide sequence encoded by the nucleic acid of the invention may be a modified sequence of a naturally-occurring (i.e., wild-type) p40 polypeptide sequence of a mammal (e.g., human, a non-human primate, a ruminant, or a rodent), preferably a primate, more preferably human. The modified p40 polypeptide sequence encoded by the nucleic acid of the invention may be a modified sequence of a polypeptide selected from the group consisting of p40 polypeptides encoded by nucleic acids having the GenBank accession numbers: M65272, M65290, U19841, U19834, Y11129, U83184, Y07762, AF054607, U49100, AF091134, U57752, U10160, AF007576, AF004024, U11815, U08317, X97019, AF082494, AF133197, U16674, M86671, S82426, AF097507, and AF046211. A modified polypeptide of the invention may comprise at least one of the substitutions Leu62Ser; Ser71Thr; Gln78His; His99(Arg or Gln); Thr127(Ser or Ile); Arg130Lys; Lys185Glu; Glu186Tyr; Tyr187(Lys or Asn); Glu188Lys; Ser190(Arg or Thr); Asp196Gly; Met211Val; Val289(Ile or Leu); Ser305Lys; Ser307Arg; Arg309Gln; and Gln311Arg. A modified polypeptide of the invention may also comprise at least one of the substitutions Lys27Glu; Asp29Asn; Asp40Asn; Met45Thr; Thr49Ala; Glu67Gly, His91Arg; Glu95(Ala or Thr), Val96Ala; Glu122Lys; Asn125Ala; Asn135Asp; Arg139His; Thr147Ala; Thr153Lys; Ser155Thr; Ser163Thr; Gln166(Arg or His), Ala172Thr; Ala173Val; Thr174Leu; Ala177Glu; Glu178Asp; Arg179Leu; Val180Gly; Ala201Ser; Val212Leu; Asp213Glu; Val215Ile; Ser226Arg; Lys244Arg; Gln251His; Val254Ile; Ser255Asn; Glu257Gly; Thr264(Ala or Ile); Thr272Met; Cys274Gly; Val275Ile; Lys280Arg; Ser281Asn; Lys285Asp; Lys286Arg; Phe290Ser; Thr291 (Met or Val); Lys293Gln; Thr297Lys; Ile299(Thr or Val); Arg301His; Asn303Asp; Ser318Phe; Glu321Asp; Pro326Ser; Cys327Leu; and Ser328(Gly or Gln).

The invention also includes an isolated or recombinant nucleic acid, comprising a polynucleotide sequence encoding a modified p40 polypeptide, wherein the modified p40 polypeptide comprises an amino acid sequence having at least about 90% amino acid sequence identity to the amino acid sequence identified herein as the mature polypeptide region (amino acid residue positions 23–328) of SEQ ID NO: IWEL-$X_{27}$-K-$X_{29}$-VYVVELDWYP-$X_{40}$-APGE-$X_{45}$-VVL-$X_{49}$-CDTPEEDGITWT-$X_{62}$-DQSS-$X_{67}$-VLG-$X_{71}$-GKTLTI-$X_{78}$-VKEFGDAGQYTC-$X_{91}$-KGG-$X_{95}$-$X_{96}$-LS-$X_{99}$-SLLLLHKKEDGIWSTDILKDQK-$X_{122}$-PK-$X_{125}$-K-$X_{127}$-FL-$X_{130}$-CEAK-$X_{135}$-YSG-$X_{139}$-FTCWWLT-$X_{147}$-ISTDL-$X_{153}$-F-$X_{155}$-VKSSRGS-$X_{163}$-DP-$X_{166}$-GVTCG-$X_{172}$-$X_{173}$-$X_{174}$-LS-$X_{177}$-$X_{178}$-$X_{179}$-$X_{180}$-X181-$X_{182}$-$X_{183}$-$X_{184}$-$X_{185}$-$X_{186}$-$X_{187}$-$X_{188}$-Y-$X_{190}$-VECQE-$X_{196}$-SACP-$X_{201}$-AEESLPIEV-$X_{211}$-$X_{212}$-$X_{213}$-A-$X_{215}$-HKLKYENYTS-$X_{226}$-FFIRDIIKPDPPKNLQL-$X_{244}$-PLKNSR-$X_{251}$-VE-$X_{254}$-$X_{255}$-W-$X_{257}$-YPDTWS-$X_{264}$-PHSYFSLTF-$X_{274}$-$X_{275}$-QVQG-$X_{280}$-$X_{281}$-KRE-$X_{285}$-$X_{286}$-$X_{287}$-$X_{288}$-$X_{289}$-F-$X_{291}$-D-$X_{293}$-TSA-$X_{297}$-V-$X_{299}$-C-$X_{301}$-K-$X_{303}$-A-$X_{305}$-I-$X_{307}$-V-$X_{309}$-A-$X_{311}$-DRY-$X_{315}$-SS-$X_{318}$-WS-$X_{321}$-WAS-V-$X_{326}$-$X_{327}$-$X_{328}$, or a conservatively substituted variation thereof, where $X_{27}$ is K or E; $X_{29}$ is D or N; $X_{40}$ is D or N; $X_{45}$ is M or T; $X_{49}$ is T or A; $X_{62}$ is S; $X_{67}$ is E or G; $X_{71}$ is T; $X_{78}$ is H; $X_{91}$ is H or R; $X_{95}$ is E, A, K, or T, $X_{96}$ is V or A; $X_{99}$ is R or Q; $X_{122}$ is E or K; $X_{125}$ is N or A; $X_{127}$ is S or I; $X_{130}$ is K; $X_{135}$ is N or D; $X_{139}$ is R or H; $X_{147}$ is T or A; $X_{153}$ is T or K; $X_{155}$ is S or T; $X_{163}$ is S or T; $X_{166}$ is Q, R, or H; $X_{172}$ is A or T; $X_{173}$ is A or V; $X_{174}$ is T or L; $X_{177}$ is A or E; $X_{178}$ is E or D; $X_{179}$ is R, L, or K; $X_{180}$ is V or G; $X_{181}$ to $X_{184}$ inclusive is deleted, or is replaced with the sequence S-(L or M)-(E or D)-H-R; $X_{185}$ is E; $X_{186}$ is Y; $X_{187}$ is K or N; $X_{187}$ is K; $X_{190}$ is R or T; $X_{196}$ is G; $X_{201}$ is A or S; $X_{211}$ is V; $X_{212}$ is V or L; $X_{213}$ is D or E; $X_{215}$ is V or I; $X_{226}$ is S or R; $X_{244}$ is K or R; $X_{251}$ is Q or H; $X_{254}$ is V or I; $X_{255}$ is S or N; $X_{257}$ is E or G; $X_{264}$ is T or A; $X_{274}$ is C or G; $X_{275}$ is V or I; $X_{280}$ is K or R; $X_{281}$ is S or N; $X_{285}$ is K or D; $X_{286}$ is K or R; $X_{287}$ is D or is deleted; $X_{288}$ is R or is deleted; $X_{289}$ is I or L; $X_{291}$ is T or M; $X_{293}$ is K or Q; $X_{297}$ is T or K; $X_{299}$ is I, T, or V; $X_{301}$ is R or H; $X_{303}$ is N or D; $X_{305}$ is K; $X_{307}$ is R; $X_{309}$ is Q; $X_{311}$ is R; $X_{315}$ is Y or H; $X_{318}$ is S or F; $X_{321}$ is E or D; $X_{326}$ is P or S; $X_{327}$ is C or L; and $X_{328}$ is S, G, or Q. As used herein and throughout the specification, each of the single letters in the amino acid sequences presented above represents a particular amino acid residue, according to standard practice known to those of ordinary skill in the art. In various embodiments, the modified p40 polypeptide encoded by the nucleic acid of the invention comprises an amino acid sequence having at least about 90%, 92%, 95%, 96%, 97%, 98%, or 99% amino acid sequence identity to the mature polypeptide region (amino acid residue positions 23–328) of SEQ ID NO:39. In another embodiment, the nucleic acid of the invention encodes a modified p40 polypeptide comprising an amino acid sequence identified herein as the mature polypeptide region (amino acid residue positions 23–328) of SEQ ID NO:39.

The modified p40 polypeptide encoded by a nucleic acid of the invention may further comprise a leader peptide sequence having at least about 90%, 92%, 95%, 96%, 97%, 98%, or 99% amino acid sequence identity to the amino acid sequence M-$X_2$-$X_3$-QQLV-$X_8$-SWFSLV-$X_{15}$-LASPL-$X_{21}$-A, identified herein as the leader peptide region (amino acid residue positions 1–22) of SEQ ID NO:39, where $X_2$ is C or H; $X_3$ is H or P; $X_8$ is I or V; $X_{15}$ is F or L; and $X_{21}$ is V or M.

The invention also includes an isolated or recombinant nucleic acid, comprising a polynucleotide sequence encoding a polypeptide comprising a leader peptide sequence having at least about 90% amino acid sequence identity to the amino acid sequence M-$X_2$-$X_3$-QQLV-$X_8$-SWFSLV-$X_{15}$-LASPL-$X_{21}$-A, identified herein as the leader peptide region (amino acid residue positions 1–22) of SEQ ID NO:39, where $X_2$ is C or H; $X_3$ is H or P; $X_8$ is I or V; $X_{15}$ is F or L; and $X_{21}$ is V or M. In various embodiments, the leader peptide sequence encoded by the nucleic acid of the invention comprises an amino acid sequence having at least about 90%, 92%, 95%, 96%, 97%, 98%, or 99% amino acid sequence identity to leader peptide region (amino acid residues 1–22) of SEQ ID NO:39.

The invention also includes an isolated or recombinant nucleic acid, comprising a polynucleotide sequence encoding a modified p35 polypeptide comprising an amino acid modification located at an amino acid position equivalent to (i.e., an equivalent position to) that in the amino acid sequence of a naturally-occurring (i.e., wild-type) p35 polypeptide (SEQ ID NO:36). The modification can include: (a) a substitution of the specified amino acid for a different amino acid at one or more equivalent position to that of SEQ ID NO:36 selected from Thr91, Met120, Ala121, Val212, Thr213, and Ala218; (b) a insertion of one or more amino acids Phe-His-Leu between equivalent positions Leu19 and Ser20; (c) a deletion of the amino acid at equivalent position Pro36. The modified p35 polypeptide may optionally include two or more of modification (a), (b) or (c). The modified p35 polypeptide sequence encoded by the nucleic acid of the invention may be a modified sequence of a naturally-occurring (i.e., wild-type) p35 polypeptide sequence of a mammal (e.g., human, a non-human primate, a ruminant, or a rodent), preferably a primate, more preferably human. The modified p35 polypeptide sequence encoded by the nucleic acid of the invention may be a modified sequence of a polypeptide selected from the group consisting of p35 polypeptides encoded by nucleic acids having the GenBank accession numbers M65271, M65291, U19842, U19835, U83185, Y07761, AF054605, U49085, L35765, Y11130, U14416, U57751, AF173557, AF003542, X97018, AF177031, M86672, and S82419. Preferred substitutions include Thr91(Ala or Ile); Met120Thr; Ala121Thr; Val212Met; Thr213Met; and Ala218Ser.

The invention also includes an isolated or recombinant nucleic acid, comprising a polynucleotide sequence encoding a modified p35 polypeptide, wherein the modified p35 polypeptide comprises an amino acid sequence having at least about 90% amino acid sequence identity to the amino acid sequence identified herein as the mature polypeptide region (amino acid residue positions 23–219) of SEQ ID NO:40: R-$X_{24}$-LP-$X_{27}$-$X_{28}$-T-$X_{30}$-$X_{31}$-PG-$X_{34}$-$X_{35}$-$X_{36}$-CL-$X_{39}$-$X_{40}$-SQNLL-$X_{46}$-A-$X_{48}$-SN-$X_{51}$-LQ-$X_{54}$-A-$X_{56}$-Q-$X_{58}$-LEFY-$X_{63}$-CTSEE-$X_{69}$-DHEDIT-$X_{76}$-DKT-STVEACLPLEL-$X_{91}$-$X_{92}$-NESCL-$X_{98}$-SR-$X_{101}$-$X_{102}$-S-$X_{104}$-ITNGSCLASRKTSFM-$X_{120}$-$X_{121}$-LC-$X_{124}$-$X_{125}$-SIYEDLKMYQ-$X_{136}$-EFK-$X_{140}$-MNAKLLM-$X_{148}$-PKRQIFLDQNML-$X_{161}$-$X_{162}$-I-$X_{164}$-EL-$X_{167}$-QALN-$X_{172}$-NSET-$X_{177}$-PQK-$X_{181}$-SLEE-$X_{186}$-DFYKTKIKLCILLHAFRIRAVTI-$X_{210}$-R-$X_{212}$-$X_{213}$-SYLN-$X_{218}$-S, or a conservatively substituted variation thereof, where $X_{24}$ is N or S; $X_{27}$ is V or T; $X_{28}$ is A or T; $X_{30}$ is P or A; $X_{31}$ is D, S, or G; $X_{34}$ is M or R; $X_{35}$ is F, S, or L; $X_{36}$ is P or is deleted; $X_{39}$ is H or D; $X_{40}$ is H or Y; $X_{46}$ is R or K; $X_{48}$ is V or A; $X_{51}$ is M or T; $X_{54}$ is K or R; $X_{56}$ is K or R; $X_{58}$ is T or I; $X_{63}$ is P or S; $X_{69}$ is I or T; $X_{76}$ is K or Q; $X_{91}$ is A or I; $X_{92}$ is K or T; $X_{98}$ is N or A; $X_{101}$ is E or G; $X_{102}$ is T or I; $X_{104}$ is F or L; $X_{120}$ is T; $X_{121}$ is T; $X_{124}$ is L or H; $X_{125}$ is S or G; $X_{136}$ is V or M; $X_{140}$ is T or A; $X_{148}$ is D or N; $X_{161}$ is A or T; $X_{162}$ is V or A; $X_{164}$ is D or A; $X_{167}$ is M or L; $X_{172}$ is F or V; $X_{177}$ is V or A; $X_{181}$ is S or P; $X_{186}$ is P or L; $X_{210}$ is D or N; $X_{212}$ is M; $X_{213}$ is M; and $X_{218}$ is S. In various embodiments, the nucleic acid of the invention encodes a modified p35 polypeptide comprising an amino acid sequence having at least about 90%, 92%, 95%, 96%, 97%, 98%, or 99% amino acid sequence identity to the mature polypeptide region (amino acid residue positions 23–219) of SEQ ID NO:40. In another embodiment, the nucleic acid of the invention encodes a modified p35 polypeptide comprising an amino acid sequence identified herein as the mature polypeptide region (amino acid residue positions 23–219) of SEQ ID NO:40.

The modified p35 polypeptide encoded by a nucleic acid of the invention may further comprise a leader peptide sequence having at least about 90%, 92%, 95%, 96%, 97%, 98%, or 99% amino acid sequence identity to the amino acid sequence M-$X_2$-P-$X_4$-R-$X_6$-LLL-$X_{10}$-$X_{11}$-TLVLL-$X_{17}$-HLSL-$X_{22}$, identified herein as the leader peptide region (amino acid residue positions 1–22) of SEQ ID NO:40, where $X_2$ is C or Y; $X_4$ is A, L or P; $X_6$ is S or G; $X_{10}$ is V or I; $X_{11}$ is A or S; $X_{17}$ is D or H; and $X_{22}$ is A or G, and optionally includes an insertion of the amino acids P-H-L between positions 18 and 19.

The invention also includes an isolated or recombinant nucleic acid, comprising a polynucleotide sequence encoding a polypeptide comprising a leader peptide sequence having at least about 90% amino acid sequence identity to the amino acid sequence M-$X_2$-P-$X_4$-R-$X_6$-LLL-$X_{10}$-$X_{11}$-TLVLL-$X_{16}$-HLSL-$X_{22}$, identified herein as the leader peptide region (amino acid residue positions 1–22) of SEQ ID NO:40, where $X_2$ is C or Y; $X_4$ is A, L, or P; $X_6$ is S or G; $X_{10}$ is V or I; $X_{11}$ is A or S; $X_{16}$ is D or H; $X_{22}$ is A or G, and optionally includes an insertion of the amino acids P-H-L between positions 18 and 19. In various embodiments, the leader peptide sequence encoded by the nucleic acid of the invention comprises an amino acid sequence having at least about 90%, 92%, 95%, 96%, 97%, 98%, or 99% amino acid sequence identity to leader peptide region (amino acid residue positions 1–22) of SEQ ID NO:40.

The invention also provides nucleotide fragments of any of SEQ NOS:1–7. In one aspect of the invention, such a nucleotide fragment encodes a polypeptide comprising an amino acid sequence comprising at least 10 contiguous amino acid residues of any one of SEQ ID NOS:8–14. The polypeptide sequence encoded by the nucleotide fragment typically comprises one or more amino acid substitution, at an equivalent position to that of SEQ ID NO:15, selected from: Leu62Ser; Ser71Thr; Gln78His; His99(Arg or Gln); Thr127(Ser or Ile); Arg130Lys; Lys185Glu; Glu186Tyr; Tyr187(Lys or Asn); Glu188Lys; Ser190(Arg or Thr); Asp196Gly; Met211Val; Val289(Ile or Leu); Ser305Lys; Ser307Arg; Arg309Gln; and Gln311Arg. The polypeptide may optionally comprises one or more substitution, at an equivalent position to that of SEQ ID NO:15, selected from: Cys2His; His3Pro; Ile8Val; Phe15Leu; Val21Met; Lys27Glu; Asp29Asn; Asp40Asn; Met45Thr; Thr49Ala; Glu67Gly, His91Arg; Glu95(Ala or Thr), Val96Ala; Glu122Lys; Asn125Ala; Asn135Asp; Arg139His; Thr147Ala; Thr153Lys; Ser155Thr; Ser163Thr; Gln166 (Arg or His), Ala172Thr; Ala173Val; Thr174Leu; Ala177Glu; Glu178Asp; Arg179Leu; Val180Gly; Ala201Ser; Val212Leu; Asp213Glu; Val215Ile; Ser226Arg; Lys244Arg; Gln251His; Val254Ile; Ser255Asn; Glu257Gly; Thr264(Ala or Ile); Thr272Met; Cys274Gly; Val275Ile; Lys280Arg; Ser281Asn; Lys285Asp; Lys286Arg; Phe290Ser; Thr291(Met or Val); Lys293Gln; Thr297Lys; Ile299(Thr or Val); Arg301His; Asn303Asp; Ser318Phe; Glu321Asp; Pro326Ser; Cys327Leu; and Ser328(Gly or Gln). In various embodiments, the nucleic acid of the invention encodes a polypeptide comprising at least 10, at least 15, at least 20, at least 30, at least 50, at least 75, at least 100, at least 150, at least 200, or at least 250 contiguous amino acid residues of any one of SEQ ID NOS:8–14. In other embodiments, the polypeptide encoded by the nucleic acid of the invention comprises at least 270, 280, 285, 290, 295, 300, 305, 310, or 320 contiguous amino acid residues of any one of SEQ ID NOS:8–14. In another embodiment, the encoded polypeptide comprises at least 290, 300, or 305 contiguous amino acid residues of the mature polypeptide region of any one of SEQ ID NOS:8–14. In other embodiments, the invention provides a nucleic acid that comprises a polynucleotide sequence selected from SEQ ID NO:1, SEQ ID NO:2, SEQ ID NO:3, SEQ ID NO:4, SEQ ID NO:5, SEQ ID NO:6, and SEQ ID NO:7.

The invention also provides nucleotide fragments of any of SEQ NOS:16–25. In one aspect of the invention, such a nucleotide fragment encodes a polypeptide comprising an amino acid sequence comprising at least 10 contiguous amino acid residues of any one of SEQ ID NOS:26–35. The polypeptide typically comprises one or more amino acid substitution, at an equivalent position to that of SEQ ID NO:36, selected from: Thr91(Ala or Ile), Met120Thr, Ala121Thr, Val212Met, Thr213Met, and Ala218Ser. The polypeptide optionally comprises one or more substitution, at an equivalent position to that of SEQ ID NO:36, selected from: Cys2Tyr; Ala4(Leu or Pro); Ser6Gly; Val10Ile; Ala11Ser; Asp17His; Ala22Gly; Asn24Ser; Val27Thr; Ala28Thr; Pro30Ala; Asp31(Ser or Gly); Met34Arg; Phe35 (Ser or Leu); Pro36(deleted); His39Asp; His40Tyr; Arg46Lys; Val48Ala; Met51Thr; Lys54Arg; Thr58Ile; Pro63Ser; Ile69Thr; Lys76Gln; Lys92Thr; Asn98Ala; Glu101Gly; Thr102Ile; Phe104Leu; Leu124His; Ser125Gly; Val136Met; Thr140Ala; Asp148Asn; Ala161Thr; Val162Ala; Asp164Ala; Met167Leu; Phe172Val; Val177Ala; Ser181Pro; Pro186Leu; Asp210Asn; and insertion of one or more of 220Leu; 221Glu; 222Ser; and 223Ser. In various embodiments, the nucleic acid of the invention encodes a polypeptide sequence comprising at least 10, at least 15, at least 20, at least 30, at least 50, at least 75, at least 100, at least 150, at least 170, or at least 180 contiguous amino acid residues of any one of SEQ ID NOS:26–35. In another embodiment, the encoded polypeptide sequence comprises at least 185, 190, 195, 200, or 205 contiguous amino acid residues of the mature polypeptide region of any one of SEQ ID NOS:26–35. In other embodiments, the invention provides a nucleic acid that comprises a polynucleotide sequence selected from SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25.

An isolated or recombinant polypeptide having a sequence encoded by any nucleic acid of the invention, such as nucleic acids embodied in SEQ ID NOS:1–7 and SEQ ID NOS:16–25, is also a feature of the invention.

An isolated or recombinant polypeptide having any of the preceding sequences, such as those embodied in SEQ ID NOS:8–14, SEQ ID NO:39, SEQ ID NOS:26–35, and SEQ ID NO:40, is also a feature of the invention.

The invention also provides polypeptide fragments of any of SEQ NOS:8–14, SEQ ID NO:39, and SEQ ID NOS:26–35, SEQ ID NO:40. In one aspect of the invention, such a polypeptide fragment exhibits T-cell proliferative activity or interferon-gamma induction activity in a T-cell based assay (such as, e.g., a human T-cell based assay). The T-cell proliferation assay and the interferon-gamma induction assay are described in greater detail below. In yet another aspect, the invention provides a polynucleotide sequence comprising a nucleotide fragment of any nucleic acid of the invention described above and below, wherein said nucleotide fragment encodes a polypeptide fragment that exhibits T-cell proliferative activity or interferon-gamma induction activity in a T-cell based assay (such as, e.g., a human T-cell based assay), as is described in greater detail below.

In other embodiments, the modified p40 polypeptide of the invention can form a dimer (i.e., the polypeptide "dimerizes") with a p35 polypeptide to form a modified p40/p35 heterodimer, or can dimerize with a p40 polypeptide to form a modified p40/p40 homodimer. In various embodiments, the modified p40 polypeptide of the invention (hetero-)dimerizes with a polypeptide comprising a naturally-occurring or "wild type" p35 polypeptide sequence (e.g., a human p35 polypeptide, such as SEQ ID NO:36; a primate p35 polypeptide; or a mammalian p35 polypeptide), or a fragment thereof. In other embodiments, the modified p40 polypeptide of the invention (hetero-)dimerizes with a modified p35 polypeptide of the invention, such as, for example, one comprising a sequence selected from SEQ ID NOS: 26–35, SEQ ID NO:40, or a fragment thereof. In various other embodiments, the modified p40 polypeptide of the invention (homo-)dimerizes with a polypeptide comprising a naturally-occurring or wild-type p40 polypeptide sequence (e.g., a human p40 polypeptide, such as SEQ ID NO:15, a primate p40 polypeptide, or a mammalian p40 polypeptide), or a fragment thereof. In other embodiments, the modified p40 polypeptide of the invention (homo-)dimerizes with itself, or with another modified p40 polypeptide of the invention, such as, for example, one comprising a sequence selected from SEQ ID NOS:8–14 or SEQ ID NO:39, or a fragment thereof.

In other embodiments, the modified p35 polypeptide of the invention forms a dimer (i.e., the polypeptide "dimerizes") with a p40 polypeptide to form a modified p40/p35 heterodimer, or with a p35 polypeptide to form a modified p35/p35 homodimer. In various embodiments, the modified p35 polypeptide of the invention (hetero-)dimerizes with a polypeptide comprising a naturally-occurring or wild-type p40 polypeptide sequence (e.g., a human p40 polypeptide, such as SEQ ID NO:15, a primate p40 polypeptide, or a mammalian p40 polypeptide), or a fragment thereof. In other embodiments, the modified p35 polypeptide of the invention (hetero-)dimerizes with a modified p40 polypeptide of the invention, such as, for example, one comprising a sequence selected from SEQ ID NOS:8–14 and SEQ ID NO:39, or a fragment thereof. In various other embodiments, the modified p35 polypeptide of the invention (homo-)dimerizes with a polypeptide comprising a naturally-occurring or wild-type p35 polypeptide sequence (e.g., a human p35 polypeptide, such as SEQ ID NO:36, a primate p35 polypeptide, or a mammalian p35 polypeptide), or a fragment thereof. In other embodiments, the modified p35 polypeptide of the invention (homo-) dimerizes with itself, or with another modified p35 polypeptide of the invention, such as, for example, one comprising a sequence selected from SEQ ID NOS:26–35 and SEQ ID NO:40, or a fragment thereof.

The invention also includes a cell comprising any nucleic acid of the invention described herein, or which expresses any polypeptide of the invention noted herein. In one embodiment, the cell expresses a polypeptide encoded by the nucleic acid of the invention as described herein.

The invention also includes a vector comprising any nucleic acid of the invention described above and below. The vector can comprise a plasmid, a cosmid, a phage, or a virus; the vector can be, e.g., an expression vector, a cloning vector, a packaging vector, an integration vector, or the like. The invention also includes a cell transduced by a vector of the invention. The invention also includes compositions comprising any nucleic acid of the invention described above and below, and an excipient, preferably a pharmaceutically acceptable excipient. Cells and transgenic animals which include any polypeptide or nucleic acid of the invention described above and below, e.g., produced by transduction of vector, are a feature of the invention.

The invention also includes compositions produced by digesting one or more nucleic acid described above with, e.g., a restriction endonuclease, an RNAse, or a DNAse; compositions produced by fragmenting one or more nucleic acid described above by mechanically shearing, by UV, or by chemical methods; and compositions produced by incubating one or more nucleic acid described above in the presence of ribonucleotide or deoxyribonucleotide triphosphates and a nucleic acid polymerase, e.g., a thermostable polymerase.

The invention also includes compositions comprising two or more nucleic acids described above. The composition may comprise a library of nucleic acids, where the library contains, e.g., at least 2, 3, 5, 10, 20 or 50 nucleic acids.

In another aspect, the invention includes an isolated or recombinant polypeptide encoded by any nucleic acid of the invention described herein. In one embodiment, the polypeptide may comprise a mature polypeptide region of a sequence selected from SEQ ID NO:8 to SEQ ID NO:14 and SEQ ID NO:39, or SEQ ID NO:26 to SEQ ID NO:35 and SEQ ID NO:40. Longer polypeptides, e.g., which comprise leader peptide sequences, purification tags, or the like, are also contemplated. Such polypeptides may display T-cell proliferative activity and/or interferon-gamma induction activity in a T-cell based assay (such as, e.g., a human T-cell based assay).

The invention also includes a polypeptide which specifically binds polyclonal antisera raised against at least one antigen, the at least one antigen comprising a polypeptide sequence selected from an amino acid sequence set forth in SEQ ID NO:8 to SEQ ID NO:14 or SEQ ID NO:26 to SEQ ID NO:35 or a fragment thereof. In particular, the invention provides polypeptides which bind a polyclonal antisera raised against at least one antigen, wherein said at least one antigen comprises at least one amino acid sequence set forth in SEQ ID NO:8 to SEQ ID NO:14, or a fragment of any of these amino sequences, wherein the polyclonal antisera is subtracted with one or more known p40 polypeptides or proteins, including, e.g., a polypeptide or protein encoded by a nucleic acid having or corresponding to one or more of the following GenBank™ accession numbers: M65272 and M65290 (human), U19841 (*Macaca mulatta*, rhesus monkey), U19834 (*Cercocebus torquatus*, sooty mangabey), Y11129 (*Equus caballus*, horse), U83184, Y07762 and AF054607 (*Felis catus*, cat), U49100 and AF091134 (*Canis familiaris*, dog), U57752 and U10160 (*Cervus elaphus*, red deer), AF007576 (*Capra hircus*, goat), AF004024 (*Ovis aries*, sheep), U11815 (*Bos taurus*, cow), U08317 (*Sus scrofa*, pig), X97019 and AF082494 (*Marmota monax*, woodchuck), AF133197 and U16674 (*Rattus norvegicus*, rat), M86671 and S82426 (*Mus musculus*, mouse), AF097507 (*Cavia porcellus*, guinea pig), and AF046211 (*Mesocricetus auratus*, golden hamster), and other similar or homologous p40 nucleic acid sequences presented in, e.g., GenBank.

The invention also provides polypeptides which bind a polyclonal antisera raised against at least one antigen, wherein said at least one antigen comprises at least one amino acid sequence set forth in SEQ ID NO:26 to SEQ ID NO:35, or a fragment of any of these amino sequences, wherein the polyclonal antisera is subtracted with one or more known p35 polypeptides or proteins, including, e.g., a polypeptide or protein encoded by a nucleic acid having or corresponding to one or more of the following GenBank accession numbers: M65271, M65291 (human); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (*Equus caballus*, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse), and other similar or homologous p35 nucleic acid sequences presented in, e.g., GenBank.

As described above, a polypeptide of the invention may form a dimer (e.g., a heterodimer or a homodimer) with either a p35 polypeptide or a p40 polypeptide. A composition comprising a polypeptide of the invention (alone or in combination with an additional p35 polypeptide or p40 polypeptide) may exhibit at least one of the following activities: (a) T-cell proliferative activity, (b) IFN-γ induction activity, (c) enhancement of NK cell-mediated toxicity. The p35 polypeptide may comprise a naturally-occurring or wild-type sequence, such as SEQ ID NO:36 or a fragment thereof, or may comprise a modified sequence, such as, for example, one of SEQ ID NO:26 to 35, SEQ ID NO:40, or a fragment thereof. Likewise, the p40 polypeptide may comprise a naturally-occurring or wild-type sequence, such as SEQ ID NO:15 or a fragment thereof, or may comprise a modified sequence, such as, for example, one of SEQ ID NO:8 to 14, SEQ ID NO:39, or a fragment thereof.

In other embodiments, any polypeptide described above may further include a secretion/localization sequence, e.g., a leader (or signal) peptide sequence, an organelle targeting sequence, a membrane localization sequence, and the like. Any polypeptide described above may further include a sequence that facilitates purification, e.g., an epitope tag (such as, a FLAG epitope or an E-Tag epitope), a polyhistidine tag, a GST fusion, and the like. The polypeptide optionally includes a methionine at the N-terminus. Any polypeptide described above optionally includes one or more modified amino acid, such as a glycosylated amino acid, a PEG-ylated amino acid, a farnesylated amino acid, an acetylated amino acid, a biotinylated amino acid, a carboxylated amino acid, a phosphorylated amino acid, an acylated amino acid, or the like.

The invention also includes compositions comprising any nucleic acid or polypeptide described above in an excipient, preferably a pharmaceutically acceptable excipient.

The invention also includes an antibody or antisera produced by administering one or more of the polypeptides of the invention described herein to a mammal, wherein the antibody or antisera does not specifically bind to a known p40 polypeptide or protein, including, e.g., any polypeptide or protein encoded by a nucleic acid having or corresponding to one or more of the following GenBank accession numbers: M65272 and M65290 (human), U19841 (*Macaca mulatta*, rhesus monkey), U19834 (*Cercocebus torquatus*, sooty mangabey), Y11129 (*Equus caballus*, horse), U83184, Y07762 and AF054607 (*Felis catus*, cat), U49100 and AF091134 (*Canis familiaris*, dog), U57752 and U10160 (*Cervus elaphus*, red deer), AF007576 (*Capra hircus*, goat), AF004024 (*Ovis aries*, sheep), U11815 (*Bos taurus*, cow), U08317 (*Sus scrofa*, pig), X97019 and AF082494 (*Marmota monax*, woodchuck), AF133197 and U16674 (*Rattus norvegicus*, rat), M86671 and S82426 (*Mus musculus*, mouse), AF097507 (*Cavia porcellus*, guinea pig), and AF046211 (*Mesocricetus auratus*, golden hamster), and other similar or homologous p40 sequences presented in, e.g., GenBank. The invention also includes antibodies or antisera produced by administering one or more of the polypeptides of the invention described herein to a mammal, wherein the antibody or antisera does not bind to a known p35 polypeptide or protein, including, e.g., any polypeptide or protein encoded by a nucleic acid having or corresponding to one or more of the following GenBank accession numbers: M65271, M65291 (*Homo sapiens*); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (*Equus caballus*, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse), and other similar or homologous p35 sequences presented in, e.g., GenBank.

The invention also includes antibodies which specifically bind a polypeptide comprising a sequence selected from SEQ ID NO:8 to SEQ ID NO:14 or SEQ ID NO:26 to SEQ ID NO:35. The antibodies are, e.g., polyclonal, monoclonal, chimeric, humanized, single chain, Fab fragments, fragments produced by an Fab expression library, or the like.

Methods for producing the polypeptides of the invention are also included. One such method comprises introducing into a population of cells any nucleic acid of the invention described above, operatively linked to a regulatory sequence effective to produce the encoded polypeptide, culturing the cells in a culture medium to produce the polypeptide, and optionally isolating the polypeptide from the cells or from the culture medium. The nucleic acid may be part of a vector, such as a recombinant expression vector.

The invention also includes compositions comprising a nucleic acid of the invention, and optionally, further comprising a second nucleic acid encoding a p35 polypeptide or a p40 polypeptide. The second nucleic acid may encode a p35 polypeptide having a naturally-occurring p35 sequence, such as a nucleic acid encoding SEQ ID NO:36, or may encode a modified p35 polypeptide sequence, such as, for example, one of nucleic acids SEQ ID NOS:16–25 encoding SEQ ID NOS:26–35, respectively. The second nucleic acid may encode a p40 polypeptide having a naturally-occurring sequence, such as a nucleic acid encoding SEQ ID NO:15, or may encode a modified p40 polypeptide sequence, such as, for example, one of nucleic acids SEQ ID NOS:1–7 encoding SEQ ID NOS:8–14, respectively.

The invention also includes compositions comprising a polypeptide of the invention, and optionally, further comprising a second p35 polypeptide or a second p40 polypeptide. The second p35 polypeptide or the second p40 polypeptide may have a naturally-occurring or wild-type sequence, or may have a modified sequence, such as a modified p35 polypeptide or a modified p40 polypeptide of the invention.

The invention also includes a method of inducing proliferation of T-cells comprising contacting the T-cells with a composition comprising a polypeptide of the invention, thereby inducing proliferation of the T-cells. In one embodiment, the T-cells are in culture. In another embodiment, the T-cells are human T-cells.

The invention also includes a method of inducing production of IFN-γ in T-cells, the method comprising contacting the T-cells with a composition comprising a polypeptide of the invention, thereby inducing production of IFN-γ in the T-cells. In one embodiment, the T-cells are in culture. In another embodiment, the T-cells are human T-cells.

In general, nucleic acids and proteins derived by mutation of the sequences herein are a feature of the invention. Similarly, those produced by diversity generation methods or recursive sequence recombination ("RSR") methods (e.g., DNA shuffling) are a feature of the invention. Mutation and recombination methods using the nucleic acids described herein are a feature of the invention. For example, one method of the invention includes recursively recombining one or more nucleic acid sequences of the invention as described above and below with one or more additional nucleic acids (including, but not limited to, those noted herein), each sequence of the one or more additional nucleic acids encoding a modified p40 polypeptide or modified p35 polypeptide or an amino acid subsequence thereof. The recombining steps are optionally performed in vivo, ex vivo, in silico or in vitro. Said diversity generation or recursive sequence recombination produces at least one library of recombinant modified p40 or modified p35 nucleic acids. Also included in the invention are a recombinant modified p40 nucleic acid produced by this method, a recombinant modified p35 nucleic acid produced by this method, a cell containing the recombinant modified p40 nucleic acid or recombinant modified p35 nucleic acid, a nucleic acid library produced by recursive sequence recombination or other diversity generation methods, a composition comprising two or more of recombinant modified p40 or modified p35 nucleic acids, and a population of cells comprising such recombinant modified p40 or modified p35 nucleic acids or containing the library. In one embodiment, the library comprises at least ten such recombinant nucleic acids.

The invention also provides a method of producing a modified or recombinant modified p40 or modified p35 nucleic acid that comprises mutating a nucleic acid of the invention as described herein.

These and other objects and features of the invention will become more fully apparent when the following detailed description is read in conjunction with the accompanying figures.

BRIEF DESCRIPTION OF THE FIGURES

FIGS. 1A–1B show an alignment of a naturally-occurring or wild-type human p40 polypeptide sequence (SEQ ID NO:15) and exemplary modified p40 polypeptide sequences according to the invention (SEQ ID NOS:8–14). Equivalent amino acid residue positions which differ from those of SEQ ID NO:15 are shaded. The arrow and the dashed horizontal line, located between the amino acid residue positions equivalent to amino acid residues 22 and 23 of SEQ ID NO:15, indicate the predicted boundary between the leader peptide region and the mature polypeptide region. The alignment was prepared using the CLUSTALW multiple sequence alignment algorithm, a part of the Vector NTI version 6 sequence analysis software package (Informax, Bethesda, Md.). The CLUSTALW program initially performs multiple pairwise comparisons between groups of sequences and then assembles the pairwise alignments into a multiple alignment based on homology. For the initial pairwise alignments, Gap Open and Gap Extension penalties were 10 and 0.1, respectively. For the multiple alignments, Gap Open penalty was 10, and the Gap Extension penalty was 0.05. The protein weight matrix employed was the BLOSUM62 matrix.

FIGS. 11A–11B show an alignment of a naturally-occurring or wild-type human p35 polypeptide sequence (SEQ ID NO:36) and exemplary modified p35 polypeptide sequences according to the invention (SEQ ID NOS:26–35). Equivalent amino acid positions which differ from those of SEQ ID NO:36 are shaded. The arrow and the dashed horizontal line, located between the amino acid residue positions equivalent to amino acid residues 22 and 23 of SEQ ID NO:36, indicate the predicted boundary between the leader peptide region and the mature polypeptide region. The alignment was prepared using the CLUSTALW algorithm and Vector NTI software as described in FIG. 1.

DETAILED DESCRIPTION OF THE INVENTION DEFINITIONS

Figure 2:
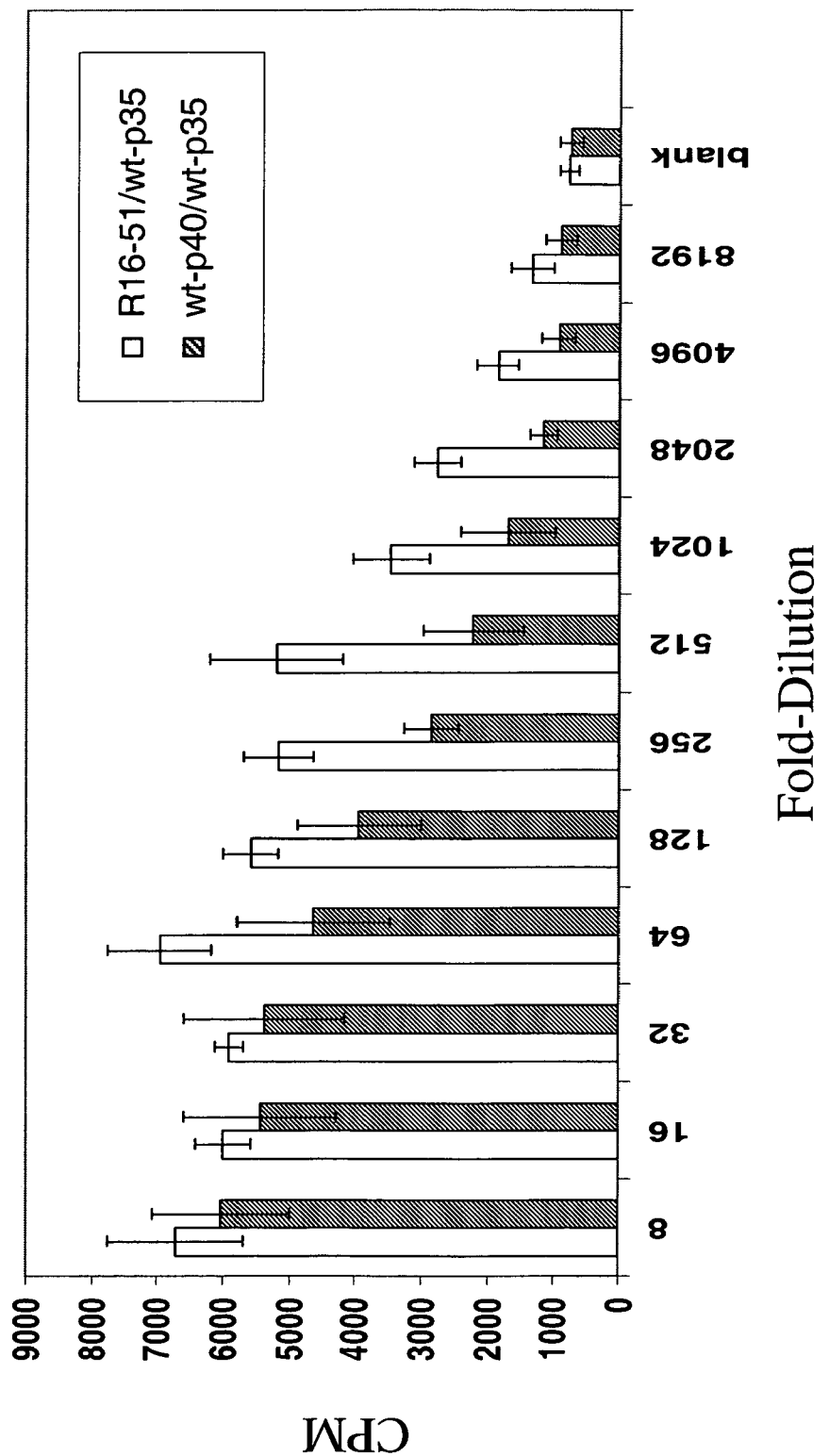
FIG. 2 shows T-cell proliferative activity of two-fold serial dilutions of culture media of mammalian cell cultures expressing a modified p40 nucleic acid of the invention (SEQ ID NO:7 encoding R16–51) co-expressed with a nucleic acid comprising a wild-type human p35 ("wt-p35") coding sequence (SEQ ID NO:38), as compared to equivalent serial dilutions of a control culture co-expressing nucleic acids comprising wt-p35 and wild-type human p40 ("wt-p40") coding sequences (SEQ ID NO:38 and SEQ ID NO:37, respectively). The X-axis ("Fold-Dilution") indicates the n-fold serial dilution of culture supernatant, and the Y-axis ("CPM") indicates the amount of $^3$H-thymidine incorporated into T-cells, expressed as counts per minute. For this and the following figures, the data bars represents the average, and the error bars represent the standard deviation, of at least three data points per assay.

Unless otherwise defined herein or below in the remainder of the specification, all technical and scientific terms used herein have the same meaning as commonly understood by those of ordinary skill in the art to which the present invention belongs.

A "polynucleotide sequence" is a nucleic acid (which is a polymer of nucleotides (A,C,T,U,G, etc. or naturally occurring or artificial nucleotide analogues) or a character string representing a nucleic acid, depending on context. Either the given nucleic acid or the complementary nucleic acid can be determined from any specified polynucleotide sequence.

Similarly, an "amino acid sequence" is a polymer of amino acids (a protein, polypeptide, etc.) or a character string representing an amino acid polymer, depending on context. Either the given nucleic acid or the complementary nucleic acid can be determined from any specified polynucleotide sequence.

A nucleic acid, protein, peptide, polypeptide, or other component is "isolated" when it is partially or completely separated from components with which it is normally associated (other peptides, polypeptides, proteins (including complexes, e.g., polymerases and ribosomes which may accompany a native sequence), nucleic acids, cells, synthetic reagents, cellular contaminants, cellular components, etc.), e.g., such as from other components with which it is normally associated in the cell from which it was originally derived. A nucleic acid, polypeptide, or other component is isolated when it is partially or completely recovered or separated from other components of its natural environment such that it is the predominant species present in a composition, mixture, or collection of components (i.e., on a molar basis it is more abundant than any other individual species in the composition). In preferred embodiments, the preparation consists of more than 70%, typically more than 80%, or preferably more than 90% of the isolated species.

In one aspect, a "substantially pure" or "isolated" nucleic acid (e.g., RNA or DNA), polypeptide, protein, or composition also means where the object species (e.g., nucleic acid or polypeptide) comprises at least about 50, 60, or 70 percent by weight (on a molar basis) of all macromolecular species present. A substantially pure or isolated composition can also comprise at least about 80, 90, or 95 percent by weight of all macromolecular species present in the composition. An isolated object species can also be purified to essential homogeneity (contaminant species cannot be detected in the composition by conventional detection methods) wherein the composition consists essentially of derivatives of a single macromolecular species.

The term "isolated nucleic acid" may refer to a nucleic acid (e.g., DNA or RNA) that is not immediately contiguous with both of the coding sequences with which it is immediately contiguous (i.e., one at the 5' and one at the 3' end) in the naturally occurring genome of the organism from which the nucleic acid of the invention is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or antisense.

A nucleic acid or polypeptide is "recombinant" when it is artificial or engineered, or derived from an artificial or engineered protein or nucleic acid. The term "recombinant" when used with reference e.g., to a cell, nucleotide, vector, or polypeptide typically indicates that the cell, nucleotide, or vector has been modified by the introduction of a heterologous (or foreign) nucleic acid or the alteration of a native nucleic acid, or that the polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g., genes) that would be abnormally expressed under-expressed, or not expressed at all. The term "recombinant nucleic acid" (e.g., DNA or RNA) molecule means, for example, a nucleotide sequence that is not naturally occurring or is made by the combatant (for example, artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. The term "recombinantly produced" refers to an artificial combination usually accomplished by either chemical synthesis means, recursive sequence recombination of nucleic acid segments or other diversity generation methods (such as, e.g., shuffling) of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated. A "recombinant polypeptide" or "recombinant protein" usually refers to polypeptide or protein, respectively, that results from a cloned or recombinant gene or nucleic acid.

A "subsequence" or "fragment" is any portion of an entire sequence, up to and including the complete sequence.

Numbering of a given amino acid or nucleotide polymer "corresponds to (the) numbering" of a selected amino acid polymer or nucleic acid when the position of any given polymer component (amino acid residue, incorporated nucleotide, etc.) is designated by reference to the same residue position in the selected amino acid or nucleotide, rather than by the actual position of the component in the given polymer.

A vector is a composition for facilitating cell transduction by a selected nucleic acid, or expression of the nucleic acid in the cell. Vectors include, e.g., plasmids, cosmids, viruses, YACs, bacteria, poly-lysine, etc. An "expression vector" is a nucleic acid construct, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed operably linked to a promoter.

"Substantially an entire length of a polynucleotide or amino acid sequence" refers to at least about 50%, at least about 60%, generally at least about 70%, generally at least about 80%, or typically at least about 85%, 90%, 92%, 95,%, 96%, 97%, 98%, or 99% or more of a length of an amino acid sequence or nucleic acid sequence.

"Naturally occurring" as applied to an object refers to the fact that the object can be found in nature. For example, a polypeptide or polynucleotide sequence that is present in an organism, including viruses, that can be isolated from a source in nature and which has not been intentionally modified by man in the laboratory is naturally occurring.

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains, respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

An "antigen-binding fragment" of an antibody is a peptide or polypeptide fragment of the antibody which binds an antigen. An antigen-binding site is formed by those amino acids of the antibody which contribute to, are involved in, or affect the binding of the antigen. See Scott, T. A. and Mercer, E. I., CONCISE ENCYCLOPEDIA: BIOCHEMISTRY AND MOLECULAR BIOLOGY (de Gruyter, 3d ed. 1997) [hereinafter "Scott, CONCISE ENCYCLOPEDIA"] and Watson, J. D. et al., RECOMBINANT DNA (2d ed. 1992) [hereinafter "Watson, RECOMBINANT DNA"], each of which is incorporated herein by reference in its entirety for all purposes.

An "immunogen" refers to a substance that is capable of provoking an immune response. Examples of immunogens include, e.g., antigens, autoantigens that play a role in induction of autoimmune diseases, and tumor-associated antigens expressed on cancer cells.

An "antigen" is a substance that is capable of eliciting the formation of antibodies in a host or generating a specific population of lymphocytes reactive with that substance. Antigens are typically macromolecules (e.g., proteins and polysaccharides) that are foreign to the host.

The term "immunoassay" includes an assay that uses an antibody or immunogen to bind or specifically bind an antigen. The immunoassay is typically characterized by the use of specific binding properties of a particular antibody to isolate, target, and/or quantify the antigen.

The term "homology" generally refers to the degree of similarity between two or more structures. The term "homologous sequences" refers to regions in macromolecules that have a similar order of monomers. When used in relation to nucleic acid sequences, the term "homology" refers to the degree of similarity between two or more nucleic acid sequences (e.g., genes) or fragments thereof. Typically, the degree of similarity between two or more nucleic acid sequences refers to the degree of similarity of the composition, order, or arrangement of two or more nucleotide bases (or other genotypic feature) of the two or more nucleic acid sequences. The term "homologous nucleic acids" generally refers to nucleic acids comprising nucleotide sequences having a degree of similarity in nucleotide base composition, arrangement, or order. The two or more nucleic acids may be of the same or different species or group. The term "percent homology" when used in relation to nucleic acid sequences, refers generally to a percent degree of similarity between the nucleotide sequences of two or more nucleic acids.

When used in relation to polypeptide (or protein) sequences, the term "homology" refers to the degree of similarity between two or more polypeptide (or protein) sequences (e.g., genes) or fragments thereof. Typically, the degree of similarity between two or more polypeptide (or protein) sequences refers to the degree of similarity of the composition, order, or arrangement of two or more amino acid of the two or more polypeptides (or proteins). The two or more polypeptides (or proteins) may be of the same or different species or group. The term "percent homology" when used in relation to polypeptide (or protein) sequences, refers generally to a percent degree of similarity between the amino acid sequences of two or more polypeptide (or protein) sequences. The term "homologous polypeptides" or "homologous proteins" generally refers to polypeptides or proteins, respectively, that have amino acid sequences and functions that are similar. Such homologous polypeptides or proteins may be related by having amino acid sequences and functions that are similar, but are derived or evolved from different or the same species using the techniques described herein.

The term "subject" as used herein includes, but is not limited to, an organism; a mammal, including, e.g., a human, non-human primate (e.g., monkey), mouse, dog, cat, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish; and a non-mammalian invertebrate.

The term "pharmaceutical composition" means a composition suitable for pharmaceutical use in a subject, including an animal or human. A pharmaceutical composition generally comprises an effective amount of an active agent and a pharmaceutically acceptable carrier.

The term "effective amount" means a dosage or amount sufficient to produce a desired result. The desired result may comprise an objective or subjective improvement in the recipient of the dosage or amount.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a nucleic acid, vector, gene, polypeptide, protein, substance, composition thereof that, when administered to a subject who does not display signs or symptoms of pathology, disease or disorder, or who displays only early signs or symptoms of pathology, disease, or disorder, diminishes, prevents, or decreases the risk of the subject developing a pathology, disease, or disorder. A "prophylactically useful" agent or compound (e.g., nucleic acid or polypeptide) refers to an agent or compound that is useful in diminishing, preventing, treating, or decreasing development of pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, diminishes when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins.

Generally, the nomenclature used hereafter and the laboratory procedures in cell culture, molecular genetics, molecular biology, nucleic acid chemistry, and protein chemistry described below are those well known and commonly employed by those of ordinary skill in the art. Standard techniques, such as described in Sambrook et al., *Molecular Cloning—A Laboratory Manual* (2nd Ed.), Vols. 1–3, Cold Spring Harbor Laboratory, Cold Spring Harbor, N.Y., 1989 (hereinafter "Sambrook") and *Current Protocols in Molecular Biology*, F. M. Ausubel et al., eds., Current Protocols, a joint venture between Greene Publishing Associates, Inc. and John Wiley & Sons, Inc. (supplemented through 1999) (hereinafter "Ausubel"), are used for recombinant nucleic acid methods, nucleic acid synthesis, cell culture methods, and transgene incorporation, e.g., electroporation, injection, and lipofection. Generally, oligonucleotide synthesis and purification steps are performed according to specifications. The techniques and procedures are generally performed according to conventional methods in the art and various general references which are provided throughout this document. The procedures therein are believed to be well known to those of ordinary skill in the art and are provided for the convenience of the reader.

A variety of additional terms are defined or otherwise characterized herein.

Polynucleotides of the Invention

Modified Cytokine Nucleic Acids

The invention provides isolated or recombinant modified p40 polypeptides and modified p35 polypeptides, collectively referred to herein as "modified cytokine polypeptides", and isolated or recombinant polynucleotides encoding the polypeptides.

As described in more detail below, in accordance with the present invention, polynucleotide sequences which encode modified cytokine polypeptides, nucleotide sequences (e.g., subsequences) that encode fragments of modified cytokine polypeptides, and nucleotide sequences that encode related fusion polypeptides or proteins, or functional equivalents thereof, are referred to herein as "modified cytokine nucleotides", "modified p40 nucleotides" or "modified p35 nucleotides," and more generally as polynucleotides of the invention. Fragments of each of the preceding terms are also intended to be included. The term "nucleic acid" is used interchangeably with the term "nucleotide."

A "corresponding partner polypeptide" or a "corresponding partner subunit" is defined herein as a polypeptide which associates with another polypeptide to form a heterodimeric protein (also referred to herein as a "p40/p35" or a "p70" heterodimer) comprising a p40 polypeptide and a p35 polypeptide. Thus, a p35 polypeptide is considered a corresponding partner polypeptide to a p40 polypeptide, and a p40 polypeptide is considered a corresponding partner polypeptide to a p35 polypeptide. Nucleic acids encoding the corresponding partner polypeptides (i.e., a p40 polypeptide and a p35 polypeptide) were generally co-transfected into mammalian cells to express and secrete biologically active p40/p35 heterodimers into the cell culture media.

In examples provided herein, wild-type p40 nucleic acid (designated herein as "wt-p40") comprises the nucleic acid sequence SEQ ID NO:37, encoding a p40 subunit polypeptide comprising the amino acid sequence SEQ ID NO:15. Likewise, wild-type p35 nucleic acid (designated herein as "wt-p35") comprises the nucleic acid sequence SEQ ID NO:38, encoding a p35 subunit polypeptide comprising the amino acid sequence SEQ ID NO:36.

Culture supernatants (also referred to herein as "test culture supernatants") from cells which comprise a modified p40 nucleic acid and/or a modified p35 nucleic acid of the invention, were generally assayed in comparison to culture supernatant (also referred to herein as "control culture supernatant") from cells (also referred to herein as "control cells") which comprise both wt-p40 and wt-p35 nucleic acids. Such "control cells" express and secrete control wild-type ("wt-p40/wt-p35") heterodimers.

In some examples provided herein, a nucleic acid of the invention, encoding a polypeptide of the invention, was co-transfected into mammalian cells with a nucleic acid encoding a corresponding wild-type (wt) partner polypeptide (e.g., a modified p40 nucleic acid of the invention was co-transfected with a wt-p35 nucleic acid, and a modified p35 nucleic acid of the invention was co-transfected with a wt-p40 nucleic acid). In other examples provided herein, a nucleic acid encoding a polypeptide of the invention was co-transfected into mammalian cells with another nucleic acid of the invention encoding a corresponding modified partner polypeptide (e.g., a modified p40 nucleic acid of the invention was co-transfected with a modified p35 nucleic acid of the invention).

Modified p35 nucleic acids of the invention and the wt-p35 nucleic acid were in some instances modified to contain a sequence encoding a combined E tag-polyhistidine sequence ("EHtag") at the extreme 3' end of the coding region (prior to the stop codon). The resulting fusion proteins comprised a p35 polypeptide (e.g., comprising a modified p35 polypeptide sequence or a wt-p35 polypeptide sequence) plus an EHtag sequence (AAAGAPVPYPD-PLERAAAHHHHHH, identified herein as SEQ ID NO:44) fused to the C-terminus. Control experiments showed no significant difference in T-cell proliferative activity in the culture media of cells comprising p35 nucleic acids with and without the EHtag modification (see, for example, Table 3).

Culture supernatants from mammalian cell transfectants expressing and secreting heterodimers comprising a modified polypeptide of the invention and its corresponding wild-type subunit partner, also referred to herein as "(modified/wt) heterodimers", were initially screened in a high-throughput human T-cell based proliferation assay as described in Example 1. Clones corresponding to culture supernatants expressing (modified/wt) heterodimers having a T-cell proliferative activity approximately equal to or greater than that of a control culture supernatant expressing a control (wt-p40/wt-p35) heterodimer were selected for further analysis. The modified p40 nucleic acids and modified p35 nucleic acids so selected were re-transfected into mammalian cells with the corresponding wild-type (wt) subunit nucleic acid as described above for more detailed activity and expression analyses.

Generally, serial dilutions of test culture supernatants containing secreted heterodimers comprising modified p40 and/or modified p35 polypeptides of the invention were assayed for proliferative activity in the human T-cell based assays as described in Example 1, and compared to activities obtained from serial dilutions of control culture supernatants (containing secreted heterodimers comprising wt-p40 and wt-p35 polypeptides).

The "EC50", which is the effective concentration of heterodimer required to achieve 50% of the maximum proliferative activity measured as, e.g., CPM (counts per minute) of $^3$H-thymidine incorporated into T-cells, was estimated from plots of serial dilution versus CPM. First, the serial dilution of control culture supernatant (comprising wt-p40 and wt-p35 polypeptides, i.e., wild-type heterodimer) needed to attain 50% of the maximum proliferative activity was determined from the plot of serial dilution versus CPM, where the maximum proliferative activity was defined as the maximum amount of $^3$H-thymidine incorporation (expressed as CPM) at the highest concentrations (lowest dilutions) of control culture supernatant. The serial dilution of test culture supernatant required to attain the same amount of $^3$H-thymidine incorporation (50% of the maximum CPM) was then estimated from the plot. The n-fold difference in dilution of test culture supernatant compared to dilution of control culture supernatant required to achieve the same amount of $^3$H-thymidine incorporation (50% of the maximum CPM) provides the "relative EC50" between the test culture supernatant and the control culture supernatant.

T-cell proliferative activities of test culture supernatants of cells co-expressing various exemplary modified p40 nucleic acids of the invention plus wt-p35 nucleic acid, in comparison to culture supernatants of control cells co-expressing wt-p40 plus wt-p35 nucleic acids, are shown in FIGS. 2–6. The relative T-cell proliferative activities, (expressed as relative EC50) of test culture supernatants as compared to control culture supernatants are presented in Table 1. The data show that cells co-expressing a modified p40 nucleic acid of the invention together with a wt-p35 nucleic acid secrete biologically active protein into the culture media which, on a volume basis, has from about 4-fold to as much as 64-fold higher T-cell proliferative activity than culture media from cells co-expressing wt-p40 plus wt-p35 nucleic acids.

TABLE 1

Relative EC50 values for T-cell proliferative activities of culture supernatants comprising modified p40/wt-p35 heterodimers

Figure 3:
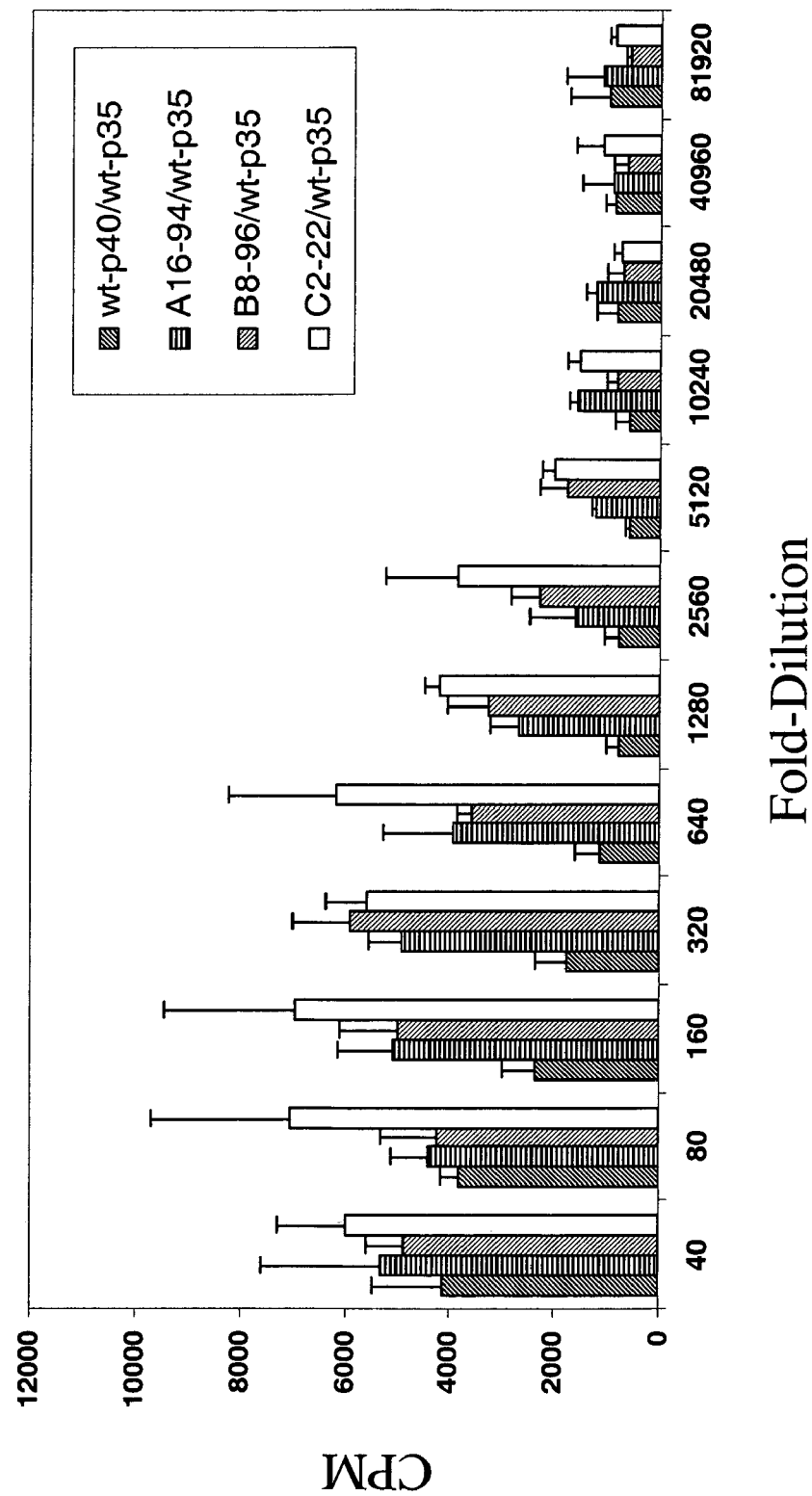
FIG. 3 shows T-cell proliferative activities of two-fold serial dilutions of culture media of mammalian cell cultures expressing the following modified p40 nucleic acids of the invention: SEQ ID NO:6 encoding A16–94; SEQ ID NO:2 encoding B8–96; and SEQ ID NO:1 encoding C2–22, all co-expressed with a nucleic acid comprising a wt-p35 coding sequence (SEQ ID NO:38), as compared to equivalent serial dilutions of a control culture co-expressing nucleic acids comprising wt-p35 and wt-p40 coding sequences (SEQ ID NO:38 and SEQ ID NO:37, respectively). X- and Y-axes are as described for FIG. 2.

| p40 subunit | p35 subunit | Relative EC50 | Figure |
|---|---|---|---|
| wt-p40 (SEQ ID NO:37) | wt-p35 (SEQ ID NO:38) | 1[1] | |
| R1-6-51 (SEQ ID NO:7) | wt-p35 | ~4 | FIG. 2 |
| A16-94 | wt-p35 | ~8 to 16 | FIG. 3 |

TABLE 1-continued

Relative EC50 values for T-cell proliferative activities of culture supernatants comprising modified p40/wt-p35 heterodimers

Figure 4:
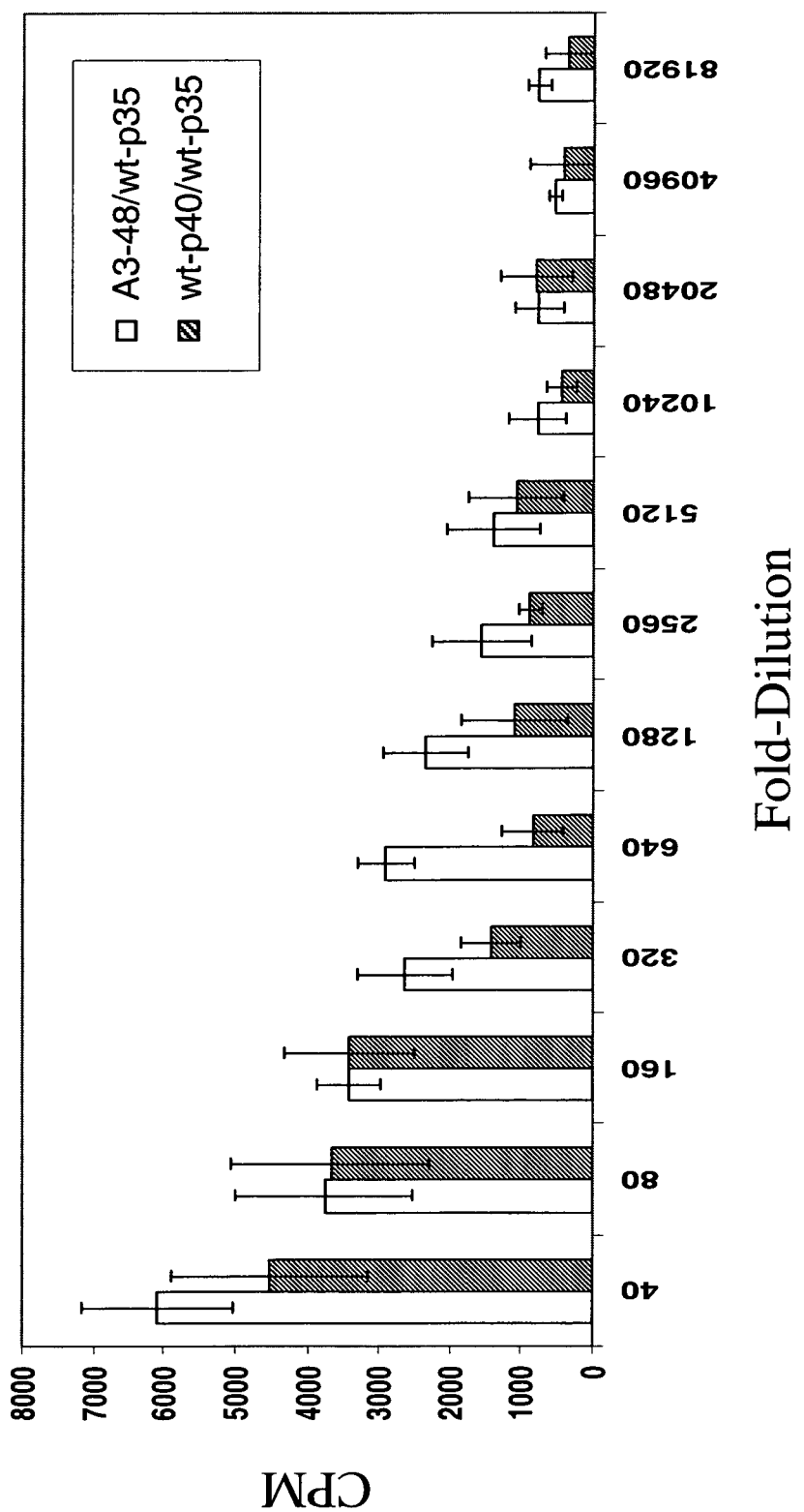
FIG. 4 shows T-cell proliferative activity of two-fold serial dilutions of culture media of mammalian cell cultures expressing a modified p40 nucleic acid of the invention (SEQ ID NO:5) encoding A3–48) co-expressed with a nucleic acid comprising a wt-p35 coding sequence, as compared to equivalent dilutions of a control culture co-expressing nucleic acids comprising wt-p35 and wt-p40 coding sequences (SEQ ID NO:38 and SEQ ID NO:37, respectively). X- and Y-axes are as described for FIG. 2.
Figure 5:
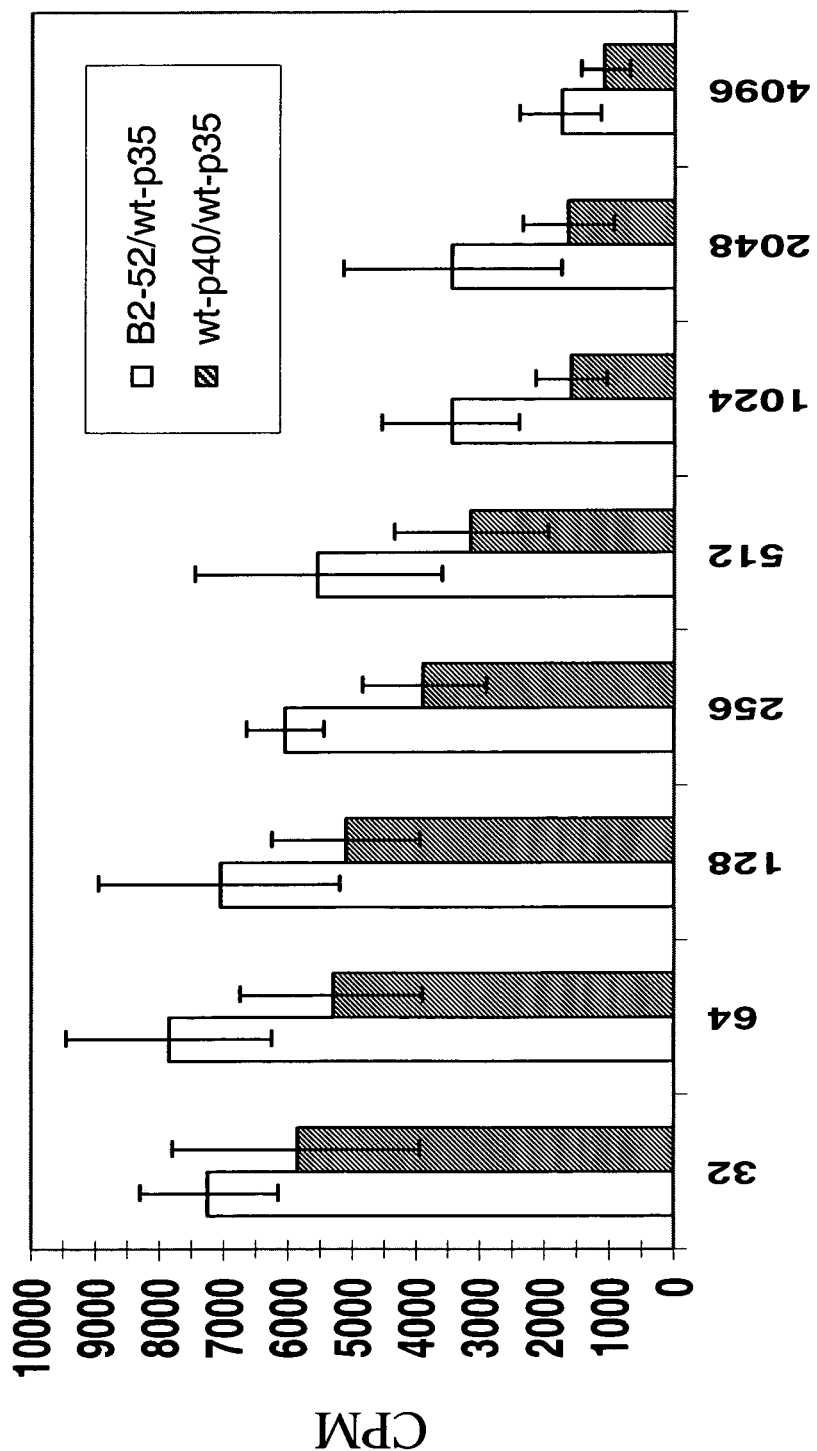
FIG. 5 shows T-cell proliferative activities of two-fold serial dilutions of culture media of mammalian cell cultures expressing a modified p40 nucleic acid of the invention (SEQ ID NO:3 encoding B2–52) co-expressed with a nucleic acid comprising a wt-p35 coding sequence (SEQ ID NO:38), as compared to equivalent dilutions of a control culture co-expressing nucleic acids comprising wt-p35 and wt-p40 coding sequences (SEQ ID NO:38 and SEQ ID NO:37, respectively). X- and Y-axes are as described for FIG. 2.
Figure 6:
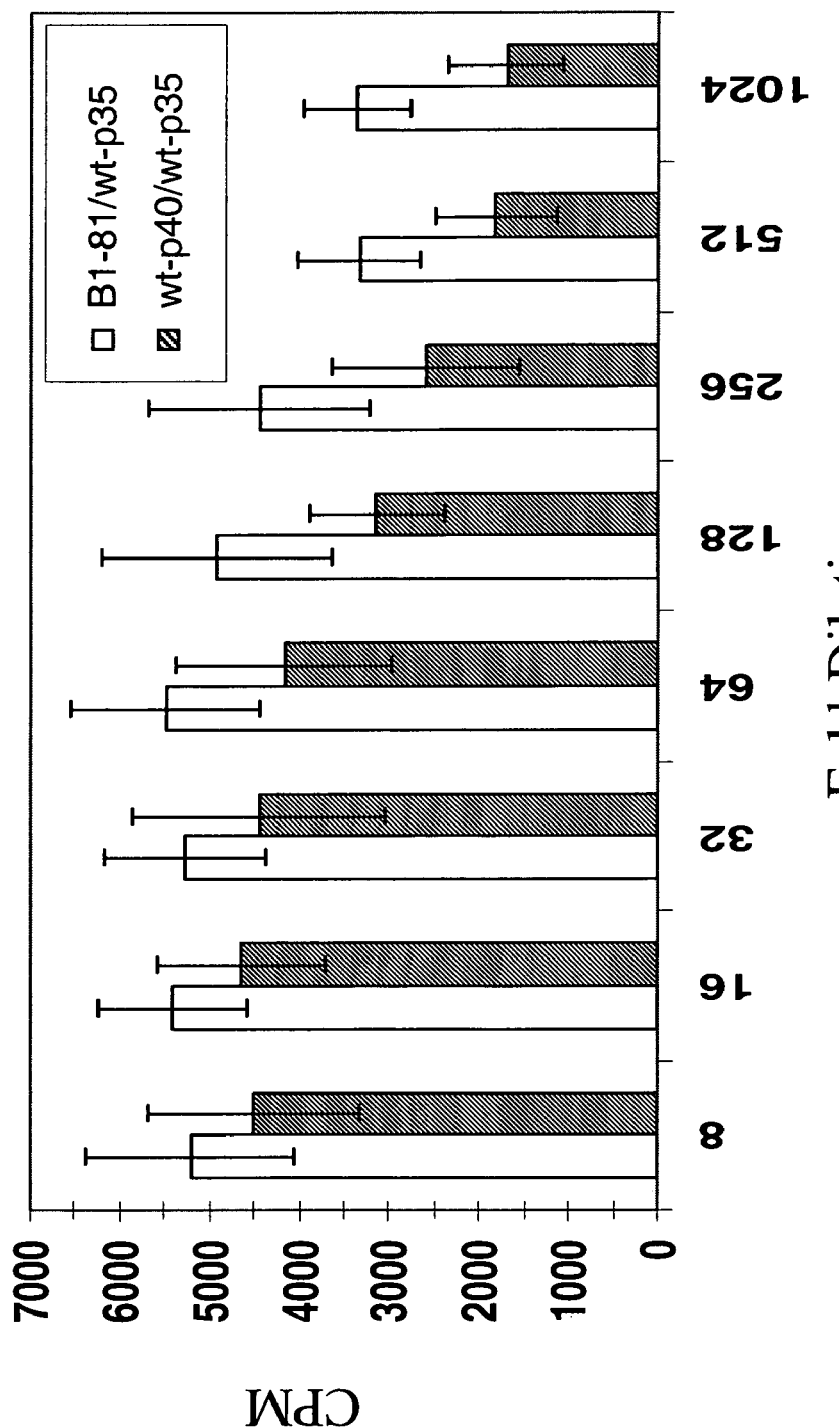
FIG. 6 shows T-cell proliferative activity of two-fold serial dilutions of culture media of mammalian cell cultures expressing a modified p40 nucleic acid of the invention (SEQ ID NO:4 encoding B1–81) co-expressed with a nucleic acid comprising a wt-p35 coding sequence (SEQ ID NO:38), as compared to equivalent dilutions of a control culture co-expressing nucleic acids comprising wt-p35 and wt-p40 coding sequences (SEQ ID NO:38 and SEQ ID NO:37, respectively). X- and Y-axes are as described for FIG. 2.

| p40 subunit | p35 subunit | Relative EC50 | Figure |
|---|---|---|---|
| (SEQ ID NO:6) | | | |
| B8-96 (SEQ ID NO:2) | wt-p35 | ~16 to 32 | FIG. 3 |
| C2-22 (SEQ ID NO:1) | wt-p35 | ~32 to 64 | FIG. 3 |
| A3-48 (SEQ ID NO:5) | wt-p35 | ~8 | FIG. 4 |
| B2-52 (SEQ ID NO:3) | wt-p35 | ~4 | FIG. 5 |
| B1-81 (SEQ ID NO:4) | wt-p35 | ~8 | FIG. 6 |

[1]relative EC50 of control (wt-p40/wt-p35) heterodimer culture supernatant is 1 by definition Culture supernatants of cells co-transfected with modified p35 nucleic acids of the invention plus wt-p40 nucleic acid also showed significantly enhanced T-cell proliferative activities over the control (wt-p40/wt-p35) culture supernatant (Table 2).

Modified p40 nucleic acids and modified p35 nucleic acids were also co-transfected into mammalian cells to generate (modified/modified) heterodimers (also referred to herein as "fully modified heterodimers"). Test culture supernatants of cells expressing and secreting fully modified heterodimers were assayed for proliferative activity in the human T-cell based assay in comparison with control supernatants of cells expressing and secreting wt-p40/wt-p35 heterodimers (Table 2).

TABLE 2

Relative EC50 values for T-cell proliferative activities of culture supernatants comprising fully modified heterodimers

| p40 subunit | p35 subunit | Relative EC50 |
|---|---|---|
| wt-p40 (SEQ ID NO:37) | wt-p35 (SEQ ID NO:38) | 1[1] |
| wt-p40 | R1-4-87 (SEQ ID NO:25) | ~2 |
| B8-96 (SEQ ID NO:2) | wt-p35 | ~16 to 32 |
| B8-96 | R2-146 (SEQ ID NO:27) | ~32 |
| B8-96 | R2-162 (SEQ ID NO:23) | ~32 |
| C2-22 (SEQ ID NO:1) | wt-p35 | ~4 to 64[2] |
| C2-22 | R2-42 (SEQ ID NO:16) | ~8 |
| C2-22 | R2-157 (SEQ ID NO:24) | ~8 |
| C2-22 | R2-631 (SEQ ID NO:19) | ~64 |
| C2-22 | R2-796 (SEQ ID NO:18) | ~64 |
| C2-22 | R2-555 (SEQ ID NO:22) | ~64 to 128 |
| C2-22 | R2-571 (SEQ ID NO:21) | ~64 to 128 |

TABLE 2-continued

Relative EC50 values for T-cell proliferative activities of culture supernatants comprising fully modified heterodimers

| p40 subunit | p35 subunit | Relative EC50 |
|---|---|---|
| C2-22 | R2-631 (SEQ ID NO:19) | ~64 |
| C2-22 | R2-796 (SEQ ID NO:18) | ~64 |

[1] Relative EC50 of control (wt-p40/wt-p35) heterodimer culture supernatant is 1 by definition.
[2] Typically, a 32- to 64-fold enhancement was observed for C2-22/wt-p35 heterodimer culture supernatants; the 4-fold enhancement reflects a possibly aberrant result from a single experiment.

Addition of an EHtag sequence to the C-termini of p35 polypeptides resulted in no significant difference in T-cell proliferative activities of the culture supernatants of cells comprising modified p35 nucleic acids with and without the added EHtag (Table 3). Furthermore, addition of four amino acids Leu-Glu-Ser-Ser (LESS in single-letter amino acid designation) to the C-terminus of the p35 polypeptide sequence also resulted in no significant difference in T-cell proliferative activities (Table 3).

TABLE 3

Effect of addition of C-terminal amino acids LESS and/or C-terminal EHtag on relative EC50 values for T-cell proliferative activities of culture supernatants

| p40 subunit | p35 subunit | Relative EC50 |
|---|---|---|
| wt-p40 | wt-p35 | 1[1] |
| C2-22 | R2-555 + LESS[2] | ~64–128 |
| C2-22 | R2-555 + LESS + EHtag | ~64 |
| C2-22 | R2-555 + EHtag | ~128 |
| C2-22 | R2-571 + LESS | ~64–128 |
| C2-22 | R2-571 + LESS + EHtag | ~128 |
| C2-22 | R2-571 + EHtag | ~128 |

Figure 7:
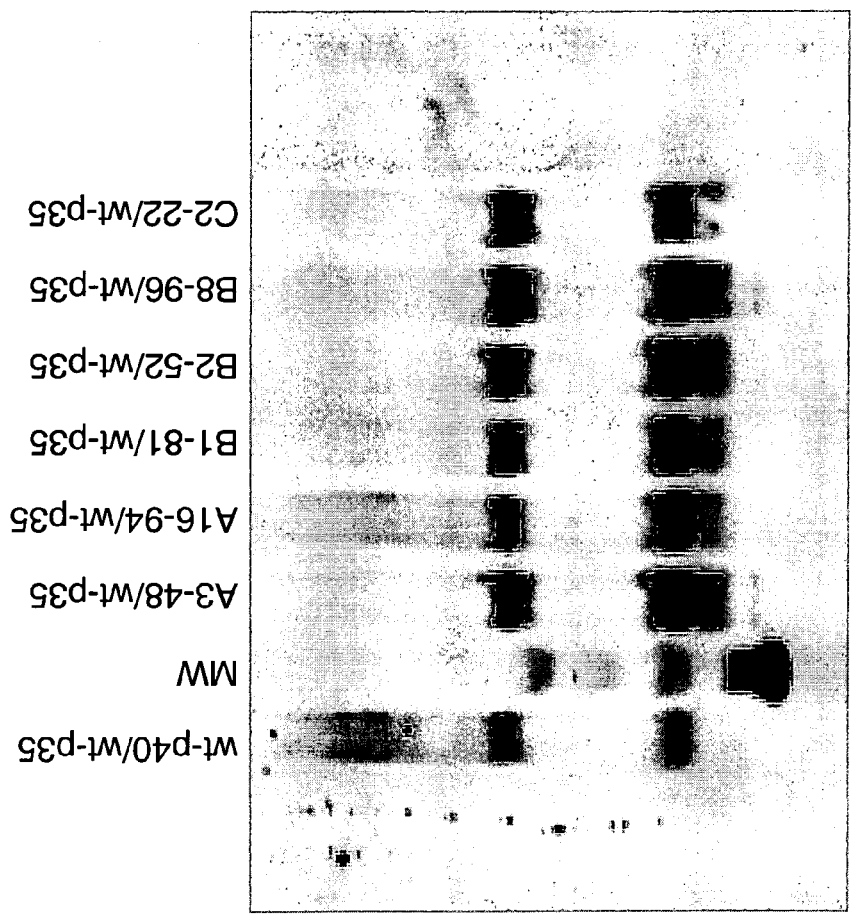
FIG. 7 shows an immunoblot, probed using an anti-p35 monoclonal antibody (mAB), of equal volumes of cell culture supernatant from a control cell culture expressing wt-p40/wt-p35 nucleic acids, and from test cell cultures expressing A16–94/wt-p35, A3–48/wt-p35, B1–81/wt-p35, B2-52/wt-p35, B8–96/wt-p35 and C2–22/wt-p35 nucleic acids. Bands corresponding to ~70 kilodalton (kDa) heterodimeric proteins are indicated by the arrow labeled "p70" and bands corresponding to ~35 kDa p35 polypeptides are indicated by the arrow labeled "p35". "MW" indicates molecular weight markers.

[1] Relative EC50 of control(wt-p40/wt-p35) heterodimer culture supernatant is 1 by definition.
[2] "+LESS" indicates addition of the amino acids Leu-Glu-Ser-Ser, and "+EHtag" indicates addition of EHtag sequence to the C-terminus of the p35 polypeptide sequence, in the order indicated The relative amounts of modified heterodimeric protein and wild-type heterodimeric protein secreted into the cell culture media was quantitated by Western blotting of culture supernatant dilutions as described in Example 1. FIG. 7 shows that a significantly larger amount of p40/p35 heterodimer (labeled "p70" in the Figure) is consistently produced by cells expressing modified p40 plus wt-p35 nucleic acids as compared to control cells expressing wt-p40 plus wt-p35 nucleic acids. Thus, modified nucleic acids of the invention appear to promote enhanced production (i.e., expression and/or secretion) of modified heterodimers as compared to wild-type (wt-p40/wt-p35) heterodimers.

As noted above and shown in FIG. 3, culture media from cells expressing and secreting the modified C2–22/wt-p35 heterodimer showed on average the highest overall proliferative activity, with an up to 64-fold increase in relative proliferative activity over that of control culture supernatant from cells expressing and secreting the wild-type (wt-p40/wt-p35) heterodimer (that is, up to a 64-fold lower volume of culture supernatant from cells expressing the modified heterodimer was required to achieve an EC50 activity level equivalent to that of a 1× volume of culture media from cells expressing the wild-type (wt-p40/wt-p35) heterodimer).

Figure 8:
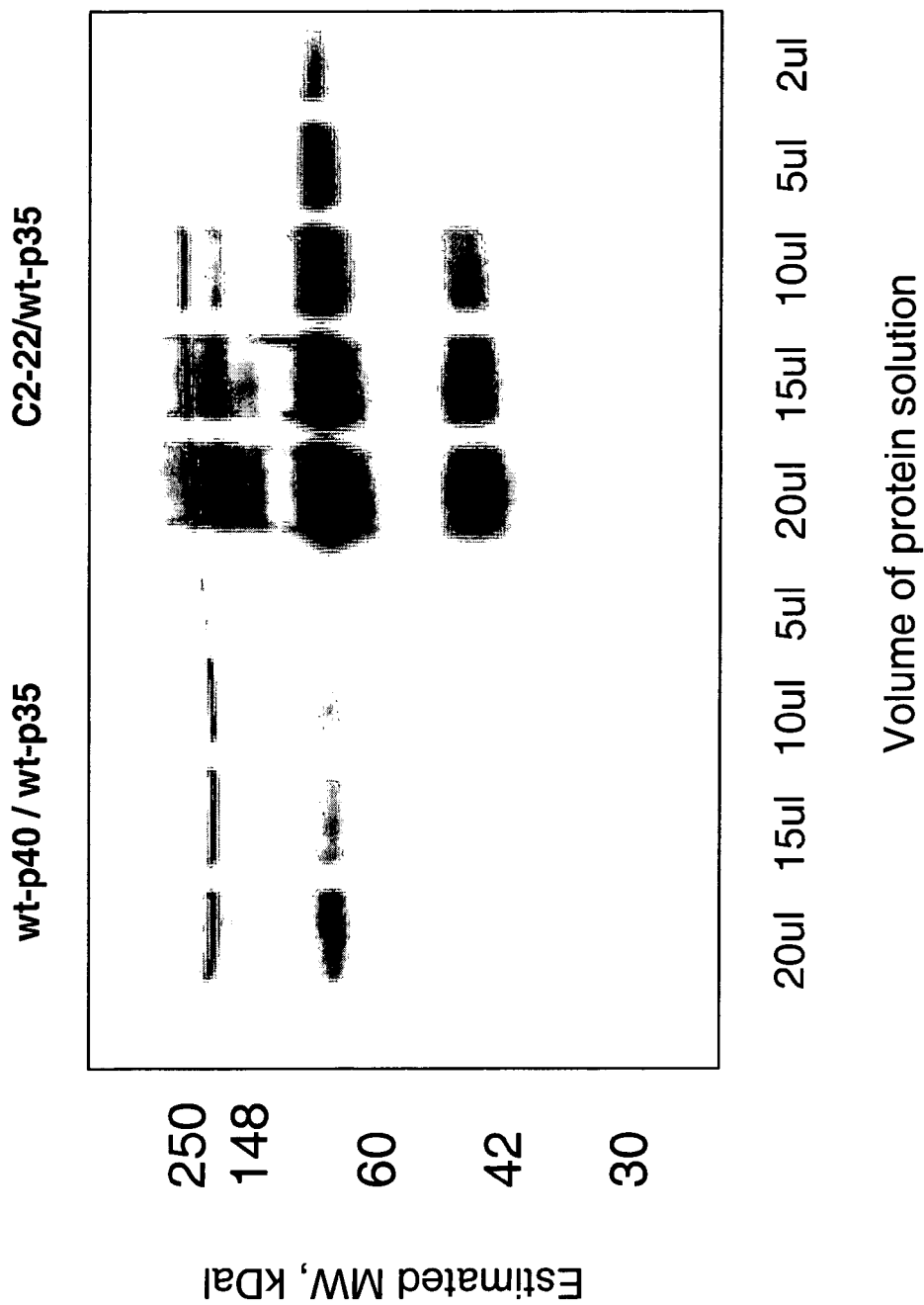
FIG. 8 shows an immunoblot, probed using an anti-p35 mAB, of dilutions of purified C2–22/wt-p35 and wt-p40/wt-p35 heterodimers. The X-axis shows the volume of purified protein solution applied to the gel, and the Y-axis shows the approximate molecular weight (in kDa).

To estimate the relative contributions of heterodimer production and activity to the overall proliferative activity observed in culture supernatants, heterodimers were first quantitated by immunoblot, using an anti-p35 monoclonal antibody (mAB), of equivalent dilutions of purified heterodimer from C2–22/wt-p35 and wt-p40/wt-p35 cultures. From densitometery analysis, an estimated 16-fold enhancement of expression of C2–22/wt-p35 heterodimer over that of the control wt-p40/wt-p35 heterodimer was observed (FIG. 8).

Figure 9:
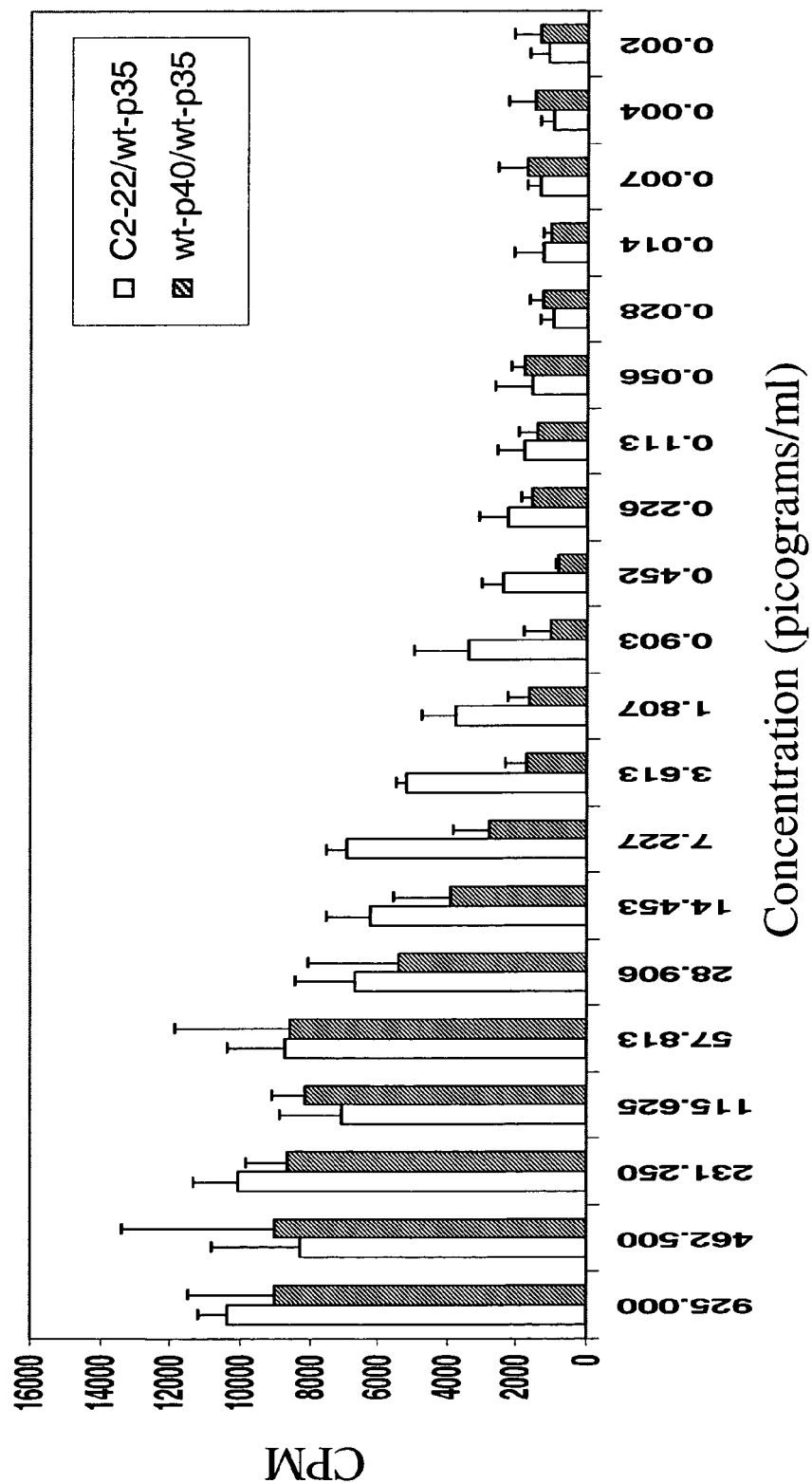
FIG. 9 shows the T-cell proliferative activity of varying concentrations of purified C2–22/wt-p35 and wt-p40/wt-p35 heterodimers. The X-axis indicates the concentration of heterodimer assayed, in picograms per milliliter (pg/ml). The Y-axis ("CPM") indicates the amount of $^3$H-thymidine incorporated into T-cells, expressed as counts per minute.

Based on this quantitation, purified C2–22/wt-p35 heterodimer exhibited about a four-fold higher proliferative activity compared to an equivalent concentration of purified control wt-p40/wt-p35 heterodimer in the human T-cell proliferation assay, after normalizing for protein concentration (FIG. 9). This result suggests that the up to 64-fold enhancement of proliferative activity in culture supernatants of cells expressing C2–22/wt-p35 heterodimers as compared to wild-type heterodimer is consistent with about a 16-fold greater concentration of active heterodimer produced, together with about a four-fold higher proliferative activity of the isolated C2–22/wt-p35 heterodimer over that of the isolated control wild-type heterodimer.

Figure 10:
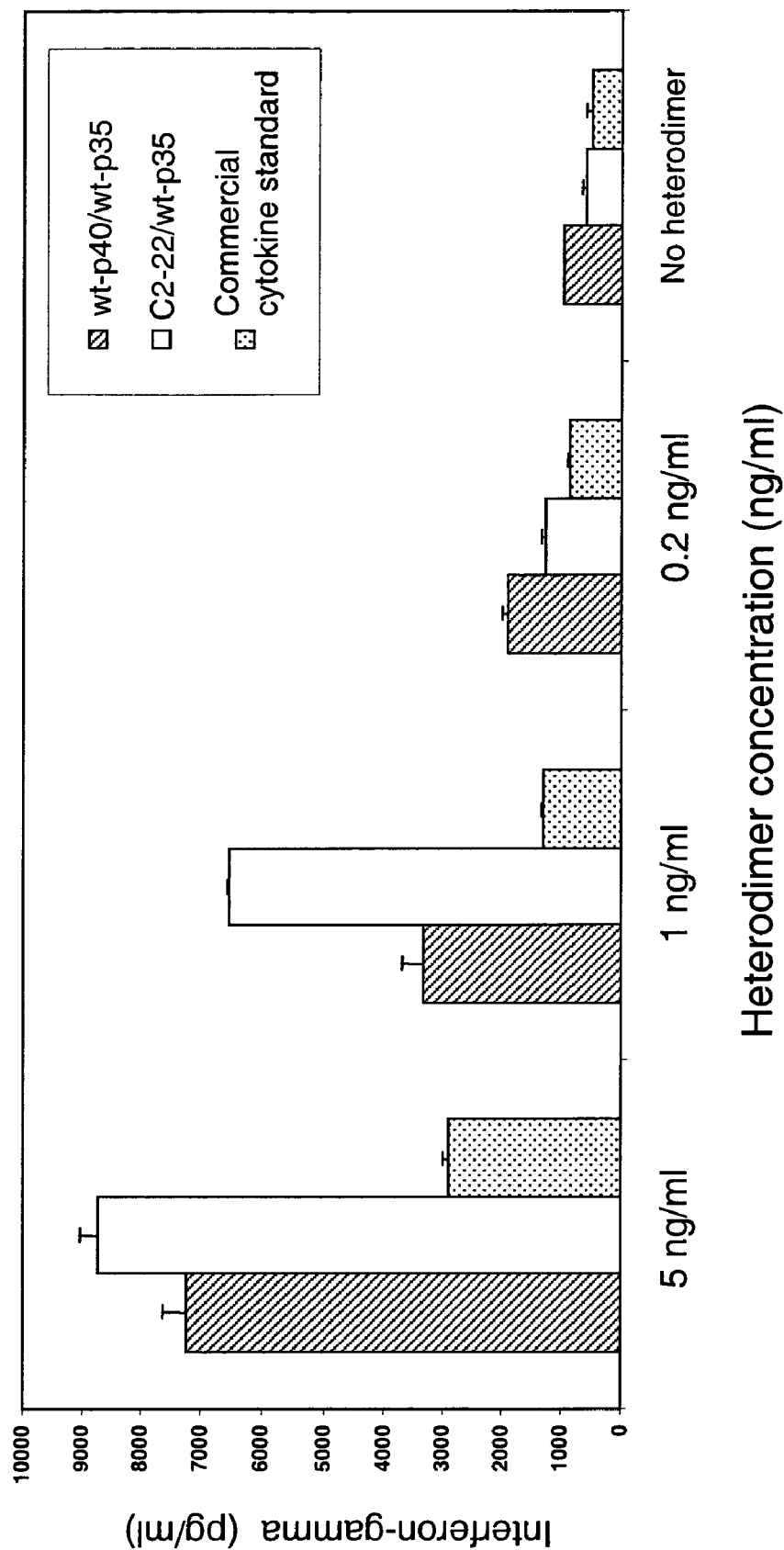
FIG. 10 shows the IFN-γ induction activity of varying concentrations of purified C2–22/wt-p35 and wt-p40/wt-p35 heterodimers and a commercially available cytokine protein. The X-axis indicates the concentration of heterodimer assayed, in nanograms per milliliter (ng/ml). The Y-axis indicates the amount of IFN-γ produced in T-cells, expressed as picograms per milliliter (pg/ml).

The ability of purified heterodimers comprising modified p35 and/or modified p40 polypeptides of the invention to induce production of the $T_H1$-specific cytokine interferon-γ in human T-cells was determined in the human $T_H1$ differentiation/IFN-γ induction assay. FIG. 10 shows the concentrations of human IFN-γ produced by human T-cells incubated in the presence or absence of purified C2–22/wt-p35 heterodimer, purified wt-p40/wt-p35 heterodimer, or a commercially available purified interleukin-12 cytokine standard, followed by activation with anti-CD3 and anti-CD28 antibodies. The concentration of IFN-γ produced by human T-cells incubated with ~1 nanogram/milliliter (ng/ml) of partially purified p40C2–22/wt-p35 heterodimer was significantly greater than that of cells treated with ~1 ng/ml of partially purified control wt-p40/wt-p35 heterodimer.

Figure 12:
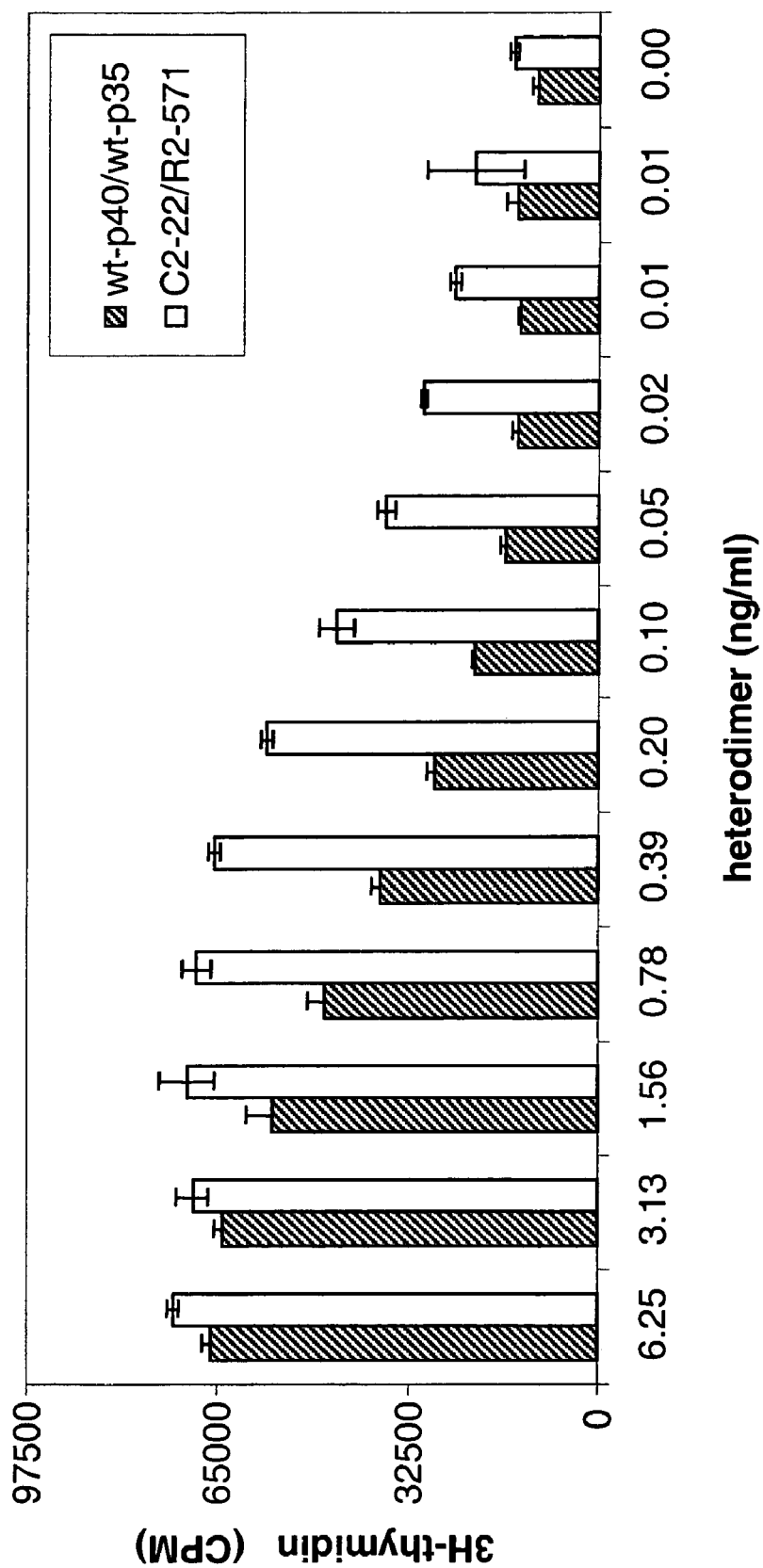
FIG. 12 shows the T-cell proliferative activity of varying concentrations of purified "fully modified" heterodimer C2–22/R2–571-EHtag and control heterodimer wt-p40/wt-p35-EHtag. X- and Y-axes are as described in FIG. 9.
Figure 13:
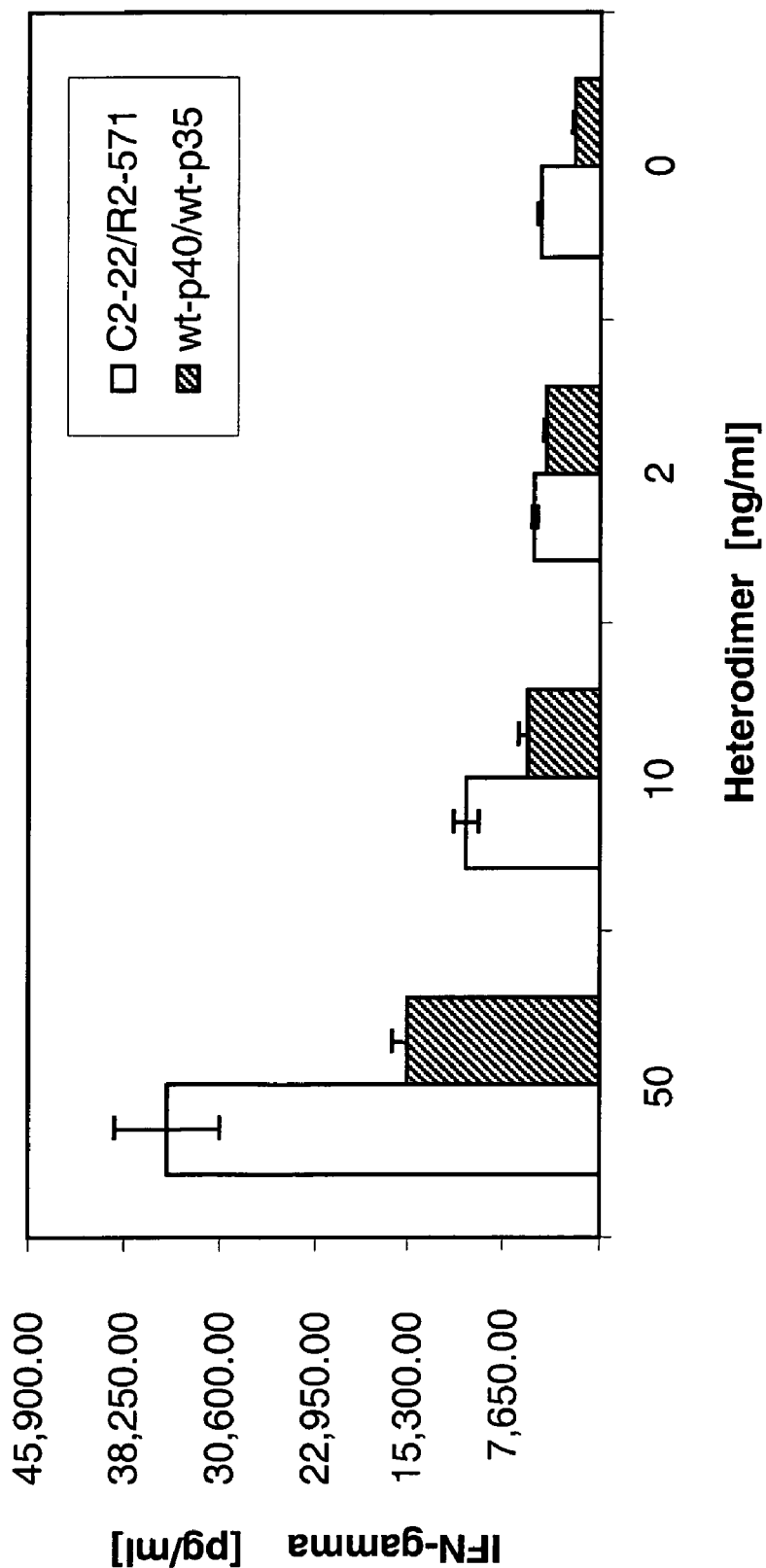
FIG. 13 shows the IFN-γ induction activity of varying concentrations of purified fully modified heterodimer C2–22/R2–571-EHtag and control heterodimer wt-p40/wt-p35-EHtag. X- and Y-axes are as described in FIG. 10.

A fully modified heterodimer of the invention, designated C2–22/R2–571-EHtag, comprising a modified p40 polypeptide of the invention comprising a sequence identified as the mature polypeptide region (amino acid residues 23–324) of SEQ ID NO:8, plus a modified p35 polypeptide of the invention comprising a sequence identified as the mature polypeptide region (amino acid residues 23–219) of SEQ ID NO:31, plus the C-terminal EHtag, was purified and quantitated by absorbance at 280 nanometers (nm) as described in Example 1. FIG. 12 shows that the T-cell proliferative activity of the purified fully modified heterodimer is about 8 times greater than that of purified wild-type (wt-p40/wt-p35-EHtag) heterodimer, after normalizing for protein concentration. FIG. 13 shows that the purified fully modified heterodimer induced a concentration level of IFN-γ production in human T-cells than that of the purified wild-type heterodimer. Because the maximum concentration of IFN-γ production could not be derived from the data, an EC50 value could not be estimated for either the purified fully modified or wild-type heterodimer preparations. However, FIG. 13 shows that a concentration of ~10 ng/ml of purified, fully modified heterodimer induces a similar concentration of IFN-γ production in the T-cell based assay as ~50 ng/ml of purified, wild-type heterodimer, suggesting that the fully modified heterodimer exhibits an estimated three-fold to five-fold greater IFN-γ induction activity than the wild-type heterodimer.

Figure 14:
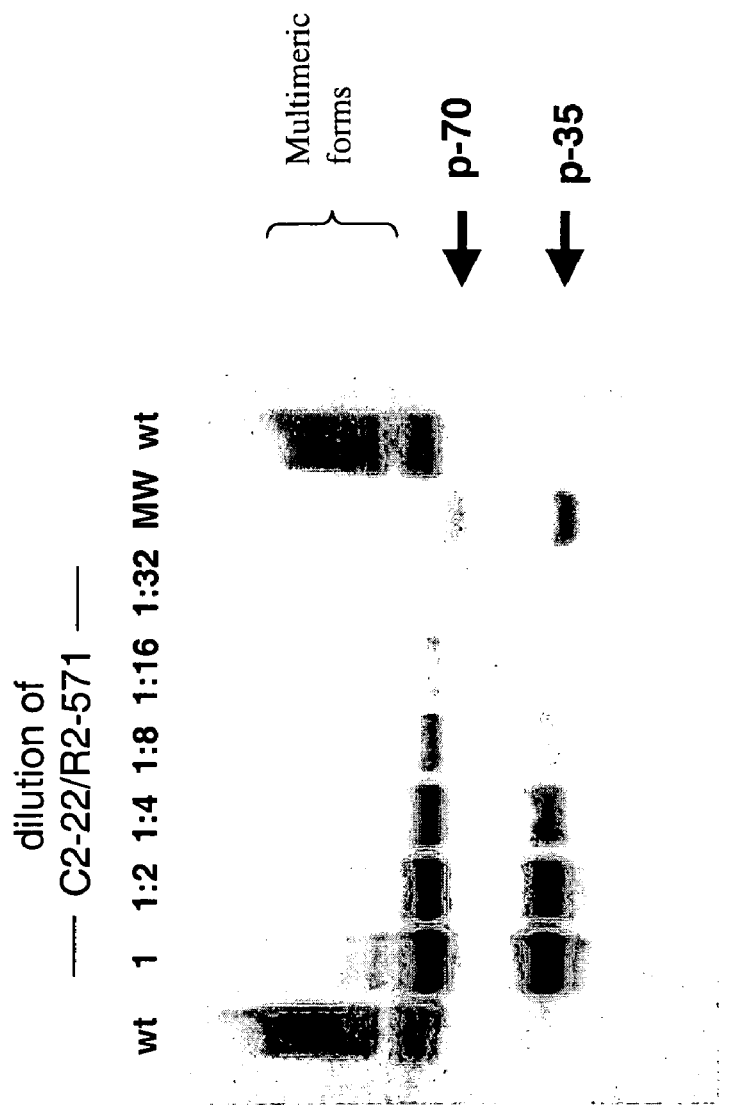
FIG. 14 shows a Western blot, probed using an anti-E tag mAB (Pharmacia-Amersham), of purified heterodimers produced by co-expressing a modified p40 nucleic acid of the invention comprising the C2–22 polynucleotide sequence SEQ ID NO:1 plus a modified p35 nucleic acid of the invention comprising the R2–571 polynucleotide sequence SEQ ID NO:21, and purified heterodimers produced by co-expressing wt-p40 and wt-p35 nucleic acids comprising the polynucleotide sequences SEQ ID NO:37 and SEQ ID NO:38, respectively. The modified p35 nucleic acid sequence and the wt-p35 nucleic acid sequence each further comprised a C-terminal EH-tag coding sequence. The modified heterodimer preparation, indicated on the figure as "C2–22/R2–571", was loaded onto the gel in serial dilutions as indicated over each lane. The wt-p40/wt-p35 heterodimer preparation, indicated on the figure as "wt", was loaded at a single dilution. Bands corresponding to ~70 kDa heterodimeric proteins are indicated by the arrow labeled "p70" and bands corresponding to ~35 kDa p35 polypeptides are indicated by the arrow labeled "p35". Higher molecular weight proteins which immunoreact with the anti-E tag antibody are indicated by the bracket labeled "multimeric forms". "MW" indicates molecular weight markers.

Co-expressing in mammalian cells a modified p40 nucleic acid of the invention plus a modified p35 nucleic acid of the invention produces a substantially more homogenous heterodimeric protein than the heterodimeric protein produced by co-expressing a wt-p40 nucleic acid and a wt-p35 nucleic acid. FIG. 14 shows a Western blot, probed using an anti-E tag mAB (Pharmacia-Amersham), of purified heterodimers produced by co-expressing a modified p40 nucleic acid of the invention (comprising the C2–22 polynucleotide sequence SEQ ID NO:1) plus a modified p35 nucleic acid of the invention (comprising the R2–571 polynucleotide sequence SEQ ID NO:21), and purified heterodimers produced by co-expressing wt-p40 and wt-p35 nucleic acids (comprising the polynucleotide sequences SEQ ID NO:37 and SEQ ID NO:38, respectively). Both the modified p35 nucleic acid and the wt-p35 nucleic acid also comprised a C-terminal EHtag coding sequence. As seen in the Figure, co-expression of the wt-p40 and wt-p35 nucleic acids produced protein which electrophoresed in multiple bands with apparent molecular weights (MW) of ~70 kDa or greater, while co-expression of the exemplary modified p40 and modified p35 nucleic acids produced protein which electrophoresed as essentially a single band with an apparent molecular weight of approximately 70 kDa.

Without being limited by theory, the observed enhancement of production (i.e., expression and/or secretion) of modified heterodimers from cells expressing nucleic acids of the invention over that of cells expressing wt-p40 plus wt-p35 nucleic acids may be attributable to one or more of a number of factors, including, but not limited to, e.g., increased expression (e.g., increased mRNA production), more efficient secretion of expressed polypeptide, more optimal folding of expressed polypeptide, more efficient processing of expressed polypeptide to mature polypeptide, enhanced dimerization affinity of expressed polypeptides, etc. For example, modified p40 and/or modified p35 polypeptides of the invention may exhibit enhanced dimerization affinity with the corresponding subunit polypeptide, resulting, for example, from an increased amount of one or both polypeptide subunits in the culture media (thus shifting monomer-heterodimer equilibrium towards heterodimer formation in solution) and/or from more favorable protein—protein interactions at the subunit interfaces. Such enhanced dimerization affinity may be manifested, for example, in a more favorable subunit association constant ($K_{assoc}$), and/or a decreased dissociation rate constant ($k_{off}$). Enhanced dimerization affinity may shift the monomer-heterodimer equilibrium towards heterodimer, resulting in the increased production of biologically active molecules. Furthermore, from FIG. 14, it is apparent that expression of nucleic acids of the invention results in the production of a highly homogeneous biologically active heterodimeric protein.

An isolated heterodimer comprising a modified p40 polypeptide and/or a modified p35 polypeptide of the invention thus exhibits proliferative activity and/or IFN-γ induction activity in human T-cells. In various embodiments, an isolated heterodimer comprising a modified p40 polypeptide and/or a modified p35 polypeptide of the invention has at least about 1.5-fold, 2-fold, 4-fold or 8-fold greater T-cell proliferative activity than an isolated heterodimer comprising a wt-p40 polypeptide and a wt-p35 polypeptide, wherein the wt-p40 polypeptide comprises the mature polypeptide sequence identified as amino acid residues 23 to 328 of SEQ ID NO:15 and the wt-p35 polypeptide comprises the mature polypeptide sequence identified as amino acid residues 23 to 219 of SEQ ID NO:36.

Modified p40 nucleic acids and modified p35 nucleic acids of the invention, compared to wt-p40 and wt-p35 nucleic acids, show enhanced production of highly homogenous, biologically active heterodimeric cytokine molecules when expressed in mammalian cells. This feature renders the modified p40 nucleic acids and the modified p35 nucleic acids of the invention particularly useful in, e.g., gene therapy or other applications where genetic delivery of localized amounts of highly active molecules is an important consideration.

Modified p40 Nucleic Acids

Exemplary nucleic acids which encode modified p40 polypeptides of the invention having proliferative activity and/or IFN-γ induction activity in a T-cell based assay (such as, e.g., a human T-cell based assay) are identified herein as SEQ ID NO:1 to SEQ ID NO:7, encoding modified p40 polypeptides identified herein as SEQ ID NO:8 to SEQ ID NO:14, respectively. These nucleic acids comprise the following mature polypeptide coding regions: nucleotides 67 to 972 of SEQ ID NO:1; nucleotides 67 to 981 of SEQ ID NO:2; nucleotides 67 to 981 of SEQ ID NO:3; nucleotides 67 to 981 of SEQ ID NO:4, nucleotides 67 to 966 of SEQ ID NO:5; nucleotides 67 to 972 of SEQ ID NO:6; and nucleotides 67 to 987 of SEQ ID NO:7, which encode the mature polypeptide regions identified as: amino acid residues 23–324 of SEQ ID NO:8; amino acid residues 23–327 of SEQ ID NO:9, amino acid residues 23–327 of SEQ ID NO:10, amino acid residues 23–327 of SEQ ID NO:11, amino acid residues 23–322 of SEQ ID NO:12, amino acid residues 23–324 of SEQ ID NO:13, and amino acid residues 23–329 of SEQ ID NO:14. These nucleic acids also comprise the following leader peptide coding regions: nucleotides 1 to 66 of SEQ ID NO:1–SEQ ID NO:7, which encode the leader peptide regions identified as amino acid residues 1–22 of SEQ ID NOS:8–14.

In one aspect, the invention provides an isolated or recombinant nucleic acid that comprises a polynucleotide sequence selected from the group of: (a) the mature polypeptide coding region of SEQ ID NO:1 to SEQ ID NO:7, or a complementary polynucleotide sequence thereof; (b) a polynucleotide sequence encoding a polypeptide sequence selected from the mature polypeptide region of SEQ ID NO:8 to SEQ ID NO:14, or a complementary polynucleotide sequence thereof; (c) a polynucleotide sequence which hybridizes under at least stringent or at least highly stringent hybridization conditions (or ultra-high stringent or ultra-ultra-high stringent hybridization conditions) over substantially the entire length of polynucleotide sequence (a) or (b), or with a 30, 50, 100, 200, 300, 400, 500, 600, 700, 800, 850, 880, 890, 900, 910, 920, 930, 940, 950, 960, 970, or 980 nucleotide base subsequence or fragment of a polynucleotide sequence of (a) or (b); (d) a polynucleotide sequence which encodes a polypeptide comprising an amino acid sequence having at least about 90%, 92%, 95%, 96%, 97%, 98%, or 99% amino acid sequence identity to a mature polypeptide region of a sequence selected from SEQ ID NO:8 to SEQ ID NO:14; and (e) a polynucleotide sequence comprising a fragment of (a), (b), (c), or (d), which fragment encodes all or a part of a polypeptide having proliferative activity or interferon-gamma induction activity in a T-cell based assay (such as, e.g., a human T-cell based assay), in the presence of a p35 polypeptide (such as, e.g., a wt-p35 polypeptide or a modified p35 polypeptide).

The invention also includes an isolated or recombinant nucleic acid, comprising a polynucleotide sequence encoding a modified p40 polypeptide sequence, the modified p40 polypeptide sequence comprising an amino acid modification located at an amino acid position equivalent to (i.e., an "equivalent position" to) that in the amino acid sequence of a wild-type p40 polypeptide (SEQ ID NO:15). The modification can include: (a) a substitution of the specified amino acid for a different amino acid at one or more position, equivalent to that of SEQ ID NO:15, selected from Leu62, Ser71, Gln78, His99, Thr127, Arg130, Lys185, Glu186, Tyr187, Glu188, Ser190, Asp196, Met211, Val289, Ser305, Ser307, Arg309, and Gln311; (b) a deletion of one or more amino acid residues at equivalent position Arg181 to Asn184 inclusive or a substitution of the amino acid residues at equivalent positions Arg181 to Asn184 inclusive for the amino acid residues Ser-(Leu or Met)-(Glu or Asp)-His-Arg; (c) a deletion of one or more amino acid at equivalent positions Asp287 and Arg288. The modified p40 polypeptide may optionally include two or more of modification (a), (b) or (c). The modified p40 polypeptide sequence encoded by the nucleic acid of the invention may be a modified sequence of a naturally-occurring or wild-type p40 polypeptide sequence of a mammal (e.g., human, primate, ruminant, or rodent), preferably primate, more preferably human. Preferred substitutions include Leu62Ser; Ser71Thr; Gln78His; His99(Arg or Gln); Thr127(Ser or Ile); Arg130Lys; Lys185Glu; Glu186Tyr; Tyr187(Lys or Asn); Glu188Lys; Ser190(Arg or Thr); Asp196Gly; Met211Val; Val289(Ile or Leu); Ser305Lys; Ser307Arg; Arg309Gln; and Gln311Arg. The invention also includes a polynucleotide sequence encoding said polypeptide or a fragment of said polypeptide having proliferative activity or IFN-γ induction activity in a T-cell based assay (such as, e.g., a human T-cell based assay), in the presence of a p35 polypeptide (such as, e.g., a wt-p35 polypeptide or a modified p35 polypeptide).

The modified p40 polypeptide sequence encoded by a nucleic acid of the invention optionally comprises an amino acid modification, located at an amino acid residue position equivalent to that in the amino acid sequence of a p40 polypeptide (SEQ ID NO:15), selected from: Cys2His; His3Pro; Ile8Val; Phe15Leu; Val21Met; Lys27Glu; Asp29Asn; Asp40Asn; Met45Thr; Thr49Ala; Glu67Gly; His91Arg; Glu95(Ala or Thr), Val96Ala; Glu122Lys; Asn125Ala; Asn135Asp; Arg139His; Thr147Ala; Thr153Lys; Ser155Thr; Ser163Thr; Gln166(Arg or His), Ala172Thr; Ala173Val; Thr174Leu; Ala177Glu; Glu178Asp; Arg179Leu; Val180Gly; Ala201Ser; Val212Leu; Asp213Glu; Val215Ile; Ser226Arg; Lys244Arg; Gln251His; Val254Ile; Ser255Asn; Glu257Gly; Thr264(Ala or Ile); Thr272Met; Cys274Gly; Val275Ile; Lys280Arg; Ser281Asn; Lys285Asp; Lys286Arg; Phe290Ser; Thr291 (Met or Val); Lys293Gln; Thr297Lys; Ile299(Thr or Val); Arg301His; Asn303Asp; Ser318Phe; Glu321Asp; Pro326Ser; Cys327Leu; and Ser328(Gly or Gln).

The invention also includes an isolated or recombinant nucleic acid, comprising a polynucleotide sequence encoding a modified p40 polypeptide, wherein the modified p40 polypeptide comprises an amino acid sequence having at least about 90% amino acid sequence identity to the amino acid sequence identified herein as the mature polypeptide region (amino acid residue positions 23–328) of SEQ ID NO:39: IWEL-$X_{27}$-K-$X_{29}$-VYVVELDWYP-$X_{40}$-APGE-$X_{45}$-VVL-$X_{49}$-CDTPEEDGITWT-$X_{62}$-DQSS-$X_{67}$-VLG-$X_{71}$-GKTLTI-$X_{78}$-VKEFGDAGQYTC-$X_{91}$-KGG-$X_{95}$-$X_{96}$-LS-$X_{99}$-SLLLLHKKEDGIWSTDILKDQK-$X_{122}$-PK-$X_{125}$-K-$X_{127}$-FL-$X_{130}$-CEAK-$X_{135}$-YSG-$X_{139}$-FTCWWLT-$X_{147}$-ISTDL-$X_{153}$-F-$X_{155}$-VKSSRGS-$X_{163}$-DP-$X_{166}$-GVTCG-$X_{172}$-$X_{173}$-$X_{174}$-LS-$X_{177}$-$X_{178}$-$X_{179}$-$X_{180}$-$X_{181}$-$X_{182}$-$X_{183}$-$X_{184}$-$X_{185}$-$X_{186}$-$X_{187}$-$X_{188}$-Y-$X_{190}$-VECQE-$X_{196}$-SACP-$X_{201}$-AEESLPIEV-$X_{211}$-$X_{212}$-$X_{213}$-A-$X_{215}$-HKLKYENYTS-$X_{226}$-FFIRDIIKPDPPKNLQL-$X_{244}$-PLKNSR-$X_{251}$-VE-$X_{254}$-$X_{255}$-W-$X_{257}$-YPDTWS-$X_{264}$-PHSYFSLTF-$X_{274}$-$X_{275}$-QVQG-$X_{280}$-$X_{281}$-KRE-$X_{285}$-$X_{286}$-$X_{287}$-$X_{288}$-$X_{289}$-F-$X_{291}$-D-$X_{293}$-TSA-$X_{297}$-V-$X_{299}$-C-$X_{301}$-K-$X_{303}$-A-$X_{305}$-I-$X_{307}$-V-$X_{309}$-A-$X_{311}$-DRY-$X_{315}$-SS-$X_{318}$-WS-$X_{321}$-WASV-$X_{326}$-$X_{327}$-$X_{328}$, or a conservatively substituted variation thereof, where $X_{27}$ is K or E; $X_{29}$ is D or N; $X_{40}$ is D or N; $X_{45}$ is M or T; $X_{49}$ is T or A; $X_{62}$ is S; $X_{67}$ is E or G; $X_{71}$ is T; $X_{78}$ is H; $X_{91}$ is H or R; $X_{95}$ is E, A, K, or T, $X_{96}$ is V or A; $X_{99}$ is R or Q; $X_{122}$ is E or K; $X_{125}$ is N or A; $X_{127}$ is S or I; $X_{130}$ is K; $X_{135}$ is N or D; $X_{139}$ is R or H; $X_{147}$ is T or A; $X_{153}$ is T or K; $X_{155}$ is S or T; $X_{163}$ is S or T; $X_{166}$ is Q, R, or H; $X_{172}$ is A or T; $X_{173}$ is A or V; $X_{174}$ is T or L; $X_{177}$ is A or E; $X_{178}$ is E or D; $X_{179}$ is R, L, or K; $X_{180}$ is V or G; $X_{181}$ to $X_{184}$ inclusive is deleted, or is replaced with the sequence S-(L or M)-(E or D)-H-R; $X_{185}$ is E; $X_{186}$ is Y; $X_{187}$ is K or N; $X_{188}$ is K; $X_{190}$ is R or T; $X_{196}$ is G; $X_{201}$ is A or S; $X_{211}$ is V; $X_{212}$ is V or L; $X_{213}$ is D or E; $X_{215}$ is V or I; $X_{226}$ is S or R; $X_{244}$ is K or R; $X_{251}$ is Q or H; $X_{254}$ is V or I; $X_{255}$ is S or N; $X_{257}$ is E or G; $X_{264}$ is T or A; $X_{274}$ is C or G; $X_{275}$ is V or I; $X_{280}$ is K or R; $X_{281}$ is S or N; $X_{285}$ is K or D; $X_{286}$ is K or R; $X_{287}$ is D or is deleted; $X_{288}$ is R or is deleted; $X_{289}$ is I or L; $X_{291}$ is T or M; $X_{293}$ is K or Q; $X_{297}$ is T or K; $X_{299}$ is I, T, or V; $X_{301}$ is R or H; $X_{303}$ is N or D; $X_{305}$ is K; $X_{307}$ is R; $X_{309}$ is Q; $X_{311}$ is R; $X_{315}$ is Y or H; $X_{318}$ is S or F; $X_{321}$ is E or D; $X_{326}$ is P or S; $X_{327}$ is C or L; and $X_{328}$ is S, G, or Q. In various embodiments, the modified p40 polypeptide encoded by the nucleic acid of the invention comprises an amino acid sequence having at least about 90%, 92%, 95%, 96%, 97%, 98%, or 99% amino acid sequence identity to the mature polypeptide region (amino acid residue positions 23–328) of SEQ ID NO:39. The invention also includes a polynucleotide sequence encoding said polypeptide or a fragment of said polypeptide having proliferative activity or IFN-γ induction activity in a T-cell based assay (such as, e.g., a human T-cell based assay), in the presence of a p35 polypeptide (such as, e.g., a wt-p35 polypeptide or a modified p35 polypeptide).

The modified p40 polypeptide encoded by a nucleic acid of the invention may further comprise a leader peptide sequence having at least about 90%, 92%, 95%, 96%, 97%, 98%, or 99% amino acid sequence identity to the amino acid sequence M-$X_2$-$X_3$-QQLV-$X_8$-SWFSLV-$X_{15}$-LASPL-$X_{21}$-A, identified herein as the leader peptide region (amino acid residue positions 1–22) of SEQ ID NO:39, where $X_2$ is C or H; $X_3$ is H or P; $X_8$ is I or V; $X_{15}$ is F or L; and $X_{21}$ is V or M.

The present invention also includes a modified p40 polypeptide comprising a conservatively modified variation of the amino acid sequence identified herein as the mature polypeptide region (amino acid residue positions 23–328) of SEQ ID NO:39, and, optionally, a conservatively modified variation of the leader peptide region (amino acid residue positions 1–22) of SEQ ID NO:39 and a polynucleotide sequence encoding said polypeptide or a fragment of said polypeptide having proliferative activity or IFN-γ induction activity in a T-cell based assay (such as, e.g., a human T-cell based assay), in the presence of a p35 polypeptide (such as, e.g., a wt-p35 polypeptide or a modified p35 polypeptide).

The invention also includes a modified p40 polypeptide comprising the amino acid sequence identified herein as the mature polypeptide region (amino acid residue positions 23–328) of SEQ ID NO:39, and, optionally, comprising the leader peptide region (amino acid residue positions 1–22) of SEQ ID NO:39, and a polynucleotide sequence encoding said polypeptide or a fragment of said polypeptide having proliferative activity or IFN-γ induction activity in a T-cell based assay (such as, e.g., a human T-cell based assay), in the presence of a p35 polypeptide (such as, e.g., a wt-p35 polypeptide or a modified p35 polypeptide).

The invention also includes an isolated or recombinant nucleic acid, comprising a polynucleotide sequence encoding a polypeptide comprising a leader peptide sequence having at least about 90% amino acid sequence identity to the amino acid sequence M-$X_2$-$X_3$-QQLV-$X_8$-SWFSLV-$X_{15}$-LASPL-$X_{21}$-A, identified herein as the leader peptide region (amino acid residue positions 1–22) of SEQ ID NO:39, where $X_2$ is C or H; $X_3$ is H or P; $X_8$ is I or V; $X_{15}$ is F or L; and $X_{21}$ is V or M. In various embodiments, the leader peptide sequence encoded by the nucleic acid of the invention comprises an amino acid sequence having at least about 90%, 92%, 95%, 96%, 97%, 98%, or 99% amino acid sequence identity to leader peptide region (amino acid residues 1–22) of SEQ ID NO:39. In other embodiments, the leader peptide sequence comprises the sequence identified as the leader peptide region (amino acid residue positions 1–22) of SEQ ID NO:39, or conservatively modified variations thereof.

Modified p35 Nucleic Acids

Exemplary nucleic acids which encode modified p35 polypeptides having proliferative activity and/or IFN-γ induction activity in the T-cell-based assay are identified herein as SEQ ID NO:16 to SEQ ID NO:25, encoding modified p35 polypeptides identified herein as SEQ ID NO:26 to SEQ ID NO:35, respectively. These nucleic acids comprise the following mature polypeptide coding regions: nucleotides 76 to 663 of SEQ ID NO:16; nucleotides 76 to 663 of SEQ ID NO:17; nucleotides 67 to 657 of SEQ ID NO:18; nucleotides 67 to 657 of SEQ ID NO:19, nucleotides 67 to 657 of SEQ ID NO:20; nucleotides 67 to 657 of SEQ ID NO:21; nucleotides 67 to 657 of SEQ ID NO:22; nucleotides 67 to 657 of SEQ ID NO:23; nucleotides 67 to 657 of SEQ ID NO:24; and nucleotides 67 to 657 of SEQ ID NO:25, which encode the mature polypeptide regions identified as: amino acid residues 26–221 of SEQ ID NO:26, amino acid residues 26–221 of SEQ ID NO:27, amino acid residues 23–219 of SEQ ID NO:28, amino acid residues 23–219 of SEQ ID NO:29, amino acid residues 23–219 of SEQ ID NO:30, amino acid residues 23–219 of SEQ ID NO:31, amino acid residues 23–219 of SEQ ID NO:32, amino acid residues 23–219 of SEQ ID NO:33, amino acid residues 23–219 of SEQ ID NO:34, and amino acid residues 23–219 of SEQ ID NO:35. These nucleic acids also comprise the following leader peptide coding regions: nucleotides 1 to 75 of SEQ ID NO: 16–SEQ ID NO:17, and nucleotides 1 to 66 of SEQ ID NO:18–SEQ ID NO:25, which encode the leader peptide regions identified as: amino acid residues 1–25 of SEQ ID NOS:26 to 27, and amino acid residues 1–22 of SEQ ID NOS:28 to 35.

In one aspect, the invention provides an isolated or recombinant nucleic acid that comprises a polynucleotide sequence selected from the group of: (a) the mature polypeptide coding region of SEQ ID NO:16 to SEQ ID NO:35, or a complementary polynucleotide sequence thereof; (b) a polynucleotide sequence encoding a polypeptide sequence selected from the mature polypeptide region of SEQ ID NO:26 to SEQ ID NO:35, or a complementary polynucleotide sequence thereof; (c) a polynucleotide sequence which hybridizes under at least stringent or at least highly stringent hybridization conditions (or ultra-high stringent or ultra-ultra-high stringent hybridization conditions) over substantially the entire length of polynucleotide sequence (a) or (b), or with a 30, 50, 100, 200, 300, 400, 500, 550, 580, 590, 600, 610, 620, 630, 640, 650, 660, or 670 nucleotide base subsequence or fragment of a polynucleotide sequence of (a) or (b); (d) a polynucleotide sequence which encodes a polypeptide comprising an amino acid sequence having at least about 90%, 92%, 95%, 96%, 97%, 98%, or 99% amino acid sequence identity to a mature polypeptide region of a sequence selected from SEQ ID NO:26 to SEQ ID NO:35; and (e) a polynucleotide sequence comprising a fragment of (a), (b), (c), or (d), which fragment encodes all or a part of a polypeptide having proliferative activity or IFN-γ induction activity in a T-cell based assay (such as, e.g., a human T-cell based assay), in the presence of a p40 polypeptide (such as, e.g., a wt-p40 polypeptide or a modified p40 polypeptide).

The invention also includes an isolated or recombinant nucleic acid, comprising a polynucleotide sequence encoding a modified p35 polypeptide comprising an amino acid modification located at an amino acid residue position equivalent to (i.e., an equivalent position to) that in the amino acid sequence of a wild-type p35 polypeptide (SEQ ID NO:36). The modification can include: (a) a substitution of the specified amino acid for a different amino acid at one or more equivalent position to that of SEQ ID NO:36 selected from Thr91, Met120, Ala121, Val212, Thr213, and Ala218; (b) a insertion of one or more amino acid residues Phe-His-Leu between equivalent positions Leu19 and Ser20; (c) a deletion of the amino acid at equivalent position Pro36. The modified p35 polypeptide may optionally include two or more of modification (a), (b), or (c). The modified p35 polypeptide sequence encoded by the nucleic acid of the invention may be a modified sequence of a naturally-occurring or wild-type p35 polypeptide sequence of a mammal (e.g., human, primate, ruminant, or rodent), preferably primate, more preferably human. Preferred substitutions include Thr91(Ala or Ile); Met120Thr; Ala121Thr; Val212Met; Thr213Met; and Ala218Ser. The invention also includes a polynucleotide sequence encoding said polypeptide or a fragment of said polypeptide having proliferative activity or IFN-γ induction activity in a T-cell based assay (such as, e.g., a human T-cell based assay), in the presence of a p40 polypeptide (such as, e.g., a wt-p40 polypeptide or a modified p40 polypeptide).

The modified p35 polypeptide sequence encoded by a nucleic acid of the invention optionally comprises an amino acid modification, located at an amino acid position equivalent to that in the amino acid sequence of a p35 polypeptide (SEQ ID NO:36), selected from: Cys2Tyr; Ala4(Leu or Pro); Ser6Gly; Val10Ile; Ala11Ser; Asp17His; Ala22Gly; Asn24Ser; Val27Thr; Ala28Thr; Pro30Ala; Asp31(Ser or Gly); Met34Arg; Phe35(Ser or Leu); Pro36(deleted); His39Asp; His40Tyr; Arg46Lys; Val48Ala; Met51Thr; Lys54Arg; Thr58Ile; Pro63Ser; Ile69Thr; Lys76Gln; Lys92Thr; Asn98Ala; Glu101Gly; Thr102Ile; Phe104Leu; Leu124His; Ser125Gly; Val136Met; Thr140Ala; Asp148Asn; Ala161Thr; Val162Ala; Asp164Ala; Met167Leu; Phe172Val; Val177Ala; Ser181Pro; Pro186Leu; Asp210Asn; and insertion of one or more of 220Leu; 221Glu; 222Ser; and 223Ser.

The invention also includes an isolated or recombinant nucleic acid comprising a polynucleotide sequence encoding a modified p35 polypeptide, wherein the modified p35 polypeptide comprises an amino acid sequence having at least about 90% amino acid sequence identity to the amino acid sequence identified herein as the mature polypeptide region (amino acid residue positions 23–219) of SEQ ID NO:40: R-$X_{24}$-LP-$X_{27}$-$X_{28}$-T-$X_{30}$-$X_{31}$-PG-$X_{34}$-$X_{35}$-$X_{36}$-CL-$X_{39}$-$X_{40}$-SQNLL-X46-A-$X_{48}$-SN-$X_{51}$-LQ-$X_{54}$-A-$X_{56}$-

Q-$X_{58}$-LEFY-$X_{63}$-CTSEE-$X_{69}$-DHEDIT-$X_{76}$-DKT-STVEAC many others. Similarly, peptides and antibodies can be custom ordered from any of a variety of sources, such as PeptidoGenic (pkim@ccnet.com), HTI Bio-products, Inc. (see htbio website with the extension of ".com"), BMA Biomedicals Ltd. (U.K.), Bio.Synthesis, Inc., and many others.

Certain polynucleotides of the invention may also obtained by screening cDNA libraries (e.g., libraries generated by recombining homologous nucleic acids as in typical diversity generation methods, such as, e.g., shuffling methods) using oligonucleotide probes which can hybridize to or PCR-amplify polynucleotides which encode the modified p40 or modified p35 polypeptides and fragments of those polypeptides. Procedures for screening and isolating cDNA clones are well-known to those of skill in the art. Such techniques are described in, for example, Sambrook et al., *Molecular Cloning—A Laboratory Manual* (2nd Ed.), Vols. 1–3, Cold Spring Harbor Laboratory, Cold Spring Harbor, N.Y., 1989 (hereinafter "Sambrook") and *Current Protocols in Molecular Biology*, F. M. Ausubel et al., eds., Current Protocols, a joint venture between Greene Publishing Associates, Inc. and John Wiley & Sons, Inc. (supplemented through 1999) (hereinafter "Ausubel").

As described in more detail herein, the polynucleotides of the invention include sequences which encode novel modified p40 polypeptides and modified p35 polypeptides, and sequences complementary to the coding sequences, and novel fragments of such coding sequences and complements thereof. The polynucleotides can be in the form of RNA or in the form of DNA, and include mRNA, cRNA, synthetic RNA and DNA, and cDNA. The polynucleotides can be double-stranded or single-stranded, and if single-stranded, can be the coding strand or the non-coding (anti-sense, complementary) strand. The polynucleotides optionally include the coding sequence of an modified 40 polypeptide or a modified p35 polypeptide (i) in isolation, (ii) in combination with additional coding sequence, so as to encode, e.g., a fusion protein, a pre-protein, a prepro-protein, or the like, (iii) in combination with non-coding sequences, such as introns, control elements such as a promoter, a terminator element, or 5' and/or 3' untranslated regions effective for expression of the coding sequence in a suitable host, and/or (iv) in a vector or host environment in which the modified p40 polypeptide or modified p35 polypeptide coding sequence is a heterologous nucleic acid sequence or gene. Sequences can also be found in combination with typical compositional formulations of nucleic acids, including in the presence of carriers, buffers, adjuvants, excipients and the like.

The term DNA or RNA encoding the respective modified p40 polypeptide or modified p35 polypeptide includes any oligodeoxynucleotide or oligodeoxyribonucleotide sequence which, upon expression in an appropriate host cell, results in production of a modified p40 polypeptide or modified p35 polypeptide of the invention. The DNA or RNA can be produced in an appropriate host cell, or in a cell-free (in vitro) system, or can be produced synthetically (e.g., by an amplification technique such as PCR) or chemically.

Using Polynucleotides of the Invention

The polynucleotides of the invention have a variety of uses in, for example: recombinant production (i.e., expression) of the modified p40 polypeptides and modified p35 polypeptides of the invention; as therapeutics and prophylactics, e.g., for use in methods of therapeutic and prophylactic treatment of a disease, disorder or condition; for use in, gene therapy methods and related applications; as immunogens; for use in diagnostic and screening assays; as diagnostic probes for the presence of complementary or partially complementary nucleic acids (including for detection of nucleic acids encoding modified p40 polypeptides or modified p35 polypeptides); as substrates for further reactions, e.g., recursive recombination or mutation reactions to produce new and/or improved modified p40 polypeptides or modified p35 polypeptides, and the like.

Expression of Polypeptides of the Invention

In accordance with the present invention, polynucleotide sequences which encode modified p35 polypeptides or modified p40 polypeptides (in mature form or comprising a leader peptide sequence), fragments of the polypeptides, related fusion proteins, or functional equivalents thereof, are collectively referred to herein as "modified cytokine polypeptides", "modified p35 polypeptides", "modified p40 polypeptides" or, simply, "polypeptides of the invention". Polypeptide or amino acid fragments of each of the preceding terms are also intended to be included and encompassed in the polypeptides or proteins of the invention. Such polynucleotide sequences of the invention are used in recombinant DNA (or RNA) molecules that direct the expression of the modified p40 polypeptides and the modified p35 polypeptides in appropriate host cells. Due to the inherent degeneracy of the genetic code, other nucleic acid sequences which encode substantially the same or a functionally equivalent amino acid sequence are also used to clone and express the modified p40 polypeptides and the modified p35 polypeptides.

Modified Coding Sequences

As will be understood by those of skill in the art, it can be advantageous to modify a coding sequence (including, e.g., a nucleotide sequence encoding a modified p40 or modified p35 polypeptide of the invention or a fragment thereof) to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang S P et al. (1991) *Gene* 105:61–72). Codons can be substituted to reflect the preferred codon usage of the host, a process called "codon optimization" or "controlling for species codon bias."

Optimized coding sequence containing codons preferred by a particular prokaryotic or eukaryotic host (see also Murray, E. et al. (1989) *Nuc. Acids Res.* 17:477–508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (Dalphin M E et al. (1996) *Nuc. Acids Res.* 24: 216–218).

The polynucleotide sequences of the present invention can be engineered in order to alter a modified p35 or modified p40 coding sequence for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to change codon preference, to introduce splice sites, etc.

Vectors, Promoters, and Expression Systems

The present invention also includes recombinant constructs comprising one or more of the nucleic acid sequences as broadly described herein (e.g., those encoding a modified p40 or modified p35 polypeptide of the invention or a fragment thereof). The constructs comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use of vectors, promoters and many other relevant topics, include Juo, P-S., CONCISE DICTIONARY OF BIOMEDICAL AND MOLECULAR BIOLOGY (CRC Press 1996); Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); Hale & Marham, THE HARPER COLLINS DICTIONARY OF BIOLOGY (1991); Scott and Mercer, CONCISE ENCYCLOPEDIA OF BIOCHEMISTRY AND MOLECULAR BIOLOGY (3d ed. 1997); Berger and Kimmel, *Guide to Molecular Cloning Techniques, Methods in Enzymology*, volume 152 Academic Press, Inc., San Diego, Calif. (hereinafter "Berger"); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc. (supplemented through 1999) ("Ausubel")). Examples of techniques sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as Mullis et al. (1987) U.S. Pat. No. 4,683,202; U.S. Pat. No. 4,683,195, issued Jul. 28, 1997; *PCR Protocols: A Guide to Methods and Applications* (Innis et al., eds.) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Nat'l Acad. Sci. USA* 86, 1173; Guatelli et al. (1990) *Proc. Nat'l Acad. Sci. USA* 87, 1874; Lomell et al. (1989) *J. Clin. Chem.* 35, 1826; Landegren et al. (1988) *Science* 241, 1077–1080; Van Brunt (1990) *Biotechnology* 8, 291–294; Wu and Wallace (1989) *Gene* 4, 560; Barringer et al. (1990) *Gene* 89, 117, and Sooknanan and Malek (1995) *Biotechnology* 13:563–564.

PCR generally refers to a procedure wherein minute amounts of a specific piece of nucleic acid, RNA, and/or DNA, are amplified by methods well known in the art (see, e.g., U.S. Pat. No. 4,683,195 and other references above). Generally, sequence information from the ends of the region of interest or beyond is used, for design of oligonucleotide primers. Such primers will be identical or similar in sequence to the opposite strands of the template to be amplified. The 5' terminal nucleotides of the opposite strands may coincide with the ends of the amplified material. PCR may be used to amplify specific RNA or specific DNA sequences, recombinant DNA or RNA sequences, DNA and RNA sequences from total genomic DNA, and cDNA transcribed from total cellular RNA, bacteriophage or plasmid sequences, etc. PCR is one example, but not the only example, of a nucleic acid polymerase reaction method for amplifying a nucleic acid test sample comprising the use of a another (e.g., known) nucleic acid as a primer. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369:684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See Ausubel, Sambrook and Berger, all supra.

The present invention also relates to host cells which are transduced with vectors of the invention, and the production of polypeptides of the invention (including fragments thereof) by recombinant techniques. Host cells are genetically engineered (i.e., transduced, transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the modified p40 or modified p35 gene. The culture conditions, such as temperature, pH and the like, are those previously used with the host cell selected for expression, and will be apparent to those skilled in the art and in the references cited herein, including, e.g., Freshney (1994) *Culture of Animal Cells, a Manual of Basic Technique*, 3d ed., Wiley-Liss, New York and the references cited therein.

The modified p40 and modified p35 polypeptides and proteins of the invention can also be produced in non-animal cells such as plants, yeast, fungi, bacteria and the like. In addition to Sambrook, Berger and Ausubel, details regarding cell culture can be found in Payne et al. (1992) *Plant Cell and Tissue Culture in Liquid Systems*, John Wiley & Sons, Inc. New York, N.Y.; Gamborg and Phillips (eds.) (1995) *Plant Cell, Tissue and Organ Culture; Fundamental Methods*, Springer Lab Manual, Springer-Verlag (Berlin Heidelberg New York) and Atlas and Parks (eds.) *The Handbook of Microbiological Media* (1993) CRC Press, Boca Raton, Fla.

The polynucleotides of the present invention may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transducers genetic material into a cell, and if replication is desired, which is replicable and viable in the relevant host can be used.

The nucleic acid sequence in the expression vector is operatively linked to an appropriate transcription control sequence (promoter) to direct mRNA synthesis. Examples of such promoters include: LTR or SV40 promoter, *E. coli* lac or trp promoter, phage lambda $P_L$ promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

The vector containing the appropriate DNA sequence as described herein, as well as an appropriate promoter or control sequence, may be employed to transform an appropriate host to permit the host to express the protein. Examples of appropriate expression hosts include: bacterial cells, such as *E. coli, Streptomyces,* and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 or Bowes melanoma; plant cells, etc. It is understood that not all cells or cell lines need to be capable of producing fully functional modified p40 or modified p35 polypeptides; for example, antigenic fragments of a modified p40 or modified p35 polypeptide may be produced in a bacterial or other expression system. The invention is not limited by the host cells employed.

In bacterial systems, a number of expression vectors may be selected depending upon the use intended for the polypeptide of the invention. For example, when large quantities of modified p40 or modified p35 polypeptide or fragments thereof are needed for the induction of antibodies, vectors which direct high level expression of fusion proteins that are readily purified may be desirable. Such vectors include, but are not limited to, multifunctional *E. coli* cloning and expression vectors such as BLUESCRIPT (Stratagene), in which the modified p40 or modified p35 coding sequence may be ligated into the vector in-frame with sequences for the amino-terminal Met and the subsequent 7 residues of beta-galactosidase so that a hybrid protein is produced; pIN vectors (Van Heeke & Schuster (1989) *J. Biol. Chem.* 264:5503–5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the modified p40 and/or modified p35 polypeptides of the invention. For reviews, see Ausubel et al. (supra) and Grant et al. (1987; *Methods in Enzymology* 153:516–544).

In mammalian host cells, a number expression systems, such as viral-based systems, may be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing modified p40 or modified p35 polypeptide in infected host cells (Logan and Shenk (1984) *Proc. Natl. Acad. Sci.* 81:3655–3659). In addition, transcription enhancers, such as the rous sarcoma virus (RSV) enhancer, may be used to increase expression in mammalian host cells.

Additional Expression Elements

Specific initiation signals can aid in efficient translation of a modified p35 or modified p40 coding sequence. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al. (1994) *Results Probl Cell Differ* 20:125–62; Bittner et al. (1987) *Methods in Enzymol* 153: 516–544).

Secretion/Localization Sequences

Polynucleotides of the invention can also be fused, for example, in-frame to nucleic acid encoding a secretion/localization sequence, to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like. Polypeptides expressed by such polynucleotides of the invention may include the amino acid sequence corresponding to the secretion and/or localization sequence(s).

Expression Hosts

In a further embodiment, the present invention relates to host cells containing the above-described constructs. The host cell can be a eukaryotic cell, such as a mammalian cell, a yeast cell, or a plant cell, or the host cell can be a prokaryotic cell, such as a bacterial cell. Introduction of the construct into the host cell can be effected by calcium phosphate transfection, DEAE-Dextran mediated transfection, electroporation, or other common techniques (Davis, L., Dibner, M., and Battey, I. (1986) *Basic Methods in Molecular Biology*). The cell may include a nucleic acid of the invention, said nucleic acid encoding a polypeptide, wherein said cells expresses a polypeptide (e.g., a modified p40 polypeptide or modified p35 polypeptide having T-cell proliferative activity, or interferon-gamma induction activity in T-cells, as measured by the assays described herein). The invention also includes a vector comprising any nucleic acid of the invention described herein and includes a cell transduced by such a vector. Furthermore, cells and transgenic animals which include any polypeptide or nucleic acid above or throughout this specification, e.g., produced by transduction of a vector of the invention, are an additional feature of the invention.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre" or a "prepro" form of the protein may also be important for correct insertion, folding and/or function. Different host cells such as CHO, HeLa, BHK, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression can be used. For example, cell lines which stably express a polypeptide of the invention are transduced using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. For example, resistant clumps of stably transformed cells can be proliferated using tissue culture techniques appropriate to the cell type.

Host cells transformed with a nucleic acid sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with leader peptide (also termed "signal peptide") sequences which direct secretion of the mature polypeptides through a prokaryotic or eukaryotic cell membrane.

Additional Polypeptide Sequences

The polynucleotides of the present invention may also comprise a coding sequence fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) Cell 37:767), maltose binding protein sequences, a FLAG epitope utilized in the FLAGS expression/affinity purification system (Immunex Corp, Seattle, Wash.), an E-epitope tag (E-tag), and the like. The inclusion of a protease-cleavable polypeptide linker sequence between the purification domain and the polypeptide sequence is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) Protein Expression and Purification 3:263–281) while the enterokinase cleavage site provides a means for separating the polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Polypeptide Production and Recovery

Following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal (especially mammalian) and archebacterial origin. See e.g., Sambrook, Ausubel, and Berger (all supra), as well as Freshney (1994) Culture of Animal Cells, a Manual of Basic Technique, Third edition, Wiley-Liss, New York and the references cited therein; Doyle and Griffiths (1997) MAMMALIAN CELL CULTURE: ESSENTIAL TECHNIQUES John Wiley and Sons, NY; Humason (1979) Animal Tissue Techniques, fourth edition W.H. Freeman and Company; and Ricciardelli, et al., (1989) In vitro Cell Dev. Biol. 25:1016–1024. For plant cell culture and regeneration, Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Plant Molecular Biology (1993) R. R. D. Croy, Ed. Bios Scientific Publishers, Oxford, U.K. ISBN 0 12 198370 6. Cell culture media in general are set forth in Atlas and Parks (eds) The Handbook of Microbiological Media (1993) CRC Press, Boca Raton, Fla. Additional information for cell culture is found in available commercial literature such as the Life Science Research Cell Culture Catalogue (1998) from Sigma-Aldrich, Inc. (St. Louis, Mo.) ("Sigma-LSRCCC") and, e.g., the Plant Culture Catalogue and supplement (1997) also from Sigma-Aldrich, Inc (St. Louis, Mo.) ("Sigma-PCCS").

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted supra, a variety of purification methods are well known in the art, including, e.g., those set forth in Sandana (1997) Bioseparation of Proteins, Academic Press, Inc.; and Bollag et al. (1996) Protein Methods, $2^{nd}$ Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice $3^{rd}$ Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ.

In vitro Expression Systems

Cell-free transcription/translation systems can also be employed to produce polypeptides using DNAs or RNAs of the present invention. Several such systems are commercially available. A general guide to in vitro transcription and translation protocols is found in Tymms (1995) In vitro Transcription and Translation Protocols: Methods in Molecular Biology (Volume 37), Garland Publishing, NY.

Modified Amino Acids: Polypeptides of the invention may contain one or more modified amino acid. The presence of modified amino acids may be advantageous in, for example, (a) increasing polypeptide serum half-life, (b) reducing polypeptide antigenicity, (c) increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) *Protein Protocols on CD-ROM* Human Press, Towata, N.J.

In Vitro, In Vivo, and Ex Vivo Uses of Polynucleotides and Polypeptides of the Invention The polynucleotides and polypeptides of the invention have a variety of uses, including, but not limited to, for example: in recombinant production (i.e., expression) of the recombinant modified p40 polypeptides and modified p35 polypeptides of the invention; as therapeutic and prophylactic agents in methods of in vivo and ex vivo treatment of a variety of diseases, disorders, and conditions in a variety of subjects; for use in in vitro methods, such as diagnostic and screening methods, to detect, diagnose, and treat a variety of diseases, disorders, and conditions (e.g., cancers, viral-based disorders, angiogenic-based disorders) in a variety of subjects (e.g., mammals); as immunogens; in gene therapy methods and DNA- or RNA-based delivery methods to deliver or administer in vivo, ex vivo, or in vitro biologically active polypeptides of the invention to a tissue, population or cells, organ, graft, bodily system of a subject (e.g., organ system, lymphatic system, blood system, etc.); as DNA vaccines, multi-component vaccines for use in prophylactic or therapeutic treatment of a variety of diseases, disorders, or other conditions (e.g., cancers, viral-based disorders, angiogenic-based disorders) in a variety of subjects (e.g., mammals); as adjuvants to enhance or augment an immune response in a subject; as a component of a multiple-step boosting vaccination method (e.g., a format comprising a prime vaccination by delivery of a DNA or RNA nucleotide (e.g., a nucleotide encoding a polypeptide of the invention or encoding another polypeptide) followed by a second boost of a polypeptide (e.g., a polypeptide of the invention or other polypeptide); as diagnostic probes for the presence of complementary or partially complementary nucleic acids (including for detection of naturally-occurring p40 and p35 coding nucleic acids); as substrates for further reactions, e.g., shuffling reactions, mutation reactions, or other diversity generation reactions to produce new and/or improved modified p40 polypeptides and modified p35 polypeptides and new modified p40 nucleic acids and modified p35 nucleic acids encoding such polypeptides, e.g., to evolve novel therapeutic or prophylactic properties, and the like; for polymerase chain reactions (PCR) or cloning methods, e.g., including digestion or ligation reactions, to identify new and/or improved naturally-occurring or non-naturally occurring p40 or p35 nucleic acids and polypeptides encoded therefrom. Polynucleotides which encode a modified p40 polypeptide or modified p35 polypeptide, or complements of the polynucleotides, are optionally administered to a cell to accomplish a therapeutically or prophylactically useful process or to express a therapeutically useful product in vivo, ex vivo, or in vitro. These applications, including in vivo or ex vivo applications, including, e.g., gene therapy, include a multitude of techniques by which gene expression may be altered in cells. Such methods include, for instance, the introduction of genes for expression of, e.g., therapeutically or prophylactically useful polypeptides, such as the modified p40 polypeptides and modified p35 polypeptides of the present invention. Such methods include, for example, infecting with a retrovirus comprising the polynucleotides and/or polypeptides of the invention. Optionally, the retrovirus further comprises additional exogenous, e.g., therapeutic or prophylactic gene construct, sequences. In one aspect, the invention provides gene therapy methods of prophylactically or therapeutically treating a disease, disorder or condition in a subject in need of such treatment by administering in vivo, ex vivo, or in vitro one or more nucleic acids of the invention described herein to one or more cells of a subject, including an organism or mammal, including, e.g., a human, primate, mouse, dog, cat, pig, cow, goat, rabbit, rat, guinea pig, hamster, horse, sheep; or a non-mammalian vertebrate such as a bird (e.g., a chicken or duck) or a fish, or invertebrate, as described in more detail below.

In another aspect, the invention provides methods of prophylactically or therapeutically treating a disease, disorder or condition in a subject in need of such treatment by administering in vivo, ex vivo, or in vitro one or more polypeptides of the invention described herein to one or more cells of a subject (including those defined herein), as described in more detail below.

Polypeptide Expression

Polynucleotides encoding polypeptides of the invention are particularly useful for in vivo or ex vivo therapeutic or prophylactic applications, using techniques well known to those skilled in the art. For example, cultured cells are engineered ex vivo with a polynucleotide (DNA or RNA), with the engineered cells then being returned to the patient. Cells may also be engineered in vivo or ex vivo for expression of a polypeptide in vivo or ex vivo, respectively.

A number of viral vectors suitable for organismal in vivo transduction and expression are known. Such vectors include retroviral vectors (see Miller, *Curr. Top. Microbiol. Immunol.* (1992) 158:1–24; Salmons and Gunzburg, (1993) *Human Gene Therapy* 4:129–141; Miller et al., (1994) *Methods in Enzymology* 217: 581–599) and adeno-associated vectors (reviewed in Carter (1992) *Curr. Opinion Biotech.* 3: 533–539; Muzcyzka (1992) *Curr. Top. Microbiol. Immunol.* 158: 97–129). Other viral vectors that are used include adenoviral vectors, herpes viral vectors and Sindbis viral vectors, as generally described in, e.g., Jolly (1994) *Cancer Gene Therapy* 1:51–64; Latchman (1994) *Molec. Biotechnol.* 2:179–195; and Johanning et al., (1995) *Nucl. Acids Res.* 23:1495–1501.

Gene therapy provides methods for combating chronic infectious diseases (e.g., HIV infection, viral hepatitis), as well as non-infectious diseases including cancer and allergic diseases and some forms of congenital defects such as enzyme deficiencies. Several approaches for introducing nucleic acids into cells in vivo, ex vivo and in vitro have been used. These include liposome based gene delivery (Debs and Zhu (1993) WO 93/24640 and U.S. Pat. No. 5,641,662; Mannino and Gould-Fogerite (1988) *BioTechniques* 6(7): 682–691; Rose, U.S. Pat. No. 5,279,833; Brigham (1991) WO 91/06309; and Felgner et al. (1987)

Proc. Natl. Acad. Sci. USA 84: 7413–7414); Brigham, et al. (1989) Am. J. Med. Sci., 298:278–281; Nabel, et al. (1990) Science, 249:1285–1288; Hazinski, et al. (1991) Am. J. Resp. Cell Molec. Biol., 4:206–209; and Wang and Huang (1987) Proc. Natl. Acad. Sci. (USA), 84:7851–7855); adenoviral vector mediated gene delivery, e.g., to treat cancer (see, e.g., Chen et al. (1994) Proc. Natl. Acad. Sci. USA 91: 3054–3057; Tong et al. (1996) Gynecol. Oncol. 61: 175–179; Clayman et al. (1995) Cancer Res. 5: 1–6; O'Malley et al. (1995) Cancer Res. 55: 1080–1085; Hwang et al. (1995) Am. J. Respir. Cell Mol. Biol. 13: 7–16; Haddada et al. (1995) Curr. Top. Microbiol. Immunol. 199 (Pt. 3): 297–306; Addison et al. (1995) Proc. Nat'l. Acad. Sci. USA 92: 8522–8526; Colak et al. (1995) Brain Res. 691: 76–82; Crystal (1995) Science 270: 404–410; Elshami et al. (1996) Human Gene Ther. 7: 141–148; Vincent et al. (1996) J. Neurosurg. 85: 648–654), and many other diseases. Replication-defective retroviral vectors harboring therapeutic polynucleotide sequence as part of the retroviral genome have also been used, particularly with regard to simple MuLV vectors. See, e.g., Miller et al. (1990) Mol. Cell. Biol. 10:4239 (1990); Kolberg (1992) J. NIH Res. 4:43, and Cornetta et al. (1991) Hum. Gene Ther. 2:215). Nucleic acid transport coupled to ligand-specific, cation-based transport systems (Wu and Wu (1988) J. Biol. Chem., 263:14621–14624) have also been used. Naked DNA expression vectors have also been described (Nabel et al. (1990), supra); Wolff et al. (1990) Science, 247:1465–1468). In general, these approaches can be adapted to the invention by incorporating nucleic acids encoding the polypeptides of the invention into the appropriate vectors.

General texts which describe gene therapy protocols, which can be adapted to the present invention by introducing the nucleic acids of the invention into patients, include Robbins (1996) Gene Therapy Protocols, Humana Press, NJ, and Joyner (1993) Gene Targeting: A Practical Approach, IRL Press, Oxford, England.

Antisense Technology

In addition to expression of the nucleic acids of the invention as gene replacement nucleic acids, the nucleic acids are also useful for sense and anti-sense suppression of expression, e.g., to down-regulate expression of a nucleic acid of the invention, once expression of the nucleic acid is no-longer desired in the cell. Similarly, the nucleic acids of the invention, or subsequences or anti-sense sequences thereof, can also be used to block expression of naturally occurring homologous nucleic acids. A variety of sense and anti-sense technologies are known in the art, e.g., as set forth in Lichtenstein and Nellen (1997) Antisense Technology: A Practical Approach IRL Press at Oxford University, Oxford, England, and in Agrawal (1996) Antisense Therapeutics Humana Press, NJ, and the references cited therein.

Pharmaceutical Compositions

The polynucleotides of the invention (including vectors, cells, antibodies, etc., comprising polynucleotides or polypeptides of the invention) may be employed for therapeutic uses in combination with a suitable pharmaceutical carrier. Such compositions comprise a therapeutically effective amount of the compound, and a pharmaceutically acceptable carrier or excipient. A pharmaceutically acceptable carrier encompasses any of the standard pharmaceutical carriers, buffers and excipients. Such a carrier or excipient includes, but is not limited to, saline, buffered saline (e.g., phosphate-buffered saline solution), dextrose, water, glycerol, ethanol, emulsions (such as an oil/water or water/oil emulsion), various types of wetting agents and/or adjuvants, and combinations thereof. Suitable pharmaceutical carriers and agents are described in REMINGTON'S PHARMACEUTICAL SCIENCES (Mack Publishing Co., Easton, 19$^{th}$ ed. 1995). The formulation should suit the mode of administration of the active agent (e.g., nucleotide, polypeptide, vector, cell, etc.). Methods of administering nucleic acids, polypeptides, vectors, cells, antibodies, and proteins are well known in the art, and further discussed below.

Use as Probes

Also contemplated are uses of polynucleotides, also referred to herein as oligonucleotides, typically having at least 12 bases, preferably at least 15, more preferably at least 20, 30, or 50 bases, which hybridize under at least highly stringent (or ultra-high stringent or ultra-ultra-high stringent conditions) to a modified p40 or modified p35 polynucleotide sequence of the invention described herein. The polynucleotides may be used as probes, primers, sense and antisense agents, and the like, according to methods as noted supra.

Sequence Variations

Silent Variations

It will be appreciated by those skilled in the art that due to the degeneracy of the genetic code, a multitude of nucleic acids sequences encoding polypeptides of the invention may be produced, some which may bear minimal sequence homology to the nucleic acid sequences explicitly disclosed herein.

TABLE 4

Codon Table

| Amino acids | | | Codon | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For instance, inspection of the codon table (Table 4) shows that codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Using, as an example, the DNA sequence corresponding to nucleotides 1–15 of SEQ ID NO:1, ATGTGTCACCAGCAG, an example of a silent variation of this sequence is ATGTGCCATCAACAA (SEQ ID NO:41), both sequences which encode the amino acid sequence MCHQQ, corresponding to amino acids 1–5 of SEQ ID NO: 8.

Such "silent variations" are one species of "conservatively modified variations", discussed below. One of skill will recognize that each codon in a nucleic acid (except AUG and UGC, which are ordinarily the only codons for methionine and tryptophan, respectively) can be modified by standard techniques to encode a functionally identical polypeptide. Accordingly, each silent variation of a nucleic acid which encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code (e.g., as set forth in Table 4) as applied to the nucleic acid sequence encoding a polypeptide of the invention. All such variations of every nucleic acid herein are specifically provided and described by consideration of the sequence in combination with the genetic code.

Conservative Variations

"Conservatively modified variations" or, simply, "conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in a deletion of an amino acid, an addition of an amino acid, or a substitution of an amino acid with a chemically similar amino acid.

Conservative substitution tables providing functionally similar amino acids are well known in the art. Table 5 sets forth six groups which contain amino acids that are "conservative substitutions" for one another.

TABLE 5

Conservative Amino Acid Substitution Groups

| Group 1 | Alanine (A) | Serine (S) | Threonine (T) | |
| Group 2 | Aspartic acid (D) | Glutamic acid (E) | | |
| Group 3 | Asparagine (N) | Glutamine (Q) | | |
| Group 4 | Arginine (R) | Lysine (K) | | |
| Group 5 | Isoleucine (I) | Leucine (L) | Methionine (M) | Valine (V) |
| Group 6 | Phenylalanine (F) | Tyrosine (Y) | Tryptophan (W) | |

Thus, "conservatively substituted variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

For example, a conservatively substituted variation of the polypeptide identified herein as SEQ ID NO:8 will contain "conservative substitutions", according to the six groups defined above, in up to about 16 residues (i.e., about 5% of the amino acids) in the 325 amino acid polypeptide.

In a further example, examples of conservatively substituted variations of the region corresponding to amino acids 23–47 of SEQ ID NO:8, IWELK KDVYV VELDW YPNAP GETVV include:
IW<u>D</u>LK <u>R</u>DVYV <u>I</u>ELDW <u>E</u>PNAP GET<u>L</u>V (SEQ ID NO:42) and <u>V</u>WE<u>I</u>K KD<u>M</u>YV VEL<u>E</u>W YPNAP GETV<u>I</u> (SEQ ID NO:43), and the like, in accordance with the exemplary conservative substitutions listed in Table 5 (in the above example, conservative substitutions are underlined). Listing of a polypeptide sequence herein, in conjunction with the above substitution table, provides an express listing of all conservatively substituted polypeptides.

Finally, the addition of sequences which do not alter the encoded activity of a nucleic acid molecule, such as the addition of a non-functional sequence, is a conservative variation of the basic nucleic acid.

One of ordinary skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

Nucleic Acid Hybridization

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, New York), as well as in Ausubel, supra, Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

"Stringent hybridization wash conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched probe. Very stringent conditions are selected to be equal to the $T_m$ for a particular probe.

The $T_m$ is the temperature of the nucleic acid duplexes indicates the temperature at which the duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increase sensitivity, but can product nonspecific hybridization signals and high background signals. Higher stringency conditions (e.g., using lower salt and higher temperature that is closer to the hybridization temperature) lowers the background signal, typically with only the specific signal remaining. See Rapley, R. and Walker, J. M. eds., *Molecular Biomethods Handbook* (Humana Press, Inc. 1998) (hereinafter "Rapley and Walker"), which is incorporated herein by reference in its entirety for all purposes.

The $T_m$ of a DNA—DNA duplex can be estimated using Equation 1 as follows:

$$T_m(° C.) = 81.5° C. + 16.6(\log_{10}M) + 0.41(\% G+C) - 0.72(\% f) - 500/n,$$

where M is the molarity of the monovalent cations (usually Na+), (% G+C) is the percentage of guanosine (G) and cystosine (C) nucleotides, (% f) is the percentage of formalize and n is the number of nucleotide bases (i.e., length) of the hybrid. See Rapley and Walker, supra.

The $T_m$ of an RNA-DNA duplex can be estimated by using Equation 2 as follows:

$$T_m(° C.) = 79.8° C. + 18.5 (\log_{10}M) + 0.58(\% G+C) - 11.8(\% G+C)^2 - 0.56 (\% f)$$

820/n, where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Id.

Equations 1 and 2 are typically accurate only for hybrid duplexes longer than about 100–200 nucleotides. Id.

The Tm of nucleic acid sequences shorter than 50 nucleotides can be calculated as follows:

$$T_m(° C.) = 4(G+C) + 2(A+T),$$

where A (adenine), C, T (thymine), and G are the numbers of the corresponding nucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see Sambrook, supra for a description of SSC buffer). Often the high stringency wash is preceded by a low stringency wash to remove background probe signal. An example low stringency wash is 2×SSC at 40° C. for 15 minutes.

In general, a signal to noise ratio of 2.5×–5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention provided in the sequence listings herein.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under highly stringency conditions. Lower stringency conditions are appropriate for sequences that are less complementary. See, e.g., Rapley and Walker, supra.

Comparative hybridization can be used to identify nucleic acids of the invention, and this comparative hybridization method is a preferred method of distinguishing nucleic acids of the invention. Detection of highly stringent hybridization between two nucleotide sequences in the context of the present invention indicates relatively strong structural similarity/homology to, e.g., the nucleic acids provided in the sequence listing herein. Highly stringent hybridization between two nucleotide sequences demonstrates a degree of similarity or homology of structure, nucleotide base composition, arrangement or order that is greater than that detected by stringent hybridization conditions. In particular, detection of highly stringent hybridization in the context of the present invention indicates strong structural similarity or structural homology (e.g., nucleotide structure, base composition, arrangement or order) to, e.g., the nucleic acids provided in the sequence listings herein. For example, it is desirable to identify test nucleic acids which hybridize to the exemplar nucleic acids herein under stringent conditions.

Thus, one measure of stringent hybridization is the ability to hybridize to one of the listed nucleic acids (e.g., nucleic acid sequences SEQ ID NO:1 to SEQ ID NO:7 and SEQ ID NO:16 to SEQ ID NO:25, and complementary polynucleotide sequences thereof), under highly stringent conditions (or very stringent conditions, or ultra-high stringency hybridization conditions, or ultra-ultra high stringency hybridization conditions). Stringent hybridization (as well as highly stringent, ultra-high stringency, or ultra-ultra high stringency hybridization conditions) and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a probe comprising one or more nucleic acid sequences selected from SEQ ID NO:1 to SEQ ID NO:7 and SEQ ID NO:16 to SEQ ID NO:25, and complementary polynucleotide sequences thereof, binds to a perfectly matched complementary target (again, a nucleic acid comprising one or more nucleic acid sequences selected from SEQ ID NO:1 to SEQ ID NO:7 and SEQ ID NO:16 to SEQ ID NO:25, and complementary polynucleotide sequences thereof), with a signal to noise ratio that is at least about 2.5×, and optionally about 5× or more as high as that observed for hybridization of the probe to an unmatched target. In this case, the unmatched target is a nucleic acid corresponding to a known p40 or p35, e.g., a p40 or p35 nucleic acid that is present in a public database such as GenBank at the time of filing of the subject application. Examples of such unmatched target nucleic acids include, e.g., p40 nucleic acids with the following GenBank accession numbers: M65272 and M65290 (human), U19841 (*Macaca mulatta*, rhesus monkey), U19834 (*Cercocebus torquatus*, sooty mangabey), Y11129 (*Equus caballus*, horse), U83184, Y07762 and AF054607 (*Felis catus*, cat), U49100 and AF091134 (*Canis familiaris*, dog), U57752 and U10160 (*Cervus elaphus*, red deer), AF007576 (*Capra hircus*, goat), AF004024 (*Ovis*

*aries*, sheep), U11815 (*Bos taurus*, cow), U08317 (*Sus scrofa*, pig), X97019 and AF082494 (*Marmota monax*, woodchuck), AF133197 and U16674 (*Rattus norvegicus*, rat), M86671 and S82426 (*Mus musculus*, mouse), AF097507 (*Cavia porcellus*, guinea pig), and AF046211 (*Mesocricetus auratus*, golden hamster). Additional such sequences can be identified in e.g., GenBank, by one of ordinary skill in the art.

Examples of such unmatched target nucleic acids also include, e.g., p35 nucleic acids having the following GenBank accession numbers: M65271, M65291 (human); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (*Equus caballus*, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse). Additional such sequences can be identified in public databases, e.g., GenBank, by one of ordinary skill in the art.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 2.5×–10×, typically about 5×–10× as high as that observed for hybridization to any of the unmatched p40 target nucleic acids represented by GenBank accession numbers M65272 and M65290 (human), U19841 (*Macaca mulatta*, rhesus monkey), U19834 (*Cercocebus torquatus*, sooty mangabey), Y11129 (*Equus caballus*, horse), U83184, Y07762 and AF054607 (*Felis catus*, cat), U49100 and AF091134 (*Canis familiaris*, dog), U57752 and U10160 (*Cervus elaphus*, red deer), AF007576 (*Capra hircus*, goat), AF004024 (*Ovis aries*, sheep), U11815 (*Bos taurus*, cow), U08317 (*Sus scrofa*, pig), X97019 and AF082494 (*Marmota monax*, woodchuck), AF133197 and U16674 (*Rattus norvegicus*, rat), M86671 and S82426 (*Mus musculus*, mouse), AF097507 (*Cavia porcellus*, guinea pig), and AF046211 (*Mesocricetus auratus*, golden hamster), or to any of the unmatched p35 target nucleic acids represented by GenBank accession numbers M65271, M65291 (human); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (*Equus caballus*, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse).

Ultra high-stringency hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched p40 or p35 target nucleic acids described above. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched p40 or p35 target nucleic acids described above can be identified. A target nucleic acid which hybridizes to a probe under such conditions, with a signal to noise ratio of at least ½ that of the perfectly matched complementary target nucleic acid is said to bind to the probe under ultra-ultra-high stringency conditions.

Target nucleic acids which hybridize to the nucleic acids represented by SEQ ID NO:1 to SEQ ID NO:7, and SEQ ID NO:16 to SEQ ID NO:25 under high, ultra-high and ultra-ultra high stringency conditions are a feature of the invention. Examples of such nucleic acids include those with one or a few silent or conservative nucleic acid substitutions as compared to a given nucleic acid sequence.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code, or when antisera or antiserum generated against one or more of SEQ ID NO:8 to SEQ ID NO:14, which has been subtracted using the polypeptides encoded by known p40 sequences, including, e.g., the those encoded by the following p40 nucleic acid sequences in GenBank: Accession numbers: M65272 and M65290 (human), U19841 (*Macaca mulatta*, rhesus monkey), U19834 (*Cercocebus torquatus*, sooty mangabey), Y11129 (*Equus caballus*, horse), U83184, Y07762 and AF054607 (*Felis catus*, cat), U49100 and AF091134 (*Canis familiaris*, dog), U57752 and U10160 (*Cervus elaphus*, red deer), AF007576 (*Capra hircus*, goat), AF004024 (*Ovis aries*, sheep), U11815 (*Bos taurus*, cow), U08317 (*Sus scrofa*, pig), X97019 and AF082494 (*Marmota monax*, woodchuck), AF133197 and U16674 (*Rattus norvegicus*, rat), M86671 and S82426 (*Mus musculus*, mouse), AF097507 (*Cavia porcellus*, guinea pig), and AF046211 (*Mesocricetus auratus*, golden hamster), or other similar p40 sequences presented in GenBank, or when antisera generated against one or more of SEQ ID NO:26 to SEQ ID NO:35, which has been subtracted using the polypeptides encoded by known p35 sequences, including, e.g., the those encoded by the following p35 nucleic acid sequences in GenBank: Accession numbers: M65271, M65291 (human); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (*Equus caballus*, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse), or other similar p35 sequences presented in GenBank. Further details on immunological identification of polypeptides of the invention are found below. Additionally, for distinguishing between duplexes with sequences of less than about 100 nucleotides, a TMAC1 hybridization procedure known to those of ordinary skill in the art can be used. See, e.g., Sorg, U. et al. 1 *Nucleic Acids Res.* (Sep. 11, 1991) 19(17), incorporated herein by reference in its entirety for all purposes.

In one aspect, the invention provides a nucleic acid which comprises a unique subsequence in a nucleic acid selected from SEQ ID NO:1 to SEQ ID NO:7, or SEQ ID NO: 16 to SEQ ID NO:25. The unique subsequence is unique as compared to a nucleic acid corresponding to any known p40 nucleic acid sequence including, e.g., the known sequences represented by GenBank accession numbers: M65272 and M65290 (human), U19841 (*Macaca mulatta*, rhesus monkey), U19834 (*Cercocebus torquatus*, sooty mangabey), Y11129 (*Equus caballus*, horse), U83184, Y07762 and AF054607 (*Felis catus*, cat), U49100 and AF091134 (*Canis familiaris*, dog), U57752 and U10160 (*Cervus elaphus*, red deer), AF007576 (*Capra hircus*, goat), AF004024 (*Ovis aries*, sheep), U11815 (*Bos taurus*, cow), U08317 (*Sus scrofa*, pig), X97019 and AF082494 (*Marmota monax*, woodchuck), AF133197 and U16674 (*Rattus norvegicus*, rat), M86671 and S82426 (*Mus musculus*, mouse), AF097507 (*Cavia porcellus*, guinea pig), and AF046211 (*Mesocricetus auratus*, golden hamster); or unique as compared to a nucleic acid corresponding to any known p35 nucleic acid sequence including, e.g., the known sequences represented by GenBank accession numbers M65271, M65291 (human); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (Equus caballus, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse). Such unique subsequences can be determined by aligning any of SEQ ID NO:1 to SEQ ID NO:7, or SEQ ID NO:16 to SEQ ID NO:25 against the complete set of nucleic acids corresponding to GenBank accession numbers of known p40 or p35 sequences, such as those listed above or other similar p40 or p35 sequences presented in GenBank. Alignment can be performed using the BLAST algorithm set to default parameters. Any unique subsequence is useful, e.g., as a probe to identify the nucleic acids of the invention.

Similarly, the invention includes a polypeptide which comprises a unique subsequence in a polypeptide selected from: SEQ ID NO:8 to SEQ ID NO:14, and SEQ ID NO: 26 to SEQ ID NO:35. Here, the unique subsequence is unique as compared to a an amino acid subsequence of a known p40 or p35 polypeptide including, e.g., an amino acid subsequence of a polypeptide encoded by a known p40 or p35 nucleic acid corresponding to any of GenBank accession numbers listed above, or other similar p40 or p35 nucleic acid or polypeptide sequences presented in GenBank. Here again, the polypeptide is aligned against the complete set of known p40 or p35 polypeptide sequences, such as those polypeptides encoded by the nucleic acids corresponding to the GenBank accession numbers listed above, or other similar p40 or p35 nucleic acid or polypeptide sequences presented in GenBank (referred to as the "control peptides"; note that where the sequence corresponds to a non-translated sequence such as a pseudo gene, the corresponding polypeptide is generated simply by in silico translation of the nucleic acid sequence into an amino acid sequence, where the reading frame is selected to correspond to the reading frame of homologous p40 or p35 nucleic acids).

The invention also provides a target nucleic acid which hybridizes under at least stringent or highly stringent conditions (or conditions of greater stringency) conditions to a unique coding oligonucleotide which encodes a unique subsequence in a polypeptide selected from: SEQ ID NO:8 to SEQ ID NO:14, and SEQ ID NO:26 to SEQ ID NO:35, wherein the unique subsequence is unique as compared to an amino acid subsequence of a known p40 or p35 polypeptide sequence shown in GenBank or to a polypeptide corresponding to any of the control polypeptides. Unique sequences are determined as noted above.

In one example, the stringent conditions are selected such that a perfectly complementary oligonucleotide to the coding oligonucleotide hybridizes to the coding oligonucleotide with at least about a 2.5×–10× higher, preferably at least about a 5–10× higher signal to noise ratio than for hybridization of the perfectly complementary oligonucleotide to a control nucleic acid corresponding to any of the control polypeptides. Conditions can be selected such that higher ratios of signal to noise are observed in the particular assay which is used, e.g., about 15×, 20×, 30×, 50× or more. In this example, the target nucleic acid hybridizes to the unique coding oligonucleotide with at least a 2× higher signal to noise ratio as compared to hybridization of the control nucleic acid to the coding oligonucleotide. Again, higher signal to noise ratios can be selected, e.g., about 2.5×, 5×, 10×, 20×, 30×, 50× or more. The particular signal will depend on the label used in the relevant assay, e.g., a fluorescent label, a colorimetric label, a radioactive label, or the like.

Substrates and Formats for Sequence Recombination

The polynucleotides of the invention are useful as substrates for a variety of diversity generation, recombination and recursive sequence recombination (e.g., DNA shuffling) reactions, as well as other diversity generating techniques, including mutagenesis techniques and standard cloning methods as set forth in, e.g., Ausubel, Berger and Sambrook, supra, i.e., to produce additional modified p40 polypeptides or modified p35 polypeptides with desired properties. Based on the screening or selection protocols employed, recombinant, e.g., shuffled, modified p40 or modified p35 polypeptides can be generated and isolated that confer a variety of desirable characteristics, e.g., enhanced T-cell proliferative activity, enhanced interferon-gamma inductive activity, enhanced $T_H1$ cell differentiation activity, reduced toxicity, reduced immunogenicity, etc.

A variety of diversity generating protocols, including nucleic acid shuffling protocols, are available and fully described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel, or in series to access diverse sequence variants.

The result of any of the diversity generating procedures described herein can be the generation of one or more nucleic acids, which can be selected or screened for nucleic acids that encode proteins with or which confer desirable properties. Following diversification by one or more of the methods herein, or otherwise available to one of skill, any nucleic acids that are produced can be selected for a desired activity or property, e.g., enhanced T-cell proliferative activity, enhanced interferon-gamma induction activity, enhanced $T_H1$ cell differentiation activity, reduced toxicity, reduced immunogenicity, etc. Methods for determining nucleic acids having enhanced T-cell proliferative activity, enhanced interferon-gamma inductive activity, enhanced $T_H1$ cell differentiation activity, reduced toxicity, reduced immunogenicity, etc., include those described herein. This can include identifying any activity that can be detected, for example, in an automated or automatable format, by any of the assays in the art. A variety of related (or even unrelated) properties can be evaluated in serial or in parallel at the discretion of the practitioner.

The following publications describe a variety of diversity generating procedures, including recursive sequence recombination procedures (also termed simply "recursive recombination), and/or methods for generating modified nucleic acid sequences for use in the procedures and methods of the present invention include the following publications and the references cited therein: Soong, N. W. et al. (2000) "Molecular Breeding of Viruses," *Nature Genetics* 25:436–439; Stemmer, W. et al. (1999) "Molecular breeding of viruses for targeting and other clinical properties," *Tumor Targeting* 4:1–4; Ness et al. (1999) "DNA Shuffling of subgenomic sequences of subtilisin," *Nature Biotechnology* 17:893–896; Chang et al. (1999) "Evolution of a cytokine using DNA family shuffling," *Nature Biotechnology* 17:793–797; Minshull and Stemmer (1999) "Protein evolution by molecular breeding," *Current Opinion in Chemical Biology* 3:284–290; Christians et al. (1999) "Directed evolution of thymidine kinase for AZT phosphorylation using DNA family shuffling," *Nature Biotechnology* 17:259–264; Crameri et al. (1998) "DNA shuffling of a family of genes from diverse species accelerates directed evolution," *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening," *Proc. Nat'l Acad. Sci. USA* 94:4504–4509; Patten et al. (1997) "Applications of DNA Shuffling to Pharmaceuticals and Vaccines," *Current Opinion in Biotechnology* 8:724–733; Crameri et al. (1996) "Construction and evolution of antibody-phage libraries by DNA shuffling," *Nature Medicine* 2:100–103; Crameri et al. (1996) "Improved green fluorescent protein by molecular evolution using DNA shuffling," *Nature Biotechnology* 14:315–319; Gates et al. (1996) "Affinity selective isolation of ligands from peptide libraries through display on a lac repressor 'headpiece dimer,'" *J. Mol. Biol.* 255:373–386; Stemmer (1996) "Sexual PCR and Assembly PCR" In: *The Encyclopedia of Molecular Biology*, VCH Publishers, New York. pp. 447–457; Crameri and Stemmer (1995) "Combinatorial multiple cassette mutagenesis creates all the permutations of mutant and wildtype cassettes," *BioTechniques* 18:194–195; Stemmer et al. (1995) "Single-step assembly of a gene and entire plasmid form large numbers of oligodeoxy-ribonucleotides" *Gene* 164:49–53; Stemmer (1995) "The Evolution of Molecular Computation," *Science* 270:1510; Stemmer (1995) "Searching Sequence Space," *Bio/Technology* 13:549–553; Stemmer (1994) "Rapid evolution of a protein in vitro by DNA shuffling," *Nature* 370:389–391; and Stemmer (1994) "DNA shuffling by random fragmentation and reassembly: In vitro recombination for molecular evolution," *Proc. Nat'l Acad. Sci. USA* 91:10747–10751.

Additional details regarding DNA shuffling and other diversity generating methods can be found in the following U.S. patents, PCT publications, and EP publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer (Nov. 10, 1998) "End-Complementary Polymerase Reaction;" U.S. Pat. No. 5,837,458 to Minshull (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz, "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al., "Antigen Library Immunization;" WO 99/41369 by Punnonen et al., "Genetic Vaccine Vector Engineering;" WO 99/41368 by Punnonen et al., "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by Del Cardayre et al. "Evolution of Whole Cells and Organisms by Recursive Sequence Recombination;" WO 98/27230 by Patten and Stemmer, "Methods and Compositions for Polypeptide Engineering;" EP 0946755 by Patten and Stemmer, "Methods and Compositions for Polypeptide Engineering;" and WO 98/13487 by Stemmer et al., "Methods for Optimization of Gene Therapy by Recursive Sequence Shuffling and Selection;" WO 00/00632, "Methods for Generating Highly Diverse Libraries," WO 00/09679, "Methods for Obtaining in vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding DNA shuffling and related techniques, as well as other diversity generating methods, including "SHUFFLING OF CODON ALTERED GENES" by Patten et al. filed Sep. 29, 1998 (U.S. Ser. No. 60/102,362), Jan. 29, 1999 (U.S. Ser. No. 60/117,729), and Sep. 28, 1999 (U.S. Ser. No. 09/407,800); "EVOLUTION OF WHOLE CELLS AND ORGANISMS BY RECURSIVE SEQUENCE RECOMBINATION", by Del Cardayre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Feb. 5, 1999 (U.S. Ser. No. 60/118,813), Jun. 24, 1999 (U.S. Ser. No. 60/141,049), and Sep. 28, 1999 (U.S. Ser. No. 09/408,392); "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov and Stemmer, filed Feb. 5, 1999 (U.S. Ser. No. 60/118,854) and Oct. 12, 1999 (U.S. Ser. No. 09/416,375); RECOMBINATION OF INSERTION MODIFIED NUCLEIC ACIDS by Patten et al., filed Mar. 5, 1999 (U.S. Ser. No. 60/122,943), Jul. 2, 1999 (U.S. Ser. No. 60/142,299), Nov. 10, 1999 (U.S. Ser. No. 60/164,618), and Nov. 10, 1999 (U.S. Ser. No. 60/164, 617); and "SINGLE-STRANDED NUCLEIC ACID TEMPLATE-MEDIATED RECOMBINATION AND NUCLEIC ACID FRAGMENT ISOLATION" by Affholter, U.S. Ser. No. 60/186,482 filed Mar. 2, 2000.

As a review of the foregoing publications, patents, published foreign applications and U.S. patent applications reveals, diversity generation methods, such as shuffling (or recursive sequence recombination) of nucleic acids to provide new nucleic acids with desired properties can be carried out by a number of established methods. Any of these methods can be adapted to the present invention to evolve the p40 and p35 polypeptides discussed herein to produce new modified p40 or modified p35 polypeptides with new or improved properties. Both the methods of making such polypeptides and the polypeptides (e.g., modified p40 polypeptides and modified p35 polypeptides) produced by these methods are a feature of the invention. In brief, several different general classes of sequence modification methods, such as recombination, are applicable to the present invention and set forth, e.g., in the references above. First, nucleic acids can be recombined in vitro by any of a variety of techniques discussed in the references above, including e.g., DNAse digestion of nucleic acids to be recombined followed by ligation and/or PCR reassembly of the nucleic acids. Second, nucleic acids can be recursively recombined in vivo or ex vivo, e.g., by allowing recombination to occur between nucleic acids in cells. Third, whole genome recombination methods can be used in which whole genomes of cells or other organisms are recombined, optionally including spiking of the genomic recombination mixtures with desired library components (e.g., genes corresponding to the pathways of the present invention). Fourth, synthetic recombination methods can be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Fifth, in silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. Any of the preceding general recombination formats can be practiced in a reiterative fashion to generate a more diverse set of recombinant nucleic acids. Sixth, methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be used. above references provide these and other basic recombination formats as well as many modifications of these formats. Regardless of the format which is used, the nucleic acids of the invention can be recombined (with each other, or with related (or even unrelated) nucleic acids to produce a diverse set of recombinant nucleic acids, including e.g., homologous nucleic acids. In general, the sequence recombination techniques described herein provide particular advantages in that they provide for recombination between the nucleic acids of SEQ ID NO:1 to SEQ ID NO:7, or SEQ ID NO:16 to SEQ ID NO:25, or fragments or variants thereof, in any available format, thereby providing a very fast way of exploring the manner in which different combinations of sequences can affect a desired result.

Following recombination, any nucleic acids which are produced can be screened or selected for a desired activity. In the context of the present invention, this can include testing for and identifying any activity that can be detected, e.g., in an automatable format, by any assay known in the art. In addition, useful properties such as low immunogenicity, increased half-life, improved solubility, oral availability, or the like can also be selected for. A variety of p40 and/or p35 related (or even unrelated) properties can be assayed for, using any available assay.

DNA mutagenesis and recursive recombination provide a robust, widely applicable, means of generating diversity useful for the engineering of proteins, pathways, cells and organisms with improved characteristics. In addition to the basic formats described above, it is sometimes desirable to combine shuffling methodologies with other techniques for generating diversity. In conjunction with (or separately from) shuffling methods, a variety of diversity generation methods can be practiced and the results (i.e., diverse populations of nucleic acids) screened for in the systems of the invention. Additional diversity can be introduced by methods which result in the alteration of individual nucleotides or groups of contiguous or non-contiguous nucleotides, i.e., mutagenesis methods. Many mutagenesis methods are found in the above-cited references; additional details regarding mutagenesis methods can be found in the references listed below.

Mutagenesis methods of generating diversity include, for example, recombination (PCT/US98/05223; Publ. No. WO98/42727); site-directed mutagenesis (Ling et al. (1997) "Approaches to DNA mutagenesis: an overview," *Anal. Biochem.* 254(2):157–178; Dale et al. (1996) "Oligonucleotide-directed random mutagenesis using the phosphorothioate method," *Methods Mol. Biol.* 57:369–374; Smith (1985) "In vitro mutagenesis," Ann. Rev. Genet. 19:423–462; Botstein & Shortle (1985) "Strategies and applications of in vitro mutagenesis," *Science* 229:1193–1201; Carter (1986) "Site-directed mutagenesis," Biochem. J. 237:1–7; and Kunkel (1987) "The efficiency of oligonucleotide directed mutagenesis," in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection," *Proc. Nat'l Acad. Sci. USA* 82:488–492; Kunkel et al. (1987) "Rapid and efficient site-specific mutagenesis without phenotypic selection," *Methods in Enzymol.* 154, 367–382; and Bass et al. (1988) "Mutant Trp repressors with new DNA-binding specificities," *Science* 242:240–245); oligonucleotide-directed mutagenesis (*Methods in Enzymol.* 100:468–500 (1983); *Methods in Enzymol.* 154:329–350 (1987); Zoller & Smith (1982) "Oligonucleotide-directed mutagenesis using M13-derived vectors: an efficient and general procedure for the production of point mutations in any DNA fragment," *Nucleic Acids Res.* 10:6487–6500; Zoller & Smith (1983) "Oligonucleotide-directed mutagenesis of DNA fragments cloned into M13 vectors," *Methods in Enzymol.* 100:468–500; and Zoller & Smith (1987) "Oligonucleotide-directed mutagenesis: a simple method using two oligonucleotide primers and a single-stranded DNA template," *Methods in Enzymol.* 154:329–350); phosphorothioate-modified DNA mutagenesis (Taylor et al. (1985) "The use of phosphorothioate-modified DNA in restriction enzyme reactions to prepare nicked DNA," *Nucl. Acids Res.* 13:8749–8764; Taylor et al. (1985) "The rapid generation of oligonucleotide-directed mutations at high frequency using phosphorothioate-modified DNA," *Nucl. Acids Res.* 13:8765–8787 (1985); Nakamaye & Eckstein (1986) "Inhibition of restriction endonuclease Nci I cleavage by phosphorothioate groups and its application to oligonucleotide-directed mutagenesis," *Nucl. Acids Res.* 14:9679–9698; Sayers et al. (1988) "Y-T Exonucleases in phosphorothioate-based oligonucleotide-directed mutagenesis," *Nucl. Acids Res.* 16:791–802; and Sayers et al. (1988) "Strand specific cleavage of phosphorothioate-containing DNA by reaction with restriction endonucleases in the presence of ethidium bromide," *Nucl. Acids Res.* 16:803–814); mutagenesis using gapped duplex DNA (Kramer et al. (1984) "The gapped duplex DNA approach to oligonucleotide-directed mutation construction," *Nucl. Acids Res.* 12:9441–9456; Kramer & Fritz (1987) "Oligonucleotide-directed construction of mutations via gapped duplex DNA," *Methods in Enzymol.* 154:350–367; Kramer et al. (1988) "Improved enzymatic in vitro reactions in the gapped duplex DNA approach to oligonucleotide-directed construction of mutations," *Nucl. Acids Res.* 16:7207; and Fritz et al. (1988) "Oligonucleotide-directed construction of mutations: a gapped duplex DNA procedure without enzymatic reactions in vitro," *Nucl. Acids Res.* 16:6987–6999).

Additional suitable methods include point mismatch repair (Kramer et al. (1984) "Point Mismatch Repair," *Cell* 38:879–887), mutagenesis using repair-deficient host strains (Carter et al. (1985) "Improved oligonucleotide site-directed mutagenesis using M13 vectors," *Nucl. Acids Res.* 13:4431–4443; and Carter (1987) "Improved oligonucleotide-directed mutagenesis using M13 vectors," *Methods in Enzymol.* 154:382–403), deletion mutagenesis (Eghtedarzadeh & Henikoff (1986) "Use of oligonucleotides to generate large deletions," *Nucl. Acids Res.* 14:5115), restriction-selection and restriction-selection and restriction-purification (Wells et al. (1986) "Importance of hydrogen-bond formation in stabilizing the transition state of subtilisin," *Phil. Trans. R. Soc. Lond. A* 317:415–423), mutagenesis by total gene synthesis (Nambiar et al. (1984) "Total synthesis and cloning of a gene coding for the ribonuclease S protein," *Science* 223:1299–1301; Sakamar and Khorana (1988) "Total synthesis and expression of a gene for the a-subunit of bovine rod outer segment guanine nucleotide-binding protein (transducing)," *Nucl. Acids Res.* 14:6361–6372; Wells et al. (1985) "Cassette mutagenesis: an efficient method for generation of multiple mutations at defined sites," *Gene* 34:315-323; and Grundström et al. (1985) "Oligonucleotide-directed mutagenesis by microscale 'shotgun' gene synthesis," *Nucl. Acids Res.* 13:3305–3316), double-strand break repair (Mandecki (1986) "Oligonucleotide-directed double-strand break repair in plasmids of *Escherichia coli*: a method for site-specific mutagenesis," *Proc. Nat'l Acad. Sci. USA,* 83:7177–7181). Additional details on many of the above methods can be found in *Methods Enzymol.*, Vol. 154, which also describes useful controls for trouble-shooting problems with various mutagenesis methods.

Random or semi-random mutagenesis using doped or degenerate oligonucleotides (Arkin and Youvan (1992) "Optimizing nucleotide mixtures to encode specific subsets of amino acids for semi-random mutagenesis," *Biotechnology* 10:297–300; Reidhaar-Olson et al. (1991) "Random mutagenesis of protein sequences using oligonucleotide cassettes," *Methods in Enzymol.* 208:564–86; Lim and Sauer (1991) "The role of internal packing interactions in determining the structure and stability of a protein," *J. Mol. Biol.* 219:359–76; Breyer and Sauer (1989) "Mutational analysis of the fine specificity of binding of monoclonal antibody 51F to lambda repressor," *J. Biol. Chem.* 264:13355–60); "Walk-Through Mutagenesis" (Crea, R.; U.S. Pat. Nos. 5,830,650 and 5,798,208, and EP Patent 0527809 B1) may also be employed to generate diversity.

In one aspect of the present invention, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11–15 and Caldwell et al. (1992) *PCR Methods Applic.* 2:28–33. Similarly, assembly PCR can be used, in a process which involves the assembly of a PCR product from a mixture of small DNA fragments. A large number of different PCR reactions can occur in parallel in the same vial, with the products of one reaction priming the products of another reaction. Sexual PCR mutagenesis can be used in which homologous recombination occurs between DNA molecules of different but related DNA sequence in vitro, by random fragmentation of the DNA molecule based on sequence homology, followed by fixation of the crossover by primer extension in a PCR reaction. This process is described in the references above, e.g., in Stemmer (1994) *Proc. Nat'l Acad. Sci. USA* 91:10747–10751. Recursive ensemble mutagenesis can be used in which an algorithm for protein mutagenesis is used to produce diverse populations of phenotypically related mutants whose members differ in amino acid sequence. This method uses a feedback mechanism to control successive rounds of combinatorial cassette mutagenesis. Examples of this approach are found in Arkin & Youvan (1992) *Proc. Nat'l Acad. Sci. USA* 89:7811–7815.

As noted, oligonucleotide directed mutagenesis can be used in a process which allows for the generation of site-specific mutations in any nucleic acid sequence of interest. Examples of such techniques are found in the references above and, e.g., in Reidhaar-Olson et al. (1988) *Science,* 241:53–57. Similarly, cassette mutagenesis can be used in a process which replaces a small region of a double stranded DNA molecule with a synthetic oligonucleotide cassette that differs from the native sequence. The oligonucleotide can contain, e.g., completely and/or partially randomized native sequence(s).

In vivo (or ex vivo) mutagenesis can be used in a process of generating random mutations in any cloned DNA of interest which involves the propagation of the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA.

Exponential ensemble mutagenesis can be used for generating combinatorial libraries with a high percentage of unique and functional mutants, where small groups of residues are randomized in parallel to identify, at each altered position, amino acids which lead to functional proteins. Examples of such procedures are found in Delegrave & Youvan (1993) *Biotechnology* Research 11:1548–1552. Similarly, random and site-directed mutagenesis can be used. Examples of such procedures are found in Arnold (1993) *Current Opinion in Biotechnology* 4:450–455.

Kits for mutagenesis, library construction, and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clontech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian *Biotechnology* Ltd (e.g., using the Carter/Winter method above).

Any of the described shuffling or mutagenesis techniques can be used in conjunction with procedures which introduce additional diversity into a genome, e.g., a bacterial, fungal, animal or plant genome. For example, in addition to the methods above, techniques have been proposed which produce chimeric nucleic acid multimers suitable for transformation into a variety of species (see, e.g., Schellenberger U.S. Pat. No. 5,756,316 and the references above). When such chimeric multimers consist of genes that are divergent with respect to one another (e.g., derived from natural diversity or through application of site directed mutagenesis, error prone PCR, passage through mutagenic bacterial strains, and the like), are transformed into a suitable host, this provides a source of nucleic acid diversity for DNA diversification.

Chimeric multimers transformed into host species are suitable as substrates for in vivo (or ex vivo) shuffling protocols. Alternatively, a multiplicity of polynucleotides sharing regions of partial sequence similarity or homology can be transformed into a host species and recombined in vivo (or ex vivo) by the host cell. Subsequent rounds of cell division can be used to generate libraries, members of which, comprise a single, homogenous population of monomeric or pooled nucleic acid. Alternatively, the monomeric nucleic acid can be recovered by standard techniques and recursively recombined in any of the described shuffling formats.

Chain termination methods of diversity generation have also been proposed (see, e.g., U.S. Pat. No. 5,965,408 and the references above). In this approach, double stranded DNAs corresponding to one or more genes sharing regions of sequence similarity or homology are combined and denature, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity or homology and which are chimeric with respect to the starting population of DNA molecules. Optionally, the products or partial pools of the products can be amplified at one or more stages in the process. Polynucleotides produced by a chain termination method, such as described above are suitable substrates for diversity generation methods (e.g., RSR, DNA shuffling) according to any of the described formats.

Diversity can be further increased by using methods which are not homology based with DNA shuffling (which, as set forth in the above publications and applications can be homology or non-homology based, depending on the precise format). For example, incremental truncation for the creation of hybrid enzymes (ITCHY) described in Ostermeier et al. (1999) "A combinatorial approach to hybrid enzymes independent of DNA homology," *Nature Biotechnol.* 17:1205, can be used to generate an initial recombinant library which serves as a substrate for one or more rounds of in vitro, ex vivo, or in vivo diversity generation methods (e.g., RSR or shuffling methods).

Methods for generating multispecies expression libraries have been described (e.g., U.S. Pat. Nos. 5,783,431; 5,824, 485 and the references above) and their use to identify protein activities of interest has been proposed (U.S. Pat. No. 5,958,672 and the references above). Multispecies expression libraries are, in general, libraries comprising cDNA or genomic sequences from a plurality of species or strains, operably linked to appropriate regulatory sequences, in an expression cassette. The cDNA and/or genomic sequences are optionally randomly concatenated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

In some applications, it is desirable to preselect or prescreen libraries (e.g., an amplified library, a genomic library, a cDNA library, a normalized library, etc.) or other substrate nucleic acids prior to shuffling, or to otherwise bias the substrates towards nucleic acids that encode functional products (shuffling procedures can also, independently have these effects). For example, in the case of antibody engineering, it is possible to bias the shuffling process toward antibodies with functional antigen binding sites by taking advantage of in vivo (or ex vivo or in vitro) recombination events prior to diversity generation (e.g., DNA shuffling) by any described method. For example, recombined CDRs derived from B cell cDNA libraries can be amplified and assembled into framework regions (e.g., Jirholt et al. (1998) "Exploiting sequence space: shuffling in vivo formed complementarity determining regions into a master framework," *Gene* 215:471) prior to diversity generation (e.g., DNA shuffling) according to any of the methods described herein.

Libraries can be biased towards nucleic acids which encode proteins with desirable activities (e.g., binding affinities, enzymatic activities, proliferative activities, cell differentiation activities, ability to induce an immune response, adjuvant properties, etc.). For example, after identifying a clone from a library which exhibits a specified activity, the clone can be mutagenized using any known method for introducing DNA alterations, including, but not restricted to, DNA shuffling or another form of recursive sequence recombination or diversity generation. A library comprising the mutagenized clones is then screened for a desired activity, which can be the same as or different from the initially specified activity. An example of such a procedure is proposed in U.S. Pat. No. 5,939,250. Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom.

Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in a shuffling-based gene reassembly process. In one such method the fragment population derived the genomic library (ies) is annealed with partial, or, often approximately full length ssDNA or RNA corresponding to the opposite strand. Assembly of complex chimeric genes from this population is the mediated by nuclease-base removal of non-hybridizing fragment ends, polymerization to fill gaps between such fragments and subsequent single stranded ligation. The parental strand can be removed by digestion (if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. As set forth in "Single-stranded nucleic acid template-mediated recombination and nucleic acid fragment isolation" by Affholter (U.S. Ser. No. 60/186,482, filed Mar. 2, 2000) and WO 98/27230, "Methods and Compositions for Polypeptide Engineering" by Patten and Stemmer, shuffling using single-stranded templates and nucleic acids of interest which bind to a portion of the template can also be performed.

In one approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for any of the shuffling reactions described herein.

"Non-Stochastic" methods of generating nucleic acids and polypeptides are alleged in Short, J. "Non-Stochastic Generation of Genetic Vaccines and Enzymes," WO 00/46344. These methods, including the proposed non-stochastic polynucleotide reassembly and gene site saturation mutagenesis and synthetic ligation polynucleotide reassembly methods outlined therein, can be applied to the present invention as well.

It will readily be appreciated that any of the above described techniques suitable for enriching a library prior to diversification can also be used to screen the products, or libraries of products, produced by the diversity generating methods.

A recombinant nucleic acid produced by recursively recombining one or more polynucleotides of the invention with one or more additional nucleic acids also forms a part of the invention. The one or more additional nucleic acids may include another polynucleotide of the invention; optionally, alternatively, or in addition, the one or more additional nucleic acids can include, e.g., a nucleic acid encoding a naturally-occurring p40 polypeptide or p35 polypeptide, or a subsequence thereof, or any homologous p40 polypeptide or p35 polypeptide sequence or subsequence thereof (e.g., a p40 or p35 sequence as found in GenBank or other available literature), or, e.g., any other homologous or non-homologous nucleic acid (certain recombination formats noted above, notably those performed synthetically or in silico, do not require homology for recombination).

The recombining steps may be performed in vivo, ex vivo, in vitro, in planta, or in silico as described in more detail in the references above. Also included in the invention is a cell containing any resulting recombinant nucleic acid, nucleic acid libraries produced by diversity generation, recombination, or recursive sequence recombination of the nucleic acids set forth herein, and populations of cells, vectors, viruses, plasmids or the like comprising the library or comprising any recombinant nucleic acid resulting from diversity generation or recombination (or recursive sequence recombination) of a nucleic acid as set forth herein with another such nucleic acid, or an additional nucleic acid. Corresponding sequence strings in a database present in a computer system or computer readable medium are a feature of the invention.

Other Polynucleotide Compositions

The invention also includes compositions comprising two or more polynucleotides of the invention (e.g., as substrates for recombination). The composition can comprise a library of recombinant nucleic acids, where the library contains at least 2, 3, 5, 10, 20, or 50 or more nucleic acids. The nucleic acids are optionally cloned into expression vectors, providing expression libraries.

The invention also includes compositions produced by digesting one or more polynucleotide of the invention with a restriction endonuclease, an RNAse, or a DNAse (e.g., as is performed in certain of the recombination formats noted above); and compositions produced by fragmenting or shearing one or more polynucleotide of the invention by radiation, chemical, or mechanical means (e.g., sonication, vortexing, and the like), which can also be used to provide substrates for recombination in the methods above. Similarly, compositions comprising sets of oligonucleotides corresponding to more than one nucleic acid of the invention are useful as recombination substrates and are a feature of the invention. For convenience, these fragmented, sheared, or oligonucleotide synthesized mixtures are referred to as fragmented nucleic acid sets.

Also included in the invention are compositions produced by incubating one or more of the fragmented nucleic acid sets in the presence of ribonucleotide- or deoxyribonucelotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (such as, VENT, TAQ, or the like).

Polypeptides of the Invention

The invention provides isolated or recombinant polypeptides, collectively referred to herein as "modified cytokine polypeptides," "modified p35 polypeptides,", "modified p40 polypeptides," or simply "polypeptides of the invention."

Modified p40 Polypeptides

An isolated or recombinant modified p40 polypeptide of the invention includes a polypeptide comprising a mature polypeptide region of a sequence selected from SEQ ID NO:8 to SEQ ID NO:14, conservatively modified variations thereof, and fragments thereof having proliferative activity or interferon-gamma induction activity in a T-cell based assay (such as, e.g., a human T-cell based assay), in the presence of a p35 polypeptide (such as, e.g., a wt-p35 polypeptide or a modified p35 polypeptide). An alignment of exemplary modified p40 polypeptide sequences according to the invention is provided in FIG. 1. Alignment of the polypeptide sequences of the invention to each other or to sequences of known or naturally-occurring p40 polypeptides is readily performed by one of ordinary skill in the art using publicly available databases and alignment programs. Sequences of known, naturally-occurring p40 polypeptides from human and non-human sources are readily available from a variety of sources, such as GenBank or SWISSPROT.

The modified p40 polypeptide of the invention comprises at least one modification at a position equivalent to that in the amino acid sequence of a human p40 polypeptide (SEQ ID NO:15). The modification can include:

(a) a substitution of the specified amino acid for a different amino acid at one or more equivalent position selected from Leu62, Ser71, Gln78, His99, Thr127, Arg130, Lys185, Glu186, Tyr187, Glu188, Ser190, Asp196, Met211, Val289, Ser305, Ser307, Arg309, and Gln311;

(b) a deletion of one or more of equivalent amino acids Arg181 to Asn184 inclusive, or a substitution of said equivalent amino acids for one or more of the amino acids Ser-(Leu or Met)-(Glu or Asp)-His-Arg; and (c) a deletion of one or more of equivalent amino acids Asp287 and Arg288.

A modified p40 polypeptide of the invention can optionally contain at least two of modifications (a), (b) or (c). For purposes of clarity, the numbering of amino acid positions corresponds to that of a human p40 (SEQ ID NO:15); however, it is understood that such modification may be made in an equivalent position of any p40 polypeptide.

An "equivalent position", or a "position equivalent to", refers to a position related by sequence homology to a specified position of the comparison sequence (in this example, SEQ ID NO:15). For example, in FIG. 1 the amino acid sequence of a human p40 (SEQ ID NO:15) and exemplary modified p40 polypeptide sequences of the invention (SEQ ID NO:8 to SEQ ID NO:14) are aligned to provide the maximum amount of homology between the sequences. A comparison of these sequences shows that there are a number of conserved residues contained in each sequence. As can be seen, there are also a number of insertions and deletions in the exemplary modified p40 sequences as compared to the human p40 sequence.

Thus, for example, inspection of FIG. 1 shows that the amino acid position equivalent to amino acid 185 in the human p40 sequence SEQ ID NO:15 (i.e., the equivalent position to amino acid 185), is 181 in the modified p40 polypeptide sequence SEQ ID NO:8, owing to the deletion of Arg-Gly-Asp-Asn at position 181 to 184 inclusive, and is 186 in the modified p40 polypeptide sequence SEQ ID NO:9, owing to the substitution of Arg-Gly-Asp-Asn for the amino acids Ser-(Leu or Met)-(Glu or Asp)-His-Arg at that same position. Likewise, the amino acid position equivalent to amino acid 289 in the human p40 sequence (SEQ ID NO:15) is 285 in the modified p40 sequence SEQ ID NO:8, and is 288 in the modified p40 sequence SEQ ID NO:9, owing to a deletion of amino acids Asp-Arg at equivalent positions 287 and 288 of SEQ ID NO:15.

In one embodiment, a modified p40 polypeptide of the invention comprises at least one substitution at a position equivalent to that of the amino acid sequence of human p40 polypeptide (SEQ ID NO:15), selected from the group consisting of: Leu62Ser; Ser71Thr; Gln78His; His99(Arg or Gln); Thr127(Ser or Ile); Arg130Lys; Lys185Glu; Glu186Tyr; Tyr187(Lys or Asn); Glu188Lys; Ser190(Arg or Thr); Asp196Gly; Met211Val; Val289(Ile or Leu); Ser305Lys; Ser307Arg; Arg309Gln; and Gln311Arg. In other embodiments, a modified p40 polypeptide comprises at least 2, 3, 4, 5, 6, 7, 8, 9, 10, 11, 12, 13, 14, 15, 16, or 17 of the above substitutions. In another embodiment, a modified p40 polypeptide of the invention comprises all of the above substitutions.

A modified p40 polypeptide of the invention optionally further comprises at least one of the following substitutions in an position equivalent to that of SEQ ID NO:15: Cys2His; His3Pro; Ile8Val; Phe15Leu; Val21Met; Lys27Glu; Asp29Asn; Asp40Asn; Met45Thr; Thr49Ala; Glu67Gly, His91Arg; Glu95 (Ala or Thr), Val96Ala; Glu122Lys; Asn125Ala; Asn135Asp; Arg139His; Thr147Ala; Thr153Lys; Ser155Thr; Ser163Thr; Gln166(Arg or His), Ala172Thr; Ala173Val; Thr174Leu; Ala177Glu; Glu178Asp; Arg179Leu; Val180Gly; Ala201Ser; Val212Leu; Asp213Glu; Val215Ile; Ser226Arg; Lys244Arg; Gln251His; Val254Ile; Ser255Asn; Glu257Gly; Thr264(Ala or Ile); Thr272Met; Cys274Gly; Val275Ile; Lys280Arg; Ser281Asn; Lys285Asp; Lys286Arg; Phe290Ser; Thr291 (Met or Val); Lys293Gln; Thr297Lys; Ile299(Thr or Val); Arg301His; Asn303Asp; Ser318Phe; Glu321Asp; Pro326Ser; Cys327Leu; and Ser328(Gly or Gln).

The modified p40 polypeptide sequence may be a modification of a naturally-occurring p40 polypeptide sequence of a mammal (e.g., human, a non-human primate, a ruminant, or a rodent), preferably a primate, more preferably human. The naturally-occurring p40 polypeptide sequence may be one encoded by one of the following nucleic acid sequences having GenBank accession number: M65272, M65290 (human); U19841 (*Macaca mulatta*, rhesus monkey); U19834 (*Cercocebus torquatus*, sooty mangabey); Y11129 (*Equus caballus*, horse); U83184, Y07762, AF054607 (*Felis catus*, cat); U49100, AF091134 (*Canis familiaris*, dog); U57752, U10160 (*Cervus elaphus*, red deer); AF007576 (*Capra hircus*, goat); AF004024 (*Ovis aries*, sheep); U11815 (*Bos taurus*, cow); U08317 (*Sus*

*scrofa*, pig); X97019, AF082494 (*Marmota monax*, woodchuck); AF133197, U16674 (*Rattus norvegicus*, rat); M86671, S82426 (*Mus musculus*, mouse); AF097507 (*Cavia porcellus*, guinea pig); and AF046211 (*Mesocricetus auratus*, golden hamster). The naturally-occurring p40 polypeptide sequence is more preferably a primate sequence, still more preferably a human sequence, most preferably a mature human p40 sequence comprising amino acid residues 23 to 328 of SEQ ID NO:15.

The invention also includes an isolated or recombinant polypeptide comprising an amino acid sequence containing at least 10 contiguous amino acid residues of any one of SEQ ID NOS:8–14. The polypeptide typically includes at least one amino acid substitution, at an equivalent position to that of SEQ ID NO:15, selected from: Leu62Ser; Ser71Thr; Gln78His; His99(Arg or Gln); Thr127(Ser or Ile); Arg130Lys; Lys185Glu; Glu186Tyr; Tyr187(Lys or Asn); Glu188Lys; Ser190(Arg or Thr); Asp196Gly; Met211Val; Val289(Ile or Leu); Ser305Lys; Ser307Arg; Arg309Gln; and Gln311Arg.

The modified p40 polypeptide may optionally comprise at least one substitution selected from: Cys2His; His3Pro; Ile8Val; Phe15Leu; Val21Met; Lys27Glu; Asp29Asn; Asp40Asn; Met45Thr; Thr49Ala; Glu67Gly, His91Arg; Glu95(Ala or Thr), Val96Ala; Glu122Lys; Asn125Ala; Asn135Asp; Arg139His; Thr147Ala; Thr153Lys; Ser155Thr; Ser163Thr; Gln166(Arg or His), Ala172Thr; Ala173Val; Thr174Leu; Ala177Glu; Glu178Asp; Arg179Leu; Val180Gly; Ala201Ser; Val212Leu; Asp213Glu; Val215Ile; Ser226Arg; Lys244Arg; Gln251His; Val254Ile; Ser255Asn; Glu257Gly; Thr264(Ala or Ile); Thr272Met; Cys274Gly; Val275Ile; Lys280Arg; Ser281Asn; Lys285Asp; Lys286Arg; Phe290Ser; Thr291 (Met or Val); Lys293Gln; Thr297Lys; Ile299(Thr or Val); Arg301His; Asn303Asp; Ser318Phe; Glu321Asp; Pro326Ser; Cys327Leu; and Ser328(Gly or Gln).

In various embodiments, the polypeptide comprises, e.g., at least 15, at least 20, at least 30, at least 50, at least 75, at least 100, at least 150, at least 200, or at least 250 contiguous amino acid residues of any one of SEQ ID NOS:8–14 or SEQ ID NO:39. In other embodiments, the encoded polypeptide is at least 270, 280, 285, 290, 295, 300, 305, 307, 310, or 320 amino acids in length. In another embodiment, the encoded polypeptide comprises at least 290, 300, 305, or 307 contiguous amino acid residues of the mature polypeptide region of any one of SEQ ID NOS:8–14 or SEQ ID NO:39.

Fragments of the modified p40 polypeptides described herein are also a feature of the invention. A modified p40 polypeptide fragment of the invention typically comprises a modified p40 polypeptide comprising at least about 20, 25, or 30, and typically at least about 40, 50, 60, 70, 80, 90, or 100 contiguous amino acids of any one of SEQ ID NOS: 8–14 or SEQ ID NO:39. In other embodiments, the fragment comprises usually at least about 100, 120, 140, 160, 180, 200, 220, 240, 260, 280, 290, 295, 296, 297, 298, 299, 300, 301, 302, 303, 304, 305, 306, or 307 contiguous amino acids of any one of SEQ ID NOS:8–14 or SEQ ID NO:39. Such polypeptide fragments may have proliferative activity in a human T-cell-based assay and/or interferon-gamma induction activity in a human T-cell-based assay.

In other embodiments, the invention provides polypeptides having a length of at least about 295 amino acids, and in some such embodiments, such polypeptides have a proliferative activity or interferon-gamma induction activity in a T-cell based assay (such as, e.g., a human T-cell based assay), in the presence of a p35 polypeptide (such as, e.g., a wt-p35 polypeptide or a modified p35 polypeptide).

In other embodiments, the invention provides a polypeptide comprising at least 280, 290, 295, or 300 contiguous amino acid residues of a protein encoded by a coding polynucleotide sequence comprising any of the following: (a) SEQ ID NO:1 to SEQ ID NO:7; (b) a coding polynucleotide sequence that encodes a first polypeptide selected from any of SEQ ID NO:8 to SEQ ID NO:14 or SEQ ID NO:39; and (c) a complementary polynucleotide sequence that hybridizes under at least highly stringent (or ultra-high stringent or ultra-ultra-high stringent conditions) hybridization conditions over substantially the entire length of a polynucleotide sequence of (a) or (b). Such polypeptides may have proliferative activity or interferon-gamma induction activity in a T-cell based assay (such as, e.g., a human T-cell based assay), in the presence of a p35 polypeptide (such as, e.g., a wt-p35 polypeptide or a modified p35 polypeptide).

The polypeptides and nucleic acids of the subject invention need not be identical, but can be substantially identical to the corresponding sequence of the target molecule or related molecule, including the polypeptides of any of SEQ ID NOS:8–14 or SEQ ID NO:39 or fragments thereof (including those having T-cell proliferative or interferon-gamma induction activities in the assays described herein), or the nucleic acids of any of SEQ ID NOS:1–7 or fragments thereof (including those having T-cell proliferative or interferon-gamma induction activities in the assays described herein). The polypeptides can be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) or having a percent identity to a sequence in the naturally occurring or known p40 polypeptide molecule.

In other embodiments, the invention provides a modified p40 polypeptide comprising an amino acid sequence having at least about 90% amino acid sequence identity to the sequence identified herein as the mature polypeptide region (amino acid residue positions 23–328) of SEQ ID NO:39: IWEL-$X_{27}$-K-$X_{29}$-VYVVELDWYP-$X_{40}$-APGE-$X_{45}$-VVL-$X_{49}$-CDTPEEDGITWT-$X_{62}$-DQSS-$X_{67}$-VLG-$X_{71}$-GK-TLTI-$X_{78}$-VKEFGDAGQYTC-$X_{91}$-KGG-$X_{95}$-$X_{96}$-LS-$X_{99}$-SLLLLHKKEDGIWSTDILKDQK-$X_{122}$-PK-$X_{125}$-K-$X_{127}$-FL-$X_{130}$-CEAK-$X_{135}$-YSG-$X_{139}$-FTCWWLT-$X_{147}$-ISTDL-$X_{153}$-F-$X_{155}$-VKSSRGS-$X_{163}$-DP-$X_{166}$-GVTCG-$X_{172}$-$X_{173}$-$X_{174}$-LS-$X_{177}$-$X_{178}$-$X_{179}$-$X_{180}$-$X_{181}$-$X_{182}$-$X_{183}$-$X_{184}$-$X_{185}$-$X_{186}$-$X_{187}$-$X_{188}$-Y-$X_{190}$-VECQE-$X_{196}$-SACP-$X_{201}$-AEESLPIEV-$X_{211}$-$X_{212}$-$X_{213}$-A-$X_{215}$-HKLKYENYTS-$X_{226}$-FFIRDIIKPDPPKNLQL-$X_{244}$-PLKNSR-$X_{251}$-VE-$X_{254}$-$X_{255}$-W-$X_{257}$-YPDTWS-$X_{264}$-PHSYFSLTF-$X_{274}$-$X_{275}$-QVQG-$X_{280}$-$X_{281}$-KRE-$X_{285}$-$X_{286}$-$X_{287}$-$X_{288}$-$X_{289}$-F-$X_{291}$-D-$X_{293}$-TSA-$X_{297}$-V-$X_{299}$-C-$X_{301}$-K-$X_{303}$-A-$X_{305}$-I-$X_{307}$-V-$X_{309}$-A-$X_{311}$-DRY-$X_{315}$-SS-$X_{318}$-WS-$X_{321}$-WASV-$X_{326}$-$X_{327}$-$X_{328}$, or a conservatively substituted variation thereof, where $X_{27}$ is K or E; $X_{29}$ is D or N; $X_{40}$ is D or N; $X_{45}$ is M or T; $X_{49}$ is T or A; $X_{62}$ is S; $X_{67}$ is E or G; $X_{71}$ is T; $X_{78}$ is H; $X_{91}$ is H or R; $X_{95}$ is E, A, K, or T, $X_{96}$ is V or A; $X_{99}$ is R or Q; $X_{122}$ is E or K; $X_{125}$ is N or A; $X_{127}$ is S or I; $X_{130}$ is K; $X_{135}$ is N or D; $X_{139}$ is R or H; $X_{147}$ is T or A; $X_{153}$ is T or K; $X_{155}$ is S or T; $X_{163}$ is S or T; $X_{166}$ is Q, R, or H; $X_{172}$ is A or T; $X_{173}$ is A or V; $X_{174}$ is T or L; $X_{177}$ is A or E; $X_{178}$ is E or D; $X_{179}$ is R, L, or K; $X_{180}$ is V or G; $X_{181}$ to $X_{184}$ inclusive is deleted, or is replaced with the sequence S-(L or M)-(E or D)-H-R; $X_{185}$ is E; $X_{186}$ is Y; $X_{187}$ is K or N; $X_{188}$ is K; $X_{190}$ is R or T; $X_{196}$ is G; $X_{201}$ is A or S; $X_{211}$ is V; $X_{212}$ is V or L; $X_{213}$ is D or E; $X_{215}$ is V or I; $X_{226}$ is S or R; $X_{244}$ is K or R; $X_{251}$ is Q or H; $X_{254}$ is V or I; $X_{255}$ is S or N; $X_{257}$ is E or G; $X_{264}$ is T or A; $X_{274}$ is C or G; $X_{275}$ is V or I; $X_{280}$ is K or R; $X_{281}$ is S or N; $X_{285}$ is K or D; $X_{286}$ is K or R; $X_{287}$ is D or is deleted; $X_{288}$ is R or is deleted; $X_{289}$ is I or L; $X_{291}$ is T or M; $X_{293}$ is K or Q; $X_{297}$ is T or K; $X_{299}$ is I, T, or V; $X_{301}$ is R or H; $X_{303}$ is N or D; $X_{305}$ is K; $X_{307}$ is R; $X_{309}$ is Q; $X_{311}$ is R; $X_{315}$ is Y or H; $X_{318}$ is S or F; $X_{321}$ is E or D; $X_{326}$ is P or S; $X_{327}$ is C or L; and $X_{328}$ is S, G, or Q. In various embodiments, the modified p40 polypeptide comprises an amino acid sequence having at least about 90%, 92%, 95%, 96%, 97%, 98%, or 99% amino acid sequence identity to the mature polypeptide region (amino acid residue positions 23–328) of SEQ ID NO:39. In another embodiment, the modified p40 polypeptide comprises an amino acid sequence identified herein as the mature polypeptide region (amino acid residue positions 23–328) of SEQ ID NO:39.

The modified p40 polypeptide may further comprise a leader peptide sequence having at least about 90%, 92%, 95%, 96%, 97%, 98%, or 99% amino acid sequence identity to the amino acid sequence M-$X_2$-$X_3$-QQLV-$X_8$-SWFSLV-$X_{15}$-LASPL-$X_{21}$-A, identified herein as the leader peptide region (amino acid residue positions 1–22) of SEQ ID NO:39, or a conservatively substituted variation thereof where $X_2$ is C or H; $X_3$ is H or P; $X_8$ is I or V; $X_{15}$ is F or L; and $X_{21}$ is V or M.

In other embodiments, the present invention provides a modified p40 polypeptide comprising a conservatively modified variation of the amino acid sequence identified herein as the mature polypeptide region (amino acid residue positions 23–328) of SEQ ID NO:39, and, optionally, comprising a conservatively modified variation of the leader peptide region (amino acid residue positions 1–22) of SEQ ID NO:39. The invention also provides a fragment of said polypeptide having proliferative activity in a human T-cell based assay or interferon-gamma induction activity in a human T-cell based assay. In other embodiments, the invention includes a modified p40 polypeptide comprising the amino acid sequence identified herein as the mature polypeptide region (amino acid residue positions 23–328) of SEQ ID NO:39, and, optionally, comprising the leader peptide region (amino acid residue positions 1–22) of SEQ ID NO:39, and a polypeptide or a fragment of said polypeptide having proliferative activity or interferon-gamma induction activity in a T-cell based assay (such as, e.g., a human T-cell based assay), in the presence of a p35 polypeptide (such as, e.g., a wt-p35 polypeptide or a modified p35 polypeptide).

The invention also provides a polypeptide comprising a leader peptide sequence having at least about 90% amino acid sequence identity to the amino acid sequence M-$X_2$-$X_3$-QQLV-$X_8$-SWFSLV-$X_{15}$-LASPL-$X_{21}$-A, identified herein as the leader peptide region (amino acid residue positions 1–22) of SEQ ID NO:39, where $X_2$ is C or H; $X_3$ is H or P; $X_8$ is I or V; $X_{15}$ is F or L; and $X_{21}$ is V or M. In various embodiments, the leader peptide sequence encoded by the nucleic acid of the invention comprises an amino acid sequence having at least about 90%, 92%, 95%, 96%, 97%, 98%, or 99% amino acid sequence identity to leader peptide region (amino acid residues 1–22) of SEQ ID NO:39. In other embodiments, the leader peptide sequence comprises the sequence identified as the leader peptide region (amino acid residue positions 1–22) of SEQ ID NO:39, or a conservatively modified variation thereof. Each of the single letters in the amino acid sequences presented above represents a particular amino acid residue, according to standard practice known to those of ordinary skill in the art.

Modified p35 Polypeptides

An isolated or recombinant modified p35 polypeptide of the invention includes a polypeptide comprising a mature polypeptide region of a sequence selected from SEQ ID NO:26 to SEQ ID NO:35, conservatively modified variations thereof, and fragments thereof having proliferative activity in a T-cell based assay or interferon-gamma induction activity in a T-cell based assay. An alignment of exemplary modified p35 polypeptide sequences according to the invention is provided in FIG. 11. Alignment of the polypeptide sequences of the invention to each other or to sequences of known, naturally-occurring p35 polypeptides is readily performed by one of ordinary skill in the art using publicly available databases and alignment programs. Sequences of known, naturally-occurring p35 polypeptides from human and non-human sources are readily available from a variety of sources, such as GenBank or SWISSPROT.

The modified p35 polypeptide of the invention comprises at least one modification at a position equivalent to that in the amino acid sequence of a human p35 polypeptide (SEQ ID NO:36). The modification can include:

(a) a substitution of the specified amino acid for a different amino acid at least one equivalent position selected from Thr91, Met120, Ala121, Val212, Thr213, and Ala218;

(b) a insertion of at least one of the amino acid residues Phe-His-Leu between equivalent positions Leu19 and Ser20;

(c) a deletion of the amino acid at equivalent position Pro36.

The modified p35 polypeptide may optionally include at least two of modification (a), (b) or (c). The modified p35 polypeptide sequence may be a modified sequence of a naturally-occurring p35 polypeptide sequence of a mammal (e.g., human, a non-human primate, a ruminant, or a rodent), preferably a primate, more preferably human. For purposes of clarity, the numbering of amino acid positions corresponds to that of a human p35 polypeptide sequence (SEQ ID NO:36); however, it is understood that such modification may be made in an equivalent position of any p35 polypeptide sequence.

An "equivalent position", or a "position equivalent to", refers to a position related by sequence homology to a specified position of the comparison sequence (in this case, SEQ ID NO:36). For example, in FIG. 11 the amino acid sequence of a human p35 polypeptide (SEQ ID NO:36) and exemplary modified p35 polypeptide sequences of the invention (SEQ ID NO:26 to SEQ ID NO:35) are aligned to provide the maximum amount of homology between the sequences. A comparison of these sequences shows that there are a number of conserved residues contained in each sequence. As can be seen, there are also a number of insertions and deletions in the exemplary modified p35 sequences as compared to the human p35 sequence.

Thus, for example, inspection of FIG. 11 shows that the amino acid position equivalent to amino acid 23 in human p35 (i.e., the "equivalent position" to amino acid 23), is 26 in the modified p35 polypeptide sequence SEQ ID NO:26 (owing to the insertion of Pro-His-Lys between equivalent position 19 and 20 of SEQ ID NO:36).

In one embodiment, a modified p35 polypeptide of the invention comprises at least one substitution at a position equivalent to that of the amino acid sequence of human p35 polypeptide (SEQ ID NO:36), selected from the group consisting of: Thr91(Ala or Ile), Met120Thr, Ala121Thr, Val212Met, Thr213Met, and Ala218Ser. In other embodiments, a modified p35 polypeptide of the invention comprises at least 2, 3, 4, or 5 of the above substitutions. In another embodiment, a modified p35 polypeptide comprises all of the above substitutions.

A modified p35 polypeptide of the invention optionally further comprises at least one of the following substitutions in a position equivalent to that of SEQ ID NO:36: Cys2Tyr; Ala4(Leu or Pro); Ser6Gly; Val10Ile; Ala11Ser; Asp17His; Ala22Gly; Asn24Ser; Val27Thr; Ala28Thr; Pro30Ala; Asp31(Ser or Gly); Met34Arg; Phe35(Ser or Leu); Pro36 (deleted); His39Asp; His40Tyr; Arg46Lys; Val48Ala; Met51Thr; Lys54Arg; Thr58Ile; Pro63Ser; Ile69Thr; Lys76Gln; Lys92Thr; Asn98Ala; Glu101Gly; Thr102Ile; Phe104Leu; Leu124His; Ser125Gly; Val136Met; Thr140Ala; Asp148Asn; Ala161Thr; Val162Ala; Asp164Ala; Met167Leu; Phe172Val; Val177Ala; Ser181Pro; Pro186Leu; Asp210Asn; and insertion of one or more of 220Leu; 221Glu; 222Ser; and 223Ser.

The modified p35 polypeptide sequence may be a modification of a naturally-occurring p35 polypeptide sequence of a mammal (e.g., human, a non-human primate, a ruminant, or a rodent), preferably a primate, more preferably human. The naturally-occurring p35 polypeptide sequence may be one encoded by one of the following nucleic acid sequences having GenBank accession number: M65271, M65291 (human); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (*Equus caballus*, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse). The naturally-occurring p35 polypeptide sequence is more preferably a primate sequence, still more preferably a human sequence, most preferably a mature human p35 sequence comprising amino acid residues 23 to 219 of SEQ ID NO:36.

The invention also includes an isolated or recombinant polypeptide comprising an amino acid sequence containing at least 10 contiguous amino acid residues of any one of SEQ ID NOS:26–35. The polypeptide typically includes one or more amino acid substitution, at an equivalent position to that of SEQ ID NO:36, selected from: Thr91(Ala or Ile), Met120Thr, Ala121Thr, Val212Met, Thr213Met, and Ala218Ser. The polypeptide optionally includes one or more substitution selected from: Cys2Tyr; Ala4(Leu or Pro); Ser6Gly; Val10Ile; Ala11Ser; Asp17His; Ala22Gly; Asn24Ser; Val27Thr; Ala28Thr; Pro30Ala; Asp31(Ser or Gly); Met34Arg; Phe35(Ser or Leu); Pro36(deleted); His39Asp; His40Tyr; Arg46Lys; Val48Ala; Met51Thr; Lys54Arg; Thr58Ile; Pro63Ser; Ile69Thr; Lys76Gln; Lys92Thr; Asn98Ala; Glu101Gly; Thr102Ile; Phe104Leu; Leu124His; Ser125Gly; Val136Met; Thr140Ala; Asp148Asn; Ala161Thr; Val162Ala; Asp164Ala; Met167Leu; Phe172Val; Val177Ala; Ser181Pro; Pro186Leu; Asp210Asn; and insertion of one or more of 220Leu; 221Glu; 222Ser; and 223Ser.

In various embodiments, the polypeptide comprises, e.g., at least 15, at least 20, at least 30, at least 50, at least 75, at least 100, at least 150, at least 170, or at least 180 contiguous amino acid residues of any one of SEQ ID NOS:26–35 and SEQ ID NO:40. In another embodiment, the polypeptide comprises at least 185, 190, 195, or 200 contiguous amino acid residues of the mature polypeptide region of any one of SEQ ID NOS:26–35 and SEQ ID NO:40.

Fragments of the modified p35 polypeptides described herein are also a feature of the invention. A modified p35 polypeptide fragment of the invention typically comprises a modified p35 polypeptide comprising at least about 20, 25, or 30, and typically at least about 40, 50, 60, 70, 80, 90, or 100 contiguous amino acid residues of any one of SEQ ID NOS:26–35 or SEQ ID NO:40. In other embodiments, the fragment comprises usually at least about 100, 110, 120, 130, 140, 150, 160, 170, 180, 185, 190, 192, 193, 194, 195, 196, 197, 198, 199, 200, 201, 202, 203, 204, or 205 contiguous amino acid residues of any one of SEQ ID NOS:8–14 or SEQ ID NO:40. Such polypeptide fragments may have proliferative activity or interferon-gamma induction activity in a T-cell based assay (such as, e.g., a human T-cell based assay), in the presence of a p40 polypeptide (such as, e.g., a wt-p40 polypeptide or a modified p40 polypeptide).

In other embodiments, the invention provides polypeptides having a length of at least about 190 amino acids, and in some such embodiments, such polypeptides have proliferative activity or interferon-gamma induction activity in a T-cell based assay (such as, e.g., a human T-cell based assay), in the presence of a p40 polypeptide (such as, e.g., a wt-p40 polypeptide or a modified p40 polypeptide).

In other embodiments, the invention provides a polypeptide comprising at least 190, 195, or 200 contiguous amino acid residues of a protein encoded by a coding polynucleotide sequence comprising any of the following: (a) SEQ ID NO:16 to SEQ ID NO:25; (b) a coding polynucleotide sequence that encodes a first polypeptide selected from any of SEQ ID NO:26 to SEQ ID NO:35 or SEQ ID NO:40; and (c) a complementary polynucleotide sequence that hybridizes under at least highly stringent (or ultra-high stringent or ultra-ultra-high stringent conditions) hybridization conditions over substantially the entire length of a polynucleotide sequence of (a) or (b). Such polypeptides may have proliferative activity in a T-cell-based assay (or other similar assay), and/or interferon-gamma induction activity in a T-cell-based assay (or other similar assay). The polypeptides and nucleic acids of the subject invention need not be identical, but can be substantially identical to the corresponding sequence of the target molecule or related molecule, including the polypeptides of any of SEQ ID NOS: 26–35 or SEQ ID NO:40 or fragments thereof (including those having T-cell proliferative or interferon-gamma induction activities in the assays described herein), or the nucleic acids of any of SEQ ID NOS:16–25 or fragments thereof (including those having T-cell proliferative or interferon-gamma induction activities in the assays described herein). The polypeptides can be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) or having a percent identity to a sequence in the naturally occurring or known p35 polypeptide molecule.

In other embodiments, the invention provides a modified p35 polypeptide comprising an amino acid sequence having at least about 90% amino acid sequence identity to the sequence identified herein as the mature polypeptide region (amino acid residue positions 23–219) of SEQ ID NO:40: R-$X_{24}$-LP-$X_{27}$-$X_{28}$-T-$X_{30}$-$X_{31}$-PG-$X_{34}$-$X_{35}$-$X_{36}$-CL-$X_{39}$-$X_{40}$-SQNLL-$X_{46}$-A-$X_{48}$-SN-$X_{51}$-LQ-$X_{54}$-A-$X_{56}$-Q-$X_{58}$-LEFY-$X_{63}$-CTSEE-$X_{69}$-DHEDIT-$X_{76}$-DKTSTVEA- CLPLEL-$X_{91}$-$X_{92}$-NESCL-$X_{98}$-SR-$X_{101}$-$X_{102}$-S-$X_{104}$-ITNGSCLASRKTSFM-$X_{120}$-$X_{121}$-LC-$X_{124}$-$X_{125}$-SIYEDLKMYQ-$X_{136}$-EFK-$X_{140}$-MNAKLLM-$X_{148}$-PKRQIFLDQNML-$X_{161}$-$X_{162}$-I-$X_{164}$-EL-$X_{167}$-QALN-$X_{172}$-NSET-$X_{177}$-PQK-$X_{181}$-SLEE-$X_{186}$-DFYKTKIKLCILLHAFRIRAVTI-$X_{210}$-R-$X_{212}$-$X_{213}$-SYLN-$X_{218}$-S, or a conservatively substituted variation thereof, where $X_{24}$ is N or S; $X_{27}$ is V or T; $X_{28}$ is A or T; $X_{30}$ is P or A; $X_{31}$ is D, S, or G; $X_{34}$ is M or R; $X_{35}$ is F, S, or L; $X_{36}$ is P or is deleted; $X_{39}$ is H or D; $X_{40}$ is H or Y; $X_{46}$ is R or K; $X_{48}$ is V or A; $X_{51}$ is M or T; $X_{54}$ is K or R; $X_{56}$ is K or R; $X_{58}$ is T or I; $X_{63}$ is P or S; $X_{69}$ is I or T; $X_{76}$ is K or Q; $X_{91}$ is A or I; $X_{92}$ is K or T; $X_{98}$ is N or A; $X_{101}$ is E or G; $X_{102}$ is T or I; $X_{104}$ is F or L; $X_{120}$ is T; $X_{121}$ is T; $X_{124}$ is L or H; $X_{125}$ is S or G; $X_{136}$ is V or M; $X_{140}$ is T or A; $X_{148}$ is D or N; $X_{161}$ is A or T; $X_{162}$ is V or A; $X_{164}$ is D or A; $X_{167}$ is M or L; $X_{172}$ is F or V; $X_{177}$ is V or A; $X_{181}$ is S or P; $X_{186}$ is P or L; $X_{210}$ is D or N; $X_{212}$ is M; $X_{213}$ is M; and $X_{218}$ is S. In various embodiments, the modified p35 polypeptide comprises an amino acid sequence having at least about 90%, 92%, %, 95%, 96%, 97%, 98%, or 99% amino acid sequence identity to the mature polypeptide region (amino acid residue positions 23–219) of SEQ ID NO:40. The invention also includes a polynucleotide sequence encoding said polypeptide or a fragment of said polypeptide having proliferative activity in a human T-cell based assay or interferon-gamma induction activity in a human T-cell based assay.

The modified p35 polypeptide of the invention may further comprise a leader peptide sequence having at least about 90%, 92%, 95%, 96%, 97%, 98%, or 99% amino acid sequence identity to the amino acid sequence M-$X_2$-P-$X_4$-R-$X_6$-LLL-$X_{10}$-$X_{11}$-TLVLL-$X_{17}$-HLSL-$X_{22}$, identified herein as the leader peptide region (amino acid residue positions 1–22) of SEQ ID NO:40, or a conservatively substituted variation thereof, where $X_2$ is C or Y; $X_4$ is A, L or P; $X_6$ is S or G; $X_{10}$ is V or I; $X_{11}$ is A or S; $X_{17}$ is D or H; and $X_{22}$ is A or G, and optionally includes an insertion of the amino acids P-H-L between positions 18 and 19. Each of the single letters in the amino acid sequences presented above represents a particular amino acid residue, according to standard practice known to those of ordinary skill in the art.

The present invention also includes a modified p35 polypeptide comprising a conservatively modified variation of the amino acid sequence identified herein as the mature polypeptide region (amino acid residue positions 23–219) of SEQ ID NO:40, and, optionally, a conservatively modified variation of the leader peptide region (amino acid residue positions 1–22) of SEQ ID NO:40, and a polynucleotide sequence encoding said polypeptide or a fragment of said polypeptide having proliferative activity in a human T-cell based assay or interferon-gamma induction activity in a human T-cell based assay. The invention also includes a modified p35 polypeptide comprising the amino acid sequence identified herein as the mature polypeptide region (amino acid residue positions 23–219) of SEQ ID NO:40, and, optionally, comprising the leader peptide region (amino acid residue positions 1–22) of SEQ ID NO:40, and a polypeptide or a fragment of said polypeptide having proliferative activity in a human T-cell based assay or interferon-gamma induction activity in a human T-cell based assay.

The invention also includes a polypeptide comprising a leader peptide sequence having at least about 90% amino acid sequence identity to the amino acid sequence M-$X_2$-P-$X_4$-R-$X_6$-LLL-$X_{10}$-$X_{11}$-TLVLL-$X_{16}$-HLSL-$X_{22}$, identified herein as the leader peptide region (amino acid residue positions 1–22) of SEQ ID NO:40, where $X_2$ is C or Y; $X_4$ is A, L, or P; $X_6$ is S or G; $X_{10}$ is V or I; $X_{11}$ is A or S; $X_{16}$ is D or H; $X_{22}$ is A or G, and optionally includes an insertion of the amino acids P-H-L between positions 18 and 19. In various embodiments, the leader peptide sequence comprises an amino acid sequence having at least about 90%, 92%, 95%, 96%, 97%, 98%, or 99% amino acid sequence identity to leader peptide region (amino acid residue positions 1–22) of SEQ ID NO:40. In another embodiment, the leader peptide sequence comprises the sequence identified as the leader peptide region (amino acid residue positions 1–22) of SEQ ID NO:40, or a conservatively modified variation thereof. Each of the single letters in the amino acid sequences presented above represents a particular amino acid residue, according to standard practice known to those of ordinary skill in the art.

Sequence Variations

The polypeptides and nucleic acids of the subject invention need not be identical, but can be substantially identical to the corresponding sequence of the target molecule or related molecule, including the polypeptides of any of SEQ ID NOS:8–14, 26–35, 37, 38 or fragments thereof (including those having T-cell proliferative or interferon-gamma induction activities in the assays described herein), or the nucleic acids of any of SEQ ID NOS:1–7, SEQ ID NOS:16–25 or fragments thereof (including those having T-cell proliferative or interferon-gamma induction activities in the assays described herein). The polypeptides can be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) or having a percent identity to a sequence in the naturally occurring or known p40 or p35 polypeptide molecule.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci.* (*USA*) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected.

The term sequence identity means that two polynucleotide sequences are identical (i.e., on a nucleotide-by-nucleotide basis) over a window of comparison. The term "percentage of sequence identity" or "percent sequence identity" is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity. In one aspect, the present invention provides modified p40 nucleic acids having at least about 90%, 92%, 95%, 96%, 97%, 98%, 99%, 99.5% or more percent sequence identity with the nucleic acids of any of SEQ ID NOS:1–7 or fragments thereof. In another aspect, the present invention provides modified p35 nucleic acids having at least about 90%, 92%, 95%, 96%, 97%, 98%, 99%, 99.5% or more percent sequence identity with the nucleic acids of any of SEQ ID NOS:16–25 or fragments thereof.

As applied to polypeptides, the term substantial identity means that two peptide sequences, when optimally aligned, such as by the programs GAP or BESTFIT using default gap weights (described in detail below), share at least about 80 percent sequence identity, preferably at least about 85 percent sequence identity, more preferably at least about 90 percent sequence identity or more (e.g., 92, 95, 96, 97, 98, or 99 percent sequence identity). Preferably, residue positions which are not identical differ by conservative amino acid substitutions. Conservative amino acid substitutions typically refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Some preferred conservative amino acids substitution groups are: valine-leucine-isoleucine, phenylalanine-tyrosine, lysine-arginine, alanine-valine, and asparagine-glutamine. In one aspect, the present invention provides modified p40 polypeptides having at least about 90%, 92%, 95%, 96%, 97%, 98% 99% 99.5% or more percent sequence identity with the polypeptides of any of SEQ ID NOS:8–14, SEQ ID NO:39, or fragments thereof. In another aspect, the present invention provides modified p35 polypeptides having at least about 80%, 85%, 90%, 92%, 95%, 96%, 97%, 98% 99% 99.5% or more percent sequence identity with the polypeptides of any of SEQ ID NOS: 26–35, SEQ ID NO:40, or fragments thereof.

A preferred example of an algorithm that is suitable for determining percent sequence identity and sequence similarity is the FASTA algorithm, which is described in Pearson, W. R. & Lipman, D. J., 1988, *Proc. Nat'l Acad. Sci. USA* 85: 2444. See also W. R. Pearson, 1996, *Methods Enzymol.* 266: 227–258. Preferred parameters used in a FASTA alignment of DNA sequences to calculate percent identity are optimized, BL50 Matrix 15: -5, k-tuple=2; joining penalty=40, optimization=28; gap penalty -12, gap length penalty=-2; and width=16.

Another preferred example of algorithm that is suitable for determining percent sequence identity and sequence similarity are the BLAST and BLAST 2.0 algorithms, which are described in Altschul et al., 1977, *Nuc. Acids Res.* 25: 3389–3402 and Altschul et al., 1990, *J. Mol. Biol.* 215: 403–410, respectively. BLAST and BLAST 2.0 are used with the parameters described herein to determine percent sequence identity for the nucleic acids and proteins of the invention. Software for performing BLAST analyses is publicly available through the National Center for Biotechnology Information (see ncbi website with the extension of "nlm.nih.gov"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff (1989) *Proc. Nat'l Acad. Sci. U.S.A.* 89: 10915) alignments (B) of 50, expectation (E) of 10, M=5, N=-4, and a comparison of both strands.

The BLAST algorithm also performs a statistical analysis of the similarity between two sequences (see, e.g., Karlin & Altschul (1993) *Proc. Nat'l Acad. Sci. U.S.A.* 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35: 351–360. The method used is similar to the method described by Higgins & Sharp (1989) *CABIOS* 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. (1984) Nuc. Acids Res. 12: 387–395.

Another preferred example of an algorithm that is suitable for multiple DNA and amino acid sequence alignments is the CLUSTALW program (Thompson, J. D. et al. (1994) Nucl. Acids. Res. 22: 4673–4680). CLUSTALW performs multiple pairwise comparisons between groups of sequences and assembles them into a multiple alignment based on homology. For the initial pairwise alignments, Gap open and Gap extension penalties were 10 and 0.1, respectively. For the multiple alignments, Gap open penalty was 10, and the Gap extension penalty was 0.05. For amino acid alignments, the BLOSUM62 substitution matrix can be used as a protein weight matrix (Henikoff and Henikoff (1992) Proc. Nat'l Acad. Sci. U.S.A. 89: 10915–10919). CLUSTALW can be obtained from, for example, the Vector NTI sequence analysis suite, e.g., version 6 (InforMax, Inc., North Bethesda, Md.).

Conservatively Modified Variations

Polypeptides of the present invention include conservatively modified variations of the sequences disclosed herein as SEQ ID NO:8 to SEQ ID NO:14 and SEQ ID NO:26 to SEQ ID NO:35. Such conservatively modified variations comprise substitutions, additions or deletions which alter, add or delete a single amino acid or a small percentage of amino acids (typically less than about 5%, more typically less than about 4%, 2%, or 1%) in any of the mature polypeptide sequences of SEQ ID NO:8 to SEQ ID NO:14 and SEQ ID NO:26 to SEQ ID NO:35.

For example, a conservatively modified variation (e.g., deletion) of the 302 amino acid mature polypeptide identified herein as amino acid residues 23 to 324 SEQ ID NO:8 will have a length of at least 287 amino acids, preferably at least 290 amino acids, more preferably at least 296 amino acids, and still more preferably at least 299 amino acids, corresponding to a deletion of less than about 5%, 4%, 2% or 1% of the polypeptide sequence.

Another example of a conservatively modified variation (e.g., a "conservatively substituted variation") of the mature portion of the polypeptide identified herein as SEQ ID NO:8 will contain "conservative substitutions," as shown, for example, in the six substitution groups set forth in Table 5 (supra), in up to about 15 residues (i.e., less than about 5%) of the 302 amino acid mature polypeptide.

The polypeptides of the invention, including conservatively substituted sequences, can be present as mature polypeptides (e.g., lacking leader sequences corresponding to amino acid residues 1–22 in each of SEQ ID NO:8 to SEQ ID NO:14 and SEQ ID NO:28 to SEQ ID NO:35, and amino acid residues 1–25 of SEQ ID NO:26 and SEQ ID NO:27); as comprising any one of the unique leader sequences identified as amino acid residues 1–22 of SEQ ID NO:8, SEQ ID NO:9, SEQ ID NO:11, SEQ ID NO:13; SEQ ID NO:28 and SEQ ID NO:29, and as amino acid residues 1–25 of SEQ ID NO:26 and SEQ ID NO:27); as part of larger polypeptide sequences such as occur upon the addition of one or more domains for purification of the protein (e.g., poly-His segments, FLAG epitope segments, etc.), e.g., where the additional functional domains have little or no effect on the activity of the p35 or p40 portion of the protein, or where the additional domains can be removed by post synthesis processing steps such as by treatment with a protease.

In another embodiment, a mature modified p40 polypeptide of the present invention comprises the following sequence (amino acid residue positions 23–238 of SEQ ID NO:39): IWEL-$X_{27}$-K-$X_{29}$-VYVVELDWYP-$X_{40}$-APGE-$X_{45}$-VVL-$X_{49}$-CDTPEEDGITWT-$X_{62}$-DQSS-$X_{67}$-VLG-$X_{71}$-GKTLTI-$X_{78}$-VKEFGDAGQYTC-$X_{91}$-KGG-$X_{95}$-$X_{96}$-LS-$X_{99}$-SLLLLHKKEDGIWSTDILKDQK-$X_{122}$-PK-$X_{125}$-K-$X_{127}$-FL-$X_{130}$-CEAK-$X_{135}$-YSG-$X_{139}$-FTCWWLT-$X_{147}$-ISTDL-$X_{153}$-F-$X_{155}$-VKSSRGS-$X_{163}$-DP-$X_{166}$-GVTCG-$X_{172}$-$X_{173}$-$X_{174}$-LS-$X_{177}$-$X_{178}$-$X_{179}$-$X_{180}$-$X_{181}$-$X_{182}$-$X_{183}$-$X_{184}$-$X_{185}$-$X_{186}$-$X_{187}$-$X_{188}$-Y-$X_{190}$-VECQE-$X_{196}$-SACP-$X_{201}$-AEESLPIEV-$X_{211}$-$X_{212}$-$X_{213}$-A-$X_{215}$-HKLKYENYTS-$X_{226}$-FFIRDIIKPDPPKNLQL-$X_{244}$-PLKNSR-$X_{251}$-VE-$X_{254}$-$X_{255}$-W-$X_{257}$-YPDTWS-$X_{264}$-PHSYFSLTF-$X_{274}$-$X_{275}$-QVQG-$X_{280}$-$X_{281}$-KRE-$X_{285}$-$X_{286}$-$X_{287}$-$X_{288}$-$X_{289}$-F-$X_{291}$-D-$X_{293}$-TSA-$X_{297}$-V-$X_{299}$-C-$X_{301}$-K-$X_{303}$-A-$X_{305}$-I-$X_{307}$-V-$X_{309}$-A-$X_{311}$-DRY-$X_{315}$-SS-$X_{318}$-WS-$X_{321}$-WASV-$X_{326}$-$X_{327}$-$X_{328}$, or a conservatively substituted variation thereof, where $X_{27}$ is K or E; $X_{29}$ is D or N; $X_{40}$ is D or N; $X_{45}$ is M or T; $X_{49}$ is T or A; $X_{62}$ is S; $X_{67}$ is E or G; $X_{71}$ is T; $X_{78}$ is H; $X_{91}$ is H or R; $X_{95}$ is E, A, K, or T, $X_{96}$ is V or A; $X_{99}$ is R or Q; $X_{122}$ is E or K; $X_{125}$ is N or A; $X_{127}$ is S or I; $X_{130}$ is K; $X_{135}$ is N or D; $X_{139}$ is R or H; $X_{147}$ is T or A; $X_{153}$ is T or K; $X_{155}$ is S or T; $X_{163}$ is S or T; $X_{166}$ is Q, R, or H; $X_{172}$ is A or T; $X_{173}$ is A or V; $X_{174}$ is T or L; $X_{177}$ is A or E; $X_{178}$ is E or D; $X_{179}$ is R, L, or K; $X_{180}$ is V or G; $X_{181}$ to $X_{184}$ inclusive is deleted or is replaced with the sequence S-(L or M)-(E or D)-H-R; $X_{185}$ is E; $X_{186}$ is Y; $X_{187}$ is K or N; $X_{188}$ is K; $X_{190}$ is R or T; $X_{196}$ is G; $X_{201}$ is A or S; $X_{211}$ is V; $X_{212}$ is V or L; $X_{213}$ is D or E; $X_{215}$ is V or I; $X_{226}$ is S or R; $X_{244}$ is K or R; $X_{251}$ is Q or H; $X_{254}$ is V or I; $X_{255}$ is S or N; $X_{257}$ is E or G; $X_{264}$ is T or A; $X_{274}$ is C or G; $X_{275}$ is V or I; $X_{280}$ is K or R; $X_{281}$ is S or N; $X_{285}$ is K or D; $X_{286}$ is K or R; $X_{287}$ is D or is deleted; $X_{288}$ is R or is deleted; $X_{289}$ is I or L; $X_{291}$ is T or M; $X_{293}$ is K or Q; $X_{297}$ is T or K; $X_{299}$ is I, T, or V; $X_{301}$ is R or H; $X_{303}$ is N or D; $X_{305}$ is K; $X_{307}$ is R; $X_{309}$ is Q; $X_{311}$ is R; $X_{315}$ is Y or H; $X_{318}$ is S or F; $X_{321}$ is E or D; $X_{326}$ is P or S; $X_{327}$ is C or L; and $X_{328}$ is S, G, or Q. As defined above, a conservatively modified variation of the above sequence can include up to a total of about 15 amino acid deletions, insertions, or conservative substitutions in the 306 amino acid sequence, excluding the positions designated X, which correspond to the amino acid explicitly defined. The polypeptide may further comprise an N-terminal leader sequence M-$X_2$-$X_3$-QQLV-$X_8$-SWFSLV-$X_{15}$-LASPL-$X_{21}$-A (amino acid residue positions 1–22 of SEQ ID NO:39), or a conservatively modified variation thereof, where $X_2$ is C or H; $X_3$ is H or P; $X_8$ is I or V; $X_{15}$ is F or L; and $X_{21}$ is V or M.

In another embodiment, a mature modified p35 polypeptide of the present invention comprises the following sequence (amino acid residue positions 23–219 of SEQ ID NO:40): R-$X_{24}$-LP-$X_{27}$-$X_{28}$-T-$X_{30}$-$X_{31}$-PG-$X_{34}$-$X_{35}$-$X_{36}$-CL-$X_{39}$-$X_{40}$-SQNLL-$X_{46}$-A-$X_{48}$-SN-$X_{51}$-LQ-$X_{54}$-A-$X_{56}$-Q-$X_{58}$-LEFY-$X_{63}$-CTSEE-$X_{69}$-DHEDIT-$X_{76}$-DKT-STVEACLPLEL-$X_{91}$-$X_{92}$-NESCL-$X_{98}$-SR-$X_{101}$-$X_{102}$-S-$X_{104}$-ITNGSCLASRKTSFM-$X_{120}$-$X_{121}$-LC-$X_{124}$-$X_{125}$-SIYEDLKMYQ-$X_{136}$-EFK-$X_{140}$-MNAKLLM-$X_{148}$-PKRQIFLDQNML-$X_{161}$-$X_{162}$-I-$X_{164}$-EL-$X_{167}$-QALN-$X_{172}$-NSET-$X_{177}$-PQK-$X_{181}$-SLEE-$X_{186}$-DFYKTKIKLCILLHAFRIRAVTI-$X_{210}$-R-$X_{212}$-$X_{213}$-SYLN-$X_{218}$-S, or a conservatively substituted variation thereof, where $X_{24}$ is N or S; $X_{27}$ is V or T; $X_{28}$ is A or T; $X_{30}$ is P or A; $X_{31}$ is D, S, or G; $X_{34}$ is M or R; $X_{35}$ is F, S, or L; $X_{36}$ is P or is deleted; $X_{39}$ is H or D; $X_{40}$ is H or Y; $X_{46}$ is R or K; $X_{48}$ is V or A; $X_{51}$ is M or T; $X_{54}$ is K or R; $X_{56}$ is K or R; $X_{58}$ is T or I; $X_{63}$ is P or S; $X_{69}$ is I or T; $X_{76}$ is K or Q; $X_{91}$ is A or I; $X_{92}$ is K or T; $X_{98}$ is N or A; $X_{101}$ is E or G; $X_{102}$ is T or I; $X_{104}$ is F or L; $X_{120}$ is T; $X_{121}$ is T; $X_{124}$ is L or H; $X_{125}$ is S or G; $X_{136}$ is V or M; $X_{140}$ is T or A; $X_{148}$ is D or N; $X_{161}$ is A or T; $X_{162}$ is V or A; $X_{164}$ is D or A; $X_{167}$ is M or L; $X_{172}$ is F or V; $X_{177}$ is V or A; $X_{181}$ is S or P; $X_{186}$ is P or L; $X_{210}$ is D or N; $X_{212}$ is M; $X_{213}$ is M; and $X_{218}$ is S. As defined above, a conservatively modified variation of the above sequence can include up to a total of about 10 amino acid deletions, insertions, or conservative substitutions in the 219 amino acid sequence, excluding the positions designated X, which correspond to the amino acid explicitly defined. The polypeptide may further comprise the N-terminal leader sequence M-$X_2$-P-$X_4$-R-$X_6$-LLL-$X_{10}$-$X_{11}$-TLVLL-$X_{17}$-HLSL-$X_{22}$ (amino acid residue positions 1–22 of SEQ ID NO:40), or a conservatively modified variation thereof, where $X_2$ is C or Y; $X_4$ is A, L or P; $X_6$ is S or G; $X_{10}$ is V or I; $X_{11}$ is A or S; $X_{17}$ is D or H; and $X_{22}$ is A or G.

Making Polypeptides of the Invention

Recombinant methods for producing and isolating polypeptides of the invention are described above. In addition to recombinant production, the polypeptides may be produced by direct peptide synthesis using solid-phase techniques (cf Stewart et al. (1969) *Solid-Phase Peptide Synthesis*, WH Freeman Co, San Francisco; Merrifield J (1963) *J. Am. Chem. Soc.* 85:2149–2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide full-length polypeptides. Fragments of the polypeptides of the invention, as discussed in greater detail above, are also a feature of the invention and may be synthesized by using the procedures described above.

Polypeptides of the invention can be produced by introducing into a population of cells a nucleic acid of the invention, wherein the nucleic acid is operatively linked to a regulatory sequence effective to produce the encoded polypeptide, culturing the cells in a culture medium to produce the polypeptide, and optionally isolating the polypeptide from the cells or from the culture medium.

In another aspect, polypeptides of the invention can be produced by introducing into a population of cells a recombinant expression vector comprising at least one nucleic acid of the invention, wherein the at least one nucleic acid is operatively linked to a regulatory sequence effective to produce the encoded polypeptide, culturing the cells in a culture medium under suitable conditions to produce the polypeptide encoded by the expression vector, and optionally isolating the polypeptide from the cells or from the culture medium.

Using Polypeptides of the Invention

Antibodies

In another aspect of the invention, a polypeptide of the invention is used to produce antibodies which have, e.g., diagnostic and therapeutic uses, e.g., related to the activity, distribution, and expression of p35 sequences or p40 sequences.

Antibodies to polypeptides of the invention may be generated by methods well known in the art. Such antibodies may include, but are not limited to, polyclonal, monoclonal, chimeric, humanized, single chain, Fab fragments and fragments produced by an Fab expression library. Antibodies, i.e., those which block receptor binding, are especially preferred for therapeutic use.

Polypeptides for antibody induction do not require biological activity; however, the polypeptide or oligopeptide must be antigenic. Peptides used to induce specific antibodies may have an amino acid sequence consisting of at least 10 amino acids, preferably at least 15 or 20 amino acids. Short stretches of a polypeptide of the invention may be fused with another protein, such as keyhole limpet hemocyanin, and antibody produced against the chimeric molecule.

Methods of producing polyclonal and monoclonal antibodies are known to those of skill in the art, and many antibodies are available. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1·M, preferably at least about 0.01·M or better, and most typically and preferably, 0.001·M or better.

Detailed methods for preparation of chimeric (humanized) antibodies can be found in U.S. Pat. No. 5,482,856. Additional details on humanization and other antibody production and engineering techniques can be found in Borrebaeck (ed) (1995) *Antibody Engineering, $2^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul).

In one useful embodiment, this invention provides for fully humanized antibodies against the polypeptides of the invention. Humanized antibodies are especially desirable in applications where the antibodies are used as therapeutics in vivo in human patients. Human antibodies consist of characteristically human immunoglobulin sequences. The human antibodies of this invention can be produced in using a wide variety of methods (see, e.g., Larrick et al., U.S. Pat. No. 5,001,065, and Borrebaeck McCafferty and Paul, supra, for a review). In one embodiment, the human antibodies of the present invention are produced initially in trioma cells. Genes encoding the antibodies are then cloned and expressed in other cells, such as nonhuman mammalian cells. The general approach for producing human antibodies by trioma technology is described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Adjuvants

In one aspect, the modified p40 polypeptides and/or the modified p35 polypeptides of the present invention or fragments thereof are useful as adjuvants to stimulate, enhance, potentiate, or augment an immune response related to an antigen when administered together with the antigen or after or before delivery of the antigen. In another aspect, the invention provides methods for administering one or more of the polypeptides invention described herein to a subject.

Therapeutic and Prophylactic Agents

As described in greater detail herein, the modified p40 polypeptides and/or the modified p35 polypeptides of the present invention or fragments thereof are useful in the prophylactic and/or therapeutic treatment of a variety of diseases, disorders, or medical conditions.

For example, the invention provides modified p40 polypeptides and/or modified p35 polypeptides (and nucleic acids which encode such polypeptides) that have both T-cell proliferation and interferon-gamma induction activities in the assays described herein.

Defining Polypeptides by Immunoreactivity

Because the polypeptides of the invention provide a variety of new polypeptide sequences as compared to other p35 and p40 sequences, the polypeptides also provide a new structural features which can be recognized, e.g., in immunological assays. The generation of antisera which specifically binds the polypeptides of the invention, as well as the polypeptides which are bound by such antisera, are a feature of the invention. The invention includes polypeptides that specifically bind to or that are specifically immunoreactive with an antibody or antisera generated against an immunogen comprising an amino acid sequence selected from one or more of SEQ ID NO:8 to SEQ ID NO:14 and SEQ ID NO:26 to SEQ ID NO:35. To eliminate cross-reactivity with other p40 polypeptides, the antibody or antisera is subtracted with available known p40 polypeptides, such as those p40 polypeptides encoded by nucleic acids represented by GenBank accession numbers: M65272 and M65290 (human), U19841 (*Macaca mulatta*, rhesus monkey), U19834 (*Cercocebus torquatus*, sooty mangabey), Y11129 (*Equus caballus*, horse), U83184, Y07762 and AF054607 (*Felis catus*, cat), U49100 and AF091134 (*Canis familiaris*, dog), U57752 and U10160 (*Cervus elaphus*, red deer), AF007576 (*Capra hircus*, goat), AF004024 (*Ovis aries*, sheep), U11815 (*Bos taurus*, cow), U08317 (*Sus scrofa*, pig), X97019 and AF082494 (*Marmota monax*, woodchuck), AF133197 and U16674 (*Rattus norvegicus*, rat), M86671 and S82426 (*Mus musculus*, mouse), AF097507 (*Cavia porcellus*, guinea pig), and AF046211 (*Mesocricetus auratus*, golden hamster) or any other known p40 polypeptides. Likewise, to eliminate cross-reactivity with other p35 polypeptides, the antibody or antisera is subtracted with available known p35 polypeptides, such as those p35 polypeptides encoded by nucleic acids represented by GenBank accession numbers M65271, M65291 (human); U19842 (*Macaca mulatta*, rhesus monkey), U19835 (*Cercocebus torquatus*, sooty mangabey), U83185, Y07761, AF054605 (*Felis catus*, cat), U49085 (*Canis familiaris*, dog), L35765 (*Sus scrofa*, pig), Y11130 (*Equus caballus*, horse), U14416 (*Bos taurus*, cow), U57751 (*Cervus elaphus*, red deer), AF173557 (*Ovis aries*, sheep), AF003542 (*Capra hircus*, goat), X97018 (*Marmota monax*, woodchuck), AF177031 (*Rattus norvegicus*, rat), and M86672, S82419 (*Mus musculus*, mouse), or any other known p35 polypeptides. These sequences are referred to herein as "the control (p40 or p35) polypeptides". Where the accession number corresponds to a nucleic acid, a polypeptide encoded by the nucleic acid is generated and used for antibody/antisera subtraction purposes. Where the nucleic acid corresponds to a non-coding sequence, e.g., a pseudo gene, an amino acid which corresponds to the reading frame of the nucleic acid is generated (e.g., synthetically), or is minimally modified to include a start codon for recombinant production.

In one typical format, the immunoassay uses a polyclonal antiserum which was raised against one or more polypeptide comprising sequences corresponding to one or more of: SEQ ID NO:8 to SEQ ID NO:14 and SEQ ID NO:26 to SEQ ID NO:35, or a substantial subsequence thereof (i.e., at least about 30%, 40%, 50%, 60%, 70%, 80%, 90%, 95% or 98% of the full length sequence provided). The full set of potential polypeptide immunogens derived from SEQ ID NO:8 to SEQ ID NO:14 and SEQ ID NO:26 to SEQ ID NO:35 are collectively referred to below as "the immunogenic polypeptides." The resulting antisera is optionally selected to have low cross-reactivity against the control p40 polypeptides or the control p35 polypeptides, and/or other known p40 or p35 polypeptides, and any such cross-reactivity is removed by immunoabsorption with one or more of the control p40 or p35 polypeptides and/or other known p40 or p35 polypeptides, prior to use of the polyclonal antiserum in the immunoassay.

In order to produce antisera for use in an immunoassay, one or more of the immunogenic polypeptides is produced and purified as described herein. For example, recombinant protein may be produced in a mammalian cell line. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, Harlow and Lane (1988) *Antibodies, A Laboratory Manual*, Cold Spring Harbor Publications, New York, for a standard description of antibody generation, immunoassay formats and conditions that can be used to determine specific immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide(s) in an immunoassay, for example, a solid phase immunoassay with one or more of the immunogenic proteins immobilized on a solid support. Polyclonal antisera with a titer of $10^6$ or greater are selected, pooled and subtracted with the control polypeptides to produce subtracted pooled titered polyclonal antisera.

The subtracted pooled titered polyclonal antisera are tested for cross reactivity against the control polypeptides. Preferably at least two of the immunogenic polypeptides are used in this determination, preferably in conjunction with at least two of the control polypeptides, to identify antibodies which are specifically bound by the immunogenic polypeptide(s).

In this comparative assay, discriminatory binding conditions are determined for the subtracted titered polyclonal antisera which result in at least about a 5–10 fold higher signal to noise ratio for binding of the titered polyclonal antisera to the immunogenic polypeptides as compared to binding to the control polypeptides. That is, the stringency of the binding reaction is adjusted by the addition of non-specific competitors such as albumin or non-fat dry milk, or by adjusting salt conditions, temperature, or the like. These binding conditions are used in subsequent assays for determining whether a test polypeptide is specifically bound by the pooled subtracted polyclonal antisera. In particular, test polypeptides which show at least a 2–5× higher signal to noise ratio than the control polypeptides under discriminatory binding conditions, and at least about a ½ signal to noise ratio as compared to the immunogenic polypeptide(s), shares substantial structural similarity with the immunogenic polypeptide as compared to known p40 or p35 polypeptides, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized polypeptide(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is determined as compared to the ability of the immunogenic polypeptide(s) to compete for binding to the antisera. Again, the percent cross-reactivity for the control polypeptides is calculated, using standard calculations. Where the percent cross-reactivity is at least 5–10× as high for the test polypeptides, the test polypeptides are said to specifically bind the pooled subtracted antisera.

In general, the immunoabsorbed and pooled antisera can be used in a competitive binding immunoassay as described herein to compare any test polypeptide to the immunogenic polypeptide(s). In order to make this comparison, the two polypeptides are each assayed at a wide range of concentrations and the amount of each polypeptide required to inhibit 50% of the binding of the subtracted antisera to the immobilized polypeptide is determined using standard techniques. If the amount of the test polypeptide required is less than twice the amount of the immunogenic polypeptide that is required, then the test polypeptide is said to specifically bind to an antibody generated to the immunogenic polypeptide, provided the amount is at least about 5–10× as high as for a control polypeptide.

As a final determination of specificity, the pooled antisera is optionally fully immunoabsorbed with the immunogenic polypeptide(s) (rather than the control polypeptides) until little or no binding of the resulting immunogenic polypeptide subtracted pooled antisera to the immunogenic polypeptide(s) used in the immunoabsorption is detectable. This fully immunoabsorbed antisera is then tested for reactivity with the test polypeptide. If little or no reactivity is observed (i.e., no more than 2× the signal to noise ratio observed for binding of the fully immunoabsorbed antisera to the immunogenic polypeptide), then the test polypeptide is specifically bound by the antisera elicited by the immunogenic polypeptide.

Properties of Modified P40 Polypeptides and Modified P35 Polypeptides of the Invention Any polypeptide of the invention may optionally form a dimer (e.g., a heterodimer or a homodimer) with either a p35 or a p40 polypeptide. As used herein, a "heterodimer" comprises a p35 and a p40 polypeptide, at least one of which may be a modified p35 polypeptide or a modified p40 polypeptide of the invention, while a "homodimer" comprises either two p40 polypeptides or two p35 polypeptides, at least one of which may be a modified p40 polypeptide or a modified p35 polypeptide of the invention. A homodimer need not comprise two identical polypeptides; for example, a p40 homodimer may comprise a naturally-occurring or wild-type p40 polypeptide and a modified p40 polypeptide, or two different modified p40 polypeptides. A heterodimer comprising a p35 polypeptide and a p40 polypeptide typically has an apparent molecular weight of ~70 to 75 kDa (see, for example, FIGS. 7 and 8); however, the apparent molecular weight may be higher or lower, depending on many factors, such as, for example, the length of the polypeptides forming the dimer, or the extent of glycosylation of the polypeptides.

A p35 polypeptide which forms a dimer (i.e., "dimerizes") with a polypeptide of the invention may be a naturally-occurring or wild-type p35 polypeptide, such as a human p35 polypeptide having a sequence comprising the mature polypeptide region of SEQ ID NO:36, or may be a modified p35 polypeptide, such as a modified p35 polypeptide of the present invention, such as, for example, a modified p35 polypeptide having a sequence comprising the mature polypeptide region of one of SEQ ID NO:26 to SEQ ID NO:35 and SEQ ID NO:40. Likewise, a p40 polypeptide which forms a dimer (i.e., "dimerizes") with a polypeptide of the invention may be a naturally-occurring or wild-type p40 polypeptide, such as a human p40 polypeptide having a sequence comprising the mature polypeptide region of SEQ ID NO:16, or may be a modified p40 polypeptide, such as a modified p40 polypeptide of the present invention, such as, for example, a modified p40 polypeptide having a sequence comprising the mature polypeptide region of one of SEQ ID NO:8 to SEQ ID NO:15 and SEQ ID NO:39.

A composition comprising a polypeptide of the invention (optionally in combination with a corresponding partner subunit polypeptide, e.g., a p35 polypeptide or p40 polypeptide as described above) may optionally exhibit one or more of the following activities: (a) T-cell proliferative activity, (b) IFN-γ induction activity, (c) Natural Killer (NK) cell-mediated toxicity enhancement activity.

A polypeptide of the invention has "T-cell proliferative activity" when the polypeptide or a composition comprising the polypeptide induces proliferation of phytohemagglutinin-activated T-lymphocytes, as evidenced by, for example, an increase in the $^3$H-thymidine incorporation of activated T-cells incubated in the presence of $^3$H-thymidine and the polypeptide or composition thereof, compared to activated T-cells incubated with $^3$H-thymidine alone.

A polypeptide of the invention has "IFN-γ induction activity" when the polypeptide or a composition comprising the polypeptide induces IFN-γ synthesis in T-lymphocytes (i.e., T-cells), as evidenced by, for example, an increase in IFN-γ in culture media of T-cells incubated in the presence of the polypeptide or composition thereof, compared to activated T-cells incubated without the polypeptide or composition thereof, respectively. IFN-γ in the culture medium may be assayed by any standard method, such as by using a commercially-available IFN-γ ELISA kit. Interferon-gamma induction activity in T-cells is indicative of differentiation of T-cells to the $T_H1$ phenotype.

A polypeptide of the invention has "NK cell toxicity enhancement activity" when the polypeptide or a composition comprising the polypeptide enhances NK cell-mediated toxicity against a target cell. Enhancement of NK cell toxicity is evidenced by, for example, an increase in $^{51}$Cr release into the culture supernatant from $^{51}$Cr-labeled target cells incubated with T-lymphocytes previously treated with the polypeptide or composition thereof, compared to that of $^{51}$Cr-labeled target cells incubated with T-lymphocytes which were not previously treated with the polypeptide or composition thereof, respectively.

The biological activities of exemplary polypeptides of the invention were examined as described in the Examples. The results indicate that a composition comprising a polypeptide of the invention may be used, for example, to induce proliferation of T-cells, to induce differentiation of naive T cells to $T_H1$ cells, to induce production of IFN-γ in lymphocytes, in in vitro, ex vivo or in vivo applications. Cytokines that induce IFN-γ production in vitro typically also enhance cytotoxicity of NK cells.

A polypeptide or nucleic acid of the invention or a composition comprising a polypeptide or a nucleic acid of the invention may be used in methods to promote cell-mediated immunity to a variety of infectious agents, such as bacterial, protozoal, intracellular parasitic, and viral infections, particularly in individuals who are highly susceptible to such infections, including patients undergoing surgery, patients with transiently or chronically impaired immune systems due to disease or drug therapy (e.g., chemotherapy, radiation or immunosuppressive treatments), individuals infected with HIV or otherwise manifest symptoms of AIDS or ARC, as well as elderly or otherwise immuno-compromised individuals who have reduced capacity to defend against opportunistic or infectious microorganisms. In particular, a composition comprising a polypeptide or a nucleic acid of the invention may be useful as a vaccine adjuvant, to enhance a vaccinated host's cell-mediated immunity for a protective response to a pathogen.

Malignant diseases are another useful target for treatment with modified p40/p35 heterodimers. Because IFN-γ activates NK cells and cytotoxic T cells, and induces cytokine production by these cells, the modified p40/p35 heterodimers are expected to have potent anti-tumor activities in vivo. Cutaneous T cell lymphoma and head and neck cancer may be particularly useful targets for the modified p40/p35 heterodimer therapies because of low p40/p35 heterodimer production by patients with cutaneous T cell lymphoma and because of good accessibility of these tumors.

Because IFN-γ enhances $T_H1$ cell differentiation (Chatelain et al. (1992) J. Immunol. 148:1182–1187; De Vries and Punnonen (1996) In Cytokine regulation of humoral immunity: basic and clinical aspects. Eds. Snapper, C. M., John Wiley & Sons, Ltd., West Sussex, UK, p. 195–215), and because the modified p40/p35 heterodimers enhanced IFN-γ production, allergies and asthma are very promising targets for modified p40/p35 heterodimer therapies.

Individuals with mutations in their genes encoding natural p40 subunit have dramatically impaired capacity to produce p40, and they are susceptible to infectious with intracellular pathogens. Treatments with a modified p40/p35 heterodimers, or with a modified p40 polypeptide or nucleic acid, provide a very specific means to treat patients with p40 deficiency.

A composition comprising a polypeptide or a nucleic acid of the invention may also be used to treat conditions resulting from hyper- or neo-vascularization, such as age-related macular degeneration or diabetic retinopathy, and to inhibit tumor growth.

An antagonist of the cellular receptor of the p40/p35 heterodimer (such as, for example, a human interleukin-12 receptor), said antagonist comprising a polypeptide of the invention or a fragment thereof, is useful in situations where downregulation of $T_H1$-mediated responses are desired. Such antagonist may include, but is not limited to, a p40 homodimer comprising at least one modified p40 polypeptide of the invention. In vitro and in vivo studies in mice have demonstrated that homodimers of the murine p40 polypeptide bind to mouse receptor (with affinity comparable to that of the heterodimer) and downregulate $T_H1$ mediated responses (Ling, et al. (1994) J. Immunol 154: 116–127 and Gately, et al. (1996) Ann. NY Acad. Sci. 795:1–12). The p40 homodimer was found to prevent induction and progression of Experimental Autoimmune Encephalomyelitis (EAE) in mice (Gately, et al. (1998) Annu. Rev. Immunol 16:495–521), an animal model for multiple sclerosis (MS) in humans. Another antagonist contemplated by the invention comprises a modified p35 polypeptide of the invention plus the Epstein-Barr virus induced gene 3 protein (EBI3). EBI3, which is structurally related to the p40 polypeptide, has been shown to associate with p35 polypeptide; the product of this association appears to antagonize the biological effects of interleukin-12 (Devergne, O. et al. (1997) Proc. Natl. Acad. Sci. USA 94:12041–12046). An antagonist comprising a polypeptide of the invention may be administered to decrease cell-mediated immune response, in the treatment of, for example, autoimmune diseases such as MS, type I diabetes mellitus, myasthenia gravis, rheumatoid arthritis, and systemic lupus erythematosus.

Modified p40 nucleic acids and/or modified p35 nucleic acids of the invention appear to effect enhanced production of biologically active heterodimers in vivo. This observed production enhancement may provide for more efficacious treatment with reduced toxicity or side-effects. Anti-tumor effects of interleukin-12 are known to be dose-dependent and require high localized concentrations for maximal efficacy (Trinchieri G. and Scott P. (1999) Curr. Top. Microbiol. Immunol. 238:57–78). Furthermore, genetic delivery of interleukin-12 nucleic acids results in less pronounced toxicity compared to systemic administration of interleukin-12 protein (Sun, Y. et al. (1998) Gene Ther. 5(4):481–90; Rakhmilevich A. L. et al. (1999) J. Immunother. 22(2): 135–44). Therefore, modified p40 nucleic acids and/or modified p35 nucleic acids of the invention that are capable of producing higher levels of biologically active heterodimeric cytokine in vivo than the corresponding wild-type nucleic acids may be useful, e.g., as antitumor agents, as a vaccine adjuvant, or as replacement therapy for interleukin-12 deficiency. In some instances, genetic delivery of modified p40 nucleic acids and/or modified p35 nucleic acids of the invention may be a preferred route of administration (intra-corneal; ARMD) and potentially less cumbersome—especially if less injections provide more sustained controlled release of biologically active heterodimer.

Therapeutic and Prophylactic Compositions

Therapeutic or prophylactic compositions comprising one or more modified p40 or modified p35 polypeptide or nucleic acid of the invention are tested in appropriate in vitro, ex vivo, and in vivo animal models of disease, to confirm efficacy, tissue metabolism, and to estimate dosages, according to methods well known in the art. In particular, dosages can be determined by activity comparison of the modified p35 and modified p40 polypeptides and nucleic acids to existing p35 and p40-based therapeutics or prophylactics, i.e., in a relevant assay. In one aspect, the invention provides methods comprising administering one or more modified p35 and/or modified p40 nucleic acids or polypeptides of the invention (or fragments thereof) described above to a mammal, including, e.g., a human, primate, mouse, pig, dog, cat, cow, goat, rabbit, rat, guinea pig, hamster, horse, sheep; or a non-mammalian vertebrate such as a bird (e.g., a chicken or duck) or a fish, or invertebrate, as described in greater detail below. Such compositions typically comprise one or more modified p35 and/or modified p40 nucleic acids or polypeptides of the invention (or fragments thereof) and an excipient, including, e.g., a pharmaceutically acceptable excipient.

In one aspect, a composition of the invention is produced by digesting one or more nucleic acids of the invention (or fragments thereof) with a restriction endonuclease, an RNase, or a DNase.

In another aspect of the invention, compositions produced by incubating one or more nucleic acids described above in the presence of deoxyribonucelotide triphosphates and a nucleic acid polymerase, e.g., a thermostable polymerase, are provided.

The invention also includes compositions comprising two or more nucleic acids described above. The composition may comprise a library of nucleic acids, where the library contains at least about 5, 10, 20, 50, 100, 150, or 200 or more such nucleic acids.

Administration is by any of the routes normally used for introducing a molecule into ultimate contact with blood or tissue cells. The modified p35 and/or modified p40 nucleic acids or polypeptides of the invention are administered in any suitable manner, preferably with pharmaceutically acceptable carriers. Suitable methods of administering such modified p35 and/or modified p40 nucleic acids or polypeptides in the context of the present invention to a patient are available, and although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered for any of the prophylactic, therapeutic, and diagnostic methods described herein by a number of routes including, but not limited to oral, intravenous, intraperitoneal, intramuscular, transdermal, subcutaneous, topical, sublingual, or rectal means, or by inhalation. Modified p35 and/or modified p40 polypeptide compositions can also be administered via liposomes. Such administration routes and appropriate formulations are generally known to those of skill in the art.

The modified p35 and/or modified p40 polypeptide or nucleic acid of the invention, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for existing p35 and/or p40 therapeutics or prophylactics, along with formulations in current use, are preferred routes of administration and formulation for the modified p35 and/or modified p40 polypeptide or nucleic acid of the invention (see, e.g., Gollob J. A. et al. (2000) Clin. Cancer Res. 6:1678–1692).

Cells transduced with modified p35 and/or modified p40 nucleic acids as described above in the context of ex vivo or in vivo therapy can also be administered intravenously or parenterally as described above. It will be appreciated that the delivery of cells to patients (e.g., human patients) is routine, e.g., delivery of cells to the blood via intravenous or intraperitoneal administration.

The dose of modified p35 and/or modified p40 polypeptide or nucleic acid of the invention administered to a subject (e.g., patient), in the context of the present invention is sufficient to effect a beneficial therapeutic or prophylactic response in the patient over time, or to inhibit infection by a pathogen, depending on the application. The dose will be determined by the efficacy of the particular vector, or formulation, and the activity of the modified p35 and/or modified p40 employed and the condition of the patient, as well as the body weight or surface area of the patient to be treated. The size of the dose also will be determined by the existence, nature, and extent of any adverse side-effects that accompany the administration of a particular vector, formulation, transduced cell type or the like in a particular patient.

In the therapeutic and prophylactic treatment methods of the invention described herein, an effective amount of a modified p40 and/or a modified p35 nucleic acid (e.g., DNA or mRNA) of the invention (e.g., nucleic acid dosage) will generally be in the range of, e.g., from about 0.05 microgram/kilogram (kg) to about 50 mg/kg, usually about 0.005–5 mg/kg. However, as will be understood, the effective amount of the nucleic acid (e.g., nucleic acid dosage) and/or polypeptide (e.g., polypeptide dosage) will vary in a manner apparent to those of ordinary skill in the art according to a number of factors, including the activity or potency of the polypeptide, the activity or potency of any nucleic acid construct (e.g., vector, promoter, expression system) to be administered, the disease or condition (e.g., particular cancer) to be treated, and the subject to which or whom the nucleic acid is delivered.

For delivery of some polypeptides, e.g., by delivering nucleic acids encoding such polypeptides, for example, adequate levels of translation and/or expression are achieved with a nucleic acid dosage of, e.g., about 0.005 mg/kg to about 5 mg/kg. Dosages for other polypeptides (and nucleic acids encoding them) having a known biological activity can be readily determined by those of skill in the art according to the factors noted above. Dosages used for other known p40 and/or p35 polypeptides (and nucleic acids encoding them) for particular diseases provide guidelines for determining dosage and treatment regimen for a nucleic acid or polypeptide of the invention. An effective amount of a heterodimeric p40/p35 polypeptide, comprising a modified p40 polypeptide and/or a modified p35 polypeptide of the invention, may be in the range of from about 1 nanogram (ng)/kg to about 1 mg/kg, and more typically from about 10 ng/kg to about 500 ng/kg (Gollob J. A. et al., supra.)

A composition for use in therapeutic and prophylactic treatment methods of the invention described herein may comprise, e.g., a concentration of a modified p40 nucleic acid and/or a modified p35 nucleic acid (e.g., DNA or mRNA) of the invention of from about 0.1 microgram/milliliter (ml) to about 20 mg/ml and a pharmaceutically acceptable carrier (e.g., aqueous carrier).

A composition for use in therapeutic and prophylactic treatment methods of the invention described herein may comprise, e.g., a concentration of a modified p40 polypeptide and/or a modified p35 polypeptide of the invention in an amount as described above and herein and a pharmaceutically acceptable carrier (e.g., aqueous carrier).

In determining the effective amount of the vector, cell type, or formulation to be administered in the treatment or prophylaxis of e.g., tumors, or infectious agents, such as bacterial, protozoal, intracellular parasitic, and viral infections, the physician evaluates circulating plasma levels, vector/cell/formulation/toxicities of the modified p35 and/or modified p40 nucleic acid or polypeptide, progression of the disease, and the production of anti-vector and/or anti-(modified p35 and/or modified p40) antibodies.

The dose administered, e.g., to a 70 kilogram patient will be in the range equivalent to dosages of currently-used p40/p35 therapeutic or prophylactic proteins, and doses of vectors or cells which produce modified p35 and/or modified p40 polypeptide sequences are calculated to yield an equivalent amount of modified p35 and/or modified p40 nucleic acid or expressed protein. The vectors of this invention can supplement treatment of e.g., tumors, or infectious agents, such as bacterial, protozoal, intracellular parasitic, and viral infections by any known conventional therapy, including cytotoxic agents, nucleotide analogues (e.g., when used for treatment of HIV infection), biologic response modifiers, and the like.

For administration, modified p40 and/or modified p35 polypeptides, nucleic acids, vectors, and transduced cells of the present invention can be administered at a rate determined by the LD-50 of the modified p40 and/or modified p35 polypeptide, vector, or transduced cell type, and the side-effects of the modified p40 and/or modified p35 polypeptide, vector or cell type at various concentrations, as applied to the mass and overall health of the patient. Administration can be accomplished via single or divided doses.

For introduction of recombinant modified p35 and/or modified p40 nucleic acid transduced cells into a subject (e.g., patient), blood samples are obtained prior to infusion, and saved for analysis. Between $1\times10^6$ and $1\times10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion are optionally repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy. Transduced cells are prepared for reinfusion according to established methods. See, Abrahamsen et al. (1991) *J. Clin. Apheresis* 6:48–53; Carter et al. (1988) *J. Clin. Arpheresis* 4:113–117; Aebersold et al. (1988), *J. Immunol. Methods* 112: 1–7; Muul et al. (1987) *J. Immunol. Methods* 101: 171–181 and Carter et al. (1987) *Transfusion* 27:362–365. After a period of about 2–4 weeks in culture, the cells should number between $1\times10^6$ and $1\times10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic or prophylactic agent.

If a subject (e.g., patient) undergoing infusion of a vector or transduced cell or protein formulation develops fevers, chills, or muscle aches, he/she receives the appropriate dose of aspirin, ibuprofen, acetaminophen or other pain/fever controlling drug. Subjects (e.g., patients) who experience reactions to the infusion such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Cell infusion is slowed or discontinued depending upon the severity of the reaction.

Therapeutic and Prophylactic Treatment Methods

The present invention also includes methods of therapeutically or prophylactically treating a disease or disorder by administering in vivo or ex vivo one or more nucleic acids or polypeptides of the invention described above (or compositions comprising a pharmaceutically acceptable excipient and one or more such nucleic acids or polypeptides) to a subject, including, e.g., a mammal, including, e.g., a human, primate, mouse, pig, cow, goat, rabbit, rat, guinea pig, hamster, horse, sheep; or a non-mammalian vertebrate such as a bird (e.g., a chicken or duck) or a fish, or invertebrate.

In one aspect of the invention, in ex vivo methods, one or more cells or a population of cells of interest of the subject (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) are obtained or removed from the subject and contacted with an amount of a polypeptide of the invention that is effective in prophylactically or therapeutically treating the disease, disorder, or other condition. The contacted cells are then returned or delivered to the subject to the site from which they were obtained or to another site (e.g., including those defined above) of interest in the subject to be treated. If desired, the contacted cells may be grafted onto a tissue, organ, or system site (including all described above) of interest in the subject using standard and well-known grafting techniques or, e.g., delivered to the blood or lymph system using standard delivery or transfusion techniques.

The invention also provides in vivo methods in which one or more cells or a population of cells of interest of the subject are contacted directly or indirectly with an amount of a polypeptide of the invention effective in prophylactically or therapeutically treating the disease, disorder, or other condition. In direct contact/administration formats, the polypeptide is typically administered or transferred directly to the cells to be treated or to the tissue site of interest (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) by any of a variety of formats, including topical administration, injection (e.g., by using a needle or syringe), or vaccine or gene gun delivery, pushing into a tissue, organ, or skin site. The polypeptide can be delivered, for example, intramuscularly, intradermally, subdermally, subcutaneously, orally, intraperitoneally, intrathecally, intravenously, or placed within a cavity of the body (including, e.g., during surgery), or by inhalation or vaginal or rectal administration.

In in vivo indirect contact/administration formats, the polypeptide is typically administered or transferred indirectly to the cells to be treated or to the tissue site of interest, including those described above (such as, e.g., skin cells, organ systems, lymphatic system, or blood cell system, etc.), by contacting or administering the polypeptide of the invention directly to one or more cells or population of cells from which treatment can be facilitated. For example, tumor cells within the body of the subject can be treated by contacting cells of the blood or lymphatic system, skin, or an organ with a sufficient amount of the polypeptide such that delivery of the polypeptide to the site of interest (e.g., tissue, organ, or cells of interest or blood or lymphatic system within the body) occurs and effective prophylactic or therapeutic treatment results. Such contact, administration, or transfer is typically made by using one or more of the routes or modes of administration described above.

In another aspect, the invention provides ex vivo methods in which one or more cells of interest or a population of cells of interest of the subject (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) are obtained or removed from the subject and transformed by contacting said one or more cells or population of cells with a polynucleotide construct comprising a target nucleic acid sequence of the invention that encodes a biologically active polypeptide of interest (e.g., a polypeptide of the invention) that is effective in prophylactically or therapeutically treating the disease, disorder, or other condition. The one or more cells or population of cells is contacted with a sufficient amount of the polynucleotide construct and a promoter controlling expression of said nucleic acid sequence such that uptake of the polynucleotide construct (and promoter) into the cell(s) occurs and sufficient expression of the target nucleic acid sequence of the invention results to produce an amount of the biologically active polypeptide effective to prophylactically or therapeutically treat the disease, disorder, or condition. The polynucleotide construct may include a promoter sequence (e.g., CMV promoter sequence) that controls expression of the nucleic acid sequence of the invention and/or, if desired, one or more additional nucleotide sequences encoding at least one or more of another polypeptide of the invention, a cytokine, adjuvant, or co-stimulatory molecule, or other polypeptide of interest.

Following transfection, the transformed cells are returned, delivered, or transferred to the subject to the tissue site or system from which they were obtained or to another site (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) to be treated in the subject. If desired, the cells may be grafted onto a tissue, skin, organ, or body system of interest in the subject using standard and well-known grafting techniques or delivered to the blood or lymphatic system using standard delivery or transfusion techniques. Such delivery, administration, or transfer of transformed cells is typically made by using one or more of the routes or modes of administration described above. Expression of the target nucleic acid occurs naturally or can be induced (as described in greater detail below) and an amount of the encoded polypeptide is expressed sufficient and effective to treat the disease or condition at the site or tissue system.

In another aspect, the invention provides in vivo methods in which one or more cells of interest or a population of cells of the subject (e.g., including those cells and cells systems and subjects described above) are transformed in the body of the subject by contacting the cell(s) or population of cells with (or administering or transferring to the cell(s) or population of cells using one or more of the routes or modes of administration described above) a polynucleotide construct comprising a nucleic acid sequence of the invention that encodes a biologically active polypeptide of interest (e.g., a polypeptide of the invention) that is effective in prophylactically or therapeutically treating the disease, disorder, or other condition.

The polynucleotide construct can be directly administered or transferred to cell(s) suffering from the disease or disorder (e.g., by direct contact using one or more of the routes or modes of administration described above). Alternatively, the polynucleotide construct can be indirectly administered or transferred to cell(s) suffering from the disease or disorder by first directly contacting non-diseased cell(s) or other diseased cells using one or more of the routes or modes of administration described above with a sufficient amount of the polynucleotide construct comprising the nucleic acid sequence encoding the biologically active polypeptide, and a promoter controlling expression of the nucleic acid sequence, such that uptake of the polynucleotide construct (and promoter) into the cell(s) occurs and sufficient expression of the nucleic acid sequence of the invention results to produce an amount of the biologically active polypeptide effective to prophylactically or therapeutically treat the disease or disorder, and whereby the polynucleotide construct or the resulting expressed polypeptide is transferred naturally or automatically from the initial delivery site, system, tissue or organ of the subject's body to the diseased site, tissue, organ or system of the subject's body (e.g., via the blood or lymphatic system). Expression of the target nucleic acid occurs naturally or can be induced (as described in greater detail below) such that an amount of the encoded polypeptide is expressed sufficient and effective to treat the disease or condition at the site or tissue system. The polynucleotide construct may include a promoter sequence (e.g., CMV promoter sequence) that controls expression of the nucleic acid sequence and/or, if desired, one or more additional nucleotide sequences encoding at least one or more of another polypeptide of the invention, a cytokine, adjuvant, or co-stimulatory molecule, or other polypeptide of interest.

In each of the in vivo and ex vivo treatment methods described above, a composition comprising an excipient and the polypeptide or nucleic acid of the invention can be administered or delivered. In one aspect, a composition comprising a pharmaceutically acceptable excipient and a polypeptide or nucleic acid of the invention is administered or delivered to the subject as described above in an amount effective to treat the disease or disorder.

In another aspect, in each in vivo and ex vivo treatment method described above, the amount of polynucleotide administered to the cell(s) or subject can be an amount sufficient that uptake of said polynucleotide into one or more cells of the subject occurs and sufficient expression of said nucleic acid sequence results to produce an amount of a biologically active polypeptide effective to enhance an immune response in the subject, including an immune response induced by an immunogen (e.g., antigen). In another aspect, for each such method, the amount of polypeptide administered to cell(s) or subject can be an amount sufficient to enhance an immune response in the subject, including that induced by an immunogen (e.g., antigen).

In yet another aspect, in an in vivo or in vivo treatment method in which a polynucleotide construct (or composition comprising a polynucleotide construct) is used to deliver a physiologically active polypeptide to a subject, the expression of the polynucleotide construct can be induced by using an inducible on- and off-gene expression system. Examples of such on- and off-gene expression systems include the Tet-On™ Gene Expression System and Tet-Off™ Gene Expression System (see, e.g., Clontech Catalog 2000, pg. 110–111 for a detailed description of each such system), respectively. Other controllable or inducible on- and off-gene expression systems are known to those of ordinary skill in the art. With such system, expression of the target nucleic of the polynucleotide construct can be regulated in a precise, reversible, and quantitative manner. Gene expression of the target nucleic acid can be induced, for example, after the stable transfected cells containing the polynucleotide construct comprising the target nucleic acid are delivered or transferred to or made to contact the tissue site, organ or system of interest. Such systems are of particular benefit in treatment methods and formats in which it is advantageous to delay or precisely control expression of the target nucleic acid (e.g., to allow time for completion of surgery and/or healing following surgery; to allow time for the polynucleotide construct comprising the target nucleic acid to reach the site, cells, system, or tissue to be treated; to allow time for the graft containing cells transformed with the construct to become incorporated into the tissue or organ onto or into which it has been spliced or attached, etc.)

Integrated Systems

The present invention provides computers, computer readable media and integrated systems comprising character strings corresponding to the sequence information herein for the polypeptides and nucleic acids herein, including, e.g., those sequences listed herein and the various silent substitutions and conservative substitutions thereof.

Various methods and genetic algorithms (GOs) known in the art can be used to detect homology or similarity between different character strings, or can be used to perform other desirable functions such as to control output files, provide the basis for making presentations of information including the sequences and the like. Examples include BLAST, discussed supra.

Thus, different types of homology and similarity of various stringency and length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package with GOs for calculating sequence similarity is BLAST, which can be adapted to the present invention by inputting character strings corresponding to the sequences herein.

Similarly, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention by inputting a character string corresponding to the modified p35 sequences and/or modified p40 sequences of the invention (either nucleic acids or polypeptides, or both). For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST can also be incorporated into the systems of the invention for alignment of nucleic acids or proteins (or corresponding character strings).

Integrated systems for analysis in the present invention typically include a digital computer with GO software for aligning sequences, as well as data sets entered into the software system comprising any of the sequences herein. The computer can be, e.g., a PC (Intel x86 or Pentium chip-compatible DOS™, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for controlling nucleic acid synthesis (e.g., based upon a sequence or an alignment of a sequences herein) or other operations which occur downstream from an alignment or other operation performed using a character string corresponding to a sequence herein.

In one embodiment, the invention provides an integrated system comprising a computer or computer readable medium comprising a database having one or more sequence records. Each of the sequence records comprises one or more character strings corresponding to a nucleic acid or polypeptide or protein sequence selected from SEQ ID NO:1 to SEQ ID NO:14, SEQ ID NO:16 to SEQ ID NO:35, SEQ ID NO:39, and SEQ ID NO:40. The integrated system further comprises a use input interface allowing a use to selectively view the one or more sequence records. In one such integrated system, the computer or computer readable medium comprises an alignment instruction set that aligns the character strings with one or more additional character strings corresponding to a nucleic acid or polypeptide or protein sequence.

One such integrated system includes an instruction set that comprises at least one of the following: a local homology comparison determination, a homology alignment determination, a search for similarity determination, and a BLAST determination. In some embodiments, the system further comprises a readable output element that displays an alignment produced by the alignment instruction set. In another embodiment, the computer or computer readable medium further comprises an instruction set that translates at least one nucleic acid sequence which comprises a sequence selected from SEQ ID NO:1 to SEQ ID NO:7 or SEQ ID NO:16 to SEQ ID NO:25 into an amino acid sequence. The instruction set may select the nucleic acid by applying a codon usage instruction set or an instruction set which determines sequence identity to a test nucleic acid sequence.

Methods of using a computer system to present information pertaining to at least one of a plurality of sequence records stored in a database are also provided. Each of the sequence records comprises at least one character string corresponding to SEQ ID NO:1 to SEQ ID NO:14, SEQ ID NO:16 to SEQ ID NO:35, SEQ ID NO:39, and SEQ ID NO:40. The method comprises determining at least one character string corresponding to one or more of SEQ ID NO:1 to SEQ ID NO:14, SEQ ID NO:16 to SEQ ID NO:35, SEQ ID NO:39, and SEQ ID NO:40 or a subsequence thereof; determining which of the at least one character string of the list are selected by a user; and displaying each of the selected character strings, or aligning each of the selected character strings with an additional character string. The method may further comprise displaying an alignment of each of the selected character strings with an additional character string and/or displaying the list.

Kits

In an additional aspect, the present invention provides kits embodying the methods, composition, systems and apparatus herein. Kits of the invention optionally comprise one or more of the following: (1) an apparatus, system, system component or apparatus component as described herein; (2) instructions for practicing the methods described herein, and/or for operating the apparatus or apparatus components herein and/or for using the compositions herein; (3) one or more modified p35 and/or modified p40 composition (such as e.g., compositions comprising at least one modified p35 and/or modified p40 nucleic acid or polypeptide or fragment thereof, cell, vector, etc., of the invention) or component (modified p35 and/or modified p40 nucleic acid or polypeptide or fragment thereof, cell, vector, etc., of the invention); (4) a container for holding one or more aspects of the invention, including such components or compositions, and (5) packaging materials.

In a further aspect, the present invention provides for the use of any apparatus, apparatus component, composition or kit herein, for the practice of any method or assay herein, and/or for the use of any apparatus or kit to practice any assay or method herein.

EXAMPLES

Example I

Preparation and Screening of Polypeptides

Nucleic acids encoding polypeptides of the invention, and nucleic acids encoding wt-p40 and wt-p35 polypeptides, were individually subcloned into the pcDNA1.3 (+) (Invitrogen) expression/secretion vector and transformed into *E. coli*. Transformants were propagated in 96-well blocks, and plasmid DNA was purified using an automated DNA purification system (Qiagen). Plasmids were transfected into COS-7 or 293 mammalian cells using a high-throughput 96-well format and Superfect Reagent (Qiagen). The culture medium was harvested and analyzed for protein expression and biological activity after a 48–72 hour incubation period.

In some instances, sequences of naturally-occurring (also referred to herein as wild-type or "wt") p35 nucleic acids and modified p35 nucleic acids were further modified to encode an EHtag (SEQ ID NO:44) at the C-terminus to facilitate purification and quantitation of the ~70 kDa heterodimers (comprising a p35 polypeptide and a p40 polypeptide).

Quantitation of Expression and Purification of Heterodimeric Proteins

Protein concentration was estimated by analyzing culture supernatants, or purified heterodimeric proteins, on a 4–12% NuPAGE gel (Novex, San Diego, Calif.) followed by either staining with SilverXpress staining kit (Novex, San Diego, Calif.) or chemiluminescent detection using anti-p35 mAB (R&D Systems, Pharmingen) or a mouse anti-polyhistidine tag mAB (Accurate, Westbury, N.Y.), followed by goat anti-mouse IgG conjugated to HRP (Pharmacia-Amersham, Piscataway, N.J.). Alternatively, concentration of purified protein was estimated by absorbance at 280 nm.

Large-scale transfections of human 293 cells were performed in 150 millimeter (mm) dishes with Superfect Reagent (Qiagen, Valencia, Calif.) using 10 microgram (ug) of each wt or modified p35-EHtag and p40 subunit expression vectors. Culture supernatant was harvested 72 hours post-transfection and centrifuged at low speed followed by filtration through a 0.2 micron (u) filter (Nalgene, Rochester, N.Y.) to remove cellular debris. The centrifuged supernatant was passed through an anti-E affinity column (Pharmacia-Amersham, Piscataway, N.J.) equilibrated in 20 milliMolar (mM) phosphate buffer pH 7.0 and protein eluted with 0.1 Molar (M) glycine pH 3.0 followed by neutralization with ¹⁄₁₀ volume of 1 M Tris pH 8.2. The sample was then buffered exchanged into phosphate-buffered saline (PBS) and concentrated with Centricon plus-80 filter devices (Millipore, Bedford, Mass.).

T-Cell Proliferation Assay

The assay was performed as described by Punnonen and de Vries (1994; *Journal of Immunology* 152: 1094). Human peripheral blood leukocytes (PBLs) were isolated from buffy coats by density-gradient centrifugation using Histopaque (Sigma), washed twice with PBS, and resuspended at a concentration of $2 \times 10^6$ cells/ml in RPMI medium (Gibco-BRL) supplemented with 10% fetal calf serum (Hyclone), 1× glutamine (Gibco-BRL) and 100 ug/ml of penicillin and streptomycin (Gibco-BRL). The isolated PBLs were then cultured in T75 flasks for 96 hours in the presence of 5 ug/ml phytohemagglutinin (PHA; Sigma) to induce activation of T-lymphocytes. Subsequently, the cells were washed twice with PBS and adjusted to $4 \times 10^5$ cells/ml in RPMI medium.

Assays were performed either (a) directly on serial dilutions of culture supernatants from transfected mammalian cells, or (b) on proteins purified from culture supernatants. Serial dilutions of expression culture medium, or of partially purified protein, were placed in 96-well round bottom plates (Costar). A 100 microliter (ul) aliquot of resuspended T-cells, activated as described above, was immediately added to each well with an automated multi-channel pipet (Matrix) and the plates were incubated at 37° C. with 5%

CO$_2$ for 48 hours. This was followed by an additional incubation period of 16 hours in the presence of 1 uCi of $^3$H-thymidine (Amersham). The cells were then harvested and the amount of $^3$H-thymidine incorporation—a measure of cytokine-dependent T$_H$1 proliferation—was measured using a 1450 micro-beta Trilux liquid scintillation counter (Wallac).

T$_H$1 Differentiation/Interferon-γ Induction Assay

Production of a human T$_H$1 specific cytokine, interferon-γ, was measured using a modification of the method described by Murphy et al. (1985; *Journal of Experimental Medicine* 164:263). Human T-cells were purified by negative selection using antibodies to CD14, CD19, CD56 and CD16 (Beckton-Dickinson). The homogenous population of T-cells was cultured at 1×10$^6$ cells/well for 5 days in Iscove medium, in the presence or absence of test proteins. Before activating the cells with soluble anti-CD3 (5 ug/ml) and anti-CD28 (5 μg/ml), the cells were harvested and washed with PBS. The cells were incubated at 37° C. with 5% CO2 for 48 hours prior to harvesting the conditioned medium and measuring the level of interferon-γ with a commercially available ELISA kit (R&D Systems).

Results

Culture media from mammalian cells expressing nucleic acids of the invention, and purified heterodimeric proteins, were tested for T-cell proliferative activity and interferon-γ induction activity as described above. Representative results are provided as follows. Nucleic acids encoding modified p40 polypeptides of the invention were co-expressed with nucleic acids encoding a wt-p35 polypeptide (SEQ ID NO:36). In general, significantly greater T-cell proliferative activities were observed in the culture media of cells expressing and secreting heterodimers comprising modified p40 polypeptides of the invention than were observed in the culture media of control cells expressing and secreting heterodimers formed of wt-p40 and wt-p35 polypeptides.

FIG. 2 shows that co-expression of a modified p40 nucleic acid of the invention, (SEQ ID NO:7 encoding R16–51), with nucleic acid encoding a wt-p35 polypeptide (SEQ ID NO:36) in COS-7 cells, results in secretion of active protein into the conditioned media. Relative T-cell proliferative activity of the modified-p40/wt-p35 heterodimer compared to that of the control wt-p40/wt-p35 heterodimer were estimated by comparing the n-fold dilution of test culture media necessary to achieve an equal level of activity to that of the control culture media. Assay of serial dilutions of the media showed that the modified p40/wt-p35 heterodimer required about an 4-fold dilution of media to achieve a level of $^3$H-thymidine incorporation (CPM) equivalent to that of a wt-p40/wt-p35 heterodimer. This is indicative of about an 4-fold greater T-cell proliferative activity of the expressed, secreted R16–51/wt-p35 heterodimer over that of the control culture expressing and secreting wt-p40/wt-p35 heterodimer. FIG. 3 shows the relative T-cell proliferative activities of culture media dilutions of human 293 cells co-expressing a nucleic acid encoding a wt-p35 polypeptide (SEQ ID NO:36) plus one of the following modified p40 nucleic acids of the invention: SEQ ID NO:6 encoding A16–94; SEQ ID NO:2 encoding B8–96; or SEQ ID NO:1 encoding C2–22; or a nucleic acid (SEQ ID NO:37) encoding a wt-p40 polypeptide. Relative activities of the modified p40/wt-p35 heterodimers compared to that of the control wt-p40/wt-p35 heterodimer were estimated by comparing the n-fold dilution of test culture media necessary to achieve an equal level of activity to that of the control culture media. Assay of serial dilutions of the media showed that the modified p40/wt-p35 heterodimers comprising modified p40 polypeptides A16–94 and B8–96 required at least about an 8-fold dilution and at least about a 16-fold dilution, respectively, of culture supernatant to achieve a level of $^3$H-thymidine incorporation (CPM) equivalent to that of wt-p40/wt-p35 heterodimer, while the modified p40/wt-p35 heterodimer comprising modified p40 polypeptide C2–22 required at least about a 32- to 64-fold dilution of media to achieve a level of $^3$H-thymidine incorporation (CPM) equivalent to that of wt-p40/wt-p35 heterodimer (as indicated by the dashed horizontal line). In other words, culture media of the expressed and secreted A16–94/wt-p35 and B8–96/wt-p35 heterodimers showed at least an 8-fold and at least a 16-fold greater T-cell proliferative activity, respectively, and the culture media of the expressed and secreted C2–22/wt-p35 heterodimer showed at least 32- to 64-fold greater T-cell proliferative activity, than that of the control culture media of the expressed and secreted wt-p40/wt-p35 heterodimer.

FIGS. 4, 5, and 6, respectively, show the T-cell proliferative activities of culture media of cells co-expressing a nucleic acid encoding a naturally-occurring (wt-)p35 polypeptide (SEQ ID NO:36) plus one of the following modified p40 nucleic acids: SEQ ID NO:5 encoding A3–48 (FIG. 4), SEQ ID NO:3 encoding B2–52 (FIG. 5), and SEQ ID NO:4 encoding B1–81 (FIG. 6), in comparison to dilutions of culture media of control cells co-expressing nucleic acids encoding naturally-occurring wt-p40/wt-p35 polypeptides. The results of FIGS. 4–6 are indicative of at least about a 4- to 8-fold greater T-cell proliferative activity of each of the expressed, secreted modified p40/wt-p35 heterodimers over that of the control expressed, secreted wt-p40/wt-p35 heterodimer.

FIG. 7 shows that COS-7 cells co-expressing nucleic acid encoding an exemplary modified p40 polypeptide of the invention plus nucleic acid encoding wt-p35 polypeptide consistently secreted more heterodimeric (~70 kDa) protein into the culture media than COS-7 cells co-expressing nucleic acids encoding wt-p40 and wt-p35 polypeptides. Heterodimer (p70) production was quantitated by immunoblot analysis, using an anti-p35 mAB, of equivalent volumes of crude culture medium from COS-7 cells co-expressing nucleic acids encoding wt-p35 polypeptide (SEQ ID NO:36) plus either a nucleic acid encoding one of the following exemplary modified p40 polypeptides, identified as A16–94 (SEQ ID NO:13), A3–48 (SEQ ID NO:12), B1–81 (SEQ ID NO:11), B2–52 (SEQ ID NO:10), B8–96 (SEQ ID NO:9) or C2–22 (SEQ ID NO:8), or a nucleic acid encoding a wt-p40 (SEQ ID NO:15). Thus, the increased proliferative activities of the modified heterodimers over the wild-type heterodimers may be in part attributable to enhanced production of modified heterodimers as compared to the wild-type counterparts.

As noted above and in FIG. 3, culture media from cells expressing the modified p40 C2–22/wt-p35 heterodimer showed an up to 64-fold increase in relative proliferative activity over that of culture media cells expressing the wild-type heterodimer (that is, up to a 64-fold lower volume of culture media from cells expressing the modified heterodimer was required to achieve an activity value equivalent to that of a 1× volume of culture media from cells expressing the wild-type heterodimer). To estimate the relative contributions of enhanced modified heterodimer production versus increased activity to this observed activity increase, heterodimers were first quantitated by immunoblot of equivalent dilutions of partially purified heterodimer from wt-p40/wt-p35 and C2–22/wt-p35 cultures using an anti-p35 mAB. From densitometry analysis, an estimated 16-fold enhancement of expression of C2–22/wt-p35 heterodimer over that of the control wt-p40/wt-p35 heterodimer was observed (FIG. 8). Based on this quantitation, equivalent concentrations of partially purified C2–22/wt-p35 heterodimer showed an approximately four-fold higher proliferative activity compared to partially purified control wt-p40/wt-p35 heterodimer in the human T-cell proliferation assay after normalizing for protein concentration (FIG. 9). Taken together, these data suggest that the observed 32- to 64-fold activity enhancement observed in the culture broth assay is consistent with about a 16-fold increase in active heterodimer production, and about a four-fold higher proliferative activity of the C2–22/wt-p35 heterodimer over that of the control wild-type heterodimer.

The ability of partially purified C2–22/wt-p35 heterodimer to induce synthesis and secretion of the $T_H1$ specific cytokine, interferon-γ, by human T-cells was determined in the human $T_H1$ differentiation/IFN-γ induction assay. FIG. 10 shows the levels of human IFN-γ produced by human T-cells incubated in the presence or absence of partially purified C2–22/wt-p35 or control wt-p40/wt-p35 heterodimers, followed by activation with anti-CD3 and anti-CD28. The amount of IFN-γ produced by human T-cells incubated with ~1 ng/ml of partially purified p40C2–22/wt-p35 heterodimer was significantly greater than that of cells treated with ~1 ng/ml of partially purified control wt-p40/wt-p35 heterodimer.

Nucleic acids encoding modified p35 polypeptides of the invention were co-expressed with nucleic acids encoding either wt-p40 or various modified p40 polypeptides of the invention. In general, significantly greater T-cell proliferative activities were observed in the culture media of cells expressing and secreting heterodimers comprising modified p35 polypeptides of the invention, and in the culture media of cells expressing and secreting heterodimers comprising both modified p35 and modified p40 polypeptides of the inventions, over T-cell proliferative activities of the culture media of control cells expressing and secreting wild-type heterodimers formed of naturally-occurring wt-p40 and wt-p35 polypeptides.

A "fully modified" heterodimer C2–22/R2–571-EHtag, comprising a modified p40 polypeptide comprising a sequence identified as the mature polypeptide region (amino acid residues 23–324) of SEQ ID NO:8, and a modified p35 polypeptide comprising a sequence identified as the mature polypeptide region (amino acid residues 23–219) of SEQ ID NO:31 plus the C-terminal EHtag, was purified and quantitated as described above. FIG. 12 shows that the T-cell proliferative activity of the purified fully modified heterodimer (C2–22/R2–571-EHtag) is about 8 times greater than that of purified control wild-type (wt-p40/wt-p35-EHtag) heterodimer, after normalizing for protein concentration. FIG. 13 shows that human T-cells incubated with the purified "fully modified" heterodimer (C2–22/R2–571-EHtag) at a concentration of either ~10 ng/ml or ~50 ng/ml produced 3 to 5 times more IFN-γ than human T-cells incubated with equal concentrations of purified control wild-type (wt-p40/wt-p35-EHtag) heterodimer.

FIG. 14 shows a western blot, probed using an anti-E tag monoclonal antibody, of purified heterodimers produced by co-expressing in 293 cells (a) a modified p40 nucleic acid of the invention (comprising the C2–22 polynucleotide sequence SEQ ID NO:1) plus a modified p35 nucleic acid of the invention (comprising the R2–571 polynucleotide sequence SEQ ID NO:21), and (b) wt-p40 and wt-p35 nucleic acids (comprising the polynucleotide sequences SEQ ID NO:37 and SEQ ID NO:38, respectively).

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

SEQUENCES

| SEQ ID | Clone ID, no. of residues, mature region | SEQUENCE |
|---|---|---|
| SEQ ID NO:1 | C2-22 1-975 mature coding sequence (CDS) 67-972 | ATGTGTCACCAGCAGTTGGTCATCTCTTGGTTTTCCCTGGTTTTGCTGGCATCTCCCC<br>TCATGGCCATATGGGAACTGAAGAAAGACGTTTATGTCGTAGAGTTGGACTGGTATCC<br>TAATGCTCCTGGAGAAACAGTGGTCCTCACGTGTGACACTCCTGAAGAAGATGGCATC<br>ACCTGGACCTCAGACCAGAGCAGTGAGGTCTTGGGCACTGGCAAAACCCTGACCATCC<br>ACGTCAAAGAGTTTGGAGATGCTGGCCAGTACACCTGTCGCAAAGGAGGCGAGGCTCT<br>GAGTCGTTCACTCCTCCTGCTGCACAAAAAGGAAGATGGAATTTGGTCCACTGATATT<br>TTAAAAGACCAGAAAGAGCCCAAAAACAAGAGCTTTCTAAAATGTGAGGCAAAGAATT<br>ACTCCGGACGTTTCACCTGCTGGTGGCTGACGACAATCAGTACTGATTTGAAATTCAG<br>TGTCAAAAGCAGCAGAGGCTCCACTGACCCCCGTGGCGTGACATGTGGCACGGCAACG<br>CTCTCAGAGGACCTCGGAGAGTATAAGAAGTACAGAGTGGAGTGTCAGGAGGGCAGTG |

SEQUENCES

| SEQ ID | Clone ID, no. of residues, mature region | SEQUENCE |
|---|---|---|
| | | CCTGCCCAGCCGCTGAGGAGAGCCTGCCCATTGAGGTCGTGCTGGAAGCTGTTCACAA |
| | | GCTCAAGTATGAAAACTACACCAGCAGCTTCTTCATCAGAGACATCATCAAACCAGAC |
| | | CCACCCAAGAACCTGCAACTGAAGCCATTGAAAAATTCTCGGCATGTGGAGGTCAGCT |
| | | GGGGGTACCCCGACACCTGGAGCACCCCACATTCCTACTTCTCCCTGACATTCTGCAT |
| | | CCAGGTCCAGGGCAAGAGCAAGAGAGAAAAGAAAGATAGAATCTTCACAGACAAGACC |
| | | TCAGCCACGGTCATCTGCCGCAAAAATGCCAAGATCCGCGTGCAAGCCCGGGACCGCT |
| | | ACTACAGCTCATTCTGGAGTGAATGGGCATCTGTGTCCTGCAGTTAG |
| SEQ ID NO:2 | B8-96 1-984 mature CDS 67-981 | ATGTGCCACCAGCAGTTGGTCATCTCTTGGTTTTCCCTGGTTTTTCTGGCATCTCCCC |
| | | TCGTGGCCATATGGGAACTGGAGAAAAACGTCTATGTTGTAGAATTGGACTGGTACCC |
| | | GGATGCCCCTGGAGAAATGGTGGTCCTCGCCTGTGACACTCCTGAAGAAGATGGCATC |
| | | ACCTGGACCTCAGACCAGAGCAGTGAGGTCTTGGGCACTGGCAAAACCCTGACCATCC |
| | | ACGTCAAAGAGTTTGGAGATGCTGGCCAGTACACCTGTCGCAAAGGAGGCGCAGTTCT |
| | | GAGCCAGTCACTCCTGCTGCTTCACAAAAAGGAAGATGGAATTTGGTCCACTGATATT |
| | | TTAAAAGACCAGAAAGAGCCCAAAAACAAGAGCTTTCTAAAATGTGAGGCAAAGAATT |
| | | ACTCCGGACGTTTCACCTGCTGGTGGCTGACAACAATCAGTACTGATTTGAAATTCAG |
| | | TGTCAAAAGCAGCAGAGGCTCCTCTGACCCCCGAGGGGTGACGTGCGGAGCAGCGTTG |
| | | CTCTCAGCAGAGAAGGTCAGCTTGGAGCATAGGGAGTATAAGAAGTACAGAGTGGAGT |
| | | GTCAGGAGGGCAGTGCCTGCCCAGCCGCTGAGGAGAGCCTGCCCATTGAGGTCGTGCT |
| | | GGAAGCTGTTCACAAGCTCAAGTATGAAAACTATACCAGCAGCTTCTTCATCAGGGAC |
| | | ATCATCAAACCGGACCCACCCAAGAACCTGCAACTGAGACCACTAAAGAATTCTCGGC |
| | | AGGTGGAGGTCAACTGGGAGTACCCTGACACGTGGAGCACCCCACATTCCTACTTCTC |
| | | CCTGACGTTTTGTGTTCAGGTCCAGGGAAAGAACAAGAGAGAAAAGAAACTCTTCATG |
| | | GACCAAACCTCAGCCAAAGTCACATGCCACAAGGATGCCAAGATCCGCGTGCAAGCCA |
| | | GAGACCGCTACTACAGCTCATCTTGGAGCGAATGGGCATCTGTGCCCTGCAGTTAG |
| SEQ ID NO:3 | B2-52 1-984 mature CDS 67-981 | ATGTGTCACCAGCAGTTGGTCATCTCTTGGTTTTCCCTGGTTTTTCTGGCATCTCCCC |
| | | TCGTGGCCATATGGGAACTGGAGAAAAATGTTTATGTTGTAGAATTGGATTGGTACCC |
| | | GGATGCCCCTGGAGAAATGGTGGTCCTCGCCTGTGACACTCCTGAAGAAGATGGCATC |
| | | ACCTGGACCTCAGACCAGAGCAGTGGGGTCTTGGGCACTGGCAAAACCCTGACCATCC |
| | | ACGTCAAAGAGTTTGGAGATGCTGGCCAGTACACCTGTCGCAAAGGAGGCGCAGTTCT |
| | | GAGCCAGTCACTCCTGCTGCTTCACAAAAAGGAAGATGGAATTTGGTCCACTGATATT |
| | | TTAAAGGACCAGAAAGAACCCAAAGCTAAGAGTTTTTTAAAATGTGAGGCAAAGGATT |
| | | ATTCTGGACACTTCACCTGCTGGTGGCTGACAACAATCAGTACTGATTTGAAATTCAG |
| | | TGTCAAAAGCAGCAGAGGCTCCTCTGACCCCCAAGGGGTGACTTGTGGAGCCGTTACA |
| | | CTCTCTGCAGAGAGGGTCAGCATGGACCACAGGGAGTATAACAAGTACACAGTGGAGT |
| | | GTCAGGAGGGCAGTGCCTGCCCCTCTGCCGAGGAGAGCCTACCCATCGAGGTCGTGGT |

| SEQ ID | Clone ID, no. of residues, mature region | SEQUENCE |
|---|---|---|
| | | GGATGCTATTCACAAGCTCAAGTATGAAAACTACACCAGCAGCTTCTTCATCAGGGAC |
| | | ATCATCAAACCGGACCCACCCAAGAACTTGCAGCTGAGACCACTAAAGAATTCTCGGC |
| | | AGGTGGAGGTCAACTGGGAGTACCCTGACACGTGGAGCACCCCACATTCCTACTTTTC |
| | | CCTGACGTTTTGTGTTCAGGTCCAGGGAAAGAACAAGAGAGAAAAGAAACTCTTCATG |
| | | GACCAAACCTCAGCCAAAGTCACATGCCACAAGGATGCCAAGATCCGCGTGCAAGCCA |
| | | GAGACCGCTACTACAGCTCATCTTGGAGCGAATGGGCATCTGTGCCCTGCAGTTAG |
| SEQ ID NO:4 | B1-81 1-984 mature CDS 67-981 | ATGCATCCTCAGCAGTTGGTCGTTTCCTGGTTTTCCCTGGTTTTGCTGGCATCTCCCC |
| | | TCGTGGCCATATGGGAACTGGAGAAAAATGTTTATGTTGTAGAATTGGATTGGTATCC |
| | | TGATGCTCCTGGAGAAACAGTGGTCCTCGCCTGTGACACTCCTGAAGAAGATGGCATC |
| | | ACCTGGACCTCAGACCAGAGCAGTGAGGTCCTGGGCACTGGCAAAACCCTGACCATCC |
| | | ACGTCAAAGAGTTTGGAGATGCTGGCCAGTACACCTGTCGCAAGGAGGCGCAGTTCT |
| | | GAGCCAGTCACTCCTGCTGCTTCACAAAAAGGAAGATGGAATTTGGTCCACTGATATT |
| | | TTAAAAGACCAGAAAAAGCCCAAAAACAAGATCTTTCTGAAATGTGAGGCAAAGAATT |
| | | ACTCCGGACGTTTCACCTGCTGGTGGCTGACAGCAATCAGTACAGATTTGAAATTCAC |
| | | TGTCAAAAGCAGCAGAGGCTCCTCTGACCCCCAAGGGGTGACTTGTGGAGCCGTTACA |
| | | CTCTCTGCAGAGAGGGTCAGCATGGACCACAGGGAGTATAACAAGTACACAGTGGAGT |
| | | GTCAAGAGGGCAGTGCCTGCCCCTCTGCCGAGGAGAGCCTACCCATCGAGGTCGTGGT |
| | | GGATGCTATTCACAAGCTCAAGTATGAAAACTACACCAGCAGGTTCTTCATCAGGGAC |
| | | ATCATCAAACCGGACCCACCCAAGAACTTGCAACTGAGACCACTAAAGAATTCTCGAC |
| | | ACGTGGAGATCAGCTGGGAGTACCCTGACACCTGGAGCACCCCACATTCCTACTTCTC |
| | | CCTGACGTTTTGTGTTCAGGTCCAGGGGAAGAACAAGAGAGAAAAGAAACTCTTCATG |
| | | GACCAAACCTCAGCCAAAGTCACATGCCACAAGGATGCCAAGATCCGCGTGCAAGCCA |
| | | GAGACCGCTACCACAGCTCATCTTGGAGCGAATGGGCATCTGTGCCCTGCAGTTAG |
| SEQ ID NO:5 | A3-48 1-969 mature CDS 67-966 | ATGTGTCACCAGCAGTTGGTCATCTCTTGGTTTTCCCTGGTTTTTCTGGCATCCCCCC |
| | | TCGTGGCCATATGGGAACTGGAGAAAAACGTTTATGTTGTAGAATTGGACTGGTACCC |
| | | GGATGCCCCTGGAGAAATGGTGGTCCTCGCCTGTGACACTCCTGAAGAAGATGGCATC |
| | | ACCTGGACCTCAGACCAGAGCAGTGAGGTCTTGGGCACTGGCAAAACCCTGACCATCC |
| | | ACGTCAAAGAGTTTGGAGATGCTGGCCAGTATACCTGCCATAAAGGAGGCAAGGTTCT |
| | | GAGCCGCTCACTCCTGCTGCTTCACAAAAAGGAAGATGGAATTTGGTCCACTGATATT |
| | | TTAAAAGACCAGAAAGAGCCCAAAAACAAGAGCTTTCTAAAATGTGAGGCAAAGAATT |
| | | ACTCCGGACGTTTCACCTGCTGGTGGCTGACGACAATCAGTACTGATCTGACATTCAG |
| | | TGTCAAAAGCAGCAGAGGCTCTACTGACCCCCATGGCGTGACATGGCACGGCAACG |
| | | CTCTCAGAGGACCTCGGAGAGTATAAGAAGTACAGAGTGGAGTGTCAGGAGGGCAGTG |
| | | CCTGCCCAGCCGCTGAGGAGAGCCTGCCTATTGAGGTCGTGCTGGAAGCTGTTCACAA |
| | | GCTCAAGTATGAAAACTACACCAGCAGCTTCTTCATCAGGGACATCATCAAACCAGAC |

-continued

SEQUENCES

| SEQ ID | Clone ID, no. of residues, mature region | SEQUENCE |
|---|---|---|
| | | CCACCCAAGAACCTGCAACTGAGACCATTAAAGAATTCTCGGCAGGTGGAGGTCAACT |
| | | GGGAGTACCCTGACACGTGGAGCACCCCACATTCCTACTTCTCCCTGACGTTTTGTGT |
| | | TCAGGTCCAGGGAAGGAACAAGAGAGAAAAGAAACTCTTCATGGACCAAACCTCAGCC |
| | | AAAGTCACGTGCCACAAGGATGCCAAGATCCGCGTGCAAGCCCGAGACCGCTACTATA |
| | | GTTCATCCTGGAGCGACTGGGCATCCGTGTCCTGCGGTTAG |
| SEQ ID NO:6 | A16-94 1-975 mature CDS 67-972 | ATGTGTCACCAGCAGTTGGTCATCTCTTGGTTTTCCCTGGTTTTTCTGGCATCTCCCC |
| | | TCATGGCCATATGGGAACTGAAGAAAGACGTTTATGTTGTAGAATTGGACTGGTACCC |
| | | GGATGCCCCTGGAGAAATGGTGGTCCTCGCCTGTGACACTCCTGAAGAAGATGGCATC |
| | | ACCTGGACCTCAGACCAGAGCAGTGAGGTCTTGGGCACTGGCAAAACCCTGACCATCC |
| | | ACGTCAAAGAGTTTGGAGATGCTGGCCAGTACACCTGTCATAAAGGAGGCACAGTTCT |
| | | GAGCCAGTCACTCCTGCTGCTTCACAAAAAGGAAGATGGAATTTGGTCCACTGATATT |
| | | TTAAAAGACCAGAAAGAGCCCAAAAACAAGAGCTTTCTAAAGTGTGAGGCAAAGAATT |
| | | ACTCCGGACGTTTCACCTGCTGGTGGCTGACGGCAATCAGTACTGATTTGAAATTCAC |
| | | TGTCAAAAGCAGCAGAGGCTCCACTGACCCCCGTGGCGTGACATGTGGCACGGCAACG |
| | | CTCTCAGAGGACCTCGGAGAGTATAAGAAGTACAGAGTGGAGTGTCAGGAGGGCAGTG |
| | | CCTGCCCAGCCGCTGAGGAGAGCCTGCCCATTGAGGTCGTGCTGGAAGCTGTTCACAA |
| | | GCTCAAGTATGAAAACTACACCAGCAGCTTCTTCATCAGGGACATCATCAAACCAGAC |
| | | CCACCCAAGAACCTGCAACTGAGACCATTAAAGAATTCTCGGCACGTGGAGGTCAGCT |
| | | GGGAGTACCCTGACACGTGGAGCGCCCCACATTCCTACTTTTCCCTGACGTTTGGTGT |
| | | TCAGGTCCAGGGCAGGAACAAGAGAGAAGATAGACTCTTCATGGACCAAACCTCAGCC |
| | | AAAGTCGTGTGCCACAAGGATGCCAAGATCCGCGTGCAAGCCAGAGACCGCTACTACA |
| | | GCTCATCTTGGAGCGAATGGGCATCTGTGTCCCTGCAGTCAGTCTAG |
| SEQ ID NO:7 | R16-51 1-990 mature CDS 67-987 | ATGTGTCACCAGCAGTTGGTCATCTCTTGGTTTTCCCTGGTTTTTCTGGCATCTCCCC |
| | | TCGTGGCCATATGGGAACTGGAGAAAAACGTTTATGTTGTAGAATTGGACTGGTACCC |
| | | GGATGCCCCTGGAGAAATGGTGGTCCTCGCCTGTGACACTCCTGAAGAAGATGGCATC |
| | | ACCTGGACCTCAGACCAGAGCAGTGAGGTCTTGGGCACTGGCAAAACCCTGACCATCC |
| | | ACGTCAAAGAGTTTGGAGATGCTGGCCAGTACACCTGTCGCAAAGGAGGCGCAGTTCT |
| | | GAGCCAGTCACTCCTGCTGCTTCACAAAAAGGAAGATGGAATTTGGTCCACTGATATT |
| | | TTAAAAGACCAGAAAGAGCCCAAAAACAAGATCTTTCTGAAATGTGAGGCAAAGAATT |
| | | ACTCCGGACGTTTCACCTGCTGGTGGCTGACAGCAATCAGTACAGATTTGAAATTCAC |
| | | TGTCAAAAGCAGCAGAGGCTCCTCTGACCCCCAAGGGGTGACTTGTGGAGCCGTTACA |
| | | CTCTCTGCAGAGGGGTCAGCATGGACCACAGGGAGTATAACAAGTACACAGTGGAGT |
| | | GTCAGGAGGGCAGTGCCTGCCCCTCTGCCGAGGAGAGCCTACCCATCGAGGTCGTGGT |
| | | GGATGCTATTCACAAGCTCAAGTATGAAAACTACACCAGCAGCTTCTTCATCAGAGAC |
| | | ATCATCAAACCTGACCCACCCAAGAACTTGCAGCTGAAGCCATTAAAGAATTCTCGAC |

-continued

SEQUENCES

| SEQ ID | Clone ID, no. of residues, mature region | SEQUENCE |
|---|---|---|
| | | ACGTGGAGATCAGCTGGGAGTACCCTGACACCTGGAGCATCCCACATTCCTACTTTTC |
| | | CCTGATGTTTGGTGTTCAAGTTCAGGGCAAGAACAAGAGAGAAAAGAAAGATAGACTC |
| | | TCCGTGGACAAGACCTCAGCCAAGGTCGTGTGCCACAAGGATGCCAAGATCCGCGTGC |
| | | AAGCCAGAGACCGCTACTACAGCTCATCTTGGAGCGAATGGGCATCTGTGCCCTGCAG |
| | | TTAG |
| SEQ ID NO:8 | C2-22 1-324; mature polypep. 23-324 | MCHQQLVISWFSLVLLASPLMAIWELKKDVYVVELDWYPNAPGETVVLTCDTPEEDGI TWTSDQSSEVLGTGKTLTIHVKEFGDAGQYTCRKGGEALSRSLLLLHKKEDGIWSTDI LKDQKEPKNKSFLKCEAKNYSGRFTCWWLTTISTDLKFSVKSSRGSTDPRGVTCGTAT LSEDLGEYKKYRVECQEGSACPAAEESLPIEVVLEAVHKLKYENYTSSFFIRDIIKPD PPKNLQLKPLKNSRHVEVSWGYPDTWSTPHSYFSLTFCIQVQGKSKREKKDRIFTDKT SATVICRKNAKIRVQARDRYYSSFWSEWASVSCS |
| SEQ ID NO:9 | B8-96 1-327; mature polypep. 23-327 | MCHQQLVISWFSLVFLASPLVAIWELEKNVYVVELDWYPDAPGEMVVLACDTPEEDGI TWTSDQSSEVLGTGKTLTIHVKEFGDAGQYTCRKGGAVLSQSLLLLHKKEDGIWSTDI LKDQKEPKNKSFLKCEAKNYSGRFTCWWLTTISTDLKFSVKSSRGSSDPRGVTCGAAL LSAEKVSLEHREYKKYRVECQEGSACPAAEESLPIEVVLEAVHKLKYENYTSSFFIRD IIKPDPPKNLQLRPLKNSRQVEVNWEYPDTWSTPHSYFSLTFCVQVQGKNKREKKLFM DQTSAKVTCHKDAKIRVQARDRYYSSSWSEWASVPCS |
| SEQ ID NO:10 | B2-52 1-327; mature polypep. 23-327 | MCHQQLVISWFSLVFLASPLVAIWELEKNVYVVELDWYPDAPGEMVVLACDTPEEDGI TWTSDQSSGVLGTGKTLTIHVKEFGDAGQYTCRKGGAVLSQSLLLLHKKEDGIWSTDI LKDQKEPKAKSFLKCEAKDYSGHFTCWWLTTISTDLKFSVKSSRGSSDPQGVTCGAVT LSAERVSMDHREYNKYTVECQEGSACPSAEESLPIEVVVDAIHKLKYENYTSSFFIRD IIKPDPPKNLQLRPLKNSRQVEVNWEYPDTWSTPHSYFSLTFCVQVQGKNKREKKLFM DQTSAKVTCHKDAKIRVQARDRYYSSSWSEWASVPCS |
| SEQ ID NO:11 | B1-81 1-327; mature polypep. 23-327 | MHPQQLVVSWFSLVLLASPLVAIWELEKNVYVVELDWYPDAPGETVVLACDTPEEDGI TWTSDQSSEVLGTGKTLTIHVKEFGDAGQYTCRKGGAVLSQSLLLLHKKEDGIWSTDI LKDQKKPKNKIFLKCEAKNYSGRFTCWWLTAISTDLKFTVKSSRGSSDPQGVTCGAVT LSAERVSMDHREYNKYTVECQEGSACPSAEESLPIEVVVDAIHKLKYENYTSRFFIRD IIKPDPPKNLQLRPLKNSRHVEISWEYPDTWSTPHSYFSLTFCVQVQGKNKREKKLFM DQTSAKVTCHKDAKIRVQARDRYHSSSWSEWASVPCS |
| SEQ ID NO:12 | A3-48 1-322; mature polypep. 23-322 | MCHQQLVISWFSLVFLASPLVAIWELEKNVYVVELDWYPDAPGEMVVLACDTPEEDGI TWTSDQSSEVLGTGKTLTIHVKEFGDAGQYTCHKGGKVLSRSLLLLHKKEDGIWSTDI LKDQKEPKNKSFLKCEAKNYSGRFTCWWLTTISTDLTFSVKSSRGSTDPHGVTCGTAT LSEDLGEYKKYRVECQEGSACPAAEESLPIEVVLEAVHKLKYENYTSSFFIRDIIKPD PPKNLQLRPLKNSRQVEVNWEYPDTWSTPHSYFSLTFCVQVQGRNKREKKLFMDQTSA KVTCHKDAKIRVQARDRYYSSSWSDWASVSCG |

-continued

SEQUENCES

| SEQ ID | Clone ID, no. of residues, mature region | SEQUENCE |
|---|---|---|
| SEQ ID NO:13 | A16-94 1-324; mature polypep. 23-324 | MCHQQLVISWFSLVFLASPLMAIWELKKDVYVVELDWYPDAPGEMVVLACDTPEEDGI<br>TWTSDQSSEVLGTGKTLTIHVKEFGDAGQYTCHKGGTVLSQSLLLLHKKEDGIWSTDI<br>LKDQKEPKNKSFLKCEAKNYSGRFTCWWLTAISTDLKFTVKSSRGSTDPRGVTCGTAT<br>LSEDLGEYKKYRVECQEGSACPAAEESLPIEVVLEAVHKLKYENYTSSFFIRDIIKPD<br>PPKNLQLRPLKNSRHVEVSWEYPDTWSAPHSYFSLTFGVQVQGRNKREDRLFMDQTSA<br>KVVCHKDAKIRVQARDRYYSSSWSEWASVSLQSV |
| SEQ ID NO:14 | 6-51 1-329; mature polypep. 23-329 | MCHQQLVISWFSLVFLASPLVAIWELEKNVYVVELDWYPDAPGEMVVLACDTPEEDGI<br>TWTSDQSSEVLGTGKTLTIHVKEFGDAGQYTCRKGGAVLSQSLLLLHKKEDGIWSTDI<br>LKDQKEPKNKIFLKCEAKNYSGRFTCWWLTAISTDLKFTVKSSRGSSDPQGVTCGAVT<br>LSAERVSMDHREYNKYTVECQEGSACPSAEESLPIEVVVDAIHKLKYENYTSSFFIRD<br>IIKPDPPKNLQLKPLKNSRHVEISWEYPDTWSIPHSYFSLMFGVQVQGKNKREKKDRL<br>SVDKTSAKVVCHKDAKIRVQARDRYYSSSWSEWASVPCS |
| SEQ ID NO:15 | p40 1-328; mature polypep. 23-328 | MCHQQLVISWFSLVFLASPLVAIWELKKDVYVVELDWYPDAPGEMVVLTCDTPEEDGI<br>TWTLDQSSEVLGSGKTLTIQVKEFGDAGQYTCHKGGEVLSHSLLLLHKKEDGIWSTDI<br>LKDQKEPKNKTFLRCEAKNYSGRFTCWWLTTISTDLTFSVKSSRGSSDPQGVTCGAAT<br>LSAERVRGDNKEYEYSVECQEDSACPAAEESLPIEVMVDAVHKLKYENYTSSFFIRDI<br>IKPDPPKNLQLKPLKNSRQVEVSWEYPDTWSTPHSYFSLTFCVQVQGKSKREKKDRVF<br>TDKTSATVICRKNASISVRAQDRYYSSSWSEWASVPCS |
| SEQ ID NO:16 | R2-42 1-666 mature CDS 76-663 | ATGTGCCCACTTCGCAGCCTCCTCCTCATATCCACCCTGGTTCTCCTCCACCACCTGC<br>CCCACCTCAGTTTGGGCAGGAGCCTCCCCACCACCACAGCAAGCCCAGGAAGGAGCTG<br>CCTCGACTACTCCCAAAACCTGTTGAAGGCCGCCAGCAACACGCTTCAGAAGGCCAGA<br>CAAATTCTAGAATTTTACCCTTGCACTTCTGAGGAGATCGATCATGAAGATATCACCA<br>AAGATAAAACCAGCACAGTGGAGGCCTGTTTACCACTGGAATTAGCCACGAATGAGAG<br>TTGCCTGGCTTCCAGAGAGATCTCTCTGATAACTAATGGGAGTTGCCTGGCTTCCAGA<br>AAGACCTCTTTTATGACAACCCTGTGCCATAGCAGCATCTATGAGGACTTGAAGATGT<br>ACCAGATGGAATTCAAGGCCATGAACGCAAAGCTTTTGATGGATCCTAAGAGGCAGAT<br>CTTTCTAGATCAAAACATGCTGGCAGTTATTGATGAGCTGATGCAGGCCCTGAATTTC<br>AACAGTGAGACTGTGCCACAGAAGCCCTCCCTGGAAGAACTGGATTTTTATAAGACTA<br>AAATCAAGCTCTGCATACTTCTTCATGCCTTCAGAATTCGTGCGGTGACCATCGACAG<br>AATGATGAGCTATCTGAATTCTTCCTAA |
| SEQ ID NO:17 | R2-146 1-666 mature CDS 76-663 | ATGTACCCACTTCGCAGCCTCCTCCTCATATCCACCCTGGTTCTCCTCCACCACCTGC<br>CCCACCTCAGTTTGGGCAGGAGCCTCCCCACCACCACAGCAAGCCCAGGAAGGAGCTG<br>CCTCGACTACTCCCAAAACCTGTTGAAGGCCGCCAGCAACACGCTTCAGAGGGCCAGA<br>CAAATTCTAGAATTTTACCCTTGCACTTCTGAGGAGATCGATCATGAAGATATCACCA<br>AAGATAAAACCAGCACAGTGGAGGCCTGTTTACCACTGGAATTAGCCACGAATGAGAG |

SEQUENCES

| SEQ ID | Clone ID, no. of residues, mature region | SEQUENCE |
|---|---|---|
| | | TTGCCTGGCTTCCAGAGAGATCTCTCTGATAACTAATGGGAGTTGCCTGGCTTCCAGA |
| | | AAGACCTCTTTTATGACAACCCTGTGCCTTAGCAGCATCTATGAGGACTTGAAGATGT |
| | | ACCAGATGGAATTCAAGGCCATGAACGCAAAGCTTTTGATGGATCCTAAGAGGCAGAT |
| | | CTTTTTAGATCAAAACATGCTGGCAGTTATTGATGAGCTGATGCAGGCCCTGAATTTC |
| | | AACAGTGAGACTGTGCCACAGAAGCCCTCCCTGGAAGAACTGGATTTTTATAAGACTA |
| | | AAATCAAGCTCTGCATACTTCTTCATGCCTTCAGAATTCGGGCAGTGACCATCAATAG |
| | | AATGATGAGCTATCTGAATTCTTCCTAG |
| SEQ ID NO:18 | R2-796 1-660 mature CDS 67-657 | ATGTGCCCGCCGCGCGGCCTCCTCCTTGTGGCTACCCTGGTCCTCCTGGACCACCTCA |
| | | GTTTGGCCAGAAACCTCCCTGTGGCCACCCCAGGCCCAGGAATGTTCCCATGCCTTCA |
| | | CCACTCCCAAAACCTGCTGAGGGCCGTCAGCAACATGCTGCAGAAGGCCAGACAAACT |
| | | CTAGAATTTTACTCCTGCACTTCCGAAGAGATTGATCATGAAGATATCACAAAAGATA |
| | | AAACCAGCACAGTGGAGGCCTGCTTACCACTGGAATTAATCAAGAATGAGAGTTGCCT |
| | | AAATTCCAGAGACTTCTTTCATAACTAATGGGAGTTGCCTAGCCTCCAGAAAGACC |
| | | TCTTTTATGACAACCCTGTGCCTTAGCAGTATCTATGAGGACTTGAAGATGTACCAGG |
| | | TGGAGTTCAAGACCATGAATGCAAAGCTTCTGATGAATCCTAAGAGGCAGATCTTTCT |
| | | GGATCAAAACATGCTGACAGCTATTGATGAGCTGTTACAGGCCCTGAATTTCAACAGT |
| | | GAGACTGTGCCACAAAAATCCTCCCTTGAAGAACCGGATTTTTATAAAACTAAAATCA |
| | | AGCTCTGCATACTTCTTCATGCTTTCAGAATTCGGGCAGTGACCATCAATAGAATGAT |
| | | GAGCTATCTGAATTCTTCCTAG |
| SEQ ID NO:19 | R2-631 1-660 mature CDS 67-657 | ATGTGTCCAGCGCGCAGCCTCCTCCTTGTGGCTACCCTGGTCCTCCTGGACCACCTCA |
| | | GTTTGGCCAGAAACCTCCCTGTGGCCACCCCAGGCCCAGGAATGCTCCCATGCCTTCA |
| | | CCACTCCCAAAACCTGCTGAGGGCTGTCAGCAACACGCTCCAGAAGGCCAAACAAACC |
| | | CTAGAATTTTACCCCTGCACTTCCGAAGAGATTGATCATGAAGATATCACACAAGATA |
| | | AAACCAGCACAGTGGAGGCCTGTTTACCACTGGAATTAGCCACGAATGAGAGTTGCCT |
| | | GGCTTCCAGAGGGATCTCTCTGATAACTAATGGGAGTTGCCTGGCCTCCAGAAAGACC |
| | | TCTTTTATGACGACCCTGTGCCTTAGCAGTATCTATGAGGACTTGAAGATGTACCAGG |
| | | TGGAGTTCAAGGCCATGAATGCAAAGCTGTTAATGGATCCTAAAAGGCAGATCTTTCT |
| | | GGATCAAAACATGCTGGCAGCTATTGCTGAGCTAATGCAGGCCCTGAATGTCAACAGT |
| | | GAGACTGCGCCACAAAAATCCTCCCTTGAAGAACCGGATTTTTATAAAACTAAAATCA |
| | | AGCTCTGCATACTTCTTCATGCTTTCAGAATTCGTGCAGTGACCATCAATAGAATGAT |
| | | GAGCTATCTGAATTCTTCCTAG |
| SEQ ID NO:20 | R2-613 1-660 mature CDS 67-657 | ATGTGTCCAGCGCGCAGCCTCCTCCTTGTGGCTACCCTGGTCCTCCTGGACCACCTCA |
| | | GTTTGGCCAGAAACCTCCCTGTGGCCACCCCAGGCCCAGGAATGTTCCCATGCCTTCA |
| | | CCACTCCCAAAACCTGCTGAGGGCCGTCAGCAACATGCTGCAGAAGGCCAGACAAACT |
| | | CTAGAATTTTACTCCTGCACTTCCGAAGAGATTGATCATGAAGATATCACAAAAGATA |

-continued

SEQUENCES

| SEQ ID | Clone ID, no. of residues, mature region | SEQUENCE |
|---|---|---|
| | | AAACCAGCACAGTGGAGGCCTGCTTACCACTGGAATTAATCAAGAATGAGAGTTGCCT |
| | | AAATTCCAGAGAGACTTCTTTCATAACTAATGGGAGTTGCCTAGCCTCCAGAAAGACC |
| | | TCTTTTATGACAACCCTGTGCCTTAGCAGTATCTATGAGGACTTGAAGATGTACCAGG |
| | | TGGAGTTCAAGGCCATGAATGCAAAGCTGTTAATGGATCCTAAAAGGCAGATCTTTCT |
| | | GGATCAAAACATGCTGGCAGCTATTGCTGAGCTAATGCAGGCCCTGAATGTCAACAGT |
| | | GAGACTGCGCCACAAAAATCCTCCCTTGAAGAACCGGATTTTTATAAAACTAAAATCA |
| | | AGCTCTGCATACTTCTTCATGCTTTCAGAATTCGTGCAGTGACCATCAATAGAATGAT |
| | | GAGCTATCTGAATTCTTCCTAG |
| SEQ ID NO:21 | R2-571 1-660 mature CDS 67-657 | ATGTGTCCAGCGCGCAGCCTCCTCCTTGTGGCTACCCTGGTCCTCCTGGACCACCTCA |
| | | GTTTGGCCAGAAACCTCCCCGTGGCCACTCCAGACCCAGGAATGTTCCCATGCCTTCA |
| | | CCACTCCCAAAACCTGCTGAGGGCCGTCAGCAACATGCTGCAGAAGGCCAGACAAACT |
| | | CTAGAATTTTACTCCTGCACTTCCGAAGAGATTGATCATGAAGATATCACAAAAGATA |
| | | AAACCAGCACAGTGGAGGCCTGTTTACCACTGGAATTAGCCACGAATGAGAGTTGCCT |
| | | GGCTTCCAGAGGGATCTCTCTGATAACTAATGGGAGTTGCCTAGCCTCCAGAAAGACC |
| | | TCTTTTATGACGACCCTGTGCCTTGGCAGTATCTATGAGGACTTGAAGATGTACCAGG |
| | | TGGAGTTCAAGACCATGAATGCAAAGCTTCTGATGAATCCTAAGAGGCAGATCTTTCT |
| | | GGATCAAAACATGCTGACAGCTATTGATGAGCTGTTACAGGCCCTGAATTTCAACAGT |
| | | GAGACTGTGCCACAAAAATCCTCCCTTGAAGAACCGGATTTTTATAAAACTAAAATCA |
| | | AGCTCTGCATACTTCTTCATGCTTTCAGAATTCGGGCAGTGACCATCAATAGAATGAT |
| | | GAGCTATCTGAATTCTTCCTAG |
| SEQ ID NO:22 | R2-555 1-660 mature CDS 67-657 | ATGTGCCCGCCGCGCGGCCTCCTCCTTGTGGCTACCCTGGTCCTCCTGGACCACCTCA |
| | | GTTTGGCCAGAAACCTCCCTGTGGCCACCCCAGGCCCAGGAATGTTCCCATGCCTTCA |
| | | CCACTCCCAAAACCTGCTGAGGGCCGTCAGCAACATGCTGCAGAAGGCCAGACAAACT |
| | | CTAGAATTTTACTCCTGCACTTCCGAAGAGACTGATCATGAAGATATCACAAAAGATA |
| | | AAACCAGCACAGTGGAGGCCTGCTTACCACTGGAATTAATCAAGAATGAGAGTTGCCT |
| | | AAATTCCAGAGAGACTTCTTTCATAACTAATGGGAGTTGCCTAGCCTCCAGAAAGACC |
| | | TCTTTTATGACAACCCTGTGCCTTAGCAGTATCTATGAGGACTTGAAGATGTACCAGG |
| | | TGGAGTTCAAGACCATGAATGCAAAGCTTCTGATGAATCCTAAGAGGCAGATCTTTCT |
| | | GGATCAAAACATGCTGACAGCTATTGATGAGCTGTTACAGGCCCTGAATTTCAACAGT |
| | | GAGACTGTGCCACAAAAATCCTCCCTTGAAGAACCGGATTTTTATAAAACTAAAATCA |
| | | AGCTCTGCATACTTCTTCATGCTTTCAGAATTCGGGCAGTGACCATCAATAGAATGAT |
| | | GAGCTATCTGAATTCTTCCTAG |
| SEQ ID NO:23 | R2-162 1-660 mature CDS 67-657 | ATGTGCCCGCCGCGCGGCCTCCTCCTTGTGGCTACCCTGGTCCTCCTGGACCACCTCA |
| | | GTTTGGCCAGAAACCTCCCCGTGGCCACCCCAGGCCCAGGAATGTTCCCATGCCTTCA |
| | | CCACTCCCAAAACCTGCTGAGGGCTGTCAGCAACACGCTCCAGAAGGCCAAACAAACC |

-continued

SEQUENCES

| SEQ ID | Clone ID, no. of residues, mature region | SEQUENCE |
|---|---|---|
| | | CTAGAATTTTACCCCTGCACTTCCGAAGAGATTGATCATGAAGATATCACAAAAGATA |
| | | AAACCAGCACAGTGGAGGCCTGTTTACCACTGGAATTAGCCACGAATGAGAGTTGCCT |
| | | GGCTTCCAGAGGGATCTCTCTGATAACTAATGGGAGTTGCCTGGCCTCCAGAAAGACC |
| | | TCTTTTATGACAACCCTGTGCCTTAGCAGCATCTATGAGGACTTGAAGATGTACCAGG |
| | | TGGAGTTCAAGGCCATGAATGCAAAGCTGTTAATGGATCCTAAAAGGCAGATCTTTCT |
| | | GGATCAAAACATGCTGGCAGCTATTGCTGAGCTAATGCAGGCCCTGAATGTCAACAGT |
| | | GAGACTGCGCCACAAAAATCCTCCCTGGAAGAACCGGATTTTTATAAAACTAAAATCA |
| | | AGCTCTGCATACTTCTTCATGCTTTCAGAATTCGGGCAGTGACCATCAATAGAATGAT |
| | | GAGCTATCTGAATTCTTCCTAG |
| SEQ ID NO:24 | R2-157 1-660 mature CDS 67-657 | ATGTGTCCAGCGCGCAGCCTCCTCCTTGTGGCTACCCTGGTCCTCCTGGACCACCTCA |
| | | GTTTGGCCAGAAACCTCCCCGTGGCCACTCCAGACCCAGGAATGTTCCCATGCCTTCA |
| | | CCACTCCCAAAACCTGCTGAGGGCTGTCAGCAACACGCTCCAGAAGGCCAAACAAACC |
| | | CTAGAATTTTACCCCTGCACTTCCGAAGAGATTGATCATGAAGATATCACAAAAGATA |
| | | AAACCAGCACAGTGGAGGCCTGTTTACCACTGGAATTAGCCACGAATGAGAGTTGCCT |
| | | GGCTTCCAGAGGGATCTCTCTGATAACTAATGGGAGTTGCCTGGCCTCCAGAAAGACC |
| | | TCTTTTATGACGACCCTGTGCCTTAGCAGCATCTATGAGGACTTGAAGATGTACCAGG |
| | | TGGAGTTCAAGGCCATGAATGCAAAGCTGTTGATGGATCCTAAAAGGCAGATCTTTCT |
| | | GGATCAAAACATGCTGGCAGCTATTGCTGAGCTAATGCAGGCCCTGAATGTCAACAGT |
| | | GAGACTGCGCCACAAAAATCCTCCCTTGAAGAACCGGATTTTTATAAGACTAAAATCA |
| | | AGCTCTGCATACTTCTTCATGCCTTCAGAATTCGTGCAGTGACCATCGATAGAATGAT |
| | | GAGCTATCTGAATTCTTCCTAG |
| SEQ ID NO:25 | R1-4-87 1-660 mature CDS 67-657 | ATGTGCCCGCCGCGCGGCCTCCTCCTTGTGGCTACCCTGGTCCTCCTGGACCACCTCA |
| | | GTTTGGCCAGAAACCTCCCCGTGGCCACCCCAGGCCCAGGAATGTTCCCATGCCTTCA |
| | | CCACTCCCAAAACCTGCTGAGGGCCGTCAGCAACATGCTGCAGAAGGCCAGACAAACT |
| | | CTAGAATTTTACTCCTGCACTTCCGAAGAGATTGATCATGAAGATATCACAAAAGATA |
| | | AAACCAGCACAGTGGAGGCCTGCTTACCACTGGAATTAATCAAGAATGAGAGTTGCCT |
| | | AAATTCCAGAGAGACTTCTTTCATAACTAATGGGAGTTGCCTAGCCTCCAGAAAGACC |
| | | TCTTTTATGACAACCCTGTGCCTTAGCAGTATCTATGAGGACTTGAAGATGTACCAGG |
| | | TGGAGTTCAAGACCATGAATGCAAAGCTTCTGATGAATCCTAAGAGGCAGATCTTTCT |
| | | GGATCAAAACATGCTGACAGCTATTGATGAGCTGTTACAGGCCCTGAATTTCAACAGT |
| | | GAGACTGTGCCACAAAAATCCTCCCTTGAAGAACCGGATTTTTATAAAACTAAAATCA |
| | | AGCTCTGCATACTTCTTCATGCTTTCAGAATTCGGGCAGTGACCATCAATAGAATGAT |
| | | GAGCTATCTGAATTCTTCCTAG |
| SEQ ID NO:26 | R2-42 1-221 mature | MCPLRSLLLISTLVLLHHLPHLSLGRSLPTTTASPGRSCLDYSQNLLKAASNTLQKAR |
| | | QILEFYPCTSEEIDHEDITKDKTSTVEACLPLELATNESCLASREISLITNGSCLASR |

-continued

SEQUENCES

| SEQ ID | Clone ID, no. of residues, mature region | SEQUENCE |
|---|---|---|
| | polypep. 26-221 | KTSFMTTLCHSSIYEDLKMYQMEFKAMNAKLLMDPKRQIFLDQNMLAVIDELMQALNF NSETVPQKPSLEELDFYKTKIKLCILLHAFRIRAVTIDRMMSYLNSS |
| SEQ ID NO:27 | R2-146 1-221 mature polypep. 26-221 | MYPLRSLLLISTLVLLHHLPHLSLGRSLPTTTASPGRSCLDYSQNLLKAASNTLQRAR QILEFYPCTSEEIDHEDITKDKTSTVEACLPLELATNESCLASREISLITNGSCLASR KTSFMTTLCLSSIYEDLKMYQMEFKAMNAKLLMDPKRQIFLDQNMLAVIDELMQALNF NSETVPQKPSLEELDFYKTKIKLCILLHAFRIRAVTINRMMSYLNSS |
| SEQ ID NO:28 | R2-796 1-219 mature polypep. 23-219 | MCPPRGLLLVATLVLLDHLSLARNLPVATPGPGMFPCLHHSQNLLRAVSNMLQKARQT LEFYSCTSEEIDHEDITKDKTSTVEACLPLELIKNESCLNSRETSFITNGSCLASRKT SFMTTLCLSSIYEDLKMYQVEFKTMNAKLLMNPKRQIFLDQNMLTAIDELLQALNFNS ETVPQKSSLEEPDFYKTKIKLCILLHAFRIRAVTINRMMSYLNSS |
| SEQ ID NO:29 | R2-631 1-219 mature polypep. 23-219 | MCPARSLLLVATLVLLDHLSLARNLPVATPGPGMLPCLHHSQNLLRAVSNTLQKAKQT LEFYPCTSEEIDHEDITQDKTSTVEACLPLELATNESCLASRGISLITNGSCLASRKT SFMTTLCLSSIYEDLKMYQVEFKAMNAKLLMDPKRQIFLDQNMLAAIAELMQALNVNS ETAPQKSSLEEPDFYKTKIKLCILLHAFRIRAVTINRMMSYLNSS |
| SEQ ID NO:30 | R2-613 1-219 mature polypep. 23-219 | MCPARSLLLVATLVLLDHLSLARNLPVATPGPGMFPCLHHSQNLLRAVSNMLQKARQT LEFYSCTSEEIDHEDITKDKTSTVEACLPLELIKNESCLNSRETSFITNGSCLASRKT SFMTTLCLSSIYEDLKMYQVEFKAMNAKLLMDPKRQIFLDQNMLAAIAELMQALNVNS ETAPQKSSLEEPDFYKTKIKLCILLHAFRIRAVTINRMMSYLNSS |
| SEQ ID NO:31 | R2-571 1-219 mature polypep. 23-219 | MCPARSLLLVATLVLLDHLSLARNLPVATPDPGMFPCLHHSQNLLRAVSNMLQKARQT LEFYSCTSEEIDHEDITKDKTSTVEACLPLELATNESCLASRGISLITNGSCLASRKT SFMTTLCLGSIYEDLKMYQVEFKTMNAKLLMNPKRQIFLDQNMLTAIDELLQALNFNS ETVPQKSSLEEPDFYKTKIKLCILLHAFRIRAVTINRMMSYLNSS |
| SEQ ID NO:32 | R2-555 1-219 mature polypep. 23-219 | MCPPRGLLLVATLVLLDHLSLARNLPVATPGPGMFPCLHHSQNLLRAVSNMLQKARQT LEFYSCTSEETDHEDITKDKTSTVEACLPLELIKNESCLNSRETSFITNGSCLASRKT SFMTTLCLSSIYEDLKMYQVEFKTMNAKLLMNPKRQIFLDQNMLTAIDELLQALNFNS ETVPQKSSLEEPDFYKTKIKLCILLHAFRIRAVTINRMMSYLNSS |
| SEQ ID NO:33 | R2-162 1-219 mature polypep. 23-219 | MCPPRGLLLVATLVLLDHLSLARNLPVATPGPGMFPCLHHSQNLLRAVSNTLQKAKQT LEFYPCTSEEIDHEDITKDKTSTVEACLPLELATNESCLASRGISLITNGSCLASRKT SFMTTLCLSSIYEDLKMYQVEFKAMNAKLLMDPKRQIFLDQNMLAAIAELMQALNVNS ETAPQKSSLEEPDFYKTKIKLCILLHAFRIRAVTINRMMSYLNSS |
| SEQ ID NO:34 | R2-157 1-219 mature polypep. 23-219 | MCPARSLLLVATLVLLDHLSLARNLPVATPDPGMFPCLHHSQNLLRAVSNTLQKAKQT LEFYPCTSEEIDHEDITKDKTSTVEACLPLELATNESCLASRGISLITNGSCLASRKT SFMTTLCLSSIYEDLKMYQVEFKAMNAKLLMDPKRQIFLDQNMLAAIAELMQALNVNS ETAPQKSSLEEPDFYKTKIKLCILLHAFRIRAVTIDRMMSYLNSS |
| SEQ ID | R1-4-87 | MCPPRGLLLVATLVLLDHLSLARNLPVATPGPGMFPCLHHSQNLLRAVSNMLQKARQT |

| SEQ ID | Clone ID, no. of residues, mature region | SEQUENCE |
|---|---|---|
| NO:35 | 1-219 mature protein 23-219 | LEFYSCTSEEIDHEDITKDKTSTVEACLPLELIKNESCLNSRETSFITNGSCLASRKT SFMTTLCLSSIYEDLKMYQVEFKTMNAKLLMNPKRQIFLDQNMLTAIDELLQALNFNS ETVPQKSSLEEPDFYKTKIKLCILLHAFRIRAVTINRMMSYLNSS |
| SEQ ID NO:36 | p35 1-219 mature polypep. 23-219 | MCPARSLLLVATLVLLDHLSLARNLPVATPDPGMFPCLHHSQNLLRAVSNMLQKARQT LEFYPCTSEEIDHEDITKDKTSTVEACLPLELTKNESCLNSRETSFITNGSCLASRKT SFMMALCLSSIYEDLKMYQVEFKTMNAKLLMDPKRQIFLDQNMLAVIDELMQALNFNS ETVPQKSSLEEPDFYKTKIKLCILLHAFRIRAVTIDRVTSYLNAS |
| SEQ ID NO:37 | wt-p40 CDS for SEQ 15 | ATGTGTCACCAGCAGTTGGTCATCTCTTGGTTTTCCCTGGTTTTTCTGGCATCTCCCC TCGTGGCCATATGGGAACTGAAGAAAGATGTTTATGTCGTAGAATTGGATTGGTATCC GGATGCCCCTGGAGAAATGGTGGTCCTCACCTGTGACACCCCTGAAGAAGATGGTATC ACCTGGACCTTGGACCAGAGCAGTGAGGTCTTAGGCTCTGGCAAAACCCTGACCATCC AAGTCAAAGAGTTTGGAGATGCTGGCCAGTACACCTGTCACAAAGGAGGCGAGGTTCT AAGCCATTCGCTCCTGCTGCTTCACAAAAAGGAAGATGGAATTTGGTCCACTGATATT TTAAAGGACCAGAAAGAACCCAAAAATAAGACCTTTCTAAGATGCGAGGCCAAGAATT ATTCTGGACGTTTCACCTGCTGGTGGCTGACGACAATCAGTACTGATTTGACATTCAG TGTCAAAAGCAGCAGAGGCTCTTCTGACCCCCAAGGGGTGACGTGCGGAGCTGCTACA CTCTCTGCAGAGAGTCAGAGGGGACAACAAGGAGTATGAGTACTCAGTGGAGTGCC AGGAGGACAGTGCCTGCCCAGCTGCTGAGGAGAGTCTGCCCATTGAGGTCATGGTGGA TGCCGTTCACAAGCTCAAGTATGAAAACTACACCAGCAGCTTCTTCATCAGGGACATC ATCAAACCTGACCCACCCAAGAACTTGCAGCTGAAGCCATTAAAGAATTCTCGGCAGG TGGAGGTCAGCTGGGAGTACCCTGACACCTGGAGTACTCCACATTCCTACTTCTCCCT GACATTCTGCGTTCAGGTCCAGGGCAAGAGCAAGAGAGAAAAGAAAGATAGAGTCTTC ACGGACAAGACCTCAGCCACGGTCATCTGCCGCAAAAATGCCAGCATTAGCGTGCGGG CCCAGGACCGCTACTATAGCTCATCTTGGAGCGAATGGGCATCTGTGCCCTGCAGTTA G |
| SEQ ID NO:38 | wt-p35 CDS for SEQ 36 | ATGTGTCCAGCGCGCAGCCTCCTCCTTGTGGCTACCCTGGTCCTCCTGGACCACCTCA GTTTGGCCAGAAACCTCCCCGTGGCCACTCCAGACCCAGGAATGTTCCCATGCCTTCA CCACTCCCAAAACCTGCTGAGGGCCGTCAGCAACATGCTCCAGAAGGCCAGACAAACT CTAGAATTTTACCCTTGCACTTCTGAAGAGATTGATCATGAAGATATCACAAAAGATA AAACCAGCACAGTGGAGGCCTGTTTACCATTGGAATTAACCAAGAATGAGAGTTGCCT AAATTCCAGAGAGACCTCTTTCATAACTAATGGGAGTTGCCTGGCCTCCAGAAAGACC TCTTTTATGATGGCCCTGTGCCTTAGTAGTATTTATGAAGACTTGAAGATGTACCAGG TGGAGTTCAAGACCATGAATGCAAAGCTTCTGATGGATCCTAAGAGGCAGATCTTTCT AGATCAAAACATGCTGGCAGTTATTGATGAGCTGATGCAGGCCCTGAATTTCAACAGT GAGACTGTGCCACAAAAATCCTCCCTTGAAGAACCGGATTTTTATAAAACTAAAATCA |

SEQUENCES

| SEQ ID | Clone ID, no. of residues, mature region | SEQUENCE |
|---|---|---|
| | | AGCTCTGCATACTTCTTCATGCTTTCAGAATTCGGGCAGTGACTATTGACAGAGTGAC GAGCTATCTGAATGCTTCCTAA |
| SEQ ID NO:39 | modif p40 1-328 mature polypep. 23-328 | M-$X_2$-$X_3$-QQLV-$X_8$-SWFSLV-$X_{15}$-LASPL-$X_{21}$-AIWEL-$X_{27}$-K-$X_{29}$- VYVVELDWYP-$X_{40}$-APGE-$X_{45}$-VVL-$X_{49}$-CDTPEEDGITWT-$X_{62}$-DQSS-$X_{67}$- VLG-$X_{71}$-GKTLTI-$X_{78}$-VKEFGDAGQYTC-$X_{91}$-KGG-$X_{95}$-$X_{96}$-LS-$X_{99}$- SLLLLHKKEDGIWSTDILKDQK-$X_{122}$-PK-$X_{125}$-K-$X_{127}$-FL-$X_{130}$-CEAK-$X_{135}$- YSG-$X_{139}$-FTCWWLT-$X_{147}$-ISTDL-$X_{153}$-F-$X_{155}$-VKSSRGS-$X_{163}$-DP-$X_{166}$- GVTCG-$X_{172}$-$X_{173}$-$X_{174}$-LS-$X_{177}$-$X_{178}$-$X_{179}$-$X_{180}$-$X_{181}$-$X_{182}$-$X_{183}$-$X_{184}$-$X_{185}$- $X_{186}$-$X_{187}$-$X_{188}$-Y-$X_{190}$-VECQE-$X_{196}$-SACP-$X_{201}$-AEESLPIEV-$X_{211}$-$X_{212}$- $X_{213}$-A-$X_{215}$-HKLKYENYTS-$X_{226}$-FFIRDIIKPDPPKNLQL-$X_{244}$-PLKNSR-$X_{251}$- VE-$X_{254}$-$X_{255}$-W-$X_{257}$-YPDTWS-$X_{264}$-PHSYFSLTF-$X_{274}$-$X_{275}$-QVQG-$X_{280}$- $X_{281}$-KRE-$X_{285}$-$X_{286}$-$X_{287}$-$X_{288}$-$X_{289}$-F-$X_{291}$-D-$X_{293}$-TSA-$X_{297}$-V-$X_{299}$-C- $X_{301}$-K-$X_{303}$-A-$X_{305}$-I-$X_{307}$-V-$X_{309}$-A-$X_{311}$-DRY-$X_{315}$-SS-$X_{318}$-WS-$X_{321}$- WASV-$X_{326}$-$X_{327}$-$X_{328}$ |
| SEQ ID NO:40 | modif p35 1-219 mature polypep 23-219 | M-$X_2$-P-$X_4$-R-$X_6$-LLL-$X_{10}$-$X_{11}$-TLVLL-$X_{17}$-HLSL-$X_{22}$-R-$X_{24}$-LP-$X_{27}$-$X_{28}$- T-$X_{30}$-$X_{31}$-PG-$X_{34}$-$X_{35}$-$X_{36}$-CL-$X_{39}$-$X_{40}$-SQNLL-$X_{46}$-A-$X_{48}$-SN-$X_{51}$-LQ- $X_{54}$-A-$X_{56}$-Q-$X_{58}$-LEFY-$X_{63}$-CTSEE-$X_{69}$-DHEDIT-$X_{76}$-DKTSTVEACLPLEL- $X_{91}$-$X_{92}$-NESCL-$X_{98}$-SR-$X_{101}$-$X_{102}$-S-$X_{104}$-ITNGSCLASRKTSFM-$X_{120}$-$X_{121}$- LC-$X_{124}$-$X_{125}$-SIYEDLKMYQ-$X_{136}$-EFK-$X_{140}$-MNAKLLM-$X_{148}$- PKRQIFLDQNML-$X_{161}$-$X_{162}$-I-$X_{164}$-EL-$X_{167}$-QALN-$X_{172}$-NSET-$X_{177}$-PQK- $X_{181}$-SLEE-$X_{186}$-DFYKTKIKLCILLHAFRIRAVTI-$X_{210}$-R-$X_{212}$-$X_{213}$-SYLN- $X_{218}$-S |
| SEQ ID NO:41 | nucleic acid | ATGTGCCATCAACAA |
| SEQ ID NO:42 | peptide | IWDLKRDVYVIELDWFPNAPGETLV |
| SEQ ID NO:43 | peptide | VWEIKKDMYVVELEWYPNAPGETVI |
| SEQ ID NO:44 | EHtag peptide | AAAGAPVPYPDPLERAAAHHHHHH |

What is claimed is:

1. A recombinant polypeptide, wherein the recombinant polypeptide induces proliferation of T cells in the presence of a mature polypeptide region of a wild-type p35 polypeptide subunit of human interleukin-12, and wherein the recombinant polypeptide comprises a sequence that is at least 95% identical to the full length of the mature polypeptide region of SEQ ID NO:8.

2. The recombinant polypeptide of claim 1, wherein the recombinant polypeptide comprises a sequence that is at least 97% identical to the full length of the mature polypeptide region of SEQ ID NO:8.

3. The recombinant polypeptide of claim 2, wherein the recombinant polypeptide comprises the mature polypeptide region of SEQ ID NO:8.

4. A composition comprising the recombinant polypeptide of claim 1 and a carrier.

5. The composition of claim 4, further comprising a mature polypeptide region of a wild-type p35 polypeptide subunit of human interleukin-12.

6. The composition of claim 4, wherein the carrier is a pharmaceutically acceptable carrier.

7. A recombinant polypeptide, wherein the recombinant polypeptide induces proliferation of T cells in the presence of a wild-type p35 polypeptide subunit of human interleukin-12, and wherein the recombinant polypeptide comprises a sequence that is at least 95% identical to the full length of the sequence of SEQ ID NO:8.

8. The recombinant polypeptide of claim 7, wherein the recombinant polypeptide comprises a sequence that is at least 97% identical to the full length of the sequence of SEQ ID NO:8.

9. The recombinant polypeptide of claim 8, wherein the recombinant polypeptide comprises the sequence of SEQ ID NO:8.

10. A composition comprising the recombinant polypeptide of claim 7 and a carrier.

11. The composition of claim 10, further comprising a wild-type p35 polypeptide subunit of human interleukin-12.

12. The composition of claim 11, wherein the carrier is a pharmaceutically acceptable carrier.

* * * * *

SEQUENCE LISTING

<160> NUMBER OF SEQ ID NOS: 44

<210> SEQ ID NO 1
<211> LENGTH: 975
<212> TYPE: DNA
<213> ORGANISM: Artificial Sequence
<220> FEATURE:
<223> OTHER INFORMATION: Synthetic Sequence

<400> SEQUENCE: 1

```
atgtgtcacc agcagttggt catctcttgg ttttccctgg ttttgctggc atctcccctc    60
atggccatat gggaactgaa gaaagacgtt tatgtcgtag agttggactg gtatcctaat   120
gctcctggag aaacagtggt cctcacgtgt gacactcctg aagaagatgg catcacctgg   180
acctcagacc agagcagtga ggtcttgggc actggcaaaa ccctgaccat ccacgtcaaa   240
gagtttggag atgctggcca gtacacctgt cgcaaaggag gcgaggctct gagtcgttca   300
ctcctcctgc tgcacaaaaa ggaagatgga atttggtcca ctgatatttt aaaagaccag   360
aaagagccca aaacaagag ctttctaaaa tgtgaggcaa agaattactc cggacgtttc   420
acctgctggt ggctgacgac aatcagtact gatttgaaat tcagtgtcaa agcagcaga   480
ggctccactg accccgtgg cgtgacatgt ggcacggcaa cgctctcaga ggacctcgga   540
gagtataaga agtacagagt ggagtgtcag gagggcagtg cctgcccagc cgctgaggag   600
agcctgccca ttgaggtcgt gctggaagct gttcacaagc tcaagtatga aaactacacc   660
agcagcttct tcatcagaga catcatcaaa ccagacccac caagaacct gcaactgaag   720
ccattgaaaa attctcggca tgtggaggtc agctgggggt accccgacac ctggagcacc   780
ccacattcct acttctccct gacattctgc atccaggtcc agggcaagag caagagagaa   840
aagaaagata gaatcttcac agacaagacc tcagccacgg tcatctgccg caaaaatgcc   900
aagatccgcg tgcaagcccg ggaccgctac tacagctcat tctggagtga atgggcatct   960
gtgtcctgca gttag                                                   975
```

<210> SEQ ID NO 2
<211> LENGTH: 984
<212> TYPE: DNA
<213> ORGANISM: Artificial Sequence
<220> FEATURE:
<223> OTHER INFORMATION: Synthetic Sequence

<400> SEQUENCE: 2

```
atgtgccacc agcagttggt catctcttgg ttttccctgg tttttctggc atctcccctc    60
gtggccatat gggaactgga gaaaaacgtc tatgttgtag aattggactg gtacccggat   120
gccccctgga gaaatggtgg tcctcgcctgt gacactcctg aagaagatgg catcacctgg   180
acctcagacc agagcagtga ggtcttgggc actggcaaaa ccctgaccat ccacgtcaaa   240
gagtttggag atgctggcca gtacacctgt cgcaaaggag cgcagttct gagccagtca   300
ctcctgctgc ttcacaaaaa ggaagatgga atttggtcca ctgatatttt aaaagaccag   360
aaagagccca aaacaagag ctttctaaaa tgtgaggcaa agaattactc cggacgtttc   420
acctgctggt ggctgacaac aatcagtact gatttgaaat tcagtgtcaa agcagcaga   480
ggctcctctg accccgagg ggtgacgtgc ggagcagcgt tgctctcagc agagaaggtc   540
agcttggagc atagggagta taagaagtac agagtggagt gtcaggaggg cagtgcctgc   600
ccagccgctg aggagagcct gcccattgag gtcgtgctgg aagctgttca caagctcaag   660
tatgaaaact ataccagcag cttcttcatc agggacatca tcaaaccgga cccacccaag   720
aacctgcaac tgagaccact aaagaattct cggcaggtgg aggtcaactg ggagtaccct   780
gacacgtgga gcaccccaca ttcctacttc tccctgacgt tttgtgttca ggtccaggga   840
aagaacaaga gagaaagaa actcttcatg gaccaaacct cagccaaagt cacatgccac   900
aaggatgcca agatccgcgt gcaagccaga gaccgctact acagctcatc ttggagcgaa   960
```

```
                                       tgggcatctg tgccctgcag ttag              984
```

<210> SEQ ID NO 3
<211> LENGTH: 984
<212> TYPE: DNA
<213> ORGANISM: Artificial Sequence
<220> FEATURE:
<223> OTHER INFORMATION: Synthetic Sequence

<400> SEQUENCE: 3

```
atgtgtcacc agcagttggt catctcttgg tttttcctgg ttttctggc atctcccctc      60
gtggccatat gggaactgga gaaaaatgtt tatgttgtag aattggattg gtacccggat    120
gccctggag aaatggtggt cctcgcctgt gacactcctg aagaagatgg catcacctgg     180
acctcagacc agagcagtgg ggtcttgggc actggcaaaa ccctgaccat ccacgtcaaa    240
gagtttggag atgctggcca gtacacctgt cgcaaaggag gcgcagttct gagccagtca    300
ctcctgctgc ttcacaaaaa ggaagatgga atttggtcca ctgatatttt aaaggaccag    360
aaagaaccca agctaagag tttttttaaaa tgtgaggcaa aggattattc tggacacttc    420
acctgctggt ggctgacaac aatcagtact gatttgaaat tcagtgtcaa agcagcaga    480
ggctcctctg accccaagg ggtgacttgt ggagccgtta cactctctgc agagagggtc    540
agcatggacc acaggagta taacaagtac acagtggagt gtcaggaggg cagtgcctgc    600
ccctctgccg aggagagcct acccatcgag gtcgtggtgg atgctattca caagctcaag    660
tatgaaaact acaccagcag cttcttcatc agggacatca tcaaaccgga cccacccaag    720
aacttgcagc tgagaccact aaagaattct cggcaggtgg aggtcaactg ggagtaccct    780
gacacgtgga gcaccccaca ttcctacttt tccctgacgt tttgtgttca ggtccaggga    840
aagaacaaga gagaaaagaa actcttcatg gaccaaacct cagccaaagt cacatgccac    900
aaggatgcca agatccgcgt gcaagccaga gaccgctact acagctcatc ttggagcgaa    960
tgggcatctg tgccctgcag ttag                                           984
```

<210> SEQ ID NO 4
<211> LENGTH: 984
<212> TYPE: DNA
<213> ORGANISM: Artificial Sequence
<220> FEATURE:
<223> OTHER INFORMATION: Synthetic Sequence

<400> SEQUENCE: 4

```
atgcatcctc agcagttggt cgtttcctgg ttttccctgg ttttgctggc atctcccctc      60
gtggccatat gggaactgga gaaaaatgtt tatgttgtag aattggattg gtatcctgat    120
gctcctggag aaacagtggt cctcgcctgt gacactcctg aagaagatgg catcacctgg    180
acctcagacc agagcagtga ggtcctgggc actggcaaaa ccctgaccat ccacgtcaaa    240
gagtttggag atgctggcca gtacacctgt cgcaaaggag gcgcagttct gagccagtca    300
ctcctgctgc ttcacaaaaa ggaagatgga atttggtcca ctgatatttt aaaagaccag    360
aaaaagccca aaaacaagat ctttctgaaa tgtgaggcaa agaattactc cggacgtttc    420
acctgctggt ggctgacagc aatcagtaca gatttgaaat tcactgtcaa agcagcaga    480
ggctcctctg accccaagg ggtgacttgt ggagccgtta cactctctgc agagagggtc    540
agcatggacc acaggagta taacaagtac acagtggagt gtcaagaggg cagtgcctgc    600
ccctctgccg aggagagcct acccatcgag gtcgtggtgg atgctattca caagctcaag    660
tatgaaaact acaccagcag gttcttcatc agggacatca tcaaaccgga cccacccaag    720
```

```
aacttgcaac tgagaccact aaagaattct cgacacgtgg agatcagctg ggagtaccct      780
gacacctgga gcaccccaca ttcctacttc tccctgacgt tttgtgttca ggtccagggg      840
aagaacaaga gagaaaagaa actcttcatg gaccaaacct cagccaaagt cacatgccac      900
aaggatgcca agatccgcgt gcaagccaga gaccgctacc acagctcatc ttggagcgaa      960
tgggcatctg tgccctgcag ttag                                             984

<210> SEQ ID NO 5
<211> LENGTH: 969
<212> TYPE: DNA
<213> ORGANISM: Artificial Sequence
<220> FEATURE:
<223> OTHER INFORMATION: Synthetic Sequence

<400> SEQUENCE: 5
atgtgtcacc agcagttggt catctcttgg ttttccctgg tttttctggc atccccctc       60 gtggccatat gggaactgga gaaaaacgtt tatgttgtag aattggactg gtacccggat     120
gcccctggag aaatggtggt cctcgcctgt gacactcctg aagaagatgg catcacctgg     180
acctcagacc agagcagtga ggtcttgggc actggcaaaa ccctgaccat ccacgtcaaa     240
gagtttggag atgctggcca gtatacctgc ataaaggag gcaaggttct gagccgctca      300
ctcctgctgc ttcacaaaaa ggaagatgga atttggtcca ctgatatttt aaaagaccag     360
aaagagccca aaacaagag ctttctaaaa tgtgaggcaa agaattactc cggacgtttc      420
acctgctggt ggctgacgac aatcagtact gatctgacat tcagtgtcaa agcagcaga     480 ggctctactg accccatgg cgtgacatgt ggcacggcaa cgctctcaga ggacctcgga     540
gagtataaga agtacagagt ggagtgtcag gagggcagtg cctgcccagc cgctgaggag     600
agcctgccta ttgaggtcgt gctggaagct gttcacaagc tcaagtatga aaactacacc     660
agcagcttct tcatcaggga catcatcaaa ccagacccac ccaagaacct gcaactgaga     720
ccattaaaga attctcggca ggtggaggtc aactgggagt accctgacac gtggagcacc     780
ccacattcct acttctccct gacgttttgt gttcaggtcc agggaaggaa caagagagaa     840
aagaaactct tcatggacca aacctcagcc aaagtcacgt gccacaagga tgccaagatc     900
cgcgtgcaag cccagagaccg ctactatagt tcatcctgga gcgactgggc atccgtgtcc     960
tgcggttag                                                             969

<210> SEQ ID NO 6
<211> LENGTH: 975
<212> TYPE: DNA
<213> ORGANISM: Artificial Sequence
<220> FEATURE:
<223> OTHER INFORMATION: Synthetic Sequence

<400> SEQUENCE: 6
atgtgtcacc agcagttggt catctcttgg ttttccctgg tttttctggc atctcccctc      60
atggccatat gggaactgaa gaaagacgtt tatgttgtag aattggactg gtacccggat     120
gcccctggag aaatggtggt cctcgcctgt gacactcctg aagaagatgg catcacctgg     180
acctcagacc agagcagtga ggtcttgggc actggcaaaa ccctgaccat ccacgtcaaa     240
gagtttggag atgctggcca gtacacctgt cataaaggag gcacagttct gagccagtca     300
ctcctgctgc ttcacaaaaa ggaagatgga atttggtcca ctgatatttt aaaagaccag     360
aaagagccca aaacaagag ctttctaaag tgtgaggcaa agaattactc cggacgtttc      420
```

-continued

| | |
|---|---|
| acctgctggt ggctgacggc aatcagtact gatttgaaat tcactgtcaa aagcagcaga | 480 |
| ggctccactg accccgtgg cgtgacatgt ggcacggcaa cgctctcaga ggacctcgga | 540 |
| gagtataaga agtacagagt ggagtgtcag gagggcagtg cctgcccagc cgctgaggag | 600 |
| agcctgccca ttgaggtcgt gctggaagct gttcacaagc tcaagtatga aaactacacc | 660 |
| agcagcttct tcatcaggga catcatcaaa ccagacccac caagaacct gcaactgaga | 720 |
| ccattaaaga attctcggca cgtggaggtc agctgggagt accctgacac gtggagcgcc | 780 |
| ccacattcct acttttccct gacgtttggt gttcaggtcc agggcaggaa caagagagaa | 840 |
| gatagactct tcatggacca aacctcagcc aaagtcgtgt gccacaagga tgccaagatc | 900 |
| cgcgtgcaag ccagagaccg ctactacagc tcatcttgga gcgaatgggc atctgtgtcc | 960 |
| ctgcagtcag tctag | 975 |

<210> SEQ ID NO 7
<211> LENGTH: 990
<212> TYPE: DNA
<213> ORGANISM: Artificial Sequence
<220> FEATURE:
<223> OTHER INFORMATION: Synthetic Sequence

<400> SEQUENCE: 7

| | |
|---|---|
| atgtgtcacc agcagttggt catctcttgg ttttccctgg tttttctggc atctcccctc | 60 |
| gtggccatat gggaactgga gaaaaacgtt tatgttgtag aattggactg gtacccggat | 120 |
| gccctggag aaatggtggt cctcgcctgt gacactcctg aagaagatgg catcacctgg | 180 |
| acctcagacc agagcagtga ggtcttgggc actggcaaaa ccctgaccat ccacgtcaaa | 240 |
| gagtttggag atgctggcca gtacacctgt cgcaaaggag cgcagttct gagccagtca | 300 |
| ctcctgctgc ttcacaaaaa ggaagatgga atttggtcca ctgatatttt aaaagaccag | 360 |
| aaagagccca aaaacaagat ctttctgaaa tgtgaggcaa agaattactc cggacgtttc | 420 |
| acctgctggt ggctgacagc aatcagtaca gatttgaaat tcactgtcaa aagcagcaga | 480 |
| ggctcctctg accccaagg ggtgacttgt ggagccgtta cactctctgc agagagggtc | 540 |
| agcatggacc acagggagta taacaagtac acagtggagt gtcaggaggg cagtgcctgc | 600 |
| ccctctgccg aggagagcct acccatcgag gtcgtggtgg atgctattca caagctcaag | 660 |
| tatgaaaact acaccagcag cttcttcatc agagacatca tcaaacctga cccacccaag | 720 |
| aacttgcagc tgaagccatt aaagaattct cgacacgtgg agatcagctg ggagtaccct | 780 |
| gacacctgga gcatcccaca ttcctacttt tccctgatgt ttggtgttca agttcagggc | 840 |
| aagaacaaga gagaaagaa agatagactc tccgtggaca agacctcagc caaggtcgtg | 900 |
| tgccacaagg atgccaagat ccgcgtgcaa gccagagacc gctactacag ctcatcttgg | 960 |
| agcgaatggg catctgtgcc ctgcagttag | 990 |

<210> SEQ ID NO 8
<211> LENGTH: 324
<212> TYPE: PRT
<213> ORGANISM: Artificial Sequence
<220> FEATURE:
<223> OTHER INFORMATION: Synthetic Sequence

<400> SEQUENCE: 8

Met Cys His Gln Gln Leu Val Ile Ser Trp Phe Ser Leu Val Leu Leu
 1               5                  10                  15

Ala Ser Pro Leu Met Ala Ile Trp Glu Leu Lys Lys Asp Val Tyr Val
             20                  25                  30

-continued

Val Glu Leu Asp Trp Tyr Pro Asn Ala Pro Gly Glu Thr Val Val Leu
             35                  40                  45

Thr Cys Asp Thr Pro Glu Glu Asp Gly Ile Thr Trp Thr Ser Asp Gln
 50                  55                  60

Ser Ser Glu Val Leu Gly Thr Gly Lys Thr Leu Thr Ile His Val Lys
65                  70                  75                  80

Glu Phe Gly Asp Ala Gly Gln Tyr Thr Cys Arg Lys Gly Gly Glu Ala
                 85                  90                  95

Leu Ser Arg Ser Leu Leu Leu His Lys Lys Glu Asp Gly Ile Trp
             100                 105                 110

Ser Thr Asp Ile Leu Lys Asp Gln Lys Glu Pro Lys Asn Lys Ser Phe
         115                 120                 125

Leu Lys Cys Glu Ala Lys Asn Tyr Ser Gly Arg Phe Thr Cys Trp Trp
    130                 135                 140

Leu Thr Thr Ile Ser Thr Asp Leu Lys Phe Ser Val Lys Ser Ser Arg
145                 150                 155                 160

Gly Ser Thr Asp Pro Arg Gly Val Thr Cys Gly Thr Ala Thr Leu Ser
                165                 170                 175

Glu Asp Leu Gly Glu Tyr Lys Lys Tyr Arg Val Glu Cys Gln Glu Gly
            180                 185                 190

Ser Ala Cys Pro Ala Ala Glu Glu Ser Leu Pro Ile Glu Val Val Leu
        195                 200                 205

Glu Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg His Val Glu Val Ser Trp Gly Tyr Pro Asp
                245                 250                 255

Thr Trp Ser Thr Pro His Ser Tyr Phe Ser Leu Thr Phe Cys Ile Gln
            260                 265                 270

Val Gln Gly Lys Ser Lys Arg Glu Lys Lys Asp Arg Ile Phe Thr Asp
        275                 280                 285

Lys Thr Ser Ala Thr Val Ile Cys Arg Lys Asn Ala Lys Ile Arg Val
    290                 295                 300

Gln Ala Arg Asp Arg Tyr Tyr Ser Ser Phe Trp Ser Glu Trp Ala Ser
305                 310                 315                 320

Val Ser Cys Ser

<210> SEQ ID NO 9
<211> LENGTH: 327
<212> TYPE: PRT
<213> ORGANISM: Artificial Sequence
<220> FEATURE:
<223> OTHER INFORMATION: Synthetic Sequence

<400> SEQUENCE: 9

Met Cys His Gln Gln Leu Val Ile Ser Trp Phe Ser Leu Val Phe Leu
 1               5                  10                  15

Ala Ser Pro Leu Val Ala Ile Trp Glu Leu Glu Lys Asn Val Tyr Val
             20                  25                  30

Val Glu Leu Asp Trp Tyr Pro Asp Ala Pro Gly Glu Met Val Val Leu
             35                  40                  45

Ala Cys Asp Thr Pro Glu Glu Asp Gly Ile Thr Trp Thr Ser Asp Gln
 50                  55                  60

```
Ser Ser Glu Val Leu Gly Thr Gly Lys Thr Leu Thr Ile His Val Lys
 65                  70                  75                  80

Glu Phe Gly Asp Ala Gly Gln Tyr Thr Cys Arg Lys Gly Gly Ala Val
                 85                  90                  95

Leu Ser Gln Ser Leu Leu Leu His Lys Lys Glu Asp Gly Ile Trp
            100                 105                 110

Ser Thr Asp Ile Leu Lys Asp Gln Lys Glu Pro Lys Asn Lys Ser Phe
            115                 120                 125

Leu Lys Cys Glu Ala Lys Asn Tyr Ser Gly Arg Phe Thr Cys Trp Trp
130                 135                 140

Leu Thr Thr Ile Ser Thr Asp Leu Lys Phe Ser Val Lys Ser Ser Arg
145                 150                 155                 160

Gly Ser Ser Asp Pro Arg Gly Val Thr Cys Gly Ala Ala Leu Leu Ser
                165                 170                 175

Ala Glu Lys Val Ser Leu Glu His Arg Glu Tyr Lys Lys Tyr Arg Val
                180                 185                 190

Glu Cys Gln Glu Gly Ser Ala Cys Pro Ala Ala Glu Glu Ser Leu Pro
            195                 200                 205

Ile Glu Val Val Leu Glu Ala Val His Lys Leu Lys Tyr Glu Asn Tyr
210                 215                 220

Thr Ser Ser Phe Phe Ile Arg Asp Ile Ile Lys Pro Asp Pro Pro Lys
225                 230                 235                 240

Asn Leu Gln Leu Arg Pro Leu Lys Asn Ser Arg Gln Val Glu Val Asn
                245                 250                 255

Trp Glu Tyr Pro Asp Thr Trp Ser Thr Pro His Ser Tyr Phe Ser Leu
                260                 265                 270

Thr Phe Cys Val Gln Val Gln Gly Lys Asn Lys Arg Glu Lys Lys Leu
            275                 280                 285

Phe Met Asp Gln Thr Ser Ala Lys Val Thr Cys His Lys Asp Ala Lys
290                 295                 300

Ile Arg Val Gln Ala Arg Asp Arg Tyr Tyr Ser Ser Ser Trp Ser Glu
305                 310                 315                 320

Trp Ala Ser Val Pro Cys Ser
                325
```

<210> SEQ ID NO 10
<211> LENGTH: 327
<212> TYPE: PRT
<213> ORGANISM: Artificial Sequence
<220> FEATURE:
<223> OTHER INFORMATION: Synthetic Sequence

<400> SEQUENCE: 10

```
Met Cys His Gln Gln Leu Val Ile Ser Trp Phe Ser Leu Val Phe Leu
  1               5                  10                  15

Ala Ser Pro Leu Val Ala Ile Trp Glu Leu Glu Lys Asn Val Tyr Val
                 20                  25                  30

Val Glu Leu Asp Trp Tyr Pro Asp Ala Pro Gly Glu Met Val Val Leu
             35                  40                  45

Ala Cys Asp Thr Pro Glu Glu Asp Gly Ile Thr Trp Thr Ser Asp Gln
 50                  55                  60

Ser Ser Gly Val Leu Gly Thr Gly Lys Thr Leu Thr Ile His Val Lys
 65                  70                  75                  80

Glu Phe Gly Asp Ala Gly Gln Tyr Thr Cys Arg Lys Gly Gly Ala Val
                 85                  90                  95
```

```
Leu Ser Gln Ser Leu Leu Leu His Lys Lys Glu Asp Gly Ile Trp
            100                 105                 110

Ser Thr Asp Ile Leu Lys Asp Gln Lys Glu Pro Lys Ala Lys Ser Phe
        115                 120                 125

Leu Lys Cys Glu Ala Lys Asp Tyr Ser Gly His Phe Thr Cys Trp Trp
130                 135                 140

Leu Thr Thr Ile Ser Thr Asp Leu Lys Phe Ser Val Lys Ser Ser Arg
145                 150                 155                 160

Gly Ser Ser Asp Pro Gln Gly Val Thr Cys Gly Ala Val Thr Leu Ser
                165                 170                 175

Ala Glu Arg Val Ser Met Asp His Arg Glu Tyr Asn Lys Tyr Thr Val
            180                 185                 190

Glu Cys Gln Glu Gly Ser Ala Cys Pro Ser Ala Glu Glu Ser Leu Pro
        195                 200                 205

Ile Glu Val Val Val Asp Ala Ile His Lys Leu Lys Tyr Glu Asn Tyr
210                 215                 220

Thr Ser Ser Phe Phe Ile Arg Asp Ile Ile Lys Pro Asp Pro Pro Lys
225                 230                 235                 240

Asn Leu Gln Leu Arg Pro Leu Lys Asn Ser Arg Gln Val Glu Val Asn
                245                 250                 255

Trp Glu Tyr Pro Asp Thr Trp Ser Thr Pro His Ser Tyr Phe Ser Leu
            260                 265                 270

Thr Phe Cys Val Gln Val Gln Gly Lys Asn Lys Arg Glu Lys Lys Leu
        275                 280                 285

Phe Met Asp Gln Thr Ser Ala Lys Val Thr Cys His Lys Asp Ala Lys
290                 295                 300

Ile Arg Val Gln Ala Arg Asp Arg Tyr Tyr Ser Ser Ser Trp Ser Glu
305                 310                 315                 320

Trp Ala Ser Val Pro Cys Ser
                325

<210> SEQ ID NO 11
<211> LENGTH: 327
<212> TYPE: PRT
<213> ORGANISM: Artificial Sequence
<220> FEATURE:
<223> OTHER INFORMATION: Synthetic Sequence

<400> SEQUENCE: 11

Met His Pro Gln Gln Leu Val Val Ser Trp Phe Ser Leu Val Leu Leu
  1               5                  10                  15

Ala Ser Pro Leu Val Ala Ile Trp Glu Leu Glu Lys Asn Val Tyr Val
            20                  25                  30

Val Glu Leu Asp Trp Tyr Pro Asp Ala Pro Gly Glu Thr Val Val Leu
        35                  40                  45

Ala Cys Asp Thr Pro Glu Glu Asp Gly Ile Thr Trp Thr Ser Asp Gln
 50                  55                  60

Ser Ser Glu Val Leu Gly Thr Gly Lys Thr Leu Thr Ile His Val Lys
 65                  70                  75                  80

Glu Phe Gly Asp Ala Gly Gln Tyr Thr Cys Arg Lys Gly Gly Ala Val
                85                  90                  95

Leu Ser Gln Ser Leu Leu Leu Leu His Lys Lys Glu Asp Gly Ile Trp
            100                 105                 110

Ser Thr Asp Ile Leu Lys Asp Gln Lys Lys Pro Lys Asn Lys Ile Phe
        115                 120                 125
```

```
Leu Lys Cys Glu Ala Lys Asn Tyr Ser Gly Arg Phe Thr Cys Trp Trp
130                 135                 140

Leu Thr Ala Ile Ser Thr Asp Leu Lys Phe Thr Val Lys Ser Ser Arg
145                 150                 155                 160

Gly Ser Ser Asp Pro Gln Gly Val Thr Cys Gly Ala Val Thr Leu Ser
                165                 170                 175

Ala Glu Arg Val Ser Met Asp His Arg Glu Tyr Asn Lys Tyr Thr Val
            180                 185                 190

Glu Cys Gln Glu Gly Ser Ala Cys Pro Ser Ala Glu Ser Leu Pro
        195                 200                 205

Ile Glu Val Val Asp Ala Ile His Lys Leu Lys Tyr Glu Asn Tyr
210                 215                 220

Thr Ser Arg Phe Phe Ile Arg Asp Ile Ile Lys Pro Asp Pro Pro Lys
225                 230                 235                 240

Asn Leu Gln Leu Arg Pro Leu Lys Asn Ser Arg His Val Glu Ile Ser
                245                 250                 255

Trp Glu Tyr Pro Asp Thr Trp Ser Thr Pro His Ser Tyr Phe Ser Leu
                260                 265                 270

Thr Phe Cys Val Gln Val Gln Gly Lys Asn Lys Arg Glu Lys Lys Leu
            275                 280                 285

Phe Met Asp Gln Thr Ser Ala Lys Val Thr Cys His Lys Asp Ala Lys
290                 295                 300

Ile Arg Val Gln Ala Arg Asp Arg Tyr His Ser Ser Ser Trp Ser Glu
305                 310                 315                 320

Trp Ala Ser Val Pro Cys Ser
                325

<210> SEQ ID NO 12
<211> LENGTH: 322
<212> TYPE: PRT
<213> ORGANISM: Artificial Sequence
<220> FEATURE:
<223> OTHER INFORMATION: Synthetic Sequence

<400> SEQUENCE: 12

Met Cys His Gln Gln Leu Val Ile Ser Trp Phe Ser Leu Val Phe Leu
 1               5                  10                  15

Ala Ser Pro Leu Val Ala Ile Trp Glu Leu Glu Lys Asn Val Tyr Val
                20                  25                  30

Val Glu Leu Asp Trp Tyr Pro Asp Ala Pro Gly Glu Met Val Val Leu
            35                  40                  45

Ala Cys Asp Thr Pro Glu Glu Asp Gly Ile Thr Trp Thr Ser Asp Gln
50                  55                  60

Ser Ser Glu Val Leu Gly Thr Gly Lys Thr Leu Thr Ile His Val Lys
65                  70                  75                  80

Glu Phe Gly Asp Ala Gly Gln Tyr Thr Cys His Lys Gly Gly Lys Val
                85                  90                  95

Leu Ser Arg Ser Leu Leu Leu His Lys Lys Glu Asp Gly Ile Trp
            100                 105                 110

Ser Thr Asp Ile Leu Lys Asp Gln Lys Glu Pro Lys Asn Lys Ser Phe
        115                 120                 125

Leu Lys Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160
```

-continued

```
Gly Ser Thr Asp Pro His Gly Val Thr Cys Gly Thr Ala Thr Leu Ser
            165                 170                 175

Glu Asp Leu Gly Glu Tyr Lys Lys Tyr Arg Val Glu Cys Gln Glu Gly
            180                 185                 190

Ser Ala Cys Pro Ala Ala Glu Glu Ser Leu Pro Ile Glu Val Val Leu
            195                 200                 205

Glu Ala Val His Lys Leu Lys Tyr Glu Asn Tyr Thr Ser Ser Phe Phe
210                 215                 220

Ile Arg Asp Ile Ile Lys Pro Asp Pro Pro Lys Asn Leu Gln Leu Arg
225                 230                 235                 240

Pro Leu Lys Asn Ser Arg Gln Val Glu Val Asn Trp Glu Tyr Pro Asp
            245                 250                 255

Thr Trp Ser Thr Pro His Ser Tyr Phe Ser Leu Thr Phe Cys Val Gln
            260                 265                 270

Val Gln Gly Arg Asn Lys Arg Glu Lys Lys Leu Phe Met Asp Gln Thr
            275                 280                 285

Ser Ala Lys Val Thr Cys His Lys Asp Ala Lys Ile Arg Val Gln Ala
            290                 295                 300

Arg Asp Arg Tyr Tyr Ser Ser Ser Trp Ser Asp Trp Ala Ser Val Ser
305                 310                 315                 320

Cys Gly

<210> SEQ ID NO 13
<211> LENGTH: 324
<212> TYPE: PRT
<213> ORGANISM: Artificial Sequence
<220> FEATURE:
<223> OTHER INFORMATION: Synthetic Sequence

<400> SEQUENCE: 13

Met Cys His Gln Gln Leu Val Ile Ser Trp Phe Ser Leu Val Phe Leu
1               5                   10                  15

Ala Ser Pro Leu Met Ala Ile Trp Glu Leu Lys Lys Asp Val Tyr Val
            20                  25                  30

Val Glu Leu Asp Trp Tyr Pro Asp Ala Pro Gly Glu Met Val Val Leu
            35                  40                  45

Ala Cys Asp Thr Pro Glu Glu Asp Gly Ile Thr Trp Thr Ser Asp Gln
50                  55                  60

Ser Ser Glu Val Leu Gly Thr Gly Lys Thr Leu Thr Ile His Val Lys
65                  70                  75                  80

Glu Phe Gly Asp Ala Gly Gln Tyr Thr Cys His Lys Gly Gly Thr Val
            85                  90                  95

Leu Ser Gln Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Ser Phe
            115                 120                 125

Leu Lys Cys Glu Ala Lys Asn Tyr Ser Gly Arg Phe Thr Cys Trp Trp
            130                 135                 140

Leu Thr Ala Ile Ser Thr Asp Leu Lys Phe Thr Val Lys Ser Ser Arg
145                 150                 155                 160

Gly Ser Thr Asp Pro Arg Gly Val Thr Cys Gly Thr Ala Thr Leu Ser
            165                 170                 175

Glu Asp Leu Gly Glu Tyr Lys Lys Tyr Arg Val Glu Cys Gln Glu Gly
            180                 185                 190

Ser Ala Cys Pro Ala Ala Glu Glu Ser Leu Pro Ile Glu Val Val Leu
```

-continued

```
            195                 200                 205
Glu Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Arg
225                 230                 235                 240

Pro Leu Lys Asn Ser Arg His Val Glu Val Ser Trp Glu Tyr Pro Asp
                245                 250                 255

Thr Trp Ser Ala Pro His Ser Tyr Phe Ser Leu Thr Phe Gly Val Gln
                260                 265                 270

Val Gln Gly Arg Asn Lys Arg Glu Asp Arg Leu Phe Met Asp Gln Thr
            275                 280                 285

Ser Ala Lys Val Val Cys His Lys Asp Ala Lys Ile Arg Val Gln Ala
    290                 295                 300

Arg Asp Arg Tyr Tyr Ser Ser Ser Trp Ser Glu Trp Ala Ser Val Ser
305                 310                 315                 320

Leu Gln Ser Val
```

<210> SEQ ID NO 14
<211> LENGTH: 329
<212> TYPE: PRT
<213> ORGANISM: Artificial Sequence
<220> FEATURE:
<223> OTHER INFORMATION: Synthetic Sequence

<400> SEQUENCE: 14

```
Met Cys His Gln Gln Leu Val Ile Ser Trp Phe Ser Leu Val Phe Leu
1               5                   10                  15

Ala Ser Pro Leu Val Ala Ile Trp Glu Leu Glu Lys Asn Val Tyr Val
                20                  25                  30

Val Glu Leu Asp Trp Tyr Pro Asp Ala Pro Gly Glu Met Val Val Leu
            35                  40                  45

Ala Cys Asp Thr Pro Glu Glu Asp Gly Ile Thr Trp Thr Ser Asp Gln
    50                  55                  60

Ser Ser Glu Val Leu Gly Thr Gly Lys Thr Leu Thr Ile His Val Lys
65                  70                  75                  80

Glu Phe Gly Asp Ala Gly Gln Tyr Thr Cys Arg Lys Gly Gly Ala Val
                85                  90                  95

Leu Ser Gln Ser Leu Leu Leu His Lys Lys Glu Asp Gly Ile Trp
                100                 105                 110

Ser Thr Asp Ile Leu Lys Asp Gln Lys Glu Pro Lys Asn Lys Ile Phe
    115                 120                 125

Leu Lys Cys Glu Ala Lys Asn Tyr Ser Gly Arg Phe Thr Cys Trp Trp
130                 135                 140

Leu Thr Ala Ile Ser Thr Asp Leu Lys Phe Thr Val Lys Ser Ser Arg
145                 150                 155                 160

Gly Ser Ser Asp Pro Gln Gly Val Thr Cys Gly Ala Val Thr Leu Ser
                165                 170                 175

Ala Glu Arg Val Ser Met Asp His Arg Glu Tyr Asn Lys Tyr Thr Val
            180                 185                 190

Glu Cys Gln Glu Gly Ser Ala Cys Pro Ser Ala Glu Glu Ser Leu Pro
    195                 200                 205

Ile Glu Val Val Val Asp Ala Ile His Lys Leu Lys Tyr Glu Asn Tyr
    210                 215                 220

Thr Ser Ser Phe Phe Ile Arg Asp Ile Ile Lys Pro Asp Pro Pro Lys
225                 230                 235                 240
```

```
Asn Leu Gln Leu Lys Pro Leu Lys Asn Ser Arg His Val Glu Ile Ser
                245                 250                 255

Trp Glu Tyr Pro Asp Thr Trp Ser Ile Pro His Ser Tyr Phe Ser Leu
            260                 265                 270

Met Phe Gly Val Gln Val Gln Gly Lys Asn Lys Arg Glu Lys Lys Asp
        275                 280                 285

Arg Leu Ser Val Asp Lys Thr Ser Ala Lys Val Val Cys His Lys Asp
    290                 295                 300

Ala Lys Ile Arg Val Gln Ala Arg Asp Arg Tyr Tyr Ser Ser Ser Trp
305                 310                 315                 320

Ser Glu Trp Ala Ser Val Pro Cys Ser
                325

<210> SEQ ID NO 15
<211> LENGTH: 328
<212> TYPE: PRT
<213> ORGANISM: Homo sapiens

<400> SEQUENCE: 15

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
```

```
                   275                 280                 285
Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 16
<211> LENGTH: 666
<212> TYPE: DNA
<213> ORGANISM: Artificial Sequence
<220> FEATURE:
<223> OTHER INFORMATION: Synthetic Sequence

<400> SEQUENCE: 16

```
atgtgcccac ttcgcagcct cctcctcata tccaccctgg ttctcctcca ccacctgccc    60
cacctcagtt tgggcaggag cctccccacc accacagcaa gcccaggaag gagctgcctc   120
gactactccc aaaacctgtt gaaggccgcc agcaacacgc ttcagaaggc cagacaaatt   180
ctagaatttt acccttgcac ttctgaggag atcgatcatg aagatatcac caaagataaa   240
accagcacag tggaggcctg tttaccactg gaattagcca cgaatgagag ttgcctggct   300
tccagagaga tctctctgat aactaatggg agttgcctgg cttccagaaa gacctctttt   360
atgacaaccc tgtgccatag cagcatctat gaggacttga agatgtacca gatggaattc   420
aaggccatga acgcaaagct tttgatggat cctaagaggc agatctttct agatcaaaac   480
atgctggcag ttattgatga gctgatgcag gccctgaatt tcaacagtga gactgtgcca   540
cagaagccct ccctggaaga actggatttt tataagacta aaatcaagct ctgcatactt   600
cttcatgcct tcagaattcg tgcggtgacc atcgacagaa tgatgagcta tctgaattct   660
tcctaa                                                             666
```

<210> SEQ ID NO 17
<211> LENGTH: 666
<212> TYPE: DNA
<213> ORGANISM: Artificial Sequence
<220> FEATURE:
<223> OTHER INFORMATION: Synthetic Sequence

<400> SEQUENCE: 17

```
atgtacccac ttcgcagcct cctcctcata tccaccctgg ttctcctcca ccacctgccc    60
cacctcagtt tgggcaggag cctccccacc accacagcaa gcccaggaag gagctgcctc   120
gactactccc aaaacctgtt gaaggccgcc agcaacacgc ttcagagggc cagacaaatt   180
ctagaatttt acccttgcac ttctgaggag atcgatcatg aagatatcac caaagataaa   240
accagcacag tggaggcctg tttaccactg gaattagcca cgaatgagag ttgcctggct   300
tccagagaga tctctctgat aactaatggg agttgcctgg cttccagaaa gacctctttt   360
atgacaaccc tgtgccttag cagcatctat gaggacttga agatgtacca gatggaattc   420
aaggccatga acgcaaagct tttgatggat cctaagaggc agatctttt agatcaaaac   480
atgctggcag ttattgatga gctgatgcag gccctgaatt tcaacagtga gactgtgcca   540
cagaagccct ccctggaaga actggatttt tataagacta aaatcaagct ctgcatactt   600
cttcatgcct tcagaattcg ggcagtgacc atcaatagaa tgatgagcta tctgaattct   660
tcctag                                                             666
```

<210> SEQ ID NO 18
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 18

```
atgtgcccgc cgcgcggcct cctccttgtg gctaccctgg tcctcctgga ccacctcagt      60
ttggccagaa acctccctgt ggccacccca gcccaggaa tgttcccatg ccttcaccac      120
tcccaaaacc tgctgagggc cgtcagcaac atgctgcaga aggccagaca aactctagaa      180
ttttactcct gcacttccga agagattgat catgaagata tcacaaaaga taaaaccagc      240
acagtggagg cctgcttacc actggaatta atcaagaatg agagttgcct aaattccaga      300
gagacttctt tcataactaa tgggagttgc ctagcctcca gaaagacctc tttttatgaca     360 accctgtgcc ttagcagtat ctatgaggac ttgaagatgt accaggtgga gttcaagacc      420
atgaatgcaa agcttctgat gaatcctaag aggcagatct ttctggatca aaacatgctg      480
acagctattg atgagctgtt acaggccctg aatttcaaca gtgagactgt gccacaaaaa      540
tcctcccttg aagaaccgga ttttttataaa actaaaatca agctctgcat acttcttcat     600
gctttcagaa ttcgggcagt gaccatcaat agaatgatga gctatctgaa ttcttcctag     660
```

<210> SEQ ID NO 19
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 19

```
atgtgtccag cgcgcagcct cctccttgtg gctaccctgg tcctcctgga ccacctcagt      60
ttggccagaa acctccctgt ggccacccca gcccaggaa tgctcccatg ccttcaccac      120
tcccaaaacc tgctgagggc tgtcagcaac acgctccaga aggccaaaca aaccctagaa      180 ttttaccct gcacttccga agagattgat catgaagata tcacacaaga taaaaccagc      240
acagtggagg cctgtttacc actggaatta gccacgaatg agagttgcct ggcttccaga      300
gggatctctc tgataactaa tgggagttgc ctggcctcca gaaagacctc tttttatgacg     360 accctgtgcc ttagcagtat ctatgaggac ttgaagatgt accaggtgga gttcaaggcc      420
atgaatgcaa agctgttaat ggatcctaaa aggcagatct ttctggatca aaacatgctg      480
gcagctattg ctgagctaat gcaggccctg aatgtcaaca gtgagactgc gccacaaaaa      540
tcctcccttg aagaaccgga ttttttataaa actaaaatca agctctgcat acttcttcat     600
gctttcagaa ttcgtgcagt gaccatcaat agaatgatga gctatctgaa ttcttcctag     660
```

<210> SEQ ID NO 20
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 20

```
atgtgtccag cgcgcagcct cctccttgtg gctaccctgg tcctcctgga ccacctcagt      60
ttggccagaa acctccctgt ggccacccca gcccaggaa tgttcccatg ccttcaccac      120
tcccaaaacc tgctgagggc cgtcagcaac atgctgcaga aggccagaca aactctagaa      180
```

```
ttttactcct gcacttccga agagattgat catgaagata tcacaaaaga taaaaccagc    240
acagtggagg cctgcttacc actggaatta atcaagaatg agagttgcct aaattccaga    300
gagacttctt tcataactaa tgggagttgc ctagcctcca gaaagacctc ttttatgaca    360
accctgtgcc ttagcagtat ctatgaggac ttgaagatgt accaggtgga gttcaaggcc    420
atgaatgcaa agctgttaat ggatcctaaa aggcagatct ttctggatca aaacatgctg    480
gcagctattg ctgagctaat gcaggccctg aatgtcaaca gtgagactgc gccacaaaaa    540
tcctcccttg aagaaccgga ttttataaa actaaaatca agctctgcat acttcttcat     600
gctttcagaa ttcgtgcagt gaccatcaat agaatgatga gctatctgaa ttcttcctag    660
```

<210> SEQ ID NO 21
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 21

```
atgtgtccag cgcgcagcct cctccttgtg gctaccctgg tcctcctgga ccacctcagt     60
ttggccagaa acctccccgt ggccactcca gacccaggaa tgttcccatg ccttcaccac    120
tcccaaaacc tgctgagggc cgtcagcaac atgctgcaga aggccagaca aactctagaa    180
ttttactcct gcacttccga agagattgat catgaagata tcacaaaaga taaaaccagc    240
acagtggagg cctgtttacc actggaatta gccacgaatg agagttgcct ggcttccaga    300
gggatctctc tgataactaa tgggagttgc ctagcctcca gaaagacctc ttttatgacg    360
accctgtgcc ttggcagtat ctatgaggac ttgaagatgt accaggtgga gttcaagacc    420
atgaatgcaa agcttctgat gaatcctaag aggcagatct ttctggatca aaacatgctg    480
acagctattg atgagctgtt acaggccctg aatttcaaca gtgagactgt gccacaaaaa    540
tcctcccttg aagaaccgga ttttataaa actaaaatca agctctgcat acttcttcat     600
gctttcagaa ttcgggcagt gaccatcaat agaatgatga gctatctgaa ttcttcctag    660
```

<210> SEQ ID NO 22
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 22

```
atgtgcccgc cgcgcggcct cctccttgtg gctaccctgg tcctcctgga ccacctcagt     60
ttggccagaa acctccctgt ggccaccca ggcccaggaa tgttcccatg ccttcaccac    120
tcccaaaacc tgctgagggc cgtcagcaac atgctgcaga aggccagaca aactctagaa    180
ttttactcct gcacttccga agagactgat catgaagata tcacaaaaga taaaaccagc    240
acagtggagg cctgcttacc actggaatta atcaagaatg agagttgcct aaattccaga    300
gagacttctt tcataactaa tgggagttgc ctagcctcca gaaagacctc ttttatgaca    360
accctgtgcc ttagcagtat ctatgaggac ttgaagatgt accaggtgga gttcaagacc    420
atgaatgcaa agcttctgat gaatcctaag aggcagatct ttctggatca aaacatgctg    480
acagctattg atgagctgtt acaggccctg aatttcaaca gtgagactgt gccacaaaaa    540
tcctcccttg aagaaccgga ttttataaa actaaaatca agctctgcat acttcttcat     600
```

```
gctttcagaa ttcgggcagt gaccatcaat agaatgatga gctatctgaa ttcttcctag    660

<210> SEQ ID NO 23
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 23
atgtgcccgc cgcgcggcct cctccttgtg gctaccctgg tcctcctgga ccacctcagt     60
ttggccagaa acctccccgt ggccacccca ggcccaggaa tgttcccatg ccttcaccac    120
tcccaaaacc tgctgagggc tgtcagcaac acgctccaga aggccaaaca aaccctagaa    180
ttttacccct gcacttccga agagattgat catgaagata tcacaaaaga taaaaccagc    240
acagtggagg cctgtttacc actggaatta gccacgaatg agagttgcct ggcttccaga    300
gggatctctc tgataactaa tgggagttgc ctggcctcca gaaagacctc ttttatgaca    360
accctgtgcc ttagcagcat ctatgaggac ttgaagatgt accaggtgga gttcaaggcc    420
atgaatgcaa agctgttaat ggatcctaaa aggcagatct ttctggatca aaacatgctg    480
gcagctattg ctgagctaat gcaggccctg aatgtcaaca gtgagactgc gccacaaaaa    540 tcctcccctgg aagaaccgga tttttataaa actaaaatca agctctgcat acttcttcat    600
gctttcagaa ttcgggcagt gaccatcaat agaatgatga gctatctgaa ttcttcctag    660

<210> SEQ ID NO 24
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 24
atgtgtccag cgcgcagcct cctccttgtg gctaccctgg tcctcctgga ccacctcagt     60
ttggccagaa acctccccgt ggccactcca gacccaggaa tgttcccatg ccttcaccac    120
tcccaaaacc tgctgagggc tgtcagcaac acgctccaga aggccaaaca aaccctagaa    180
ttttacccct gcacttccga agagattgat catgaagata tcacaaaaga taaaaccagc    240
acagtggagg cctgtttacc actggaatta gccacgaatg agagttgcct ggcttccaga    300
gggatctctc tgataactaa tgggagttgc ctggcctcca gaaagacctc ttttatgacg    360
accctgtgcc ttagcagcat ctatgaggac ttgaagatgt accaggtgga gttcaaggcc    420
atgaatgcaa agctgttgat ggatcctaaa aggcagatct ttctggatca aaacatgctg    480
gcagctattg ctgagctaat gcaggccctg aatgtcaaca gtgagactgc gccacaaaaa    540
tcctcccttg aagaaccgga tttttataag actaaaatca agctctgcat acttcttcat    600
gccttcagaa ttcgtgcagt gaccatcgat agaatgatga gctatctgaa ttcttcctag    660

<210> SEQ ID NO 25
<211> LENGTH: 660
<212> TYPE: DNA
<213> ORGANISM: Artificial Sequence
<220> FEATURE:
<223> OTHER INFORMATION: Synthetic Sequence

<400> SEQUENCE: 25
atgtgcccgc cgcgcggcct cctccttgtg gctaccctgg tcctcctgga ccacctcagt     60
ttggccagaa acctccctgt ggccacccca ggcccaggaa tgttcccatg ccttcaccac    120
```

```
tcccaaaacc tgctgagggc cgtcagcaac atgctgcaga aggccagaca aactctagaa    180
ttttactcct gcacttccga agagattgat catgaagata tcacaaaaga taaaaccagc    240
acagtggagg cctgcttacc actggaatta atcaagaatg agagttgcct aaattccaga    300
gagacttctt tcataactaa tgggagttgc ctagcctcca gaaagacctc ttttatgaca    360
accctgtgcc ttagcagtat ctatgaggac ttgaagatgt accaggtgga gttcaagacc    420
atgaatgcaa agcttctgat gaatcctaag aggcagatct ttctggatca aaacatgctg    480
acagctattg atgagctgtt acaggccctg aatttcaaca gtgagactgt gccacaaaaa    540
tcctcccttg aagaaccgga tttttataaa actaaaatca agctctgcat acttcttcat    600
gctttcagaa ttcgggcagt gaccatcaat agaatgatga gctatctgaa ttcttcctag    660
```

<210> SEQ ID NO 26
<211> LENGTH: 221
<212> TYPE: PRT
<213> ORGANISM: Artificial Sequence
<220> FEATURE:
<223> OTHER INFORMATION: Synthetic Sequence
<400> SEQUENCE: 26

```
Met Cys Pro Leu Arg Ser Leu Leu Ile Ser Thr Leu Val Leu Leu
 1               5                  10                  15

His His Leu Pro His Leu Ser Leu Gly Arg Ser Leu Pro Thr Thr Thr
             20                  25                  30

Ala Ser Pro Gly Arg Ser Cys Leu Asp Tyr Ser Gln Asn Leu Leu Lys
         35                  40                  45

Ala Ala Ser Asn Thr Leu Gln Lys Ala Arg Gln Ile Leu Glu Phe Tyr
 50                  55                  60

Pro Cys Thr Ser Glu Glu Ile Asp His Glu Asp Ile Thr Lys Asp Lys
65                   70                  75                  80

Thr Ser Thr Val Glu Ala Cys Leu Pro Leu Glu Leu Ala Thr Asn Glu
                 85                  90                  95

Ser Cys Leu Ala Ser Arg Glu Ile Ser Leu Ile Thr Asn Gly Ser Cys
            100                 105                 110

Leu Ala Ser Arg Lys Thr Ser Phe Met Thr Thr Leu Cys His Ser Ser
        115                 120                 125

Ile Tyr Glu Asp Leu Lys Met Tyr Gln Met Glu Phe Lys Ala Met Asn
    130                 135                 140

Ala Lys Leu Leu Met Asp Pro Lys Arg Gln Ile Phe Leu Asp Gln Asn
145                 150                 155                 160

Met Leu Ala Val Ile Asp Glu Leu Met Gln Ala Leu Asn Phe Asn Ser
                165                 170                 175

Glu Thr Val Pro Gln Lys Pro Ser Leu Glu Glu Leu Asp Phe Tyr Lys
            180                 185                 190

Thr Lys Ile Lys Leu Cys Ile Leu Leu His Ala Phe Arg Ile Arg Ala
        195                 200                 205

Val Thr Ile Asp Arg Met Met Ser Tyr Leu Asn Ser Ser
    210                 215                 220
```

<210> SEQ ID NO 27
<211> LENGTH: 221
<212> TYPE: PRT
<213> ORGANISM: Artificial Sequence
<220> FEATURE:
<223> OTHER INFORMATION: Synthetic Sequence -continued

```
<400> SEQUENCE: 27

Met Tyr Pro Leu Arg Ser Leu Leu Ile Ser Thr Leu Val Leu Leu
 1               5                  10                  15

His His Leu Pro His Leu Ser Leu Gly Arg Ser Leu Pro Thr Thr Thr
            20                  25                  30

Ala Ser Pro Gly Arg Ser Cys Leu Asp Tyr Ser Gln Asn Leu Leu Lys
        35                  40                  45

Ala Ala Ser Asn Thr Leu Gln Arg Ala Arg Gln Ile Leu Glu Phe Tyr
    50                  55                  60

Pro Cys Thr Ser Glu Glu Ile Asp His Glu Asp Ile Thr Lys Asp Lys
65                  70                  75                  80

Thr Ser Thr Val Glu Ala Cys Leu Pro Leu Glu Leu Ala Thr Asn Glu
                85                  90                  95

Ser Cys Leu Ala Ser Arg Glu Ile Ser Leu Ile Thr Asn Gly Ser Cys
            100                 105                 110

Leu Ala Ser Arg Lys Thr Ser Phe Met Thr Thr Leu Cys Leu Ser Ser
        115                 120                 125

Ile Tyr Glu Asp Leu Lys Met Tyr Gln Met Glu Phe Lys Ala Met Asn
    130                 135                 140

Ala Lys Leu Leu Met Asp Pro Lys Arg Gln Ile Phe Leu Asp Gln Asn
145                 150                 155                 160

Met Leu Ala Val Ile Asp Glu Leu Met Gln Ala Leu Asn Phe Asn Ser
                165                 170                 175

Glu Thr Val Pro Gln Lys Pro Ser Leu Glu Glu Leu Asp Phe Tyr Lys
            180                 185                 190

Thr Lys Ile Lys Leu Cys Ile Leu Leu His Ala Phe Arg Ile Arg Ala
        195                 200                 205

Val Thr Ile Asn Arg Met Met Ser Tyr Leu Asn Ser Ser
    210                 215                 220

<210> SEQ ID NO 28
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 28

Met Cys Pro Pro Arg Gly Leu Leu Val Ala Thr Leu Val Leu Leu
 1               5                  10                  15

Asp His Leu Ser Leu Ala Arg Asn Leu Pro Val Ala Thr Pro Gly Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Ser Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Ile Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Thr Thr Leu Cys Leu Ser Ser Ile Tyr
        115                 120                 125

Glu Asp Leu Lys Met Tyr Gln Val Glu Phe Lys Thr Met Asn Ala Lys
```

```
            130                 135                 140
Leu Leu Met Asn Pro Lys Arg Gln Ile Phe Leu Asp Gln Asn Met Leu
145                 150                 155                 160

Thr Ala Ile Asp Glu Leu Leu Gln Ala Leu Asn Phe Asn Ser Glu Thr
                165                 170                 175

Val Pro Gln Lys Ser Ser Leu Glu Glu Pro Asp Phe Tyr Lys Thr Lys
                180                 185                 190

Ile Lys Leu Cys Ile Leu Leu His Ala Phe Arg Ile Arg Ala Val Thr
                195                 200                 205

Ile Asn Arg Met Met Ser Tyr Leu Asn Ser Ser
    210                 215

<210> SEQ ID NO 29
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 29

Met Cys Pro Ala Arg Ser Leu Leu Leu Val Ala Thr Leu Val Leu Leu
 1               5                  10                  15

Asp His Leu Ser Leu Ala Arg Asn Leu Pro Val Ala Thr Pro Gly Pro
                20                  25                  30

Gly Met Leu Pro Cys Leu His His Ser Gln Asn Leu Leu Arg Ala Val
                35                  40                  45

Ser Asn Thr Leu Gln Lys Ala Lys Gln Thr Leu Glu Phe Tyr Pro Cys
    50                  55                  60

Thr Ser Glu Glu Ile Asp His Glu Asp Ile Thr Gln Asp Lys Thr Ser
65                  70                  75                  80

Thr Val Glu Ala Cys Leu Pro Leu Glu Leu Ala Thr Asn Glu Ser Cys
                85                  90                  95

Leu Ala Ser Arg Gly Ile Ser Leu Ile Thr Asn Gly Ser Cys Leu Ala
                100                 105                 110

Ser Arg Lys Thr Ser Phe Met Thr Thr Leu Cys Leu Ser Ser Ile Tyr
                115                 120                 125

Glu Asp Leu Lys Met Tyr Gln Val Glu Phe Lys Ala Met Asn Ala Lys
    130                 135                 140

Leu Leu Met Asp Pro Lys Arg Gln Ile Phe Leu Asp Gln Asn Met Leu
145                 150                 155                 160

Ala Ala Ile Ala Glu Leu Met Gln Ala Leu Asn Val Asn Ser Glu Thr
                165                 170                 175

Ala Pro Gln Lys Ser Ser Leu Glu Glu Pro Asp Phe Tyr Lys Thr Lys
                180                 185                 190

Ile Lys Leu Cys Ile Leu Leu His Ala Phe Arg Ile Arg Ala Val Thr
                195                 200                 205

Ile Asn Arg Met Met Ser Tyr Leu Asn Ser Ser
    210                 215

<210> SEQ ID NO 30
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 30
```

```
Met Cys Pro Ala Arg Ser Leu Leu Val Ala Thr Leu Val Leu Leu
 1               5                  10                  15

Asp His Leu Ser Leu Ala Arg Asn Leu Pro Val Ala Thr Pro Gly Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Ser Cys
 50                  55                  60

Thr Ser Glu Glu Ile Asp His Glu Asp Ile Thr Lys Asp Lys Thr Ser
 65                  70                  75                  80

Thr Val Glu Ala Cys Leu Pro Leu Glu Leu Ile Lys Asn Glu Ser Cys
                85                  90                  95

Leu Asn Ser Arg Glu Thr Ser Phe Ile Thr Asn Gly Ser Cys Leu Ala
                100                 105                 110

Ser Arg Lys Thr Ser Phe Met Thr Thr Leu Cys Leu Ser Ser Ile Tyr
            115                 120                 125

Glu Asp Leu Lys Met Tyr Gln Val Glu Phe Lys Ala Met Asn Ala Lys
        130                 135                 140

Leu Leu Met Asp Pro Lys Arg Gln Ile Phe Leu Asp Gln Asn Met Leu
145                 150                 155                 160

Ala Ala Ile Ala Glu Leu Met Gln Ala Leu Asn Val Asn Ser Glu Thr
                165                 170                 175

Ala Pro Gln Lys Ser Ser Leu Glu Glu Pro Asp Phe Tyr Lys Thr Lys
                180                 185                 190

Ile Lys Leu Cys Ile Leu Leu His Ala Phe Arg Ile Arg Ala Val Thr
            195                 200                 205

Ile Asn Arg Met Met Ser Tyr Leu Asn Ser Ser
            210                 215
```

<210> SEQ ID NO 31
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 31

```
Met Cys Pro Ala Arg Ser Leu Leu Val Ala Thr Leu Val Leu Leu
 1               5                  10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Ser Cys
 50                  55                  60

Thr Ser Glu Glu Ile Asp His Glu Asp Ile Thr Lys Asp Lys Thr Ser
 65                  70                  75                  80

Thr Val Glu Ala Cys Leu Pro Leu Glu Leu Ala Thr Asn Glu Ser Cys
                85                  90                  95

Leu Ala Ser Arg Gly Ile Ser Leu Ile Thr Asn Gly Ser Cys Leu Ala
                100                 105                 110

Ser Arg Lys Thr Ser Phe Met Thr Thr Leu Cys Leu Gly Ser Ile Tyr
            115                 120                 125

Glu Asp Leu Lys Met Tyr Gln Val Glu Phe Lys Thr Met Asn Ala Lys
        130                 135                 140
```

```
Leu Leu Met Asn Pro Lys Arg Gln Ile Phe Leu Asp Gln Asn Met Leu
145                 150                 155                 160

Thr Ala Ile Asp Glu Leu Leu Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asn Arg Met Met Ser Tyr Leu Asn Ser Ser
        210                 215

<210> SEQ ID NO 32
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 32

Met Cys Pro Pro Arg Gly Leu Leu Leu Val Ala Thr Leu Val Leu Leu
1               5                   10                  15

Asp His Leu Ser Leu Ala Arg Asn Leu Pro Val Ala Thr Pro Gly Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Ser Cys
    50                  55                  60

Thr Ser Glu Glu Thr Asp His Glu Asp Ile Thr Lys Asp Lys Thr Ser
65                  70                  75                  80

Thr Val Glu Ala Cys Leu Pro Leu Glu Leu Ile Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Thr Thr Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asn Pro Lys Arg Gln Ile Phe Leu Asp Gln Asn Met Leu
145                 150                 155                 160

Thr Ala Ile Asp Glu Leu Leu Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asn Arg Met Met Ser Tyr Leu Asn Ser Ser
        210                 215

<210> SEQ ID NO 33
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 33

Met Cys Pro Pro Arg Gly Leu Leu Leu Val Ala Thr Leu Val Leu Leu
1               5                   10                  15
```

```
Asp His Leu Ser Leu Ala Arg Asn Leu Pro Val Ala Thr Pro Gly Pro
            20                  25                  30

Gly Met Phe Pro Cys Leu His His Ser Gln Asn Leu Leu Arg Ala Val
        35                  40                  45

Ser Asn Thr Leu Gln Lys Ala Lys Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Ala Thr Asn Glu Ser Cys
                85                  90                  95

Leu Ala Ser Arg Gly Ile Ser Leu Ile Thr Asn Gly Ser Cys Leu Ala
            100                 105                 110

Ser Arg Lys Thr Ser Phe Met Thr Thr Leu Cys Leu Ser Ser Ile Tyr
            115                 120                 125

Glu Asp Leu Lys Met Tyr Gln Val Glu Phe Lys Ala Met Asn Ala Lys
    130                 135                 140

Leu Leu Met Asp Pro Lys Arg Gln Ile Phe Leu Asp Gln Asn Met Leu
145                 150                 155                 160

Ala Ala Ile Ala Glu Leu Met Gln Ala Leu Asn Val Asn Ser Glu Thr
                165                 170                 175

Ala Pro Gln Lys Ser Ser Leu Glu Pro Asp Phe Tyr Lys Thr Lys
            180                 185                 190

Ile Lys Leu Cys Ile Leu Leu His Ala Phe Arg Ile Arg Ala Val Thr
            195                 200                 205

Ile Asn Arg Met Met Ser Tyr Leu Asn Ser Ser
    210                 215
```

<210> SEQ ID NO 34
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 34

```
Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Thr Leu Gln Lys Ala Lys Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Ala Thr Asn Glu Ser Cys
                85                  90                  95

Leu Ala Ser Arg Gly Ile Ser Leu Ile Thr Asn Gly Ser Cys Leu Ala
            100                 105                 110

Ser Arg Lys Thr Ser Phe Met Thr Thr Leu Cys Leu Ser Ser Ile Tyr
            115                 120                 125

Glu Asp Leu Lys Met Tyr Gln Val Glu Phe Lys Ala Met Asn Ala Lys
    130                 135                 140

Leu Leu Met Asp Pro Lys Arg Gln Ile Phe Leu Asp Gln Asn Met Leu
145                 150                 155                 160
```

```
Ala Ala Ile Ala Glu Leu Met Gln Ala Leu Asn Val Asn Ser Glu Thr
            165                 170                 175

Ala Pro Gln Lys Ser Ser Leu Glu Glu Pro Asp Phe Tyr Lys Thr Lys
        180                 185                 190

Ile Lys Leu Cys Ile Leu Leu His Ala Phe Arg Ile Arg Ala Val Thr
    195                 200                 205

Ile Asp Arg Met Met Ser Tyr Leu Asn Ser Ser
    210                 215

<210> SEQ ID NO 35
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 35

Met Cys Pro Pro Arg Gly Leu Leu Leu Val Ala Thr Leu Val Leu Leu
 1               5                  10                  15

Asp His Leu Ser Leu Ala Arg Asn Leu Pro Val Ala Thr Pro Gly Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Ser Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Ile Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Thr Thr Leu Cys Leu Ser Ser Ile Tyr
        115                 120                 125

Glu Asp Leu Lys Met Tyr Gln Val Glu Phe Lys Thr Met Asn Ala Lys
130                 135                 140

Leu Leu Met Asn Pro Lys Arg Gln Ile Phe Leu Asp Gln Asn Met Leu
145                 150                 155                 160

Thr Ala Ile Asp Glu Leu Leu Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asn Arg Met Met Ser Tyr Leu Asn Ser Ser
    210                 215

<210> SEQ ID NO 36
<211> LENGTH: 219
<212> TYPE: PRT
<213> ORGANISM: Homo sapiens

<400> SEQUENCE: 36

Met Cys Pro Ala Arg Ser Leu Leu Leu Val Ala Thr Leu Val Leu Leu
 1               5                  10                  15

Asp His Leu Ser Leu Ala Arg Asn Leu Pro Val Ala Thr Pro Asp Pro
            20                  25                  30
```

```
Gly Met Phe Pro Cys Leu His His Ser Gln Asn Leu Leu Arg Ala Val
         35                  40                  45
Ser Asn Met Leu Gln Lys Ala Arg Gln Thr Leu Glu Phe Tyr Pro Cys
 50                  55                  60
Thr Ser Glu Glu Ile Asp His Glu Asp Ile Thr Lys Asp Lys Thr Ser
 65                  70                  75                  80
Thr Val Glu Ala Cys Leu Pro Leu Glu Leu Thr Lys Asn Glu Ser Cys
                 85                  90                  95
Leu Asn Ser Arg Glu Thr Ser Phe Ile Thr Asn Gly Ser Cys Leu Ala
                100                 105                 110
Ser Arg Lys Thr Ser Phe Met Met Ala Leu Cys Leu Ser Ser Ile Tyr
            115                 120                 125
Glu Asp Leu Lys Met Tyr Gln Val Glu Phe Lys Thr Met Asn Ala Lys
130                 135                 140
Leu Leu Met Asp Pro Lys Arg Gln Ile Phe Leu Asp Gln Asn Met Leu
145                 150                 155                 160
Ala Val Ile Asp Glu Leu Met Gln Ala Leu Asn Phe Asn Ser Glu Thr
                165                 170                 175
Val Pro Gln Lys Ser Ser Leu Glu Glu Pro Asp Phe Tyr Lys Thr Lys
            180                 185                 190
Ile Lys Leu Cys Ile Leu Leu His Ala Phe Arg Ile Arg Ala Val Thr
        195                 200                 205
Ile Asp Arg Val Thr Ser Tyr Leu Asn Ala Ser
    210                 215
```

<210> SEQ ID NO 37
<211> LENGTH: 987
<212> TYPE: DNA
<213> ORGANISM: Homo sapiens

<400> SEQUENCE: 37

```
atgtgtcacc agcagttggt catctcttgg ttttccctgg ttttctggc atctcccctc       60
gtggccatat gggaactgaa gaaagatgtt tatgtcgtag aattggattg gtatccggat      120
gcccctggag aaatggtggt cctcacctgt gacacccctg aagaagatgg tatcacctgg      180
accttggacc agagcagtga ggtcttaggc tctggcaaaa ccctgaccat ccaagtcaaa      240
gagtttggag atgctggcca gtacacctgt cacaaaggag gcgaggttct aagccattcg      300
ctcctgctgc ttcacaaaaa ggaagatgga atttggtcca ctgatatttt aaaggaccag      360
aaagaaccca aaaataagac ctttctaaga tgcgaggcca agaattattc tggacgtttc      420
acctgctggt ggctgacgac aatcagtact gatttgacat tcagtgtcaa aagcagaga       480
ggctcttctg accccaagg ggtgacgtgc ggagctgcta cactctctgc agagagagtc      540
agagggaca acaaggagta tgagtactca gtggagtgcc aggaggacag tgcctgccca       600
gctgctgagg agagtctgcc cattgaggtc atggtggatg ccgttcacaa gctcaagtat      660
gaaaactaca ccagcagctt cttcatcagg acatcatca aacctgaccc acccaagaac       720
ttgcagctga agccattaaa gaattctcgg caggtggagg tcagctggga gtaccctgac      780
acctggagta ctccacattc ctacttctcc ctgacattct gcgttcaggt ccagggcaag      840
agcaagagag aaaagaaaga tagagtcttc acgacaagaa cctcagccac ggtcatctgc      900
cgcaaaatg ccagcattag cgtgcgggcc caggaccgct actatagctc atcttggagc       960
gaatgggcat ctgtgccctg cagttag                                          987
```

```
<210> SEQ ID NO 38
<211> LENGTH: 660
<212> TYPE: DNA
<213> ORGANISM: Homo sapiens

<400> SEQUENCE: 38
atgtgtccag cgcgcagcct cctccttgtg gctaccctgg tcctcctgga ccacctcagt      60
ttggccagaa acctccccgt ggccactcca gacccaggaa tgttcccatg ccttcaccac     120
tcccaaaacc tgctgagggc cgtcagcaac atgctccaga aggccagaca aactctagaa     180 ttttacccett gcacttctga agagattgat catgaagata tcacaaaaga taaaaccagc     240
acagtggagg cctgtttacc attggaatta accaagaatg agagttgcct aaattccaga     300
gagacctctt tcataactaa tgggagttgc ctggcctcca gaaagacctc ttttatgatg     360
gccctgtgcc ttagtagtat ttatgaagac ttgaagatgt accaggtgga gttcaagacc     420
atgaatgcaa agcttctgat ggatcctaag aggcagatct ttctagatca aaacatgctg     480
gcagttattg atgagctgat gcaggccctg aatttcaaca gtgagactgt gccacaaaaa     540
tcctcccttg aagaaccgga ttttataaa actaaaatca agctctgcat acttcttcat     600
gctttcagaa ttcgggcagt gactattgac agagtgacga gctatctgaa tgcttcctaa     660

<210> SEQ ID NO 39
<211> LENGTH: 328
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (2)...(2)
<223> OTHER INFORMATION: C or H
<220> FEATURE:
<221> NAME/KEY: VARIANT
<222> LOCATION: (3)...(3)
<223> OTHER INFORMATION: H or P
<220> FEATURE:
<221> NAME/KEY: VARIANT
<222> LOCATION: (8)...(8)
<223> OTHER INFORMATION: I or V
<220> FEATURE:
<221> NAME/KEY: VARIANT
<222> LOCATION: (15)...(15)
<223> OTHER INFORMATION: F or L
<220> FEATURE:
<221> NAME/KEY: VARIANT
<222> LOCATION: (21)...(21)
<223> OTHER INFORMATION: V or M
<220> FEATURE:
<221> NAME/KEY: VARIANT
<222> LOCATION: (27)...(27)
<223> OTHER INFORMATION: K or E
<220> FEATURE:
<221> NAME/KEY: VARIANT
<222> LOCATION: (29)...(29)
<223> OTHER INFORMATION: D or N
<220> FEATURE:
<221> NAME/KEY: VARIANT
<222> LOCATION: (40)...(40)
<223> OTHER INFORMATION: D or N
<220> FEATURE:
<221> NAME/KEY: VARIANT
<222> LOCATION: (45)...(45)
<223> OTHER INFORMATION: M or T
<220> FEATURE:
<221> NAME/KEY: VARIANT
<222> LOCATION: (49)...(49)
<223> OTHER INFORMATION: T or A
<220> FEATURE:
<221> NAME/KEY: VARIANT
<222> LOCATION: (62)...(62)
```

```
<223> OTHER INFORMATION: S
<220> FEATURE:
<221> NAME/KEY: VARIANT
<222> LOCATION: (67)...(67)
<223> OTHER INFORMATION: E or G
<220> FEATURE:
<221> NAME/KEY: VARIANT
<222> LOCATION: (71)...(71)
<223> OTHER INFORMATION: T
<220> FEATURE:
<221> NAME/KEY: VARIANT
<222> LOCATION: (78)...(78)
<223> OTHER INFORMATION: H
<220> FEATURE:
<221> NAME/KEY: VARIANT
<222> LOCATION: (91)...(91)
<223> OTHER INFORMATION: H or R
<220> FEATURE:
<221> NAME/KEY: VARIANT
<222> LOCATION: (95)...(95)
<223> OTHER INFORMATION: E, A, K, or T
<220> FEATURE:
<221> NAME/KEY: VARIANT
<222> LOCATION: (96)...(96)
<223> OTHER INFORMATION: V or A
<220> FEATURE:
<221> NAME/KEY: VARIANT
<222> LOCATION: (99)...(99)
<223> OTHER INFORMATION: R or Q
<220> FEATURE:
<221> NAME/KEY: VARIANT
<222> LOCATION: (122)...(122)
<223> OTHER INFORMATION: E or K
<220> FEATURE:
<221> NAME/KEY: VARIANT
<222> LOCATION: (125)...(125)
<223> OTHER INFORMATION: N or A
<220> FEATURE:
<221> NAME/KEY: VARIANT
<222> LOCATION: (127)...(127)
<223> OTHER INFORMATION: S or I
<220> FEATURE:
<221> NAME/KEY: VARIANT
<222> LOCATION: (130)...(130)
<223> OTHER INFORMATION: K
<220> FEATURE:
<221> NAME/KEY: VARIANT
<222> LOCATION: (135)...(135)
<223> OTHER INFORMATION: N or D
<220> FEATURE:
<221> NAME/KEY: VARIANT
<222> LOCATION: (139)...(139)
<223> OTHER INFORMATION: R or H
<220> FEATURE:
<221> NAME/KEY: VARIANT
<222> LOCATION: (147)...(147)
<223> OTHER INFORMATION: T or A
<220> FEATURE:
<221> NAME/KEY: VARIANT
<222> LOCATION: (153)...(153)
<223> OTHER INFORMATION: T or K
<220> FEATURE:
<221> NAME/KEY: VARIANT
<222> LOCATION: (155)...(155)
<223> OTHER INFORMATION: S or T
<220> FEATURE:
<221> NAME/KEY: VARIANT
<222> LOCATION: (163)...(163)
<223> OTHER INFORMATION: S or T
<220> FEATURE:
<221> NAME/KEY: VARIANT
<222> LOCATION: (166)...(166)
<223> OTHER INFORMATION: Q, R, or H
<220> FEATURE:
<221> NAME/KEY: VARIANT
<222> LOCATION: (172)...(172)
<223> OTHER INFORMATION: A or T
<220> FEATURE:
<221> NAME/KEY: VARIANT
```

```
<222> LOCATION: (173)...(173)
<223> OTHER INFORMATION: A or V
<220> FEATURE:
<221> NAME/KEY: VARIANT
<222> LOCATION: (174)...(174)
<223> OTHER INFORMATION: T or L
<220> FEATURE:
<221> NAME/KEY: VARIANT
<222> LOCATION: (177)...(177)
<223> OTHER INFORMATION: A or E
<220> FEATURE:
<221> NAME/KEY: VARIANT
<222> LOCATION: (178)...(178)
<223> OTHER INFORMATION: E or D
<220> FEATURE:
<221> NAME/KEY: VARIANT
<222> LOCATION: (179)...(179)
<223> OTHER INFORMATION: R, L, or K
<220> FEATURE:
<221> NAME/KEY: VARIANT
<222> LOCATION: (180)...(180)
<223> OTHER INFORMATION: V or G
<220> FEATURE:
<221> NAME/KEY: VARIANT
<222> LOCATION: (181)...(184)
<223> OTHER INFORMATION: deleted, or replaced with
      S-(L or M)-(E or D)-H-R
<220> FEATURE:
<221> NAME/KEY: VARIANT
<222> LOCATION: (185)...(185)
<223> OTHER INFORMATION: E
<220> FEATURE:
<221> NAME/KEY: VARIANT
<222> LOCATION: (186)...(186)
<223> OTHER INFORMATION: Y
<220> FEATURE:
<221> NAME/KEY: VARIANT
<222> LOCATION: (187)...(187)
<223> OTHER INFORMATION: K or N
<220> FEATURE:
<221> NAME/KEY: VARIANT
<222> LOCATION: (188)...(188)
<223> OTHER INFORMATION: K
<220> FEATURE:
<221> NAME/KEY: VARIANT
<222> LOCATION: (190)...(190)
<223> OTHER INFORMATION: R or T
<220> FEATURE:
<221> NAME/KEY: VARIANT
<222> LOCATION: (196)...(196)
<223> OTHER INFORMATION: G
<220> FEATURE:
<221> NAME/KEY: VARIANT
<222> LOCATION: (201)...(201)
<223> OTHER INFORMATION: A or S
<220> FEATURE:
<221> NAME/KEY: VARIANT
<222> LOCATION: (211)...(211)
<223> OTHER INFORMATION: V
<220> FEATURE:
<221> NAME/KEY: VARIANT
<222> LOCATION: (212)...(212)
<223> OTHER INFORMATION: V or L
<220> FEATURE:
<221> NAME/KEY: VARIANT
<222> LOCATION: (213)...(213)
<223> OTHER INFORMATION: D or E
<220> FEATURE:
<221> NAME/KEY: VARIANT
<222> LOCATION: (215)...(215)
<223> OTHER INFORMATION: V or I
<220> FEATURE:
<221> NAME/KEY: VARIANT
<222> LOCATION: (226)...(226)
<223> OTHER INFORMATION: S or R
<220> FEATURE:
<221> NAME/KEY: VARIANT
<222> LOCATION: (244)...(244)
<223> OTHER INFORMATION: K or R
```

```
<220> FEATURE:
<221> NAME/KEY: VARIANT
<222> LOCATION: (251)...(251)
<223> OTHER INFORMATION: Q or H
<220> FEATURE:
<221> NAME/KEY: VARIANT
<222> LOCATION: (254)...(254)
<223> OTHER INFORMATION: V or I
<220> FEATURE:
<221> NAME/KEY: VARIANT
<222> LOCATION: (255)...(255)
<223> OTHER INFORMATION: S or N
<220> FEATURE:
<221> NAME/KEY: VARIANT
<222> LOCATION: (257)...(257)
<223> OTHER INFORMATION: E or G
<220> FEATURE:
<221> NAME/KEY: VARIANT
<222> LOCATION: (264)...(264)
<223> OTHER INFORMATION: T or A
<220> FEATURE:
<221> NAME/KEY: VARIANT
<222> LOCATION: (274)...(274)
<223> OTHER INFORMATION: C or G
<220> FEATURE:
<221> NAME/KEY: VARIANT
<222> LOCATION: (275)...(275)
<223> OTHER INFORMATION: V or I
<220> FEATURE:
<221> NAME/KEY: VARIANT
<222> LOCATION: (280)...(280)
<223> OTHER INFORMATION: K or R
<220> FEATURE:
<221> NAME/KEY: VARIANT
<222> LOCATION: (281)...(281)
<223> OTHER INFORMATION: S or N
<220> FEATURE:
<221> NAME/KEY: VARIANT
<222> LOCATION: (285)...(285)
<223> OTHER INFORMATION: K or D
<220> FEATURE:
<221> NAME/KEY: VARIANT
<222> LOCATION: (286)...(286)
<223> OTHER INFORMATION: K or R
<220> FEATURE:
<221> NAME/KEY: VARIANT
<222> LOCATION: (287)...(287)
<223> OTHER INFORMATION: D or deleted
<220> FEATURE:
<221> NAME/KEY: VARIANT
<222> LOCATION: (288)...(288)
<223> OTHER INFORMATION: R or deleted
<220> FEATURE:
<221> NAME/KEY: VARIANT
<222> LOCATION: (289)...(289)
<223> OTHER INFORMATION: I or L
<220> FEATURE:
<221> NAME/KEY: VARIANT
<222> LOCATION: (291)...(291)
<223> OTHER INFORMATION: T or M
<220> FEATURE:
<221> NAME/KEY: VARIANT
<222> LOCATION: (293)...(293)
<223> OTHER INFORMATION: K or Q
<220> FEATURE:
<221> NAME/KEY: VARIANT
<222> LOCATION: (297)...(297)
<223> OTHER INFORMATION: T or K
<220> FEATURE:
<221> NAME/KEY: VARIANT
<222> LOCATION: (299)...(299)
<223> OTHER INFORMATION: I, T, or V
<220> FEATURE:
<221> NAME/KEY: VARIANT
<222> LOCATION: (301)...(301)
<223> OTHER INFORMATION: R or H
<220> FEATURE:
<221> NAME/KEY: VARIANT
<222> LOCATION: (303)...(303)
```

-continued

```
<223> OTHER INFORMATION: N or D
<220> FEATURE:
<221> NAME/KEY: VARIANT
<222> LOCATION: (305)...(305)
<223> OTHER INFORMATION: K
<220> FEATURE:
<221> NAME/KEY: VARIANT
<222> LOCATION: (307)...(307)
<223> OTHER INFORMATION: R
<220> FEATURE:
<221> NAME/KEY: VARIANT
<222> LOCATION: (309)...(309)
<223> OTHER INFORMATION: Q
<220> FEATURE:
<221> NAME/KEY: VARIANT
<222> LOCATION: (311)...(311)
<223> OTHER INFORMATION: R
<220> FEATURE:
<221> NAME/KEY: VARIANT
<222> LOCATION: (315)...(315)
<223> OTHER INFORMATION: Y or H
<220> FEATURE:
<221> NAME/KEY: VARIANT
<222> LOCATION: (318)...(318)
<223> OTHER INFORMATION: S or F
<220> FEATURE:
<221> NAME/KEY: VARIANT
<222> LOCATION: (321)...(321)
<223> OTHER INFORMATION: E or D
<220> FEATURE:
<221> NAME/KEY: VARIANT
<222> LOCATION: (326)...(326)
<223> OTHER INFORMATION: P or S
<220> FEATURE:
<221> NAME/KEY: VARIANT
<222> LOCATION: (327)...(327)
<223> OTHER INFORMATION: C or L
<220> FEATURE:
<221> NAME/KEY: VARIANT
<222> LOCATION: (328)...(328)
<223> OTHER INFORMATION: S, G, or Q

<400> SEQUENCE: 39

Met Xaa Xaa Gln Gln Leu Val Xaa Ser Trp Phe Ser Leu Val Xaa Leu
 1               5                  10                  15

Ala Ser Pro Leu Xaa Ala Ile Trp Glu Leu Xaa Lys Xaa Val Tyr Val
            20                  25                  30

Val Glu Leu Asp Trp Tyr Pro Xaa Ala Pro Gly Glu Xaa Val Val Leu
        35                  40                  45

Xaa Cys Asp Thr Pro Glu Glu Asp Gly Ile Thr Trp Thr Xaa Asp Gln
 50                  55                  60

Ser Ser Xaa Val Leu Gly Xaa Gly Lys Thr Leu Thr Ile Xaa Val Lys
65                  70                  75                  80

Glu Phe Gly Asp Ala Gly Gln Tyr Thr Cys Xaa Lys Gly Gly Xaa Xaa
                85                  90                  95

Leu Ser Xaa Ser Leu Leu Leu His Lys Lys Glu Asp Gly Ile Trp
            100                 105                 110

Ser Thr Asp Ile Leu Lys Asp Gln Lys Xaa Pro Lys Xaa Lys Xaa Phe
            115                 120                 125

Leu Xaa Cys Glu Ala Lys Xaa Tyr Ser Gly Xaa Phe Thr Cys Trp Trp
    130                 135                 140

Leu Thr Xaa Ile Ser Thr Asp Leu Xaa Phe Xaa Val Lys Ser Ser Arg
145                 150                 155                 160

Gly Ser Xaa Asp Pro Xaa Gly Val Thr Cys Gly Xaa Xaa Xaa Leu Ser
                165                 170                 175

Xaa Xaa Xaa Xaa Xaa Xaa Xaa Xaa Xaa Xaa Xaa Xaa Tyr Xaa Val Glu
            180                 185                 190
```

-continued

```
Cys Gln Glu Xaa Ser Ala Cys Pro Xaa Ala Glu Glu Ser Leu Pro Ile
            195                 200                 205

Glu Val Xaa Xaa Xaa Ala Xaa His Lys Leu Lys Tyr Glu Asn Tyr Thr
        210                 215                 220

Ser Xaa Phe Phe Ile Arg Asp Ile Ile Lys Pro Asp Pro Pro Lys Asn
225                 230                 235                 240

Leu Gln Leu Xaa Pro Leu Lys Asn Ser Arg Xaa Val Glu Xaa Xaa Trp
                245                 250                 255

Xaa Tyr Pro Asp Thr Trp Ser Xaa Pro His Ser Tyr Phe Ser Leu Thr
            260                 265                 270

Phe Xaa Xaa Gln Val Gln Gly Xaa Xaa Lys Arg Glu Xaa Xaa Xaa Xaa
        275                 280                 285

Xaa Phe Xaa Asp Xaa Thr Ser Ala Xaa Val Xaa Cys Xaa Lys Xaa Ala
        290                 295                 300

Xaa Ile Xaa Val Xaa Ala Xaa Asp Arg Tyr Xaa Ser Ser Xaa Trp Ser
305                 310                 315                 320

Xaa Trp Ala Ser Val Xaa Xaa Xaa
                325

<210> SEQ ID NO 40
<211> LENGTH: 219
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (2)...(2)
<223> OTHER INFORMATION: C or Y
<220> FEATURE:
<221> NAME/KEY: VARIANT
<222> LOCATION: (4)...(4)
<223> OTHER INFORMATION: A, L, or P
<220> FEATURE:
<221> NAME/KEY: VARIANT
<222> LOCATION: (6)...(6)
<223> OTHER INFORMATION: S or G
<220> FEATURE:
<221> NAME/KEY: VARIANT
<222> LOCATION: (10)...(10)
<223> OTHER INFORMATION: V or I
<220> FEATURE:
<221> NAME/KEY: VARIANT
<222> LOCATION: (11)...(11)
<223> OTHER INFORMATION: A or S
<220> FEATURE:
<221> NAME/KEY: VARIANT
<222> LOCATION: (16)...(16)
<223> OTHER INFORMATION: D or H
<220> FEATURE:
<221> NAME/KEY: VARIANT
<222> LOCATION: (22)...(22)
<223> OTHER INFORMATION: A or G
<220> FEATURE:
<221> NAME/KEY: VARIANT
<222> LOCATION: (24)...(24)
<223> OTHER INFORMATION: N or S
<220> FEATURE:
<221> NAME/KEY: VARIANT
<222> LOCATION: (27)...(27)
<223> OTHER INFORMATION: V or T
<220> FEATURE:
<221> NAME/KEY: VARIANT
<222> LOCATION: (28)...(28)
<223> OTHER INFORMATION: A or T
<220> FEATURE:
<221> NAME/KEY: VARIANT
<222> LOCATION: (30)...(30)
<223> OTHER INFORMATION: P or A
```

```
<220> FEATURE:
<221> NAME/KEY: VARIANT
<222> LOCATION: (31)...(31)
<223> OTHER INFORMATION: D, S, or G
<220> FEATURE:
<221> NAME/KEY: VARIANT
<222> LOCATION: (34)...(34)
<223> OTHER INFORMATION: M or R
<220> FEATURE:
<221> NAME/KEY: VARIANT
<222> LOCATION: (35)...(35)
<223> OTHER INFORMATION: F, S, or L
<220> FEATURE:
<221> NAME/KEY: VARIANT
<222> LOCATION: (36)...(36)
<223> OTHER INFORMATION: P or deleted
<220> FEATURE:
<221> NAME/KEY: VARIANT
<222> LOCATION: (39)...(39)
<223> OTHER INFORMATION: H or D
<220> FEATURE:
<221> NAME/KEY: VARIANT
<222> LOCATION: (40)...(40)
<223> OTHER INFORMATION: H or Y
<220> FEATURE:
<221> NAME/KEY: VARIANT
<222> LOCATION: (46)...(46)
<223> OTHER INFORMATION: R or K
<220> FEATURE:
<221> NAME/KEY: VARIANT
<222> LOCATION: (48)...(48)
<223> OTHER INFORMATION: V or A
<220> FEATURE:
<221> NAME/KEY: VARIANT
<222> LOCATION: (51)...(51)
<223> OTHER INFORMATION: M or T
<220> FEATURE:
<221> NAME/KEY: VARIANT
<222> LOCATION: (54)...(54)
<223> OTHER INFORMATION: K or R
<220> FEATURE:
<221> NAME/KEY: VARIANT
<222> LOCATION: (56)...(56)
<223> OTHER INFORMATION: K or R
<220> FEATURE:
<221> NAME/KEY: VARIANT
<222> LOCATION: (58)...(58)
<223> OTHER INFORMATION: T or I
<220> FEATURE:
<221> NAME/KEY: VARIANT
<222> LOCATION: (63)...(63)
<223> OTHER INFORMATION: P or S
<220> FEATURE:
<221> NAME/KEY: VARIANT
<222> LOCATION: (69)...(69)
<223> OTHER INFORMATION: I or T
<220> FEATURE:
<221> NAME/KEY: VARIANT
<222> LOCATION: (76)...(76)
<223> OTHER INFORMATION: K or Q
<220> FEATURE:
<221> NAME/KEY: VARIANT
<222> LOCATION: (91)...(91)
<223> OTHER INFORMATION: A or I
<220> FEATURE:
<221> NAME/KEY: VARIANT
<222> LOCATION: (92)...(92)
<223> OTHER INFORMATION: K or T
<220> FEATURE:
<221> NAME/KEY: VARIANT
<222> LOCATION: (98)...(98)
<223> OTHER INFORMATION: N or A
<220> FEATURE:
<221> NAME/KEY: VARIANT
<222> LOCATION: (101)...(101)
<223> OTHER INFORMATION: E or G
<220> FEATURE:
<221> NAME/KEY: VARIANT
<222> LOCATION: (102)...(102)
```

-continued

```
<223> OTHER INFORMATION: T or I
<220> FEATURE:
<221> NAME/KEY: VARIANT
<222> LOCATION: (104)...(104)
<223> OTHER INFORMATION: F or L
<220> FEATURE:
<221> NAME/KEY: VARIANT
<222> LOCATION: (120)...(120)
<223> OTHER INFORMATION: T
<220> FEATURE:
<221> NAME/KEY: VARIANT
<222> LOCATION: (121)...(121)
<223> OTHER INFORMATION: T
<220> FEATURE:
<221> NAME/KEY: VARIANT
<222> LOCATION: (124)...(124)
<223> OTHER INFORMATION: L or H
<220> FEATURE:
<221> NAME/KEY: VARIANT
<222> LOCATION: (125)...(125)
<223> OTHER INFORMATION: S or G
<220> FEATURE:
<221> NAME/KEY: VARIANT
<222> LOCATION: (136)...(136)
<223> OTHER INFORMATION: V or M
<220> FEATURE:
<221> NAME/KEY: VARIANT
<222> LOCATION: (140)...(140)
<223> OTHER INFORMATION: T or A
<220> FEATURE:
<221> NAME/KEY: VARIANT
<222> LOCATION: (148)...(148)
<223> OTHER INFORMATION: D or N
<220> FEATURE:
<221> NAME/KEY: VARIANT
<222> LOCATION: (161)...(161)
<223> OTHER INFORMATION: A or T
<220> FEATURE:
<221> NAME/KEY: VARIANT
<222> LOCATION: (162)...(162)
<223> OTHER INFORMATION: V or A
<220> FEATURE:
<221> NAME/KEY: VARIANT
<222> LOCATION: (164)...(164)
<223> OTHER INFORMATION: D or A
<220> FEATURE:
<221> NAME/KEY: VARIANT
<222> LOCATION: (167)...(167)
<223> OTHER INFORMATION: M or L
<220> FEATURE:
<221> NAME/KEY: VARIANT
<222> LOCATION: (172)...(172)
<223> OTHER INFORMATION: F or V
<220> FEATURE:
<221> NAME/KEY: VARIANT
<222> LOCATION: (177)...(177)
<223> OTHER INFORMATION: V or A
<220> FEATURE:
<221> NAME/KEY: VARIANT
<222> LOCATION: (181)...(181)
<223> OTHER INFORMATION: S or P
<220> FEATURE:
<221> NAME/KEY: VARIANT
<222> LOCATION: (186)...(186)
<223> OTHER INFORMATION: P or L
<220> FEATURE:
<221> NAME/KEY: VARIANT
<222> LOCATION: (210)...(210)
<223> OTHER INFORMATION: D or N
<220> FEATURE:
<221> NAME/KEY: VARIANT
<222> LOCATION: (212)...(212)
<223> OTHER INFORMATION: M
<220> FEATURE:
<221> NAME/KEY: VARIANT
<222> LOCATION: (213)...(213)
<223> OTHER INFORMATION: M
<220> FEATURE:
<221> NAME/KEY: VARIANT
```

<222> LOCATION: (218)...(218)
<223> OTHER INFORMATION: S

<400> SEQUENCE: 40

Met Xaa Pro Xaa Arg Xaa Leu Leu Xaa Xaa Thr Leu Val Leu Leu
1               5                   10                  15

Xaa His Leu Ser Leu Xaa Arg Xaa Leu Pro Xaa Xaa Thr Xaa Xaa Pro
        20              25                  30

Gly Xaa Xaa Xaa Cys Leu Xaa Xaa Ser Gln Asn Leu Leu Xaa Ala Xaa
        35              40                  45

Ser Asn Xaa Leu Gln Xaa Ala Xaa Gln Xaa Leu Glu Phe Tyr Xaa Cys
50                  55                  60

Thr Ser Glu Glu Xaa Asp His Glu Asp Ile Thr Xaa Asp Lys Thr Ser
65                  70                  75                  80

Thr Val Glu Ala Cys Leu Pro Leu Glu Leu Xaa Xaa Asn Glu Ser Cys
                85                  90                  95

Leu Xaa Ser Arg Xaa Xaa Ser Xaa Ile Thr Asn Gly Ser Cys Leu Ala
        100                 105                 110

Ser Arg Lys Thr Ser Phe Met Xaa Xaa Leu Cys Xaa Xaa Ser Ile Tyr
        115                 120                 125

Glu Asp Leu Lys Met Tyr Gln Xaa Glu Phe Lys Xaa Met Asn Ala Lys
130                 135                 140

Leu Leu Met Xaa Pro Lys Arg Gln Ile Phe Leu Asp Gln Asn Met Leu
145                 150                 155                 160

Xaa Xaa Ile Xaa Glu Leu Xaa Gln Ala Leu Asn Xaa Asn Ser Glu Thr
                165                 170                 175

Xaa Pro Gln Lys Xaa Ser Leu Glu Glu Xaa Asp Phe Tyr Lys Thr Lys
            180                 185                 190

Ile Lys Leu Cys Ile Leu Leu His Ala Phe Arg Ile Arg Ala Val Thr
        195                 200                 205

Ile Xaa Arg Xaa Xaa Ser Tyr Leu Asn Xaa Ser
        210                 215

<210> SEQ ID NO 41
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 41
atgtgccatc aacaa                                                15

<210> SEQ ID NO 42
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 42

Ile Trp Asp Leu Lys Arg Asp Val Tyr Val Ile Glu Leu Asp Trp Phe
1               5                   10                  15

Pro Asn Ala Pro Gly Glu Thr Leu Val
            20                  25

<210> SEQ ID NO 43
<211> LENGTH: 25
<212> TYPE: PRT

```
<213> ORGANISM: Artificial Sequence
<220> FEATURE:
<223> OTHER INFORMATION: Synthetic Sequence

<400> SEQUENCE: 43

Val Trp Glu Ile Lys Lys Asp Met Tyr Val Val Glu Leu Glu Trp Tyr
 1               5                  10                  15

Pro Asn Ala Pro Gly Glu Thr Val Ile
            20                  25

<210> SEQ ID NO 44
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 44

Ala Ala Ala Gly Ala Pro Val Pro Tyr Pro Asp Pro Leu Glu Arg Ala
 1               5                  10                  15

Ala Ala His His His His His His
            20
```